(12) United States Patent
Hipsley

(10) Patent No.: US 11,844,570 B2
(45) Date of Patent: *Dec. 19, 2023

(54) SYSTEM AND METHODS USING REAL-TIME PREDICTIVE VIRTUAL 3D EYE FINITE ELEMENT MODELING FOR SIMULATION OF OCULAR STRUCTURE BIOMECHANICS

(71) Applicant: ACE VISION GROUP, INC., Silver Lake, OH (US)

(72) Inventor: Annmarie Hipsley, Silver Lake, OH (US)

(73) Assignee: ACE VISION GROUP, INC., Silver Lake, OH (US)

( * ) Notice: Subject to any disclaimer, the term of this patent is extended or adjusted under 35 U.S.C. 154(b) by 50 days.

This patent is subject to a terminal disclaimer.

(21) Appl. No.: 17/376,157

(22) Filed: Jul. 15, 2021

(65) Prior Publication Data

US 2022/0000357 A1 Jan. 6, 2022

Related U.S. Application Data

(63) Continuation of application No. 15/638,346, filed on Jun. 29, 2017, now Pat. No. 11,071,450.

(Continued)

(51) Int. Cl.
*A61B 3/00* (2006.01)
*G06F 17/18* (2006.01)
*G16H 50/20* (2018.01)
*A61F 9/008* (2006.01)
*G16H 20/40* (2018.01)
*G06N 3/04* (2023.01)
*G16H 50/50* (2018.01)

(Continued)

(52) U.S. Cl.
CPC ............ *A61B 3/0025* (2013.01); *A61B 3/102* (2013.01); *A61B 34/10* (2016.02); *A61F 9/008* (2013.01); *G06F 17/18* (2013.01); *G06F 30/23* (2020.01); *G06N 3/006* (2013.01); *G06N 3/04* (2013.01); *G16H 20/40* (2018.01); *G16H 50/20* (2018.01); *G16H 50/50* (2018.01); *A61B 2034/104* (2016.02); *A61B 2034/105* (2016.02); *A61F 2009/00865* (2013.01); *G06F 2111/10* (2020.01)

(58) Field of Classification Search
CPC ....... A61B 3/0025; A61B 34/10; A61B 3/102; A61B 2034/104; A61B 2034/105; G06F 17/18; G16H 20/40; G16H 50/50
See application file for complete search history.

(56) References Cited

U.S. PATENT DOCUMENTS 7,096,166 B2   8/2006   Tang et al.
7,798,641 B2   9/2010   Bille
(Continued)

OTHER PUBLICATIONS

Jamshid Ghaboussi, Accurate intraocular pressure prediction from applanation response data using genetic algorithm and neural networks Journal of Biomechanics 42 (2009) 2301-2306 (Year: 2009).*

(Continued)

*Primary Examiner* — Chuen-Meei Gan
(74) *Attorney, Agent, or Firm* — ONE LLP

(57) ABSTRACT

Disclosed are systems, devices and methods for performing simulations using a multi-component Finite Element Model (FEM) of ocular structures involved in ocular accommodation.

20 Claims, 96 Drawing Sheets

Related U.S. Application Data

(60) Provisional application No. 62/356,467, filed on Jun. 29, 2016.

(51) Int. Cl.
| | | |
|---|---|---|
| *G06N 3/006* | (2023.01) | |
| *G06F 30/23* | (2020.01) | |
| *A61B 34/10* | (2016.01) | |
| *A61B 3/10* | (2006.01) | |
| *G06F 111/10* | (2020.01) | |

(56) References Cited

U.S. PATENT DOCUMENTS

| | | | |
|---|---|---|---|
| 7,871,404 B2 | 1/2011 | Hipsley | |
| 8,346,518 B2 | 1/2013 | Dupps et al. | |
| 8,348,932 B2 | 1/2013 | Hipsley | |
| 2002/0077797 A1* | 6/2002 | Hall | A61B 3/0025 703/11 |
| 2003/0208190 A1 | 11/2003 | Roberts et al. | |
| 2006/0058592 A1 | 3/2006 | Bouma et al. | |
| 2007/0027667 A1 | 2/2007 | Osborn et al. | |
| 2007/0203478 A1* | 8/2007 | Herekar | A61F 9/008 606/4 |
| 2008/0058779 A1 | 3/2008 | Hipsley et al. | |
| 2010/0049447 A1 | 2/2010 | Peyman et al. | |
| 2010/0130967 A1* | 5/2010 | Glasmacher | A61F 9/008 606/5 |
| 2010/0134760 A1* | 6/2010 | Salvati | A61B 3/117 351/246 |
| 2011/0190798 A1 | 8/2011 | Hipsley | |
| 2012/0059465 A1 | 3/2012 | Brady et al. | |
| 2012/0069298 A1 | 3/2012 | Ng | |
| 2014/0037063 A1 | 2/2014 | Gertner et al. | |
| 2014/0111765 A1* | 4/2014 | DeBoer | A61F 2/1618 351/205 |
| 2014/0163597 A1 | 6/2014 | Hipsley | |
| 2014/0316388 A1* | 10/2014 | Hipsley | A61F 9/00802 606/4 |
| 2014/0368792 A1 | 12/2014 | Friedman et al. | |
| 2015/0157406 A1 | 6/2015 | Hipsley | |
| 2016/0113816 A1 | 4/2016 | Herekar et al. | |
| 2016/0183961 A1 | 6/2016 | Hipsley | |
| 2017/0231697 A1 | 8/2017 | Hipsley | |
| 2018/0052972 A1* | 2/2018 | Hipsley | G06F 30/23 |
| 2019/0105200 A1* | 4/2019 | Hipsley | A61F 9/00802 |

OTHER PUBLICATIONS

Pitkow Xaq, Haim Sompolinsky, and Markus Meister. 2007. A neural computation for visual acuity in the presence of eye movements. PLOS Biology 5(12): e331. (Year: 2007).*

Ljubimova, Darja, Anders Eriksson, and Svetlana Bauer. "Aspects of eye accommodation evaluated by finite elements." Biomechanics and modeling in mechanobiology 7, No. 2 (2008): 139-150. (Year: 2008).*

Wilkes RP, Reilly MA. A pre-tensioned finite element model of ocular accommodation and presbyopia. International Journal of Advances in Engineering Sciences and Applied Mathematics. Mar. 2016;8:25-38. (Year: 2016).*

Croft, Mary Ann, Jared P. McDonald, Alexander Katz, Ting-Li Lin, Elke Lütjen-Drecoll, and Paul L. Kaufman. "Extralenticular and lenticular aspects of accommodation and presbyopia in human versus monkey eyes." Investigative ophthalmology & visual science 54, No. 7 (2013): 5035-5048. (Year: 2013).*

Grytz R, Fazio MA, Girard MJ, Libertiaux V, Bruno L, Gardiner S, Girkin CA, Downs JC. Material properties of the posterior human sclera. Journal of the mechanical behavior of biomedical materials. Jan. 1, 2014;29:602-17. (Year: 2014).*

WO, PCT/US2017/040146 ISR and Written Opinion, dated Dec. 20, 2017.

Croft, Mary Ann, Jared P. McDonald, Alexander Katz, Ting-Li Lin, Elke U.itjen-Drecoll, and Paul L. Kaufman. "Extralenticular and lenticular aspects of accommodation and presbyopia in human versus monkey eyes." Investigative ophthalmology & visual science 54, No. 7 (2013): 5035-5048. (Year: 2013).

Goldrick, Benjamin. "Modelling the human accommodation system using finite element analysis." PhD diss., Aston University, 2013. (Year: 2013).

Grytz, Rafael, Massimo A. Fazio, Michael JA Girard, Vincent Libertiaux, Luigi Bruno, Stuart Gardiner, Christopher A. Girkin, and J. Crawford Downs. "Material properties of the posterior human sclera." Journal of the mechanical behavior of biomedical materials 29 (2014): 602-617. (Year: 2014).

Ljubimova, Darja, Anders Eriksson, and Svetlana Bauer. "Aspects of eye accommodation evaluated by finite elements." Biomechanics and modeling in mechanobiology 7, No. 2 (2008): 139-150. (Year: 2008).

Roy, Abhijit Sinha, and William J. Dupps. "Effects of altered corneal stiffness on native and postoperative LASIK corneal biomechanical behavior: a whole-eye finite element analysis." Journal of refractive surgery 25, No. 10 (2009): 875-887. (Year: 2009).

Talisa Mohammad Nejad, Finite element modelling of cornea mechanics: a review, Arq Bras Oftalmol. 2014;77(1):60-5 (Year: 2014).

Weeber, Henk A., Gabriele Eckert, Wolfgang Pechhold, and Rob GL van der Heijde. "Stiffness gradient in the crystalline lens." Graefe's Archive for Clinical and Experimental Ophthalmology 245, No. 9 (2007): 1357-1366. (Year: 2007).

Whitford, C., et al., "Biomechanical model of the human cornea: Considering shear stiffness and regional variation of collagen anisotropy and density", J. Mech. Behav. Biomed. Mat., 2015, vol. 42, pp. 76-87.

Wilkes, Robert P., and Matthew A. Reilly. "A pre-tensioned finite element model of ocular accommodation and presbyopia." International Journal of Advances in Engineering Sciences and Applied Mathematics 8, No. 1 (2016): 25-38. (Year: 2016).

* cited by examiner

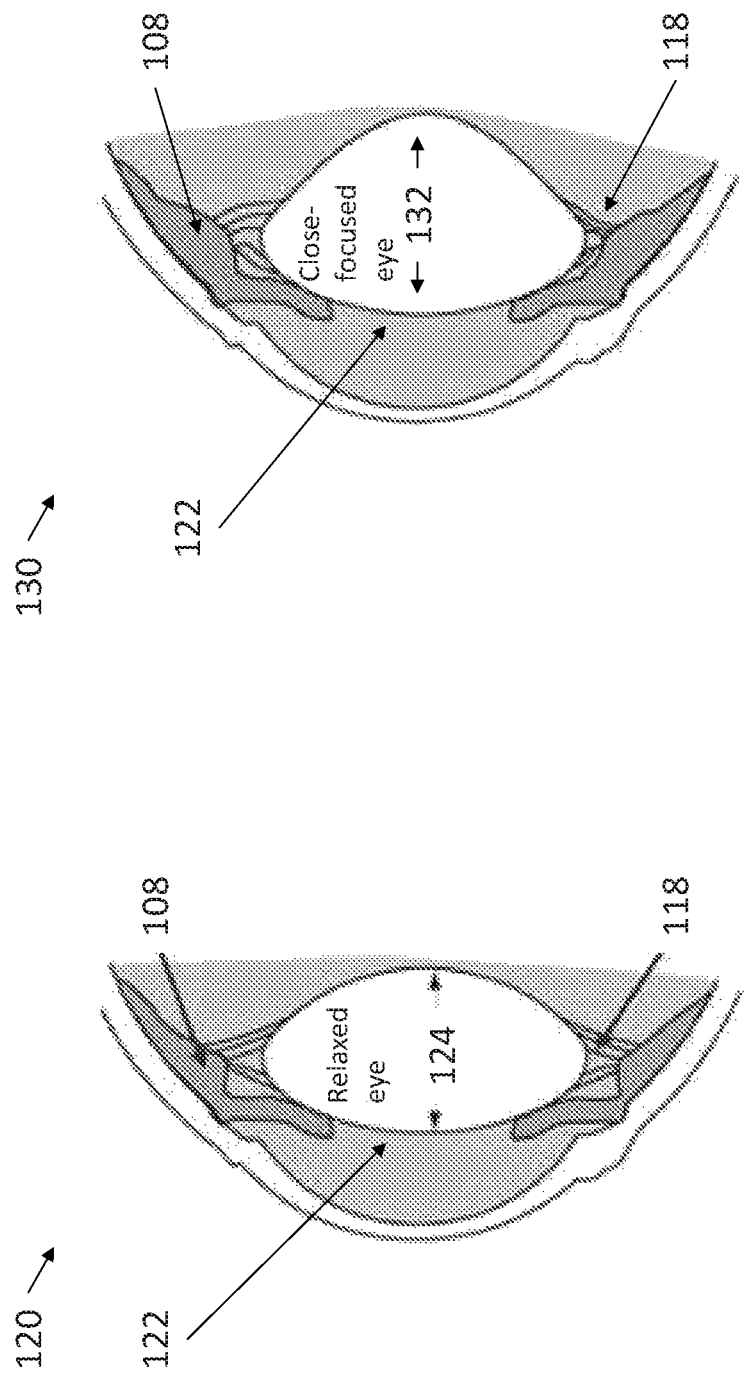

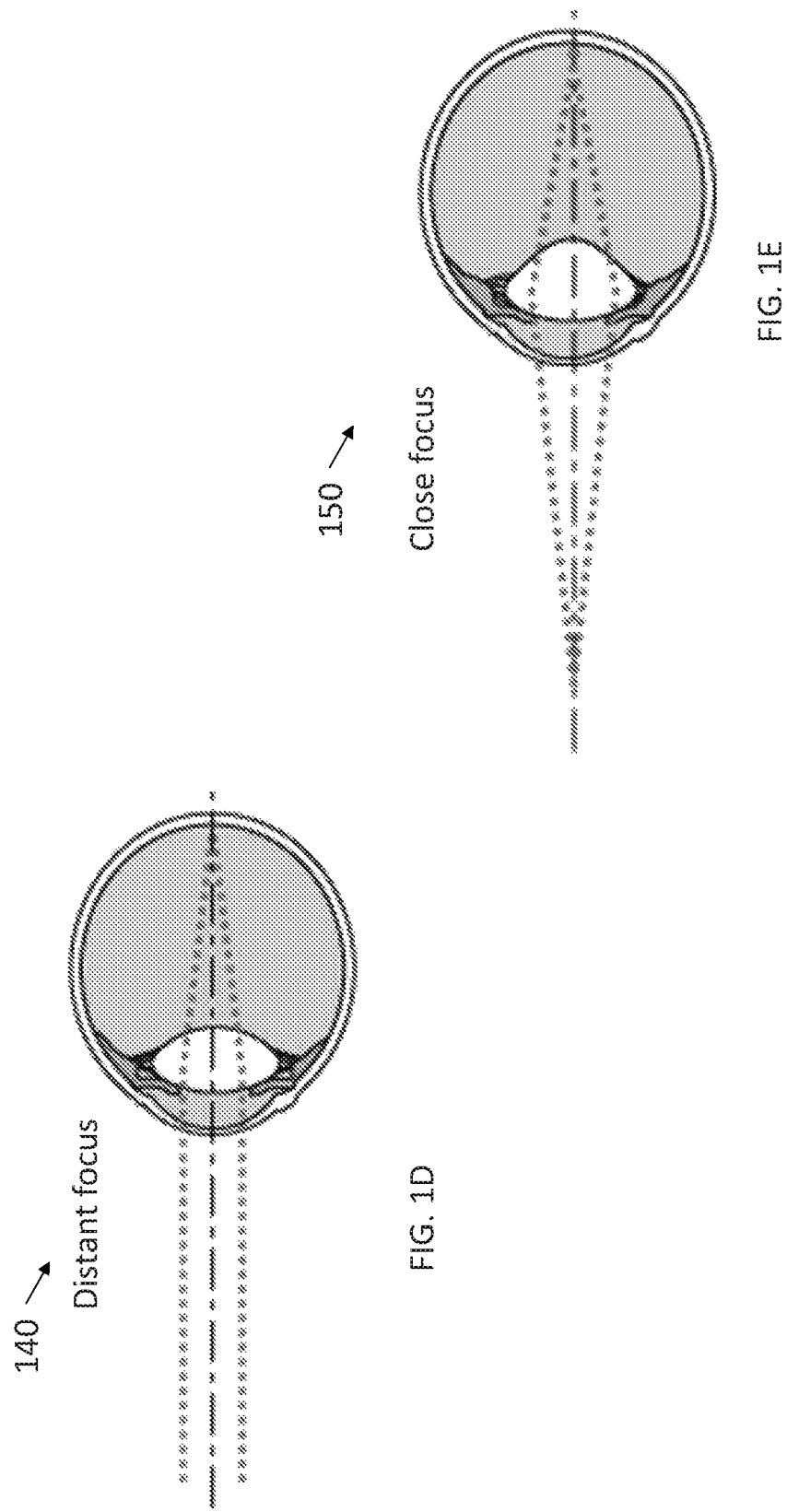

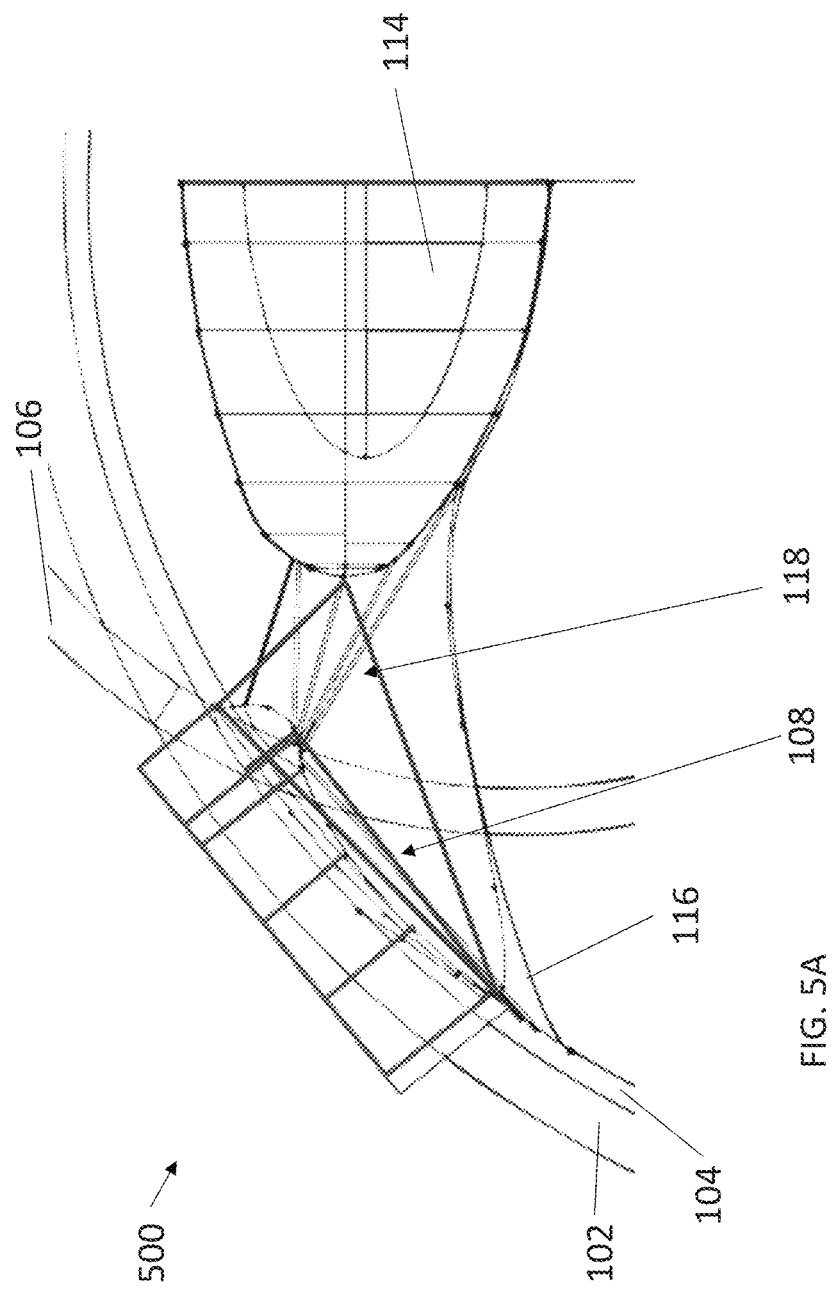

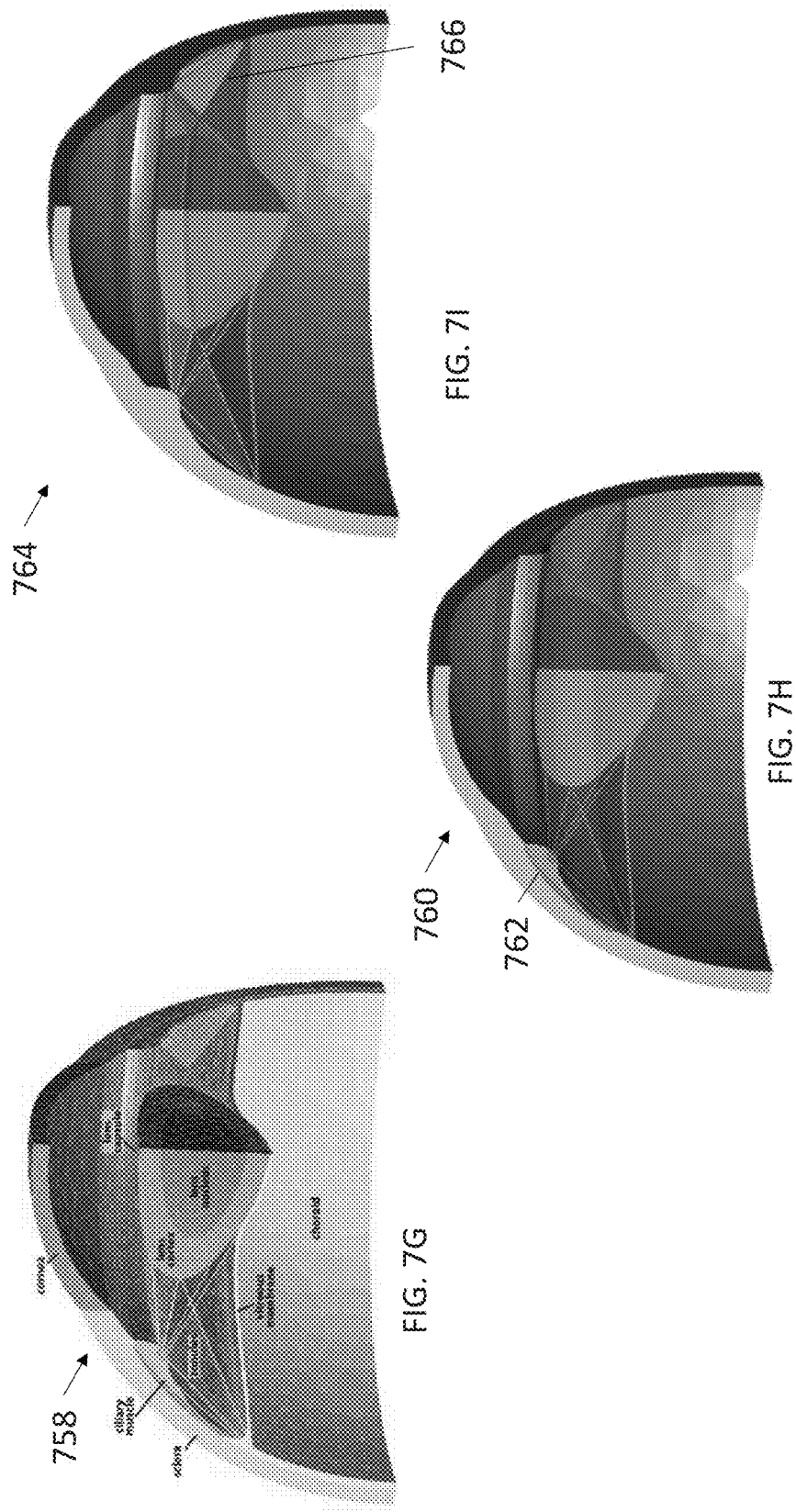

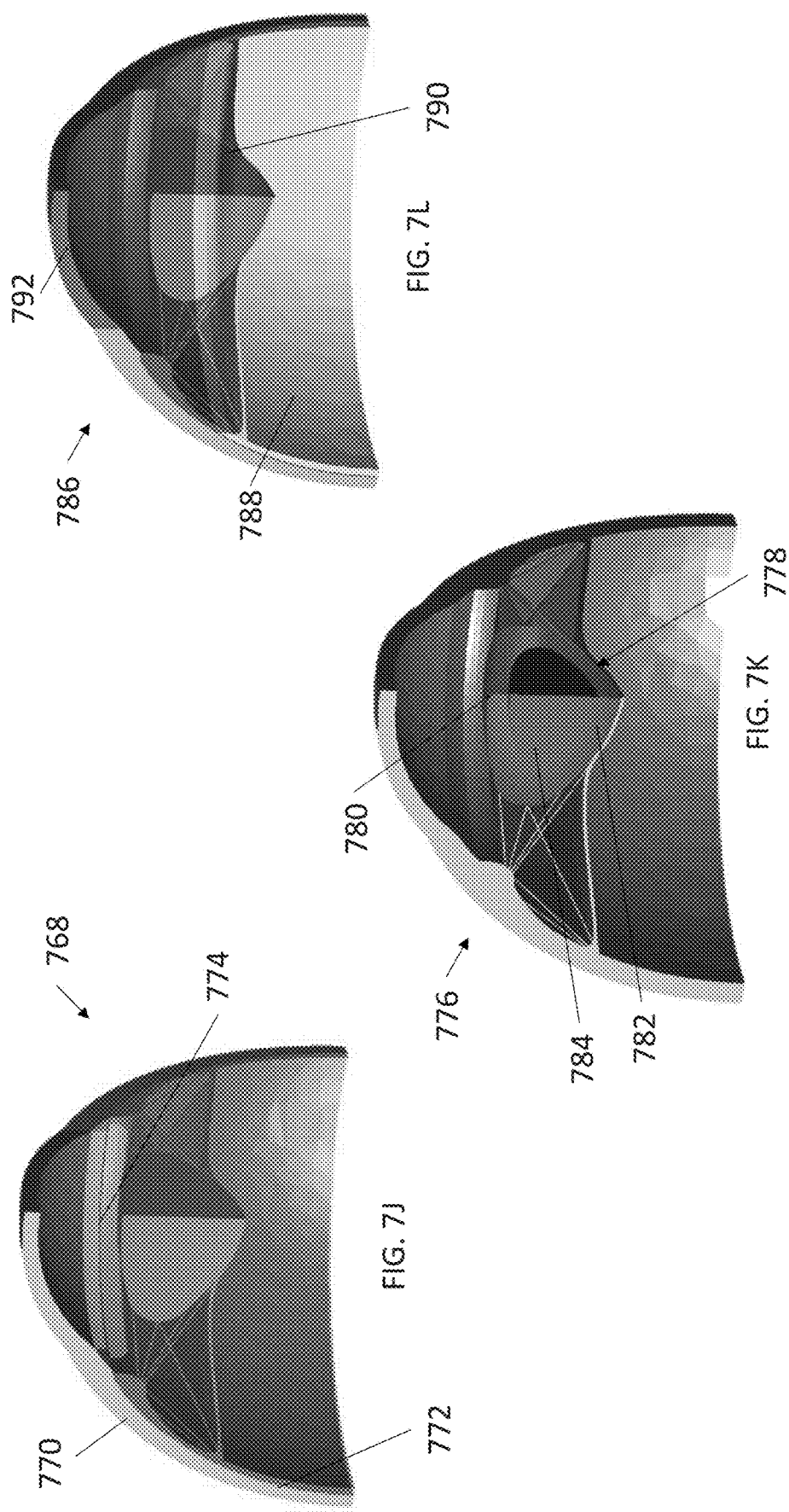

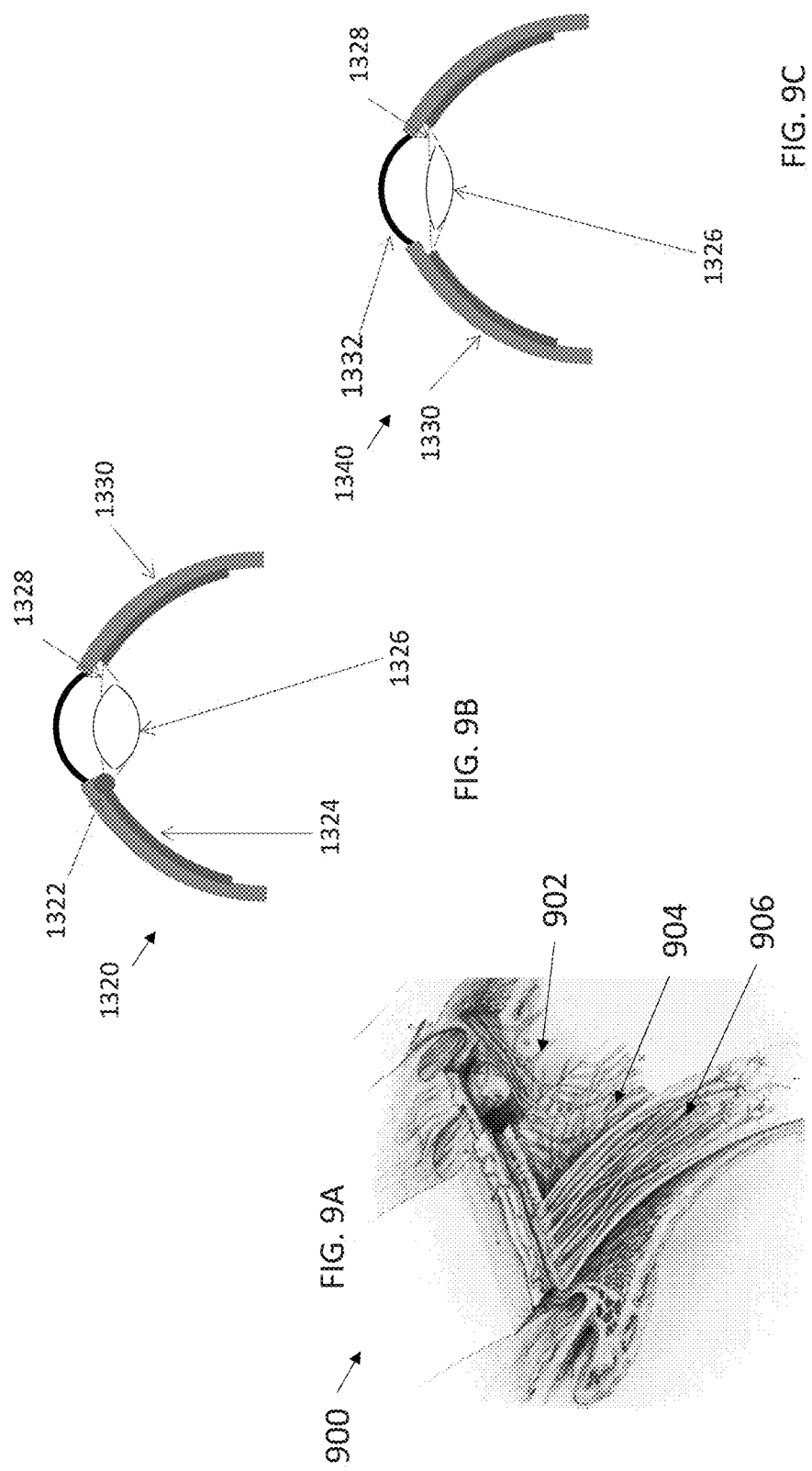

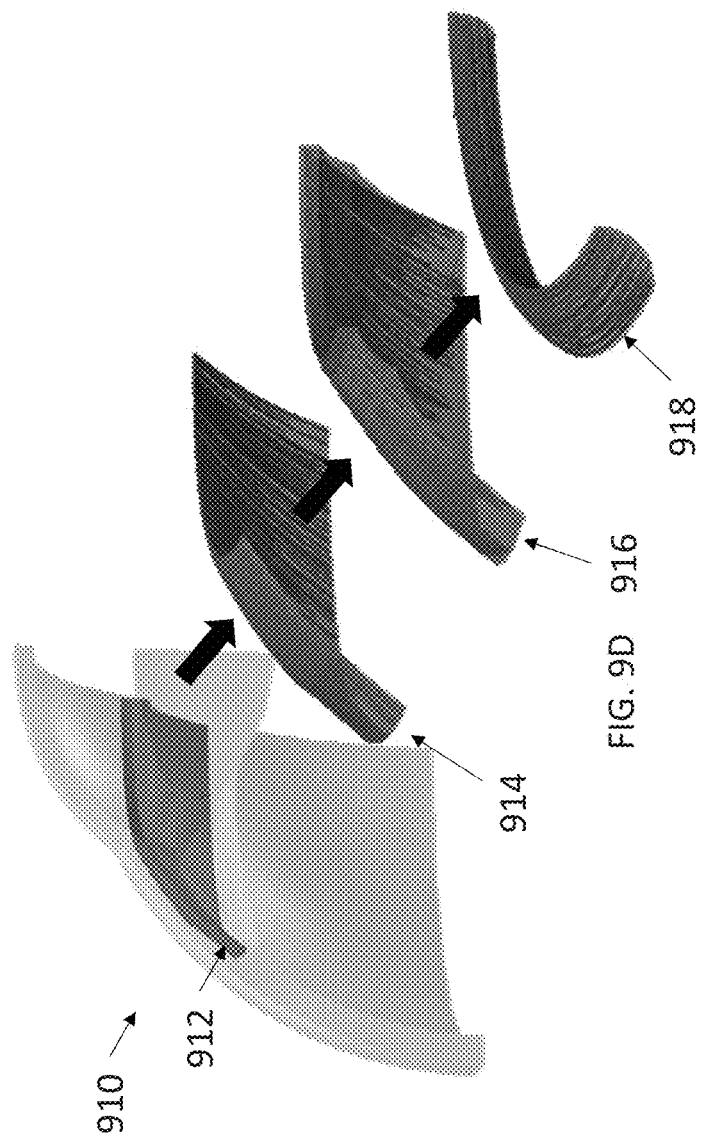

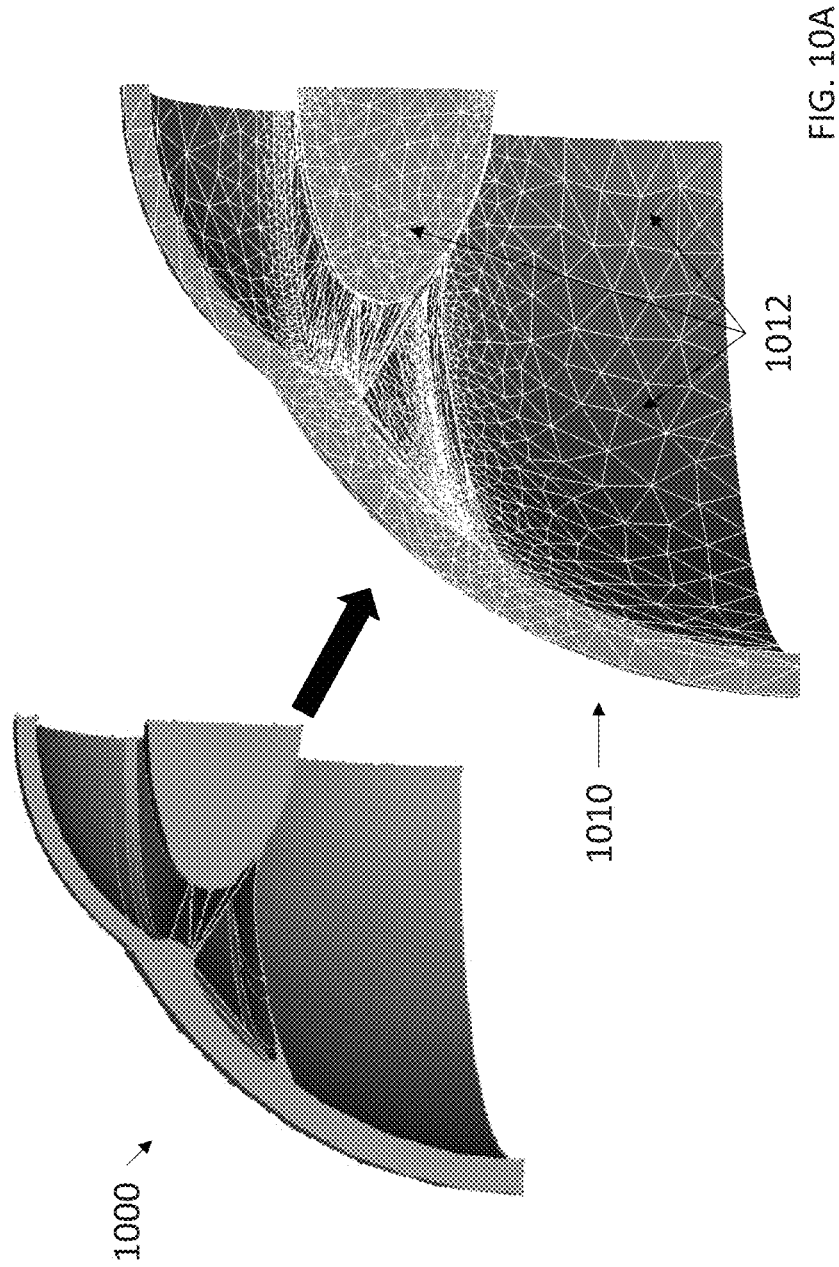

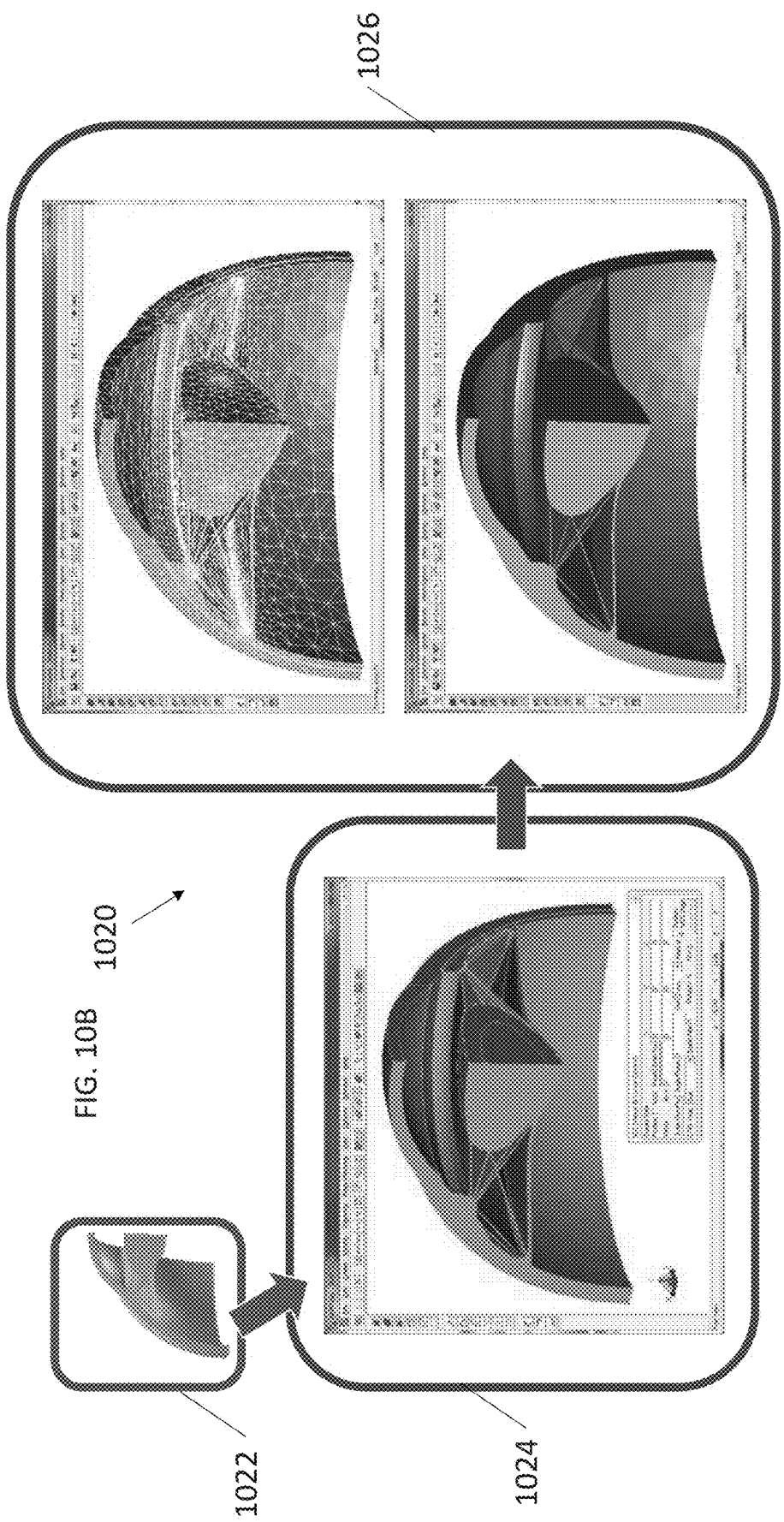

FIG. 10C

Isotropic Neo-Hookean materials    $W(C) = C_1(I_1 - 3)$    $C_1 = \dfrac{E}{4(1+\nu)}$

| | cornea | sclera | scleral spur | subchoroid lamellae | choroid | vitreous membrane | lens cortex | lens nucleus | lens capsule |
|---|---|---|---|---|---|---|---|---|---|
| Elastic modulus: E (MPa) | 5.3 | 1.61 | 13.7 | 6e-10 | 5.4e-3 | 0.033 | 3.4e-4 | 6e-4 | 1.2 |
| Poisson's ratio: $\nu$ | 0.49 | 0.49 | 0.49 | 0.2 | 0.49 | 0.49 | 0.49 | 0.49 | 0.47 |
| Source | Wang 1996 | Eliosh 2010 Friberg 1988 | Moses 1977 | Moses 1987 | Worthingt on 2013 | Sharei Kashani 2011 | Burd 2002 Krag 2003 | Burd 2002 Krag 2003 | Burd 2002 Krag 2003 |

Transversely isotropic materials strain energy density:    $a_0$ = fiber direction, $\alpha$ = activation, $p$ = tension level    $C$ = Cauchy-Green deformation tensor $$\Phi_{iso}^{ciliary} = W_1(C, a_0) + W_1(C, a_0) + W_3(C, a_0, \alpha)$$

$$\Phi_{iso}^{zonulus} = W_1(C, a_0) + W_1(C, a_0) + W_3(C, a_0, p)$$

stress and strain related by: $S = 2\dfrac{\partial \Phi}{\partial C}$    $S$ = 2$^{nd}$ Piola-Kirchoff stress tensor

| | $P_1$ | $P_2$ | $\lambda_{of1}$ | $\lambda^*$ | $K$ | $\sigma_{max}$ | $G_1$ | $A_0$ | $G_2$ |
|---|---|---|---|---|---|---|---|---|---|
| ciliary | 0.05 MPa | 6.6 | 1.0 | 1.3 | 500 kPa | 0.3 MPa | 3e-3 kPa | 2 | 3e-4 MPa |
| zonules | 0.27 MPa | 46.4 | N/A | 1.0 3 | 50 MPa | N/A | 5e-4 MPa | 2 | 5e-4 MPa |

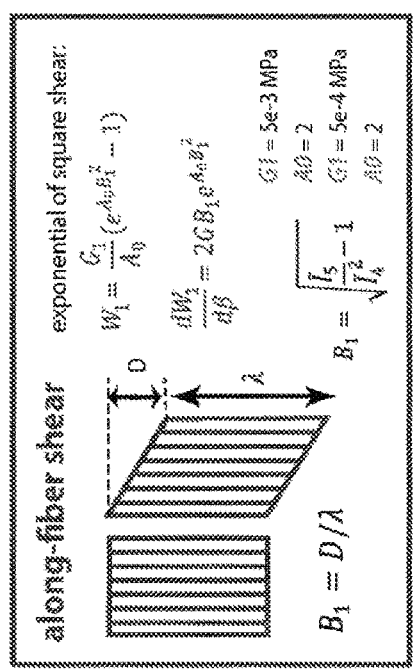

along-fiber shear exponential of square shear:

$W_1 = \frac{G_1}{A_0}(e^{A_0 B_1^2} - 1)$ $\frac{dW_2}{d\beta} = 2G_1 B_1 e^{A_0 B_1^2}$ $B_1 = \sqrt{\frac{I_5}{I_4^2} - 1}$ $G1 = 5e\text{-}3$ MPa   $A0 = 2$
$G1 = 5e\text{-}4$ MPa   $A0 = 2$ $B_1 = D/\lambda$

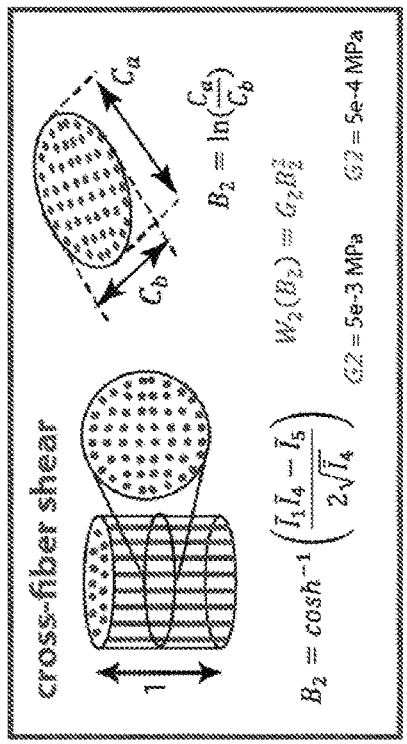

cross-fiber shear $B_2 = \ln\left(\frac{c_a}{c_b}\right)$ $W_2(B_2) = G_2 B_2^2$ $B_2 = \cosh^{-1}\left(\frac{I_1 I_4 - I_5}{2\sqrt{I_4}}\right)$ $W_2(B_2) = G_2 B_2^2$ $G2 = 5e\text{-}3$ MPa   $G2 = 5e\text{-}4$ MPa

FIG. 10J

1048 → strain energy density *(physically based strain invariants)*:

$\phi^{ciliary}(B_1, B_2, \lambda, \alpha, J) = W_1(B_1) + W_2(B_2) + W_3^{ciliary}(\lambda, \alpha) + \phi^{vol}(J)$ $\phi^{zonules}(B_1, B_2, \lambda, p, J) = W_1(B_1) + W_2(B_2) + W_3^{zonules}(\lambda, p) + \phi^{vol}(J)$

FIG. 10G

1050 → dilatational strain $\phi^{vol}(J) = \frac{K}{2} \text{Ln}(J)^2 \qquad J = \sqrt{\det(C)}$ $K = 5e2 \qquad K = 5e3$

FIG. 10H

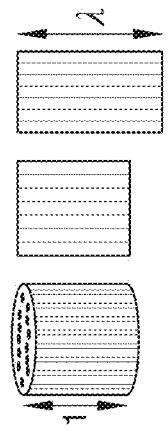
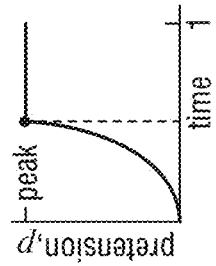
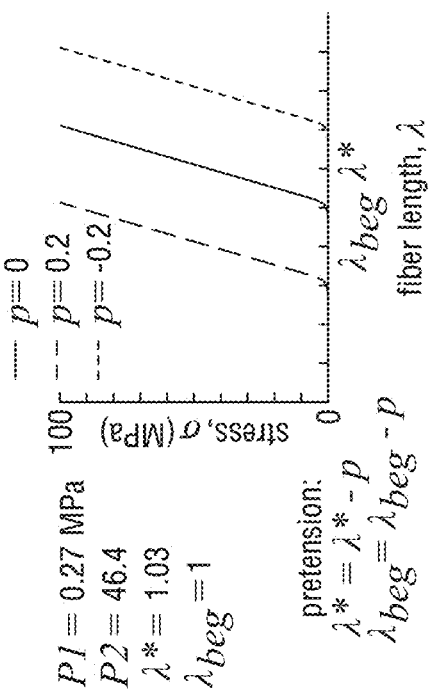
FIG. 10L

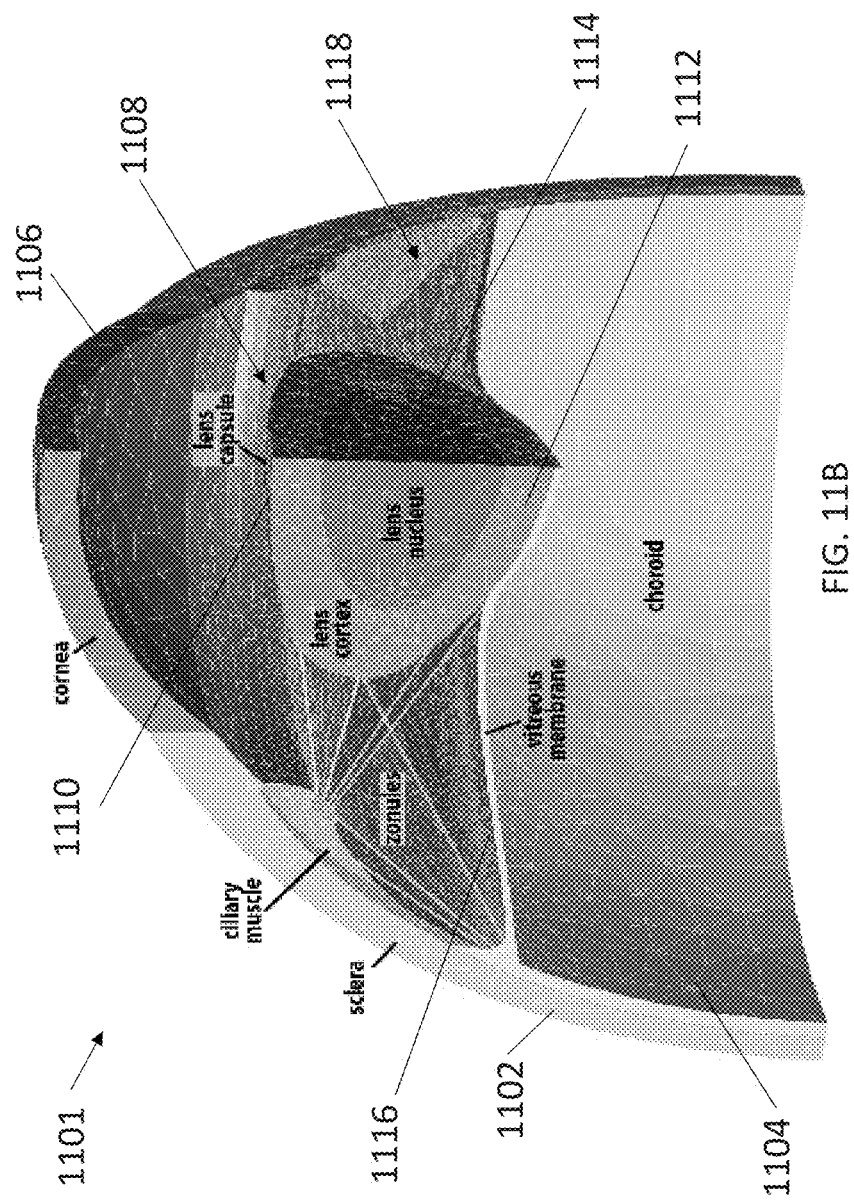

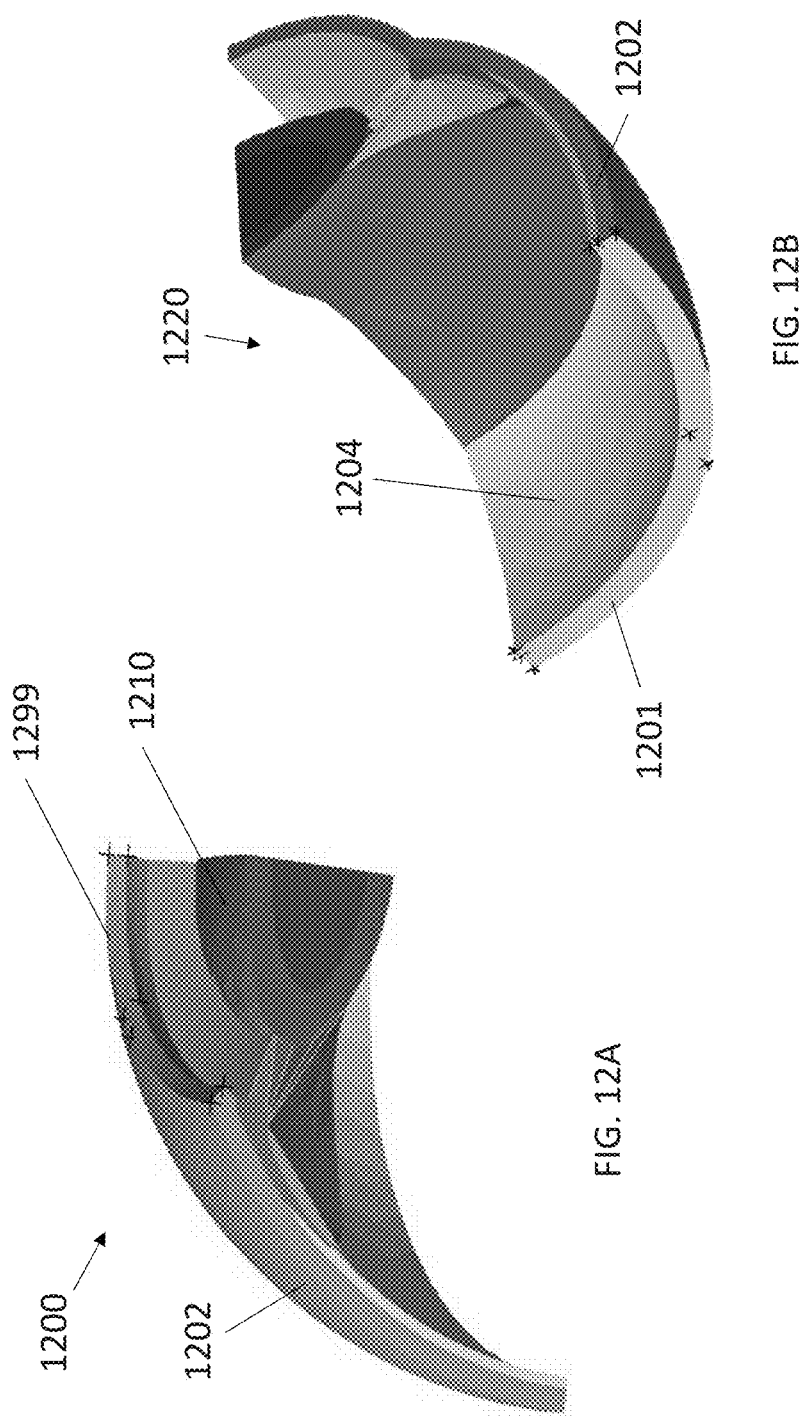

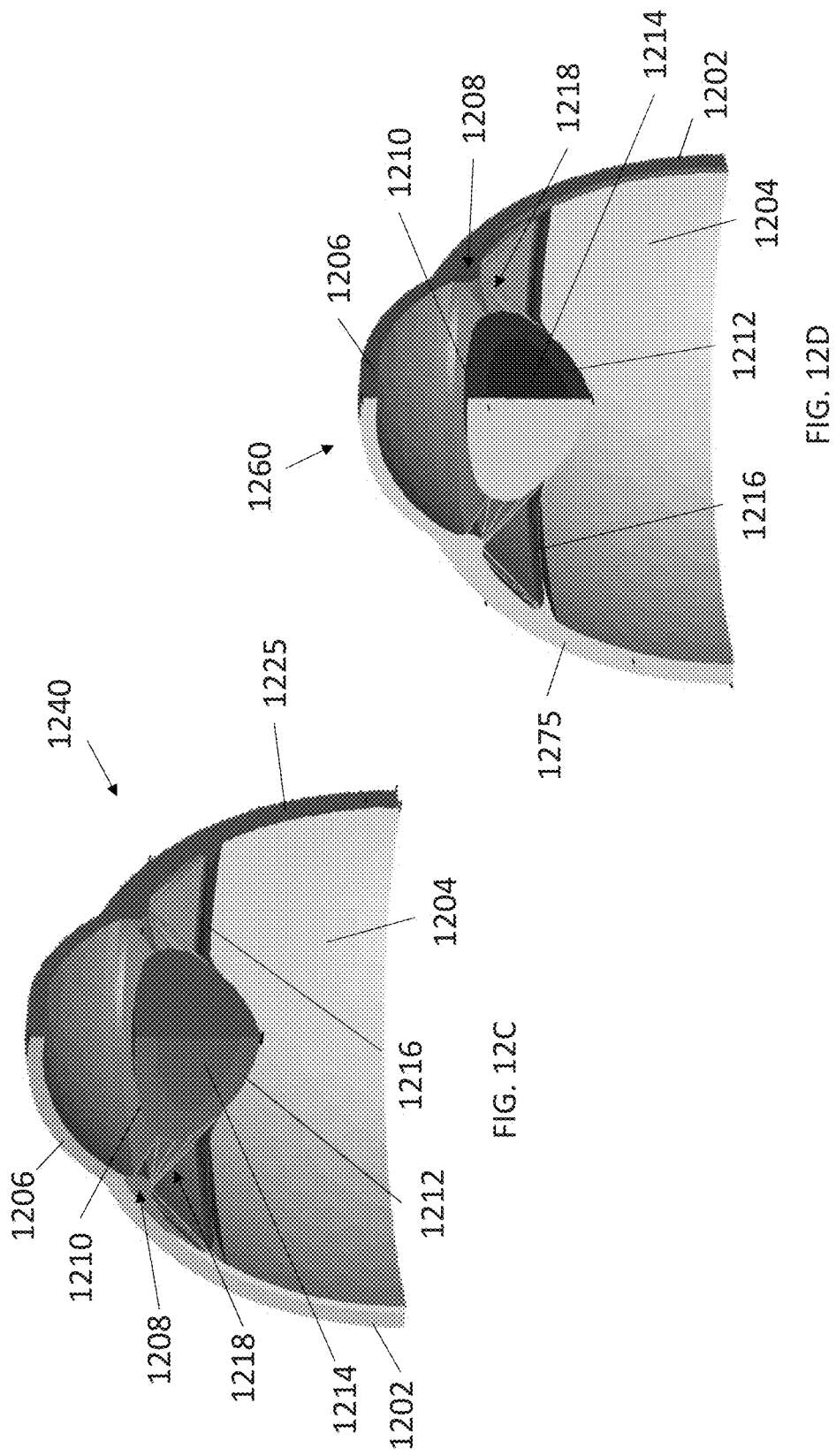

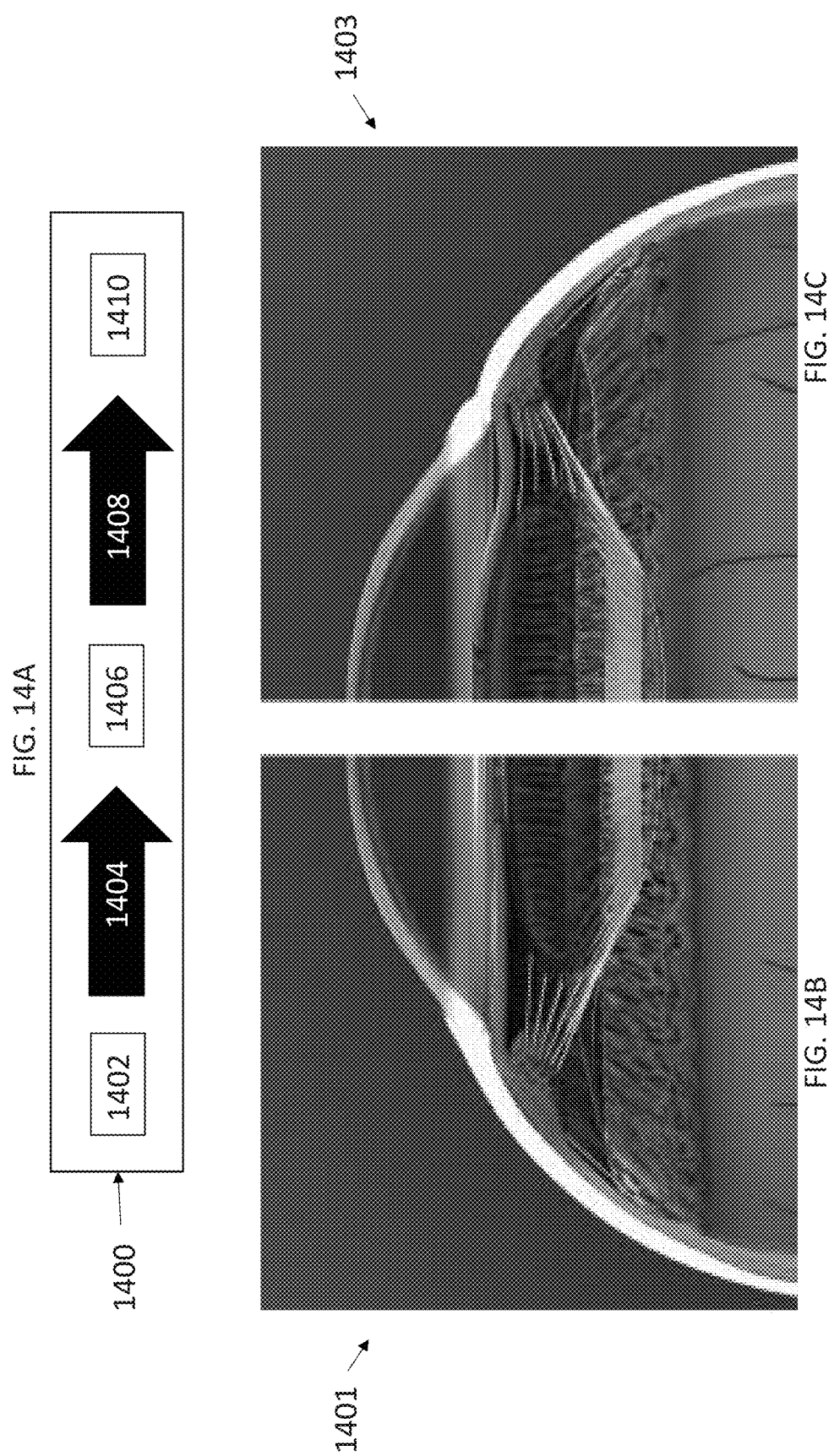

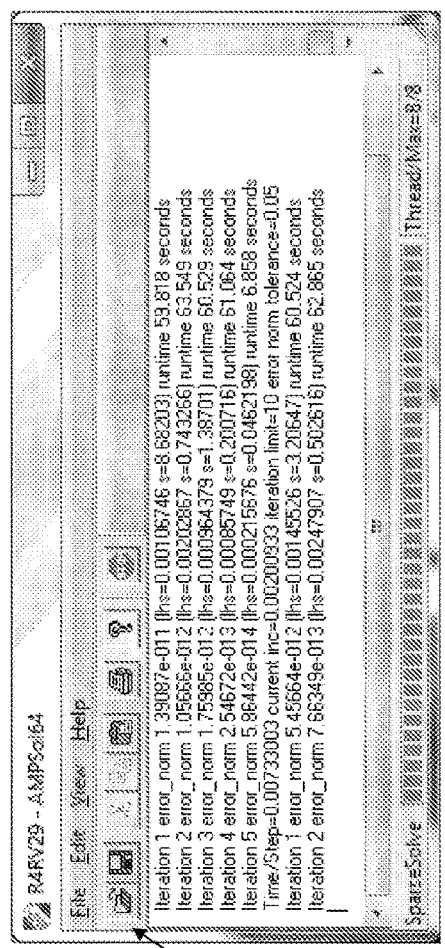
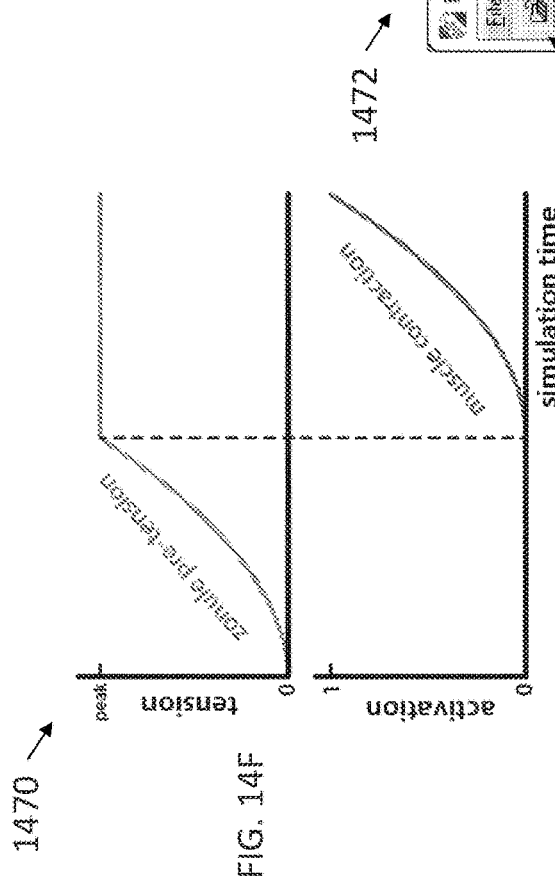
FIG. 14F
FIG. 14G

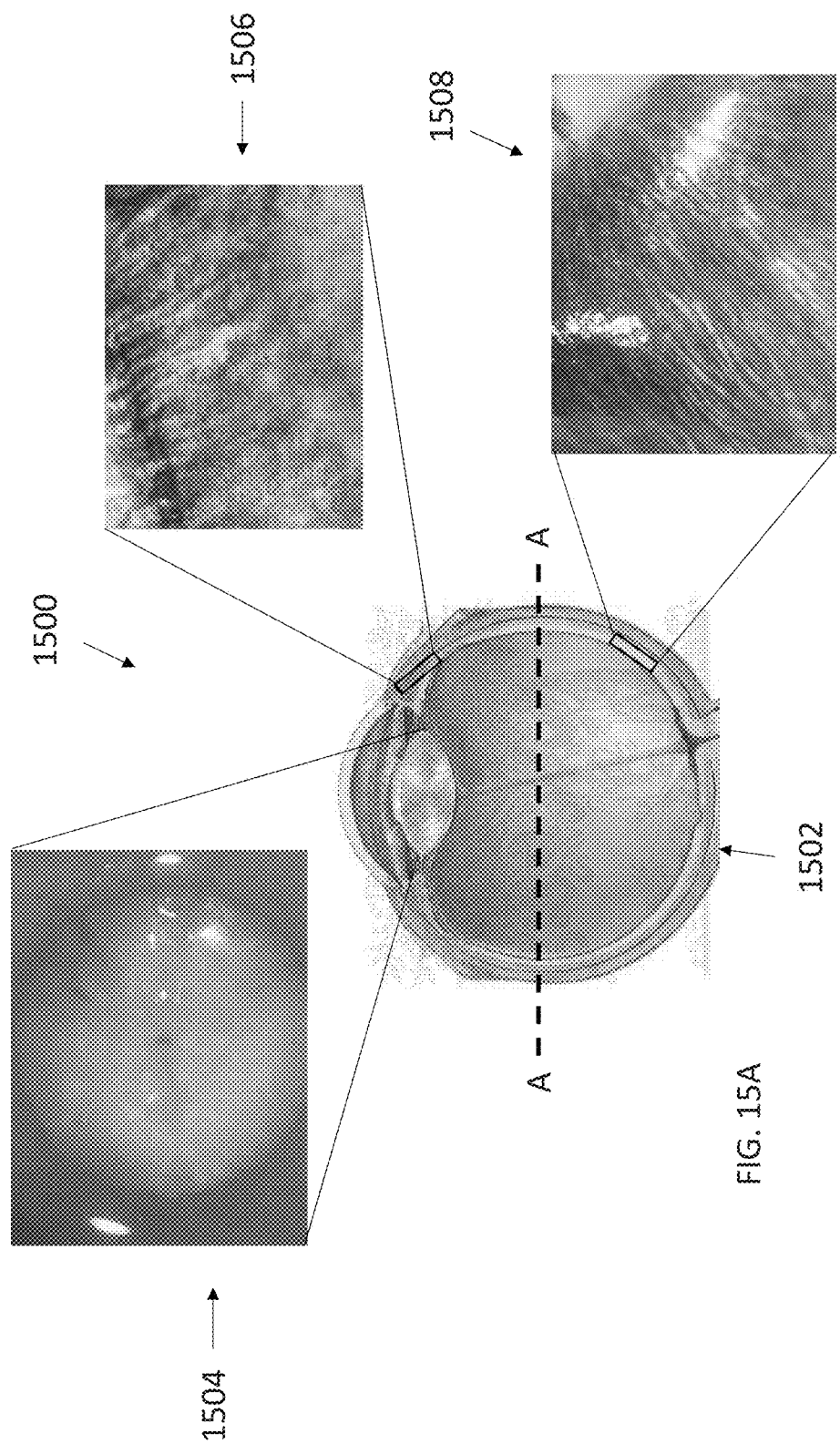

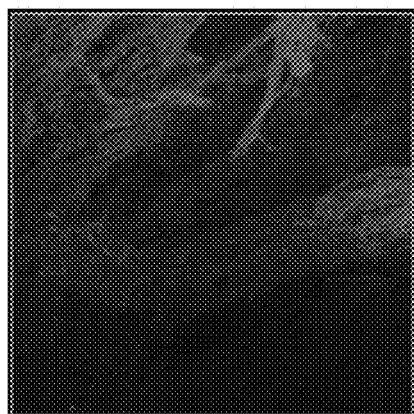
FIG. 16B — 1602
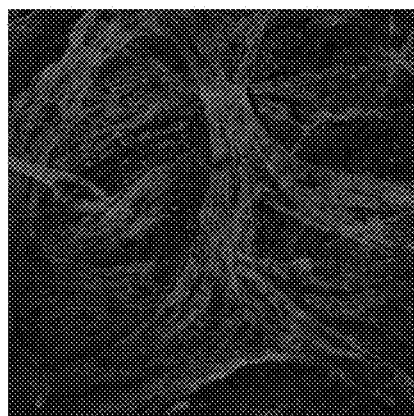
FIG. 16C — 1604
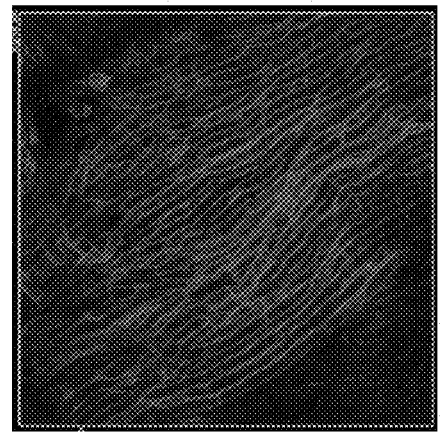
FIG. 16A — 1600

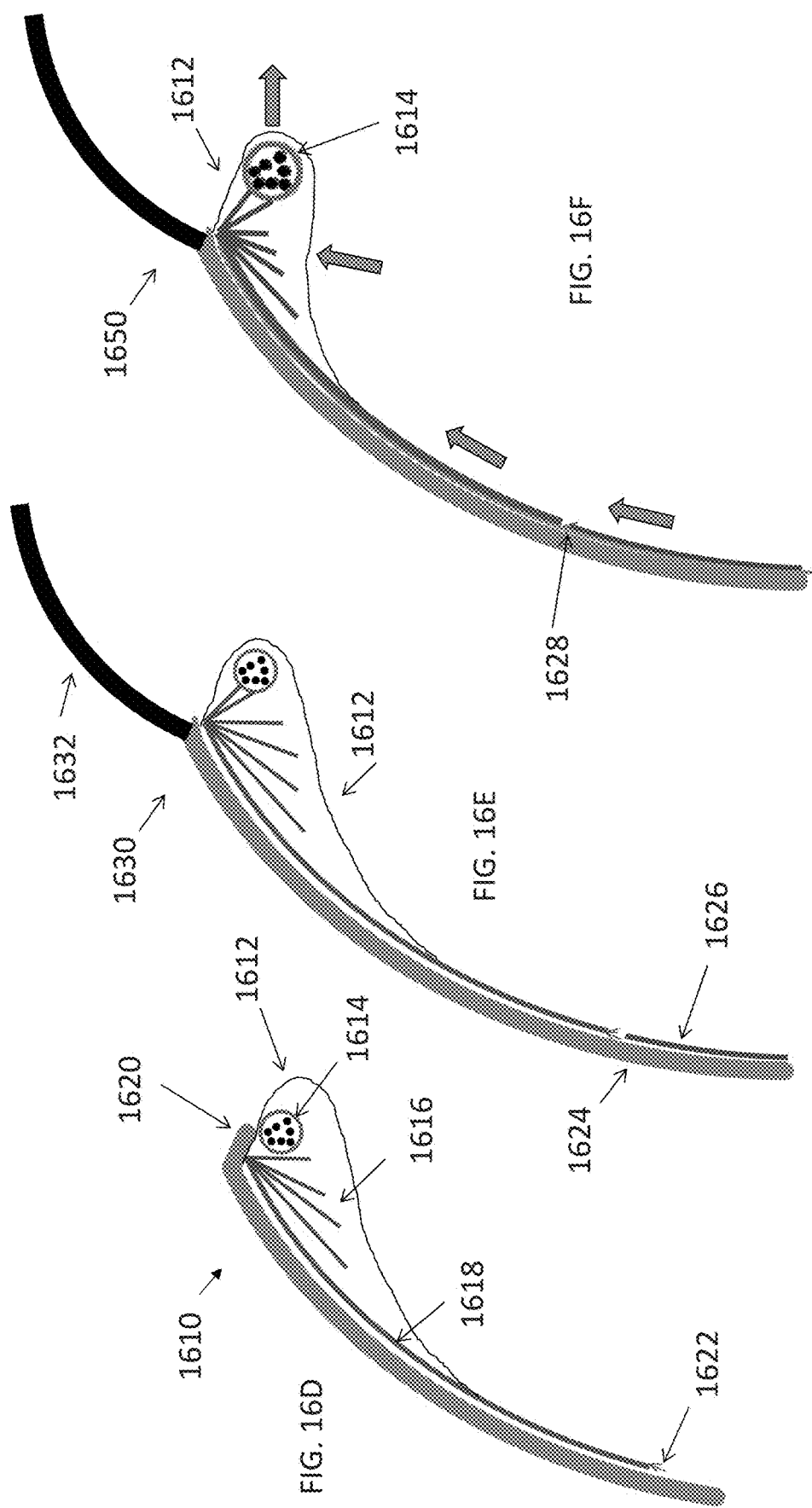

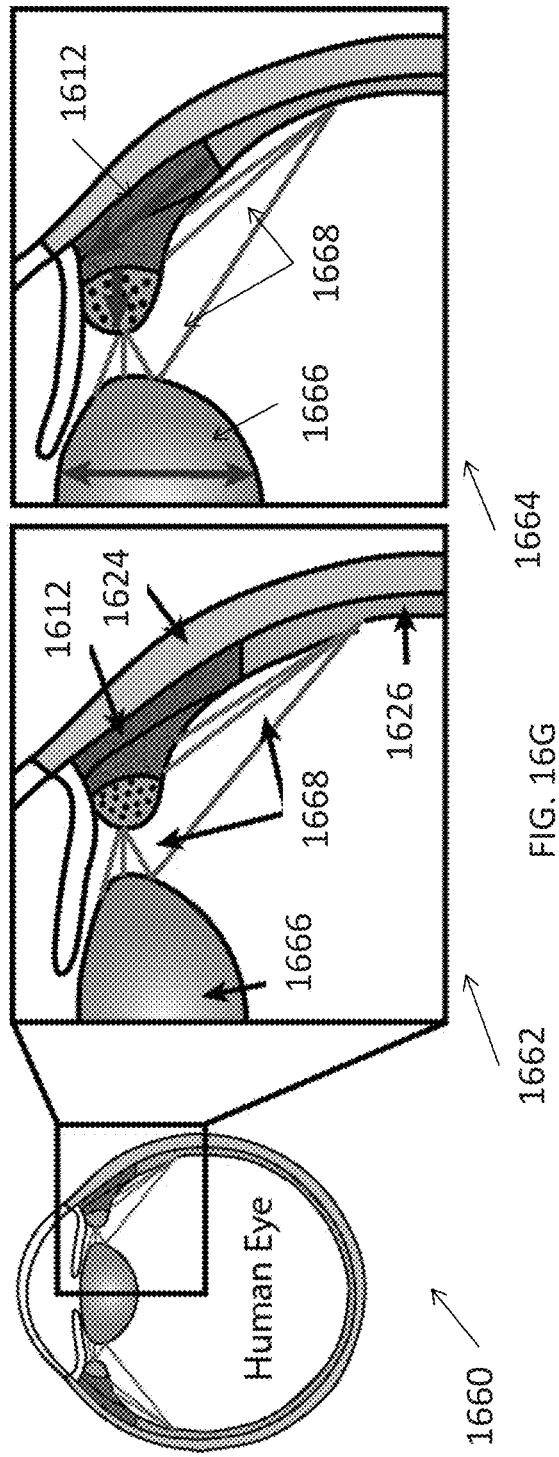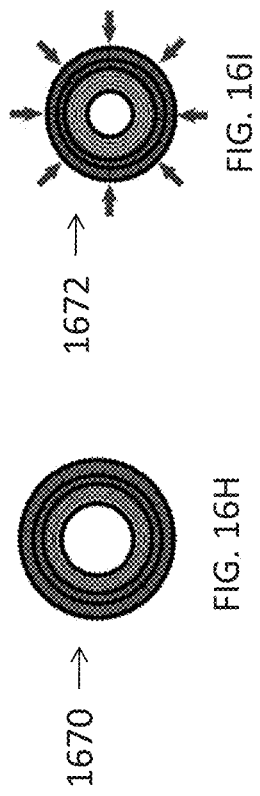

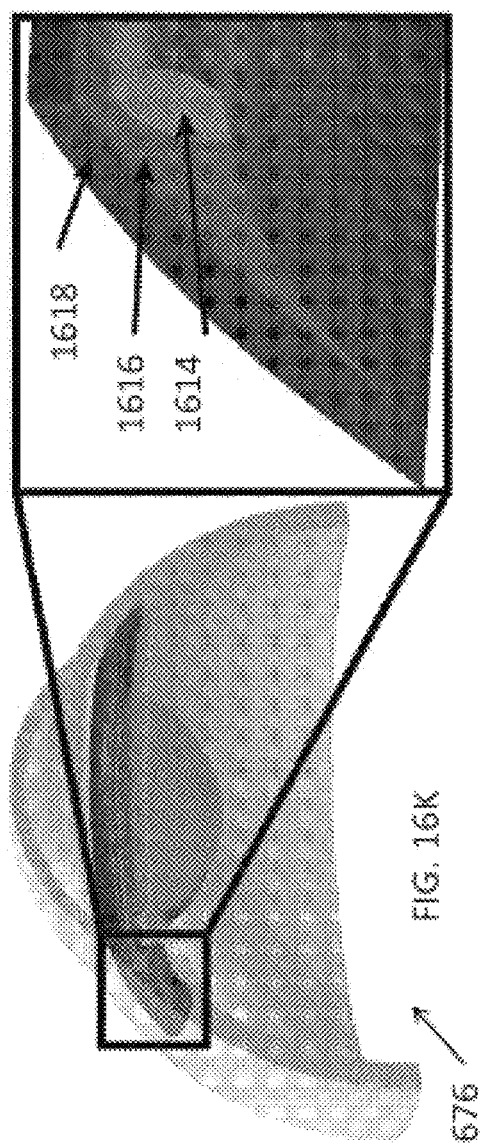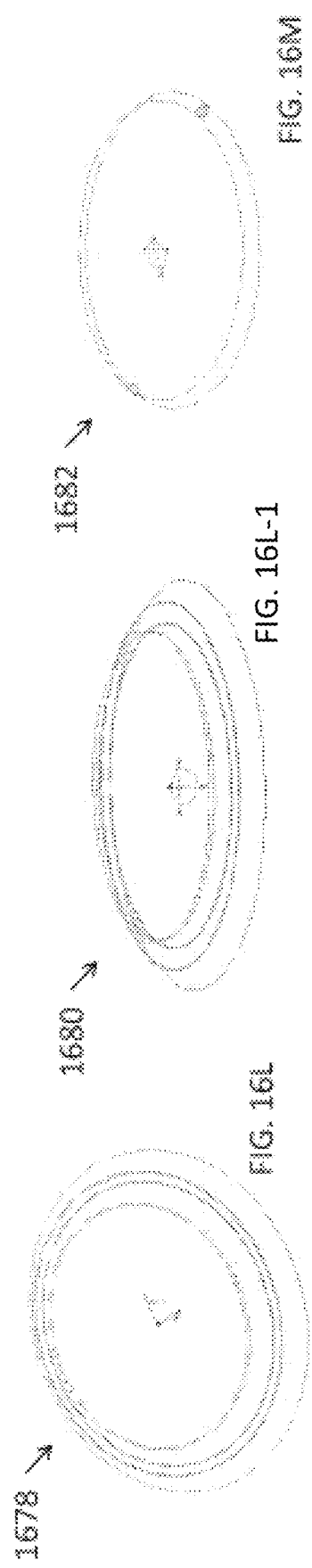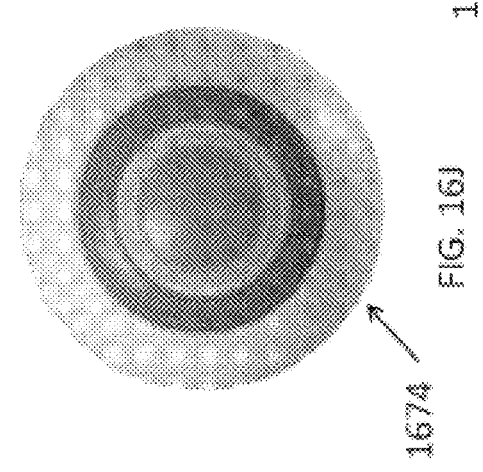

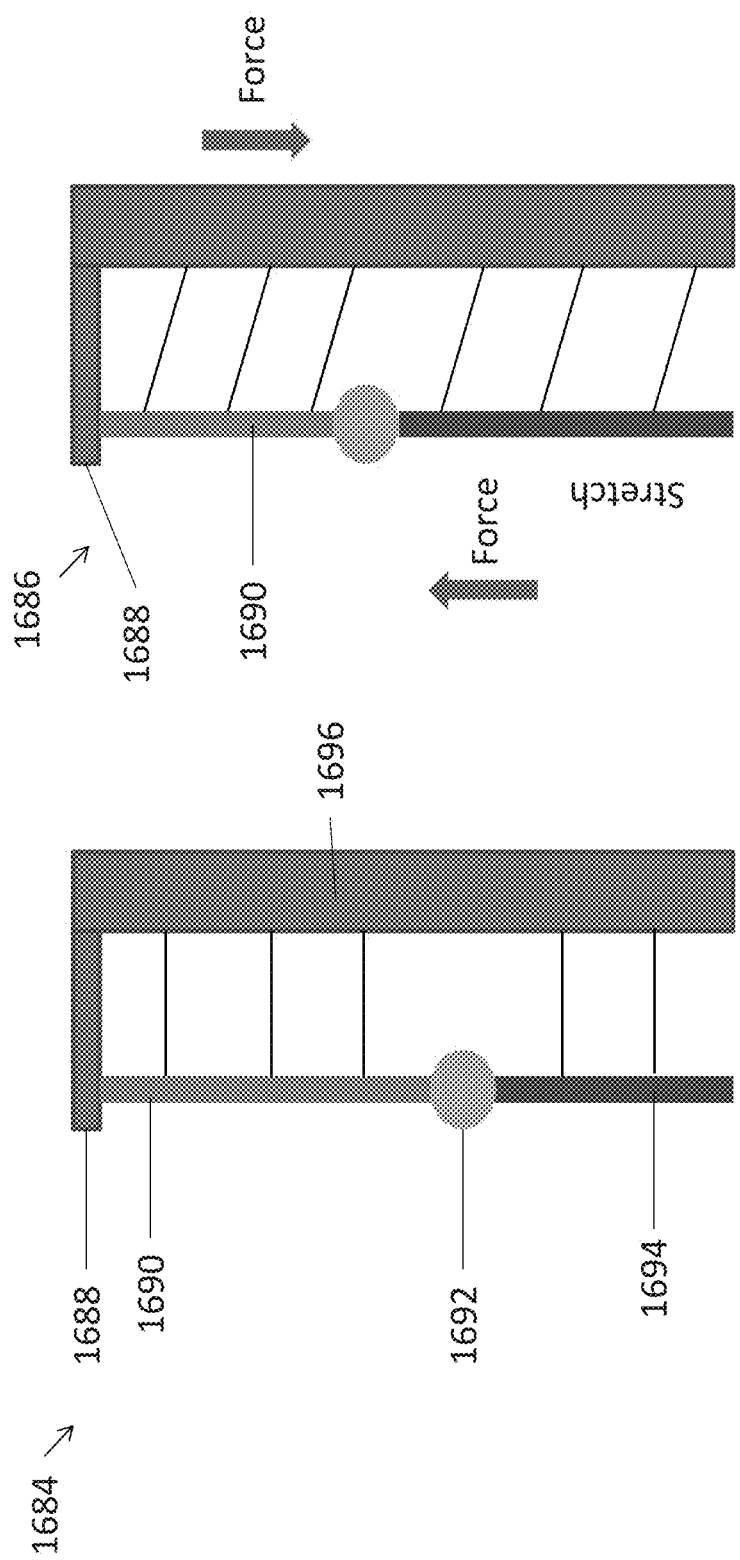

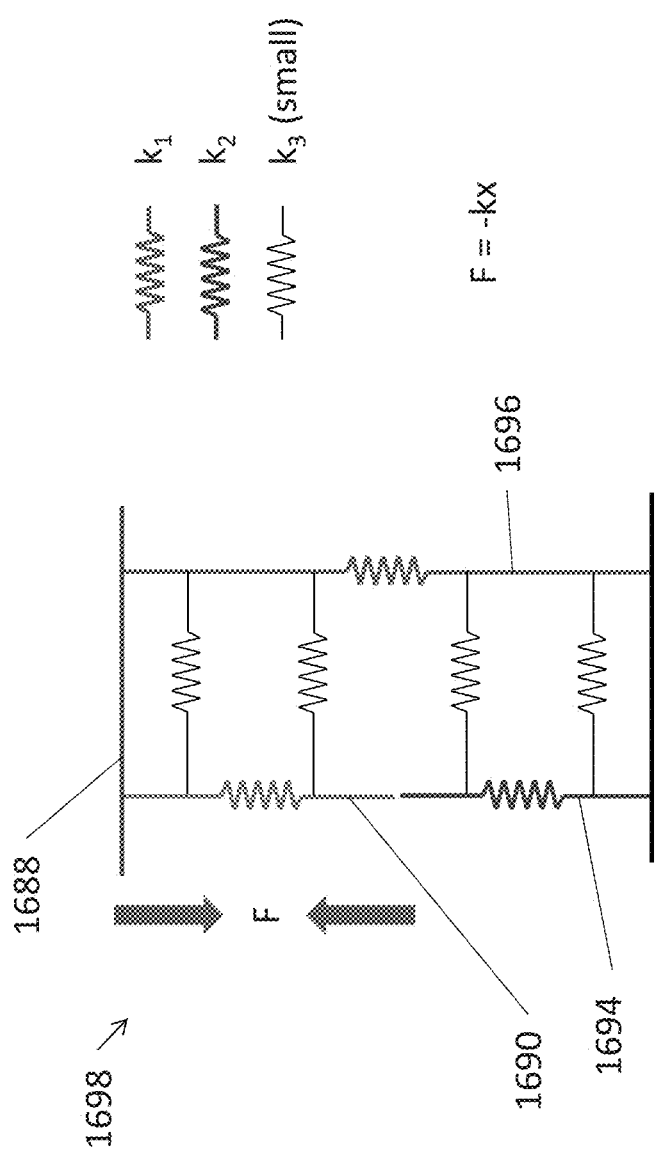

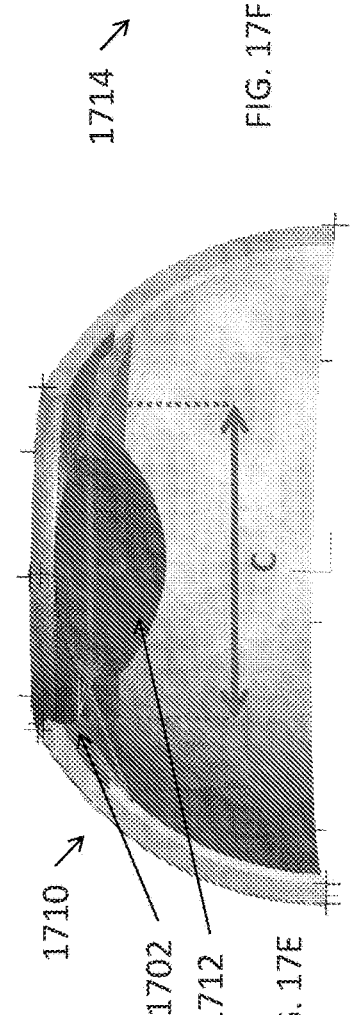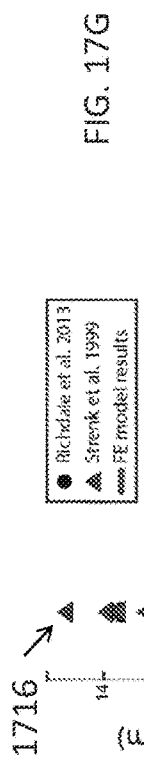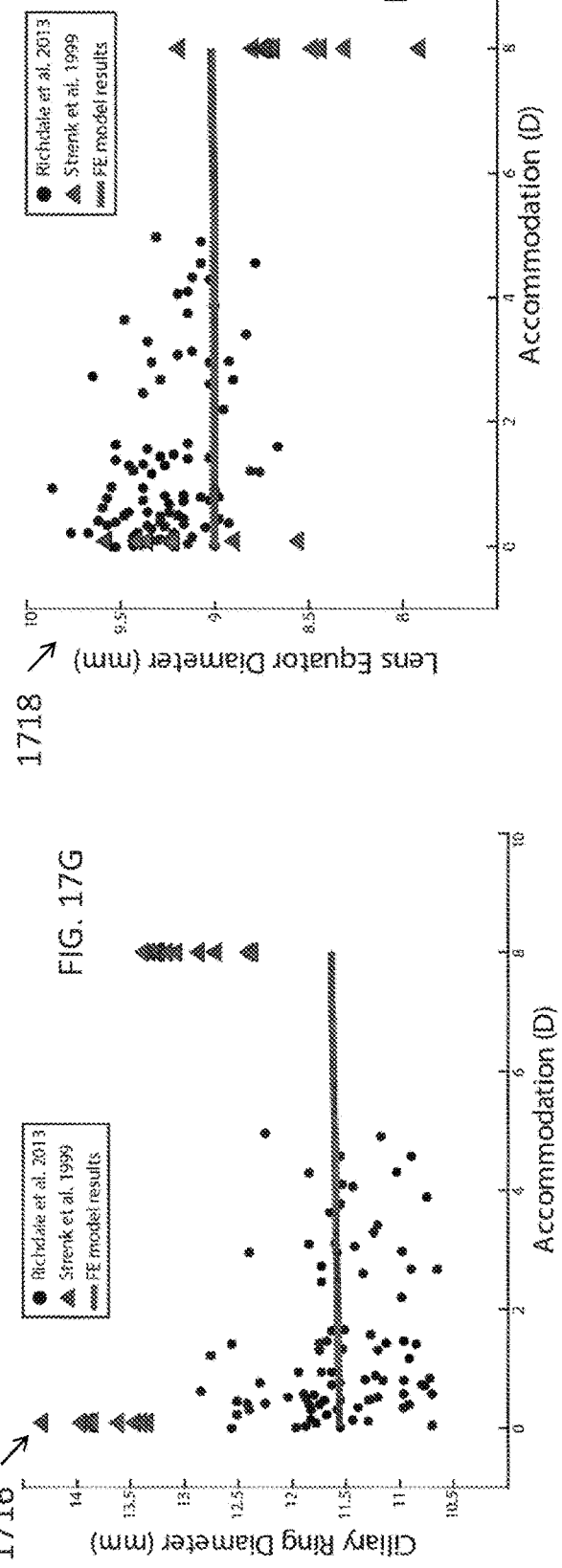
FIG. 17E
FIG. 17F
FIG. 17G
FIG. 17H

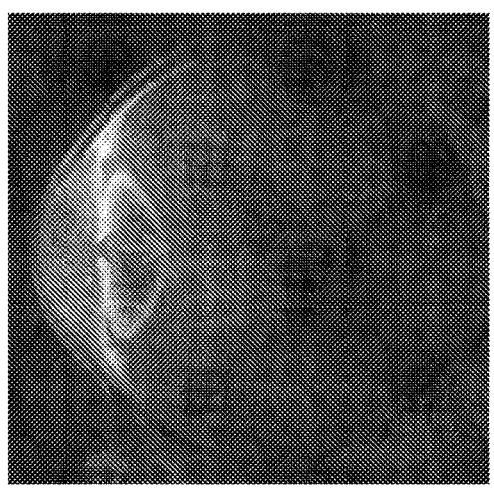
FIG. 17M
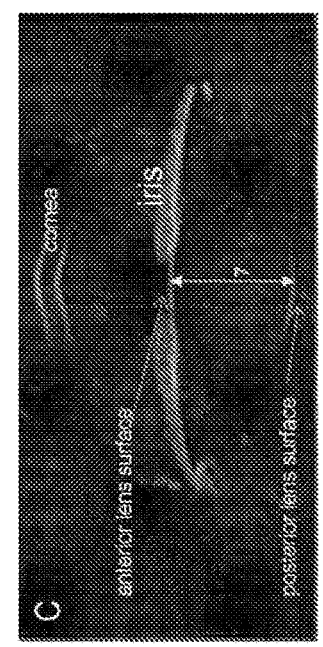
FIG. 17N
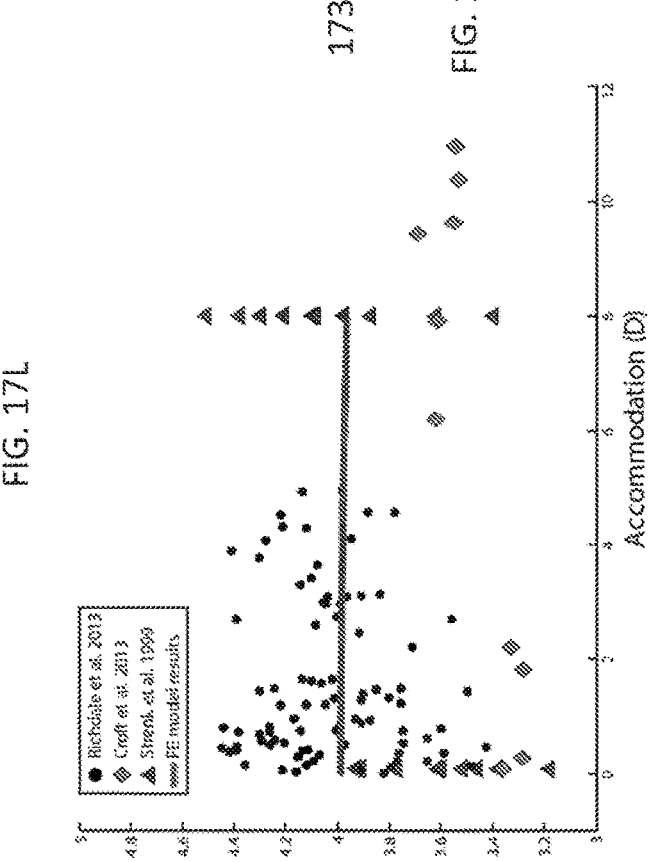
FIG. 17L
FIG. 17O

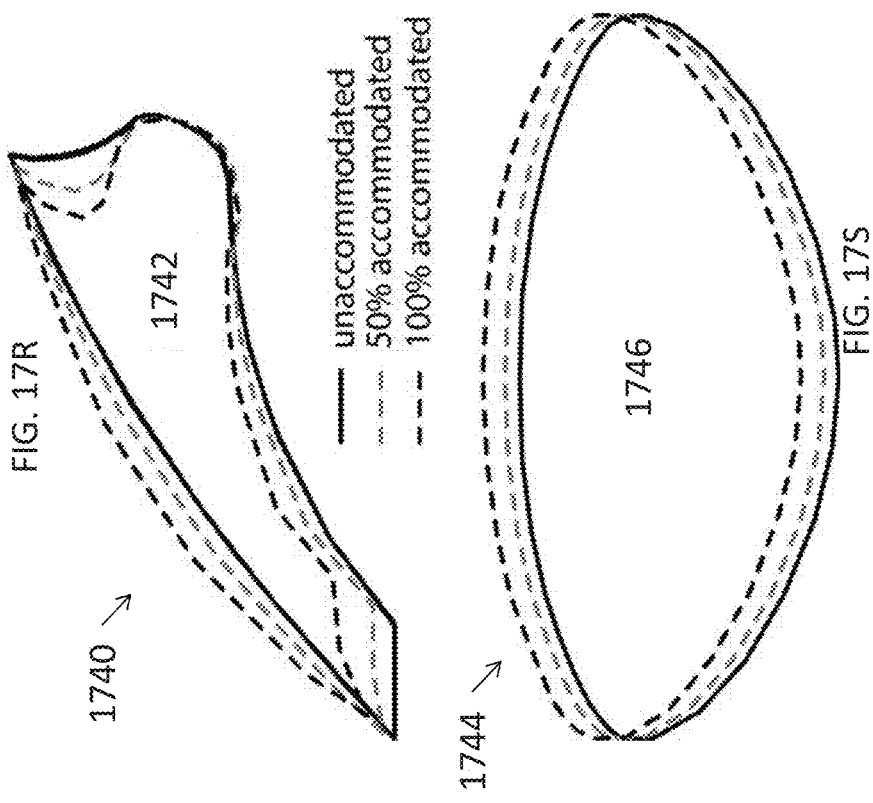
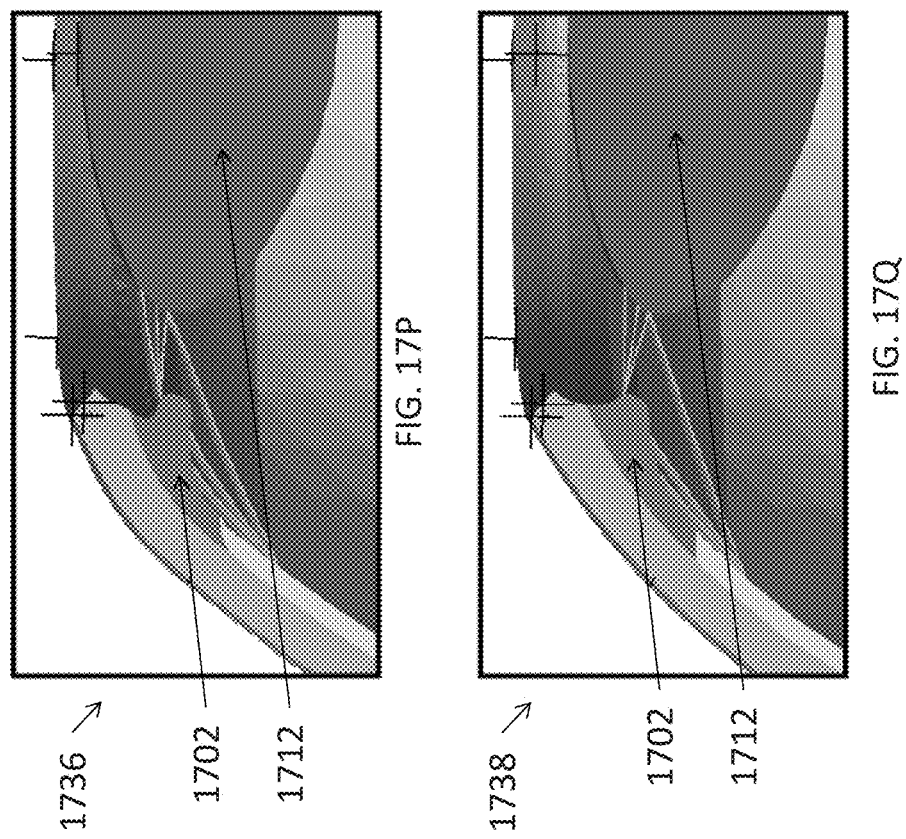

| Inquire Distance | | | | |
|---|---|---|---|---|
| L-click:Base,Ctrl-L-Click-deactivate ☐ Use Displaced Nodes | | | Activate Mouse Select | |
| | | | Node(1..111971) | |
| X | Y | Z | | Base position |
| 9.83143 | 5.30117 | 6.02002e-016 | 3099 | |
| 10.5107 | 5.63154 | 6.43594e-016 | 6339 | Current position |
| LX | LY | LZ | dPlane | dRadial |
| 0 | 0 | 1 | 4.1592e-017 | 0.755349 |
| dX | dY | dZ | Distance from Base to Current | |
| 0.67927 | 0.33037 | 4.1592e-017 | 0.755349 | |

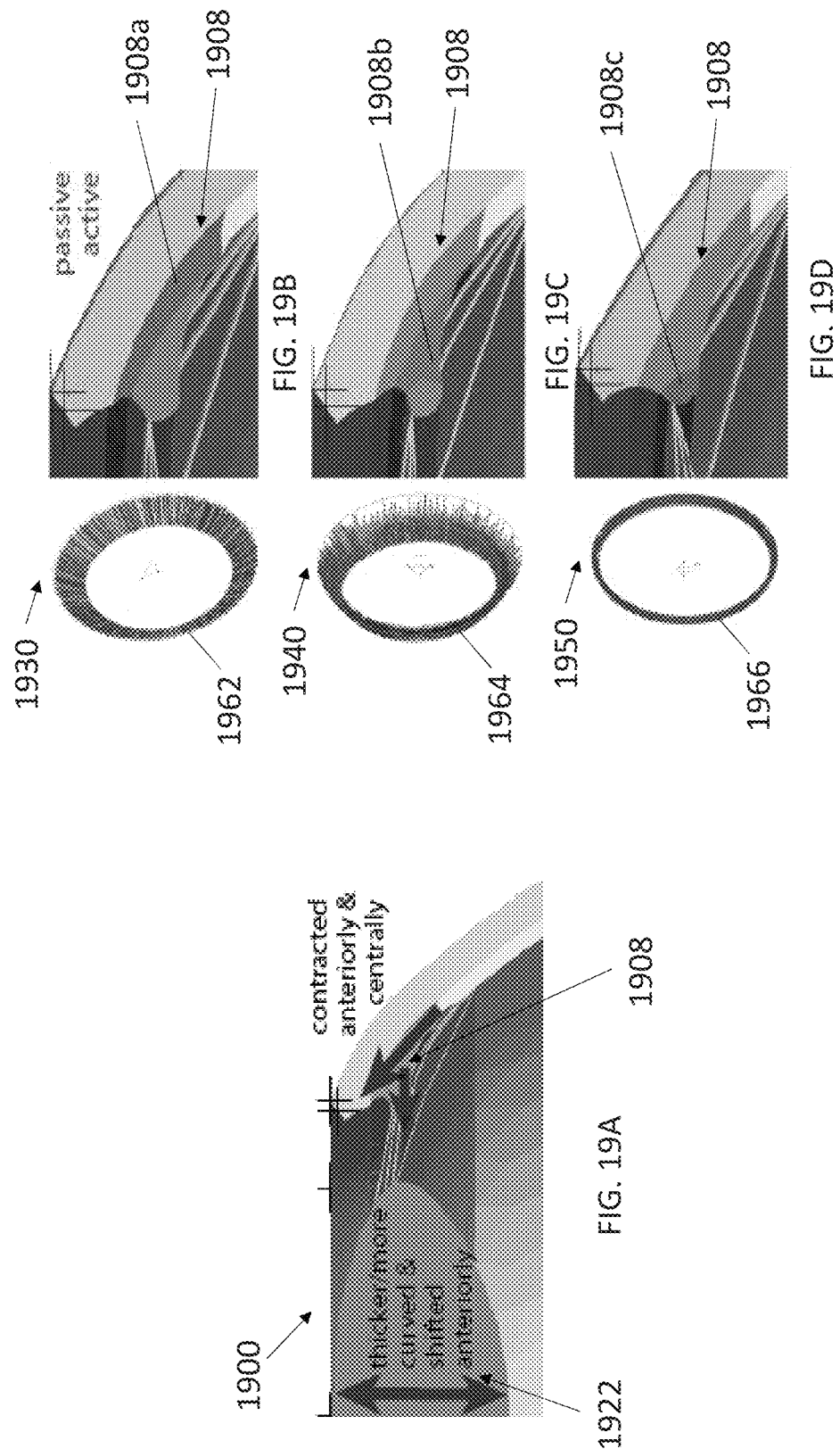

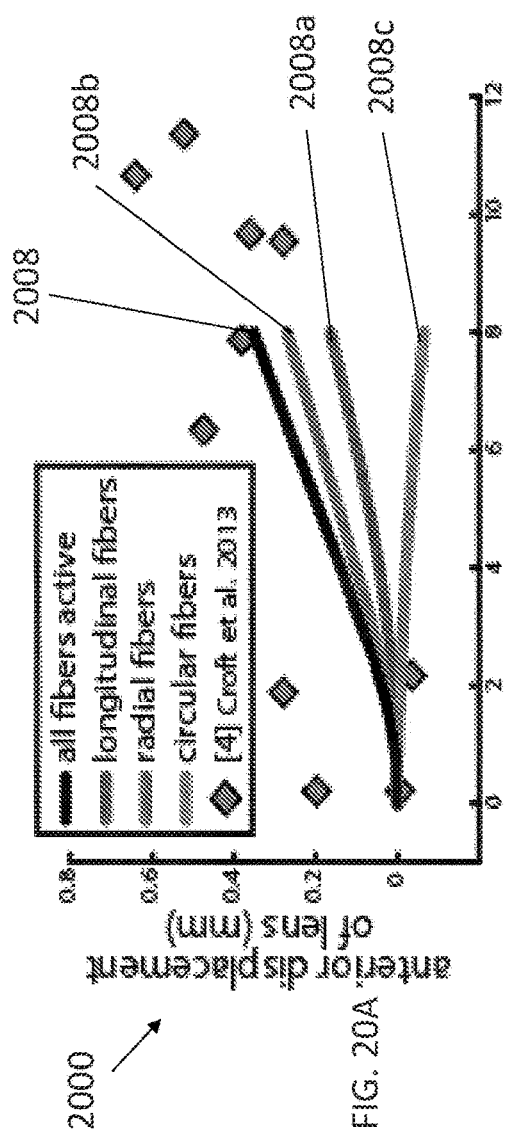
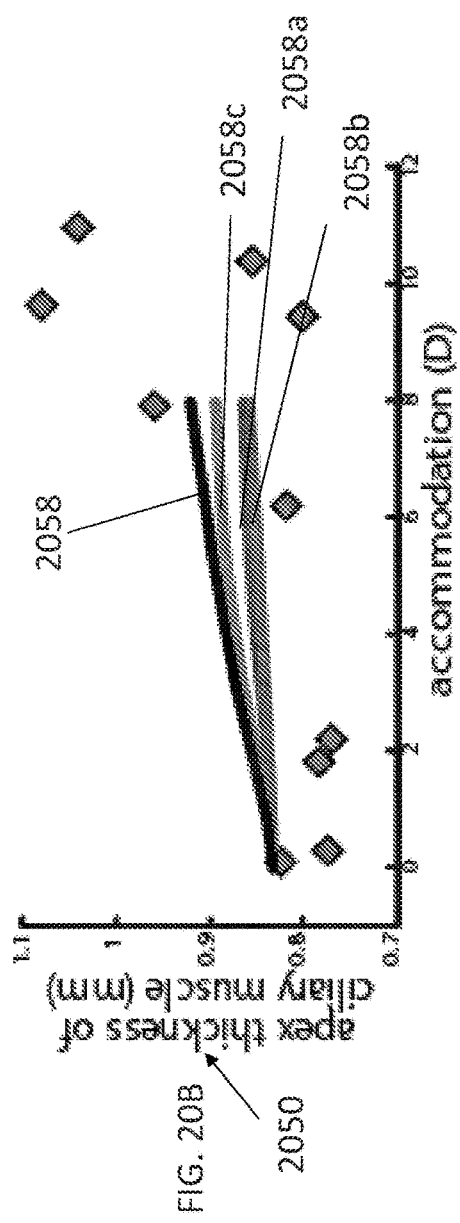
FIG. 20A
FIG. 20B

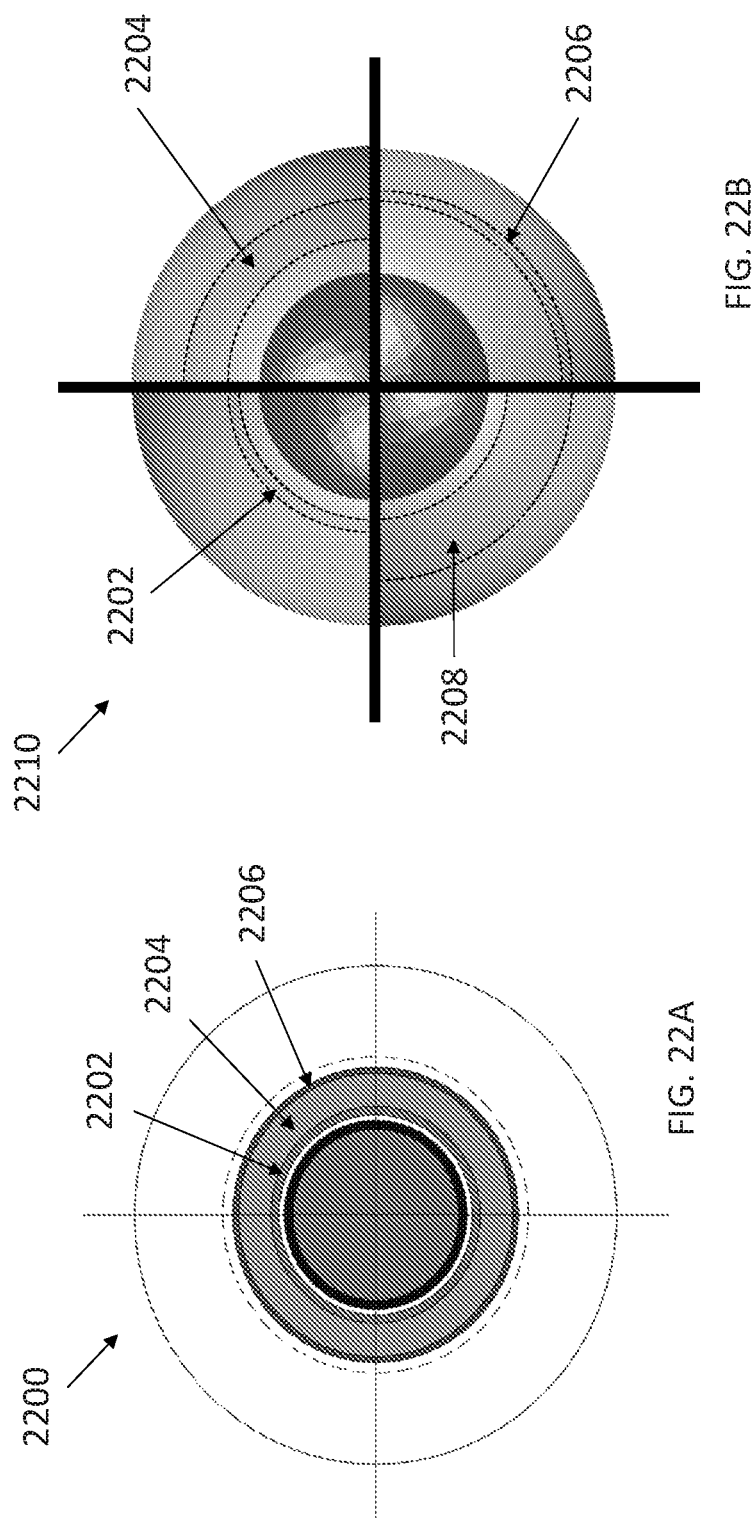

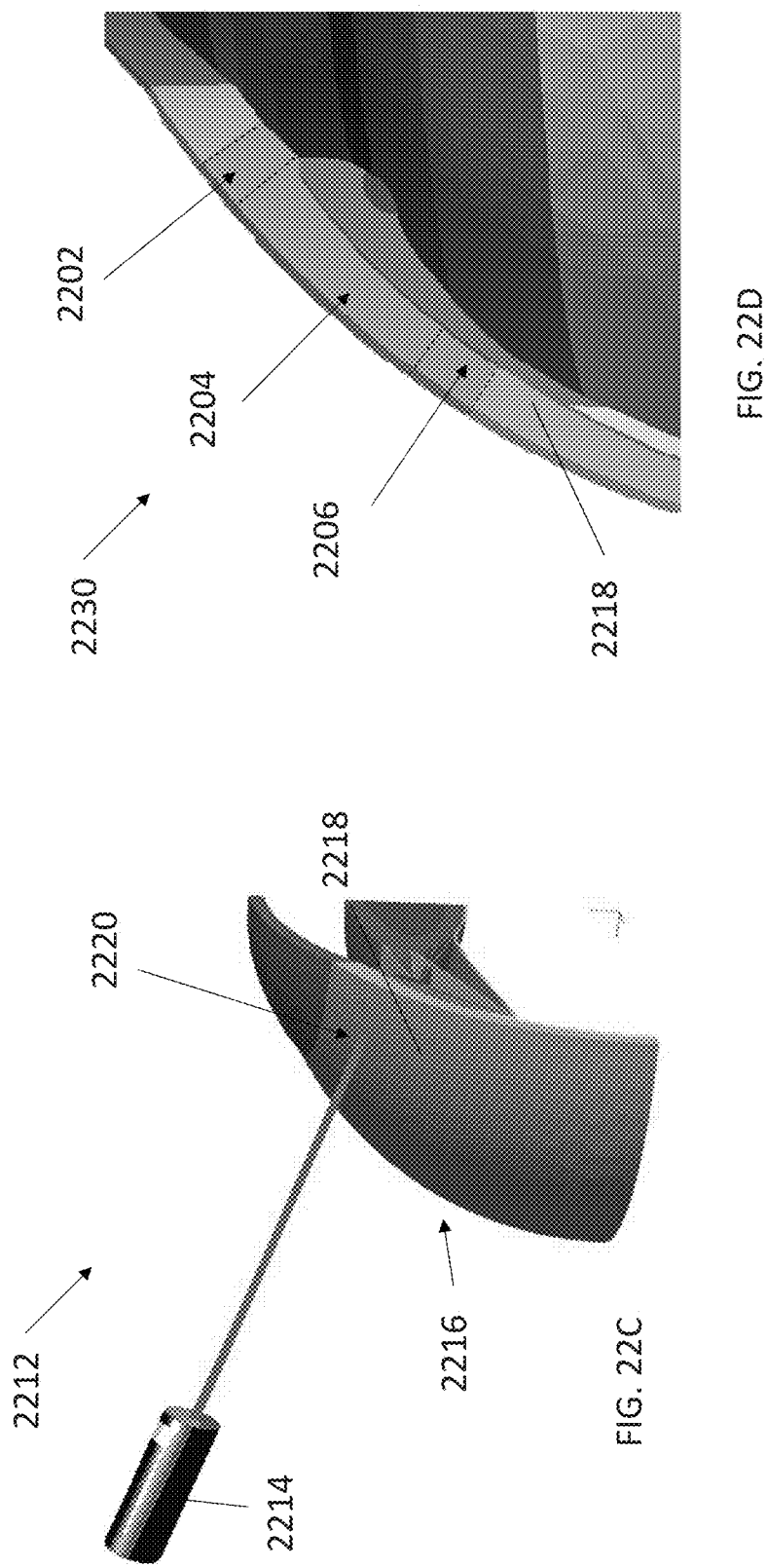

| therapy region | baseline | zones 1+2+3 |
|---|---|---|
| zone 1: sclera | stiff | restored |
| zone 2: sclera | stiff | restored |
| zone 3: sclera | stiff | restored |
| zone 2: matrix | tight | tight |
| zone 3: matrix | tight | tight |

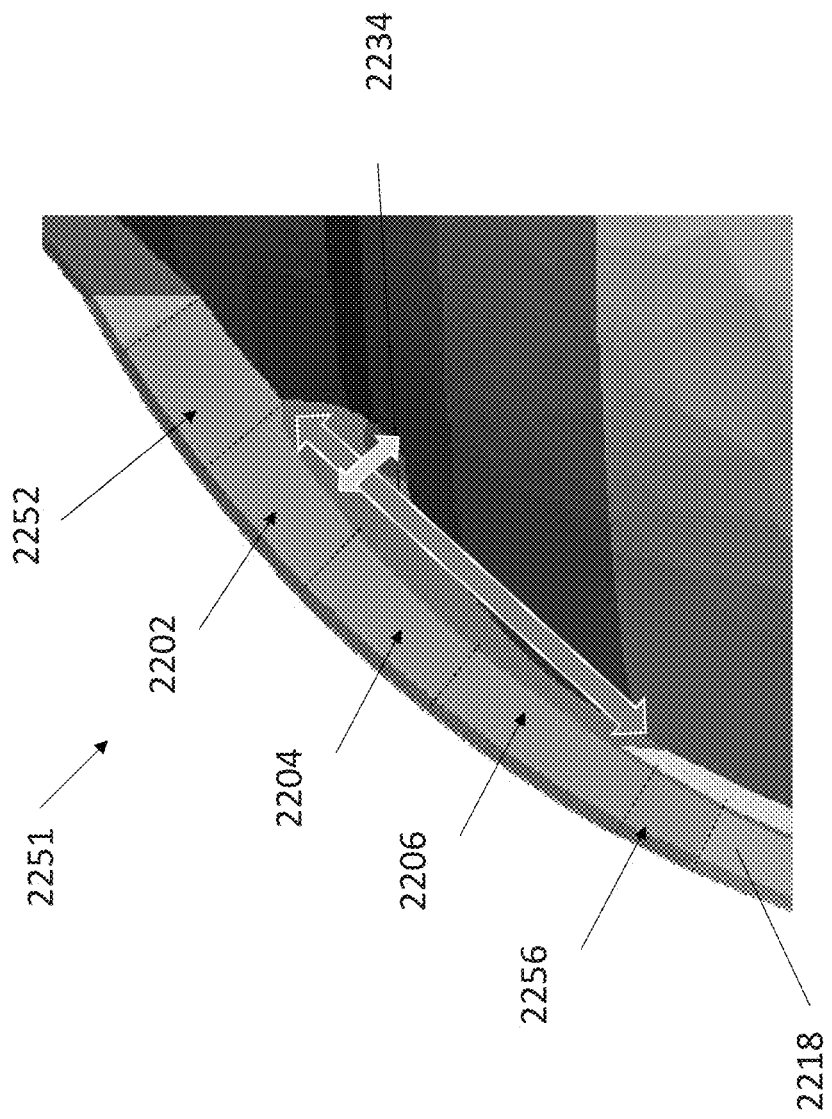

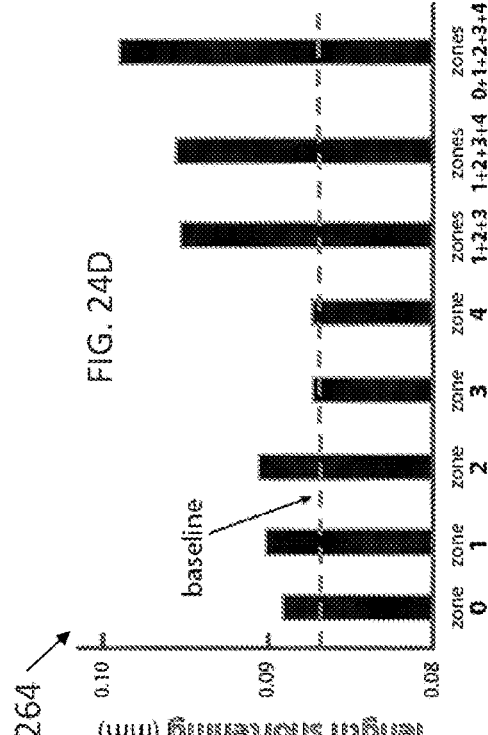
| Therapy Parameters | baseline | zone 0 | zone 1 | zone 2 | zone 3 | zone 4 | zones 1+2+3 | zones 1+2+3+4 | zones 0+1+2+3+4 |
|---|---|---|---|---|---|---|---|---|---|
| zone 0: sclera (MPa) | 2.85 | 1.61 | 2.85 | 2.85 | 2.85 | 2.85 | 2.85 | 2.85 | 1.61 |
| zone 1: sclera (MPa) | 2.85 | 2.85 | 1.61 | 2.85 | 2.85 | 2.85 | 1.61 | 1.61 | 1.61 |
| zone 2: sclera (MPa) | 2.85 | 2.85 | 2.85 | 1.61 | 2.85 | 2.85 | 1.61 | 1.61 | 1.61 |
| zone 3: sclera (MPa) | 2.85 | 2.85 | 2.85 | 2.85 | 1.61 | 2.85 | 1.61 | 1.61 | 1.61 |
| zone 4: sclera (MPa) | 2.85 | 2.85 | 2.85 | 2.85 | 2.85 | 1.61 | 2.85 | 1.61 | 1.61 |
FIG. 24B
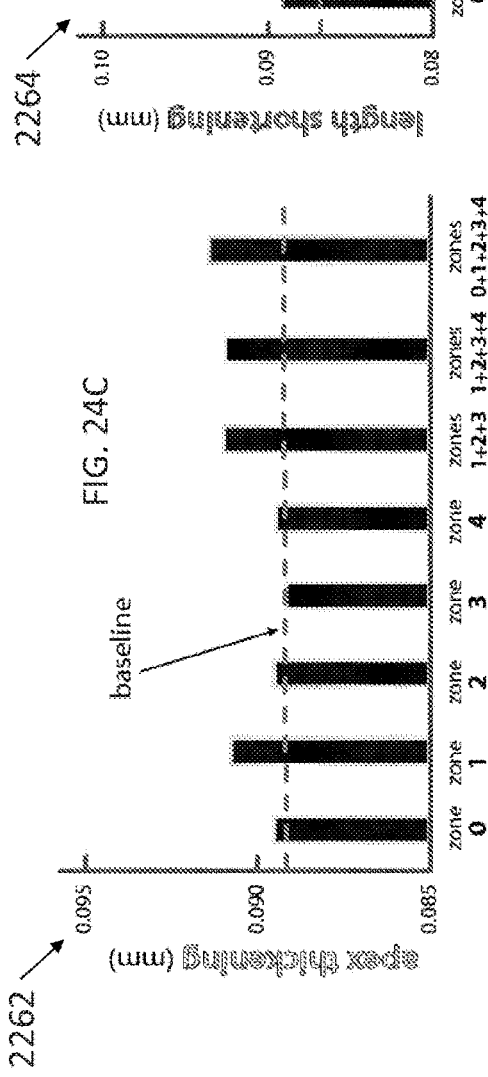
FIG. 24C
FIG. 24D

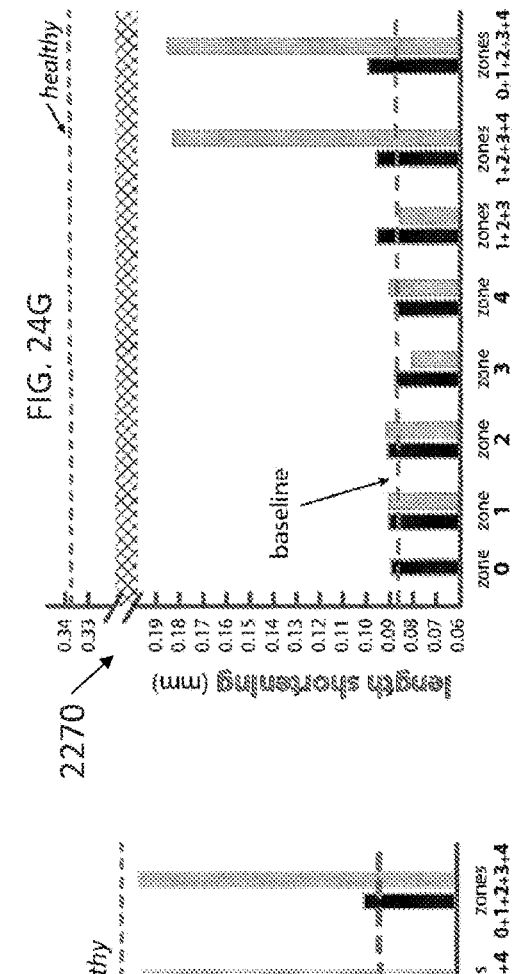
FIG. 24E
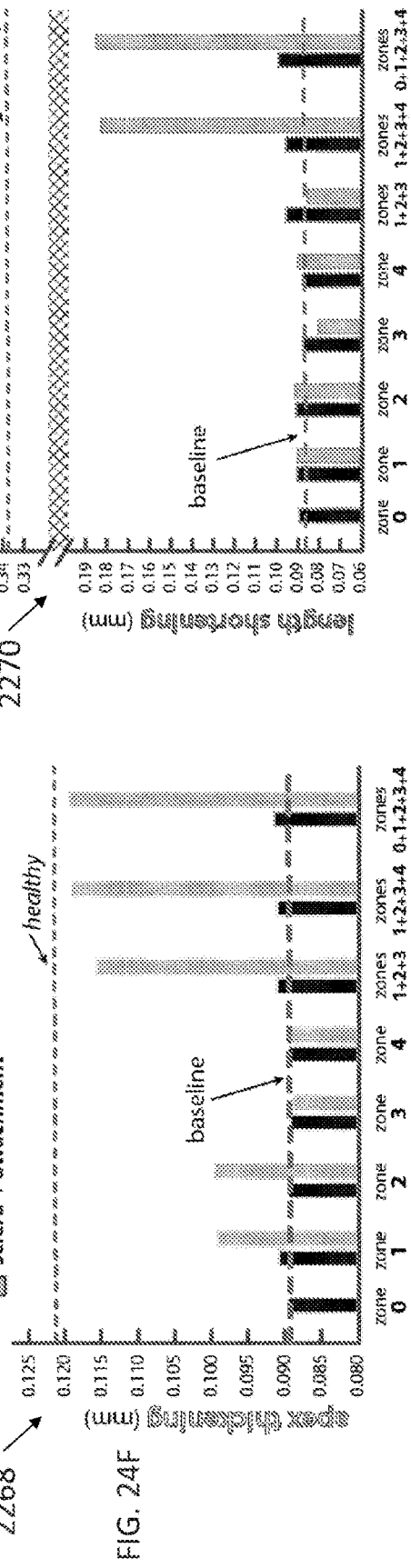
FIG. 24F
FIG. 24G

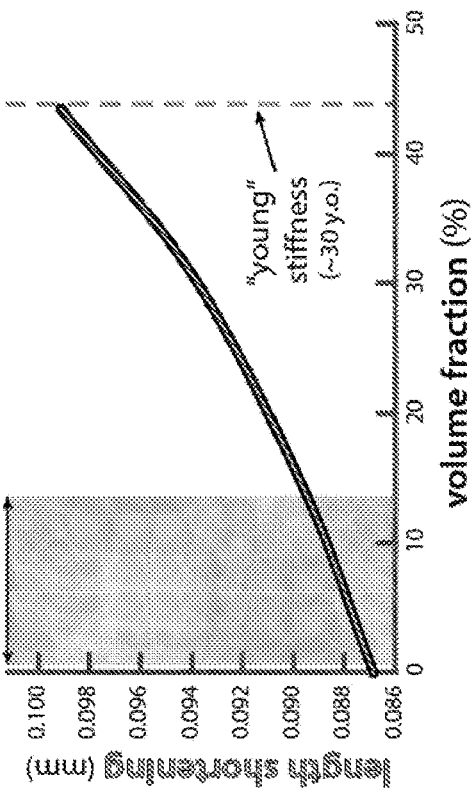
FIG. 24H
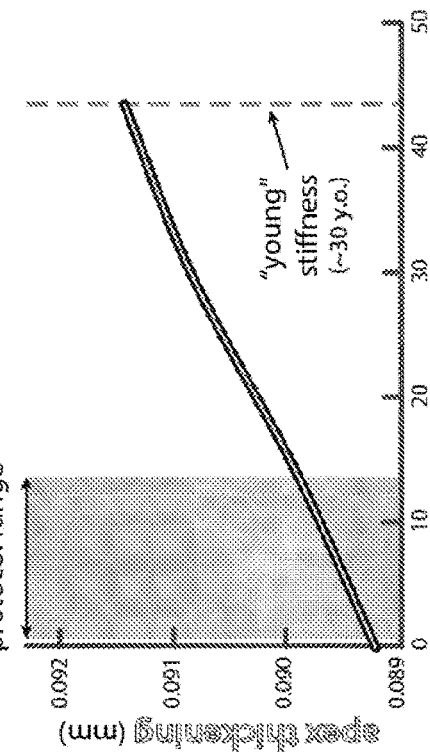
FIG. 24I
FIG. 24J

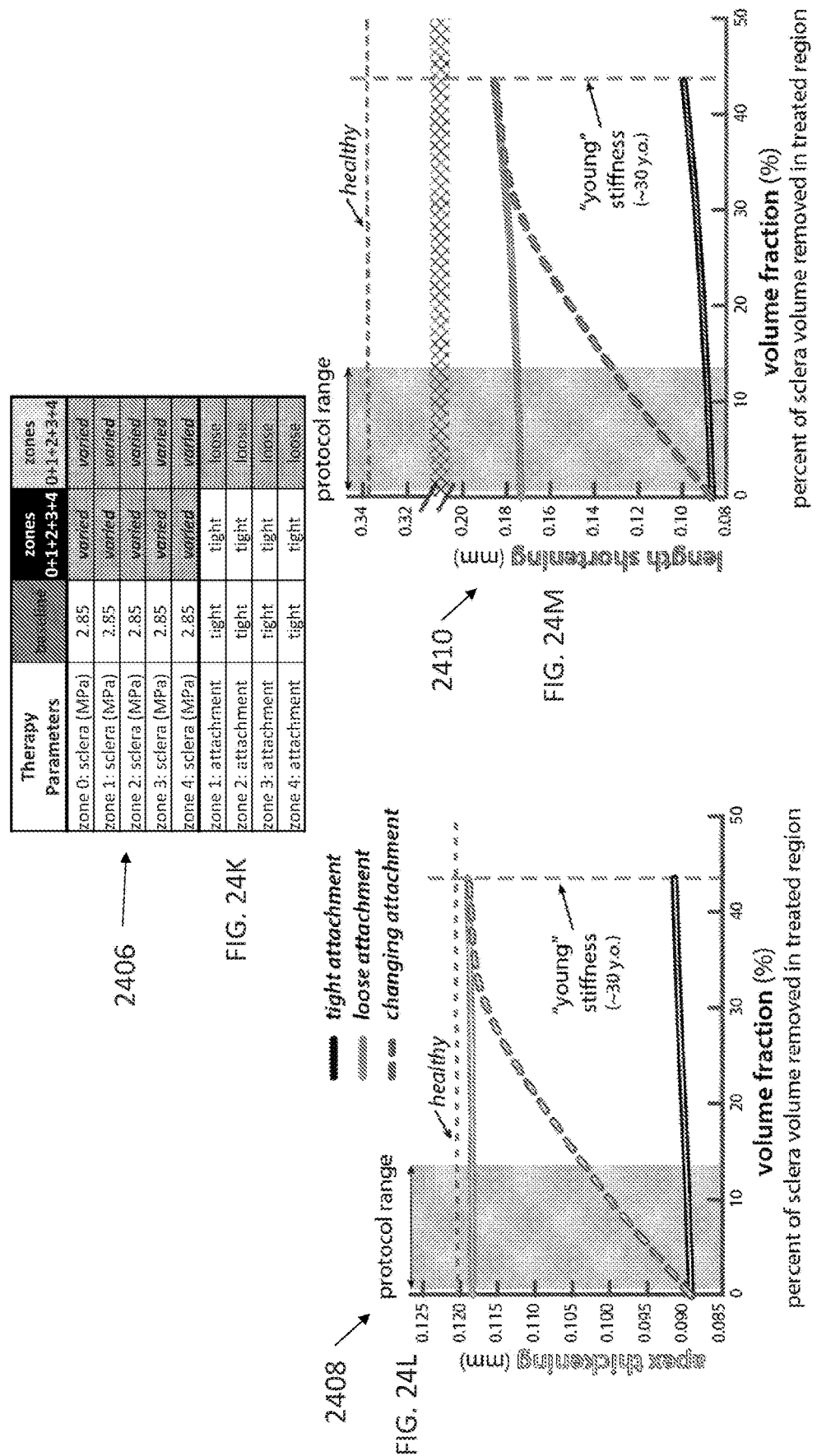

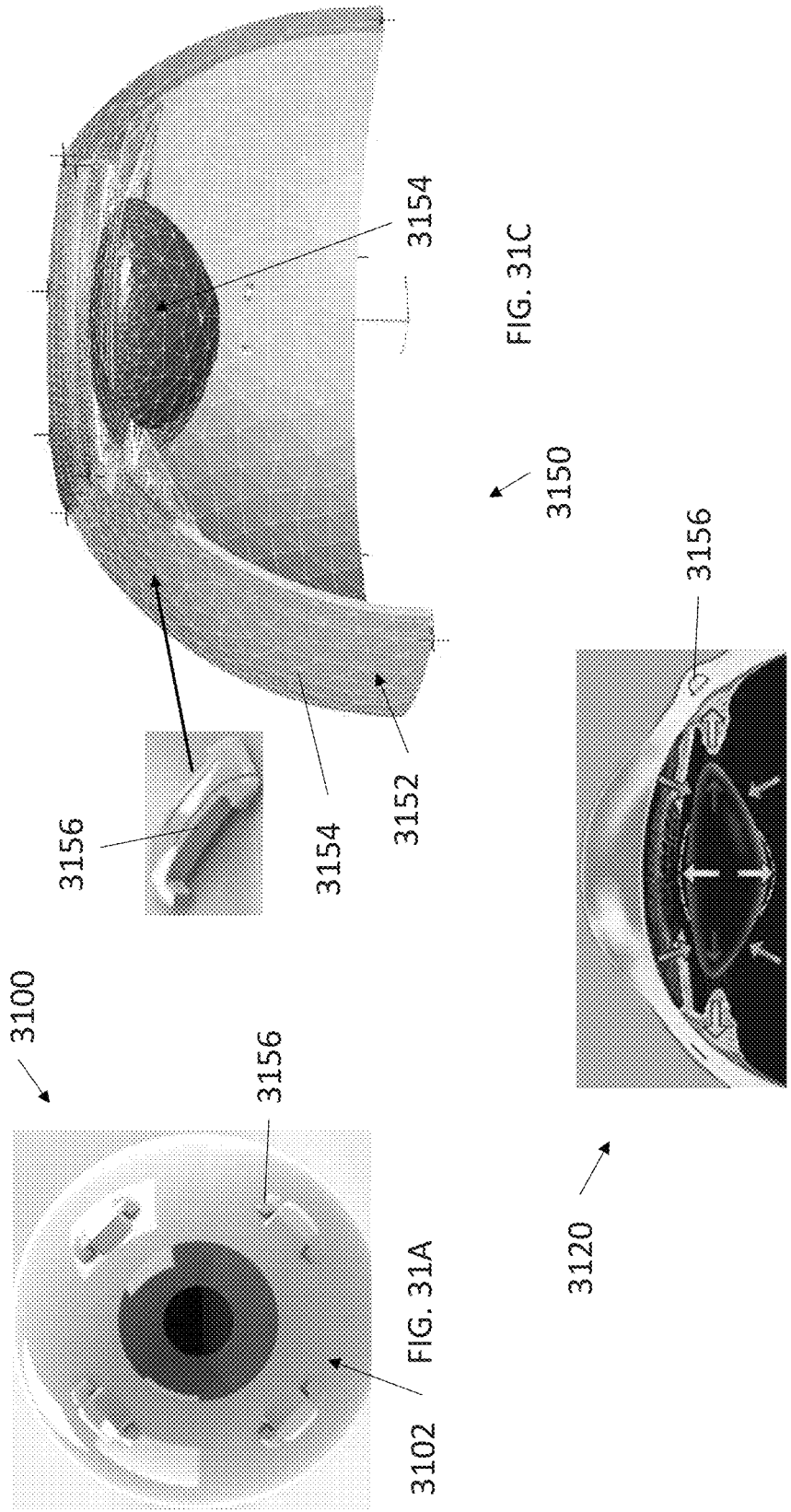

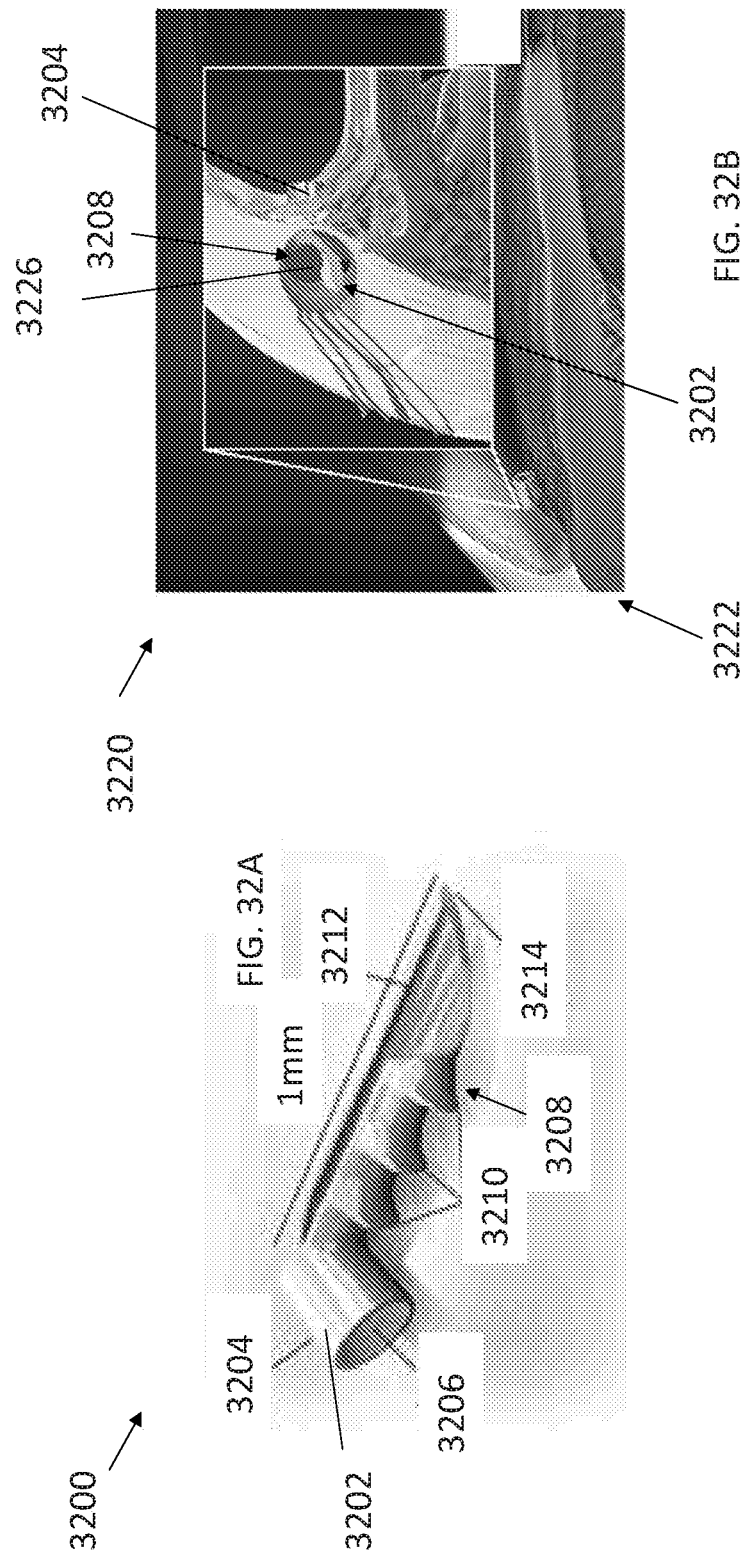

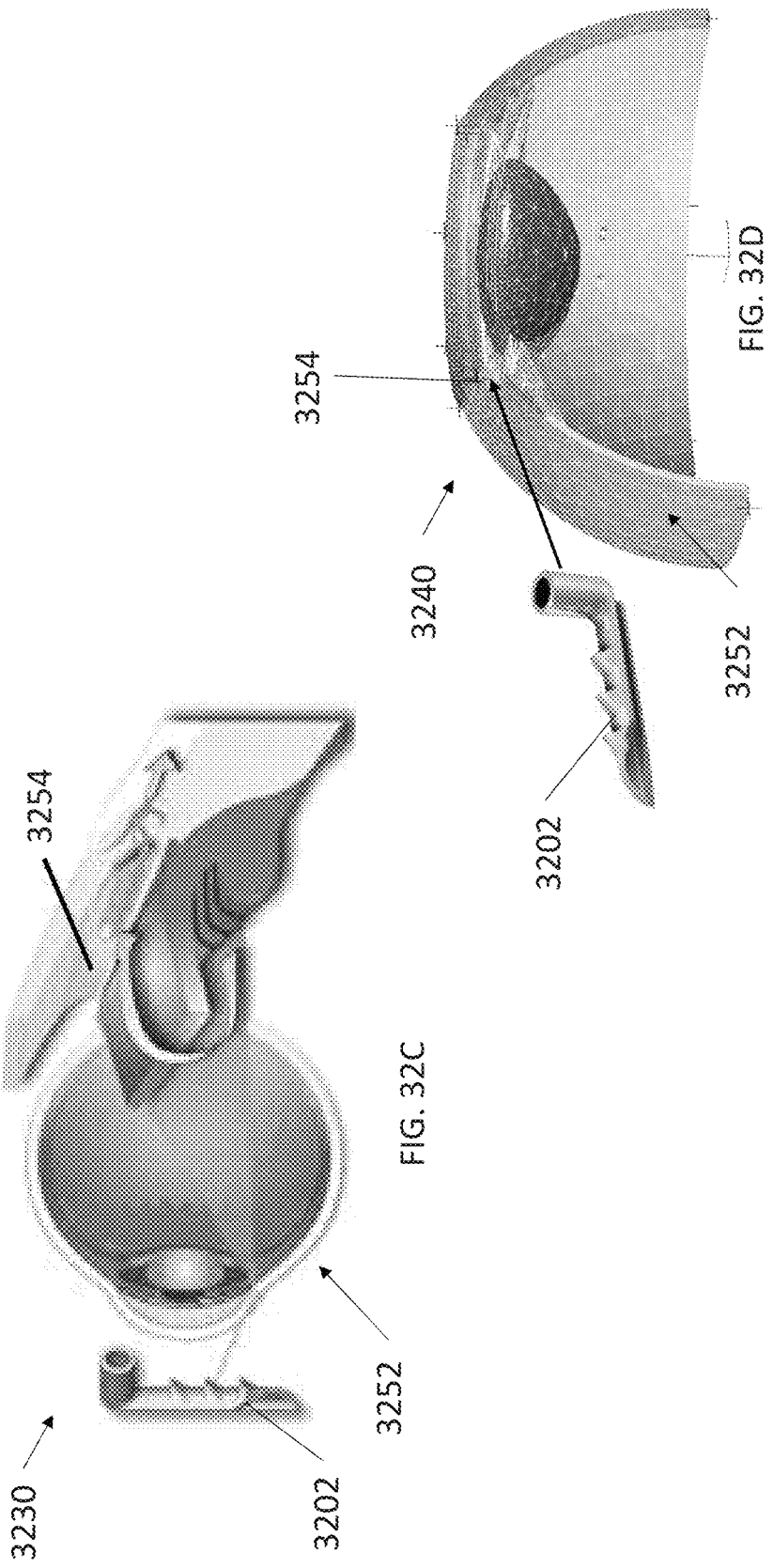

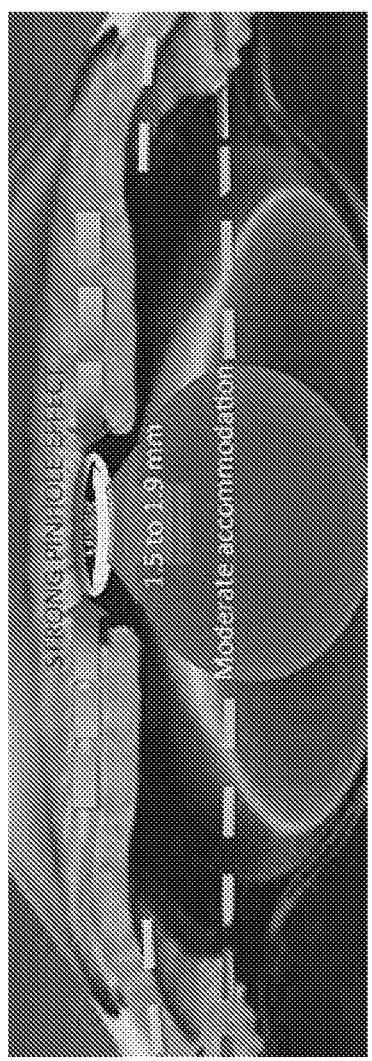
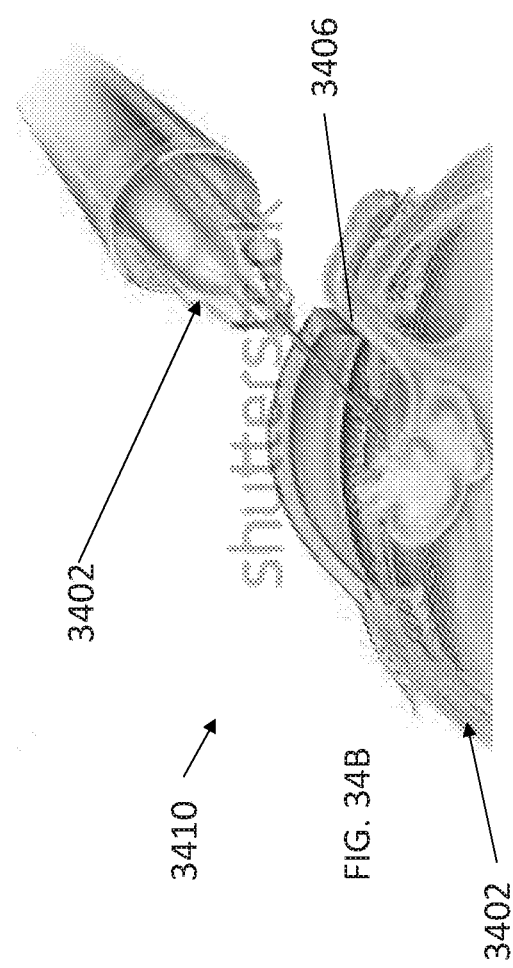
FIG. 34B
FIG. 34C

SYSTEM AND METHODS USING REAL-TIME PREDICTIVE VIRTUAL 3D EYE FINITE ELEMENT MODELING FOR SIMULATION OF OCULAR STRUCTURE BIOMECHANICS

CROSS REFERENCE TO RELATED APPLICATIONS

This application is a continuation of U.S. patent application Ser. No. 15/638,346, filed Jun. 29, 2017, which claims priority to U.S. Provisional Application No. 62/356,467, filed Jun. 29, 2016, the disclosures of both of which are hereby incorporated by reference in their entireties.

This application is related to the subject matter disclosed in U.S. Appl. No. 61/798,379, filed Mar. 15, 2013; U.S. Appl. No. 60/662,026, filed Mar. 15, 2005; U.S. application Ser. No. 11/376,969, filed Mar. 15, 2006; U.S. Appl. No. 60/842,270, filed Sep. 5, 2006; U.S. Appl. No. 60/865,314, filed Nov. 10, 2006; U.S. Appl. No. 60/857,821, filed Nov. 10, 2006; U.S. application Ser. No. 11/850,407, filed Sep. 5, 2007; U.S. application Ser. No. 11/938,489, filed Nov. 12, 2007; U.S. application Ser. No. 12/958,037, filed Dec. 1, 2010; U.S. application Ser. No. 13/342,441, filed Jan. 3, 2012; U.S. application Ser. No. 14/526,426, filed Oct. 28, 2014; U.S. application Ser. No. 14/861,142, filed Sep. 22, 2015; U.S. application Ser. No. 11/850,407, filed Sep. 5, 2007; U.S. application Ser. No. 14/213,492, filed Mar. 14, 2014; and to U.S. Appl. No. 62/356,457, filed Jun. 29, 2016, each of which are incorporated herein by reference in their entirety

FIELD OF THE INVENTION

The subject matter described herein relates generally to systems, methods and devices for simulation and analysis of human ocular structures using 3-dimensional models of complete ocular FEM of human ocular accommodation that can be used in simulating the biomechanical properties, optics, physiology, anatomy and functions of connective and other tissues. This can be implemented using systems, methods, and devices for creating 3-dimensional models of complete ocular FEM of human ocular accommodation which provide for simulation of the biomechanical properties of connective tissue structure and function. Further, systems, methods and devices are disclosed for modeling connective tissue changes by analyzing and experimentation on the underlying biomechanical properties of the connective tissue. As described herein, these features can be used in systems, methods, and devices for simulating ocular tissue changes by virtually analyzing and experimentation on the underlying biomechanical properties of the connective tissue, optical properties of optical tissues, hydrodynamics of fluids and a plurality of other biological, anatomical, and physiological functions of the eye organ.

BACKGROUND OF THE INVENTION

Development of accurate computational models is critical in order to advance scientific understanding regarding how ocular ciliary muscle movements result in changes during accommodative processes and their results on associated ocular lenses. Particularly, these models can help to understand how age-related changes in ocular structures lead to presbyopia, age-related glaucoma, cataract formation, and other age-related ocular diseases such as age-related macular degeneration. Further application of this system could be used to study pathophysiological processes of the eye organ as well as other inflictions of the eye organ such as progressive myopia, ocular nerve head entrapment, closed/open angle glaucoma and a multitude of other eye pathology. As the accommodative complex is the primary dynamic mover of the eye organ driving nearly every physiological function of the eye organ as it contracts (accommodates) and relaxes (dis-accommodates), the understanding of the movements and forces of the ciliary muscle in relationship to the biomechanics of these functions of the eye organ could illuminate many unknown interactions and causes of biomechanical dysfunctions of the eye. These types of ciliary movements are highly complex and difficult to analyze. Moreover, it is impossible in experimental in vivo or ex vivo to analyze the ciliary muscles individually in order to determine how they impact the eye functions. As such, the lack of well-designed intraocular accommodating lenses has prevented these technologies from being successful in living humans and, consequently, the market.

Most prior art accommodation models focus solely on the actions of lenses and zonules, while simplifying ciliary movement as a single muscular displacement. Furthermore, lack of a functional structural whole eye model failed to allow further development of previous technology because this deficiency failed to allow for adequate consideration of the biomechanical impacts, forces, and effects on the sclera, the ciliary muscle influences, other extra-lenticular components' influence on the accommodative system, including the choroid, zonules, and even the retina. Previous studies only looked at the ocular lens in a vacuum without the sclera or other extra-lenticular structures.

In particular, the emphasis on affecting ocular accommodation to date has typically been focused on identifying and creating changes in ocular lens properties while failing to address underlying ciliary muscle operations or other extra-lenticular tissues, forces and structures. To date, there have been no models established to include a 'whole eye Finite Element Model (FEM)'. Previous models have simulated the transition from an accommodated state, where a lens is un-stretched but the associated ciliary muscle is contracted, to an unaccommodated state, where the ciliary muscle is at rest and the lens is stretched. Unfortunately, these models depend on a simplified arrangement of zonule attachments and ignore or otherwise neglect the uniquely complex behaviors of the ciliary muscle, whose movements are constrained by attachments to the lens capsule, ocular sclera and choroid structures. As such, value and novelty would be provided for researchers, students, and medical practitioners by demonstrating accommodation more accurately during the accommodative process in vivo than currently exists, as well as pretension on the lens when the system is in disaccommodation. This would allow for better understand of various different forces that are translated to the lens during accommodation through other structures.

Due to the simplification of the ciliary muscle behaviors as applied in these prior art models, attempts to apply pre-tensioning of zonules prior to ciliary muscle contraction have not been successful. This has led not only to a gap in the understanding of the accommodation mechanism but also to a lack of effective treatment of in restoring the accommodative functions that the conditions created by presbyopia and other age-related eye afflictions.

Also contributing to the lack of effective treatment for deteriorated accommodative function is the fact that there is an overall scarcity of data with respect to the functioning accommodative mechanisms for healthy human eyes, especially in vivo or dynamic data. Since accommodative functioning is difficult to measure because of the delicate nature of the human eye, most current measurement techniques have relied on data gathered from experimentation on the ocular systems of human cadavers and other primates. Gathering this data usually requires isolating or disturbing at least a portion of the accommodative ocular system, making procedures difficult and dangerous for live human test subjects.

As a result of insufficient data regarding the accommodative ocular system, its underlying mechanisms and the related problem of incomplete modeling, analysis of existing data provides a disjointed and incomplete understanding of ocular accommodation in humans and any implications resulting from age-related changes to ocular structures.

Various examples of prior art creating meshed finite element models include U.S. Patent Pub. No. 2007/0027667, U.S. Pat. Nos. 8,346,518, 7,798,641, and 7,096,166. U.S. Patent Publ. No. 2007/0027667 in particular serves as a general example how to specify "Computational Model of Human ocular accommodative biomechanics in young and old adults." These prior art applications generally do not perform simulations on an entire eye, particularly an entire human eye, and do not include simulations, analyzers, artificial intelligence and machine learning and other important concepts and aspects disclosed herein.

Since there is a lack of knowledge about the complex biomechanical relationships between the various ocular structures, their motions, and their relation to age related dysfunction, new systems, such as those disclosed herein, can illuminate previously unknown features about biomechanical property changes of various ocular structures and their physics, in addition to the biomechanical relationship changes they undergo due to the natural aging process. Further, various therapy simulations can be simulated to determine potential effects, including their potential benefits and drawbacks for patients of different ages.

It is therefore desirable to provide improved systems, devices and methods for performing simulations using a multi-component Finite Element Model (FEM) of ocular biomechanics of the eye organ and interrelationships of physiological and optical functions of the eye. One preferred embodiment of this model is the demonstration of the accommodative mechanism that includes ocular structures including the ciliary muscle, lens, zonules, sclera, and choroid, in order to characterize the role of complex ciliary muscle action in producing ocular lens changes required for accommodative function between young and presbyopic adults.

As people age, they develop presbyopia and lose accommodative ability, leaving people over the age of 50 with an almost complete lack of focusing ability for near vision. Although scientists have studied accommodation for centuries the functional mechanism is not well understood. Most presbyopia research has focused on property changes of the aging lens without examining the accommodative mechanism as a whole, basically ignoring the complicated role of the ciliary muscle. Without understanding the interactions of the muscle, lens, and other structures that alter the eye's optic power, treatments for presbyopia that effectively restore this ability cannot be successfully developed. This lack of understanding is also in part due to the limited data, especially in vivo or dynamic, of healthy human eyes; most current measurement techniques require isolating or disturbing some portion of the accommodative system and are limited to cadavers or monkey models. These data provide a disjointed comprehension of the accommodative mechanism and the implications of age-related changes to eye structure.

Regarding glaucoma, aqueous humor drains from the eye via two routes, the so-called conventional and or unconventional uveo-scleral routes. Uveo-scleral outflow normally carries only approximately 10% of total outflow. Most aqueous humor instead drains via specialized tissues situated in the angle of the anterior chamber, located at the conjunction of the iris, cornea, and sclera. Beginning at the anterior chamber and moving exteriorly, these tissues are the trabecular meshwork, a porous connective tissue; Schlemm's canal, a collecting duct lined by a vascular-like endothelium; and the collector channels/aqueous veins. Direct pressure measurements and circumstantial evidence in the prior art indicate that most of the flow resistance in the normal non-glaucomatous eye is in the juxtacanalicular tissue (JCT) or the endothelial lining of Schlemm's canal. After leaving the aqueous veins, the aqueous humor mixes with blood in the episcleral veins, eventually draining back to the right heart. The episcleral venous pressure is has been measured at approximately 8-10 mmHg and the resistance of the conventional aqueous drainage tissues has been measured at approximately 3-4 mmHg/μl/min, resulting in an IOP of 15.5±2.6 mmHg (mean±SD) in the general population.

It is generally known that elevated IOP is the main risk factor for glaucoma that lowering IOP helps preserve visual function. In the vast majority of glaucoma conditions, the elevation in IOP is due to too much aqueous humor drainage resistance, and in the majority of these cases the elevated resistance is due to pathologic changes in the conventional drainage tissues. Despite years of intensive research, there is little understanding of how aqueous drainage resistance is controlled in normal eyes, glaucomatous eyes, and how they compare. Thus, it would be beneficial to develop models and simulations that could shed light on these issues.

Further, it is generally unknown where aqueous flow resistance originates. Existing models of Schlemm's canal as a compliant chamber with a porous, elastic wall suggest negligible flow resistance within the canal itself, except at extreme intraocular pressures (>50 mmHg) when the canal collapses. Known concentrations of proteoglycan-rich gels within the extracellular spaces of the juxtacanalicular tissue are consistent with the generation of significant flow resistance and existing data suggests that the turnover of this matrix is modulated by stretch-induced matrix metalloproteinases (MMP) activity within the trabecular meshwork. However, the evidence supporting a primary role for extracellular matrix is far from iron-clad and researchers have looked elsewhere. The other "candidate" for generating flow resistance is the endothelial lining of Schlemm's canal. This cellular layer is unusual; for example, it has the highest permeability of any endothelium, with $Lp \geq 4 \times 10\text{-}8$ cm2 s/g, however it is non-fenestrated. As such, the cells are joined by tight junctions that become less tight as IOP increases and are permeated by membrane-lined openings or pores that, although poorly understood, are almost certainly involved in aqueous humor transport. These pores represent only approximately 0.1% of the total endothelial area and have a mean diameter just slightly over 1 μm. Some models of the pores in the endothelial lining modulating the flow through a porous juxtacanalicular tissue suggest that overall flow resistance may depend on an interaction between the endothelial pores and extracellular matrix.

Additionally, the endothelial cells lining Schlemm's canal bulge prominently into the lumen of the canal, forming the so-called giant vacuoles. Existing evidence suggests these are passive structures that form in response to the "backward" basal-to-apical pressure gradient that is always present across the cells. The extreme cases occur when an individual rubs their eyes, instantaneously generating pressures as high as 80 mmHg. These large IOPs form so many giant vacuoles that inner wall endothelial cells may stretch by as much as 50%, a harsh biomechanical environment.

The biomechanics of aqueous humor flow within the anterior chamber are also interesting because as a result of the cornea being normally exposed to ambient air, the temperature at the posterior corneal surface is slightly less than body temperature, thus creating a temperature gradient across the anterior ocular chamber. The resulting convection patterns tend to transport particles in vertical paths along the mid-peripheral cornea). The clinical correlation of this effect is pigment particles that are seen to accumulate along such paths in patients whose irises release abnormal amounts of pigments.

Additionally, there is a form of glaucoma in which the elevated IOP is not due to changes in the drainage system of the eye per se. This is angle-closure glaucoma, when the iris pivots forward and blocks access to the drainage structures in the angle of the anterior chamber. There appears to be an anatomic predisposition to this situation. The iris is extremely pliable and modeling has shown interesting interactions between iris deformation and aqueous flow through the pupil and between the lens and the iris, especially when the eye is perturbed by blinking.

Currently Goldberg's Postulate incorporates all elements of the zonular apparatus into the phenomenon of accommodation. Biometry has shown lens thickness increases and the anterior chamber depth decreases upon contraction of the ciliary muscles, the lens capsule steepens, as the posterior-lens surface moves backwards. There is a decrease in the distance from scleral spur to the ora serrata, the Nasal sclera compresses inward and the Choroid also stretches forward.

A computational model is critical to understanding how the complex movements of the ciliary muscle drive the lens changes necessary for accommodation, and to understand how age-related changes lead to presbyopia. Most previous models focused solely on the actions of lens and zonules, simplifying ciliary movement to a single displacement, and simulating the transition from the accommodated state where the lens is un-stretched but the muscle is contracted, to the unaccommodated state where the muscle is at rest and the lens is stretched. This method depends on a simplified arrangement of the zonule attachments and also ignores the complex behaviors of the ciliary muscle, whose movements are constrained by its attachments to the sclera and choroid. The goal of this study was to develop a multi-component finite element (FE) model of the accommodative mechanism that includes the ciliary muscle, lens, zonules, sclera, and choroid, to characterize the role of complex ciliary muscle action in producing the lens changes required for accommodative function.

Development of accurate computational models is critical in order to advance scientific understanding regarding how ocular ciliary muscle movements result in changes during accommodative processes and their results on an associated ocular lens. Particularly, these models can help to understand how age-related changes in ocular structures lead to age-related dysfunctions and pathophysiology such as presbyopia, age-related glaucoma, age related macular degeneration, cataract formation and others. Accommodation mechanisms are highly complex and difficult to analyze, especially those of the ciliary body (muscles) which are under emphasized and grossly overlooked and not well characterized to date.

Most prior art accommodation models focus solely on the actions of lenses and zonules in isolation of extralenticular structures and whole eye biomechanics, and thus, oversimplify ciliary movement as a single muscular displacement. In particular, the emphasis for ocular accommodation to date has typically been focused on identifying and creating changes in ocular lens properties, while not addressing underlying ciliary muscle operations. These models simulate the transition from an accommodated state, where a lens is un-stretched but the associated ciliary muscle is contracted, to an unaccommodated state, where the ciliary muscle is at rest and the lens is stretched. Unfortunately, these models depend on a simplified arrangement of zonule attachments and ignore or otherwise neglect the uniquely complex behaviors of the ciliary muscle, whose movements are constrained by attachments to the ocular sclera and choroid structures.

Due to the simplification of the ciliary muscle behaviors as applied in these prior art models, attempts to apply pre-tensioning of zonules prior to ciliary muscle contraction have not been successful. This has led not only to a gap in the understanding of the accommodation mechanism but also to a lack of effective treatment in restoring the accommodative functions that the conditions created by presbyopia and other age-related eye afflictions, including proper aqueous flow hydrodynamics and normal organ function to name a few.

Also contributing to the lack of effective treatment for deteriorated accommodative function is the fact that there is an overall scarcity of data with respect to the functioning accommodative mechanisms for healthy human eyes, especially in vivo or dynamic data. Since accommodative functioning is difficult to measure because of the delicate nature of the human eye, most current measurement techniques have relied on data gathered from experimentation on the ocular systems of human cadavers and other primates. Gathering this data usually requires isolating or disturbing at least a portion of the accommodative ocular system, making procedures difficult and dangerous for live human test subjects.

As a result of insufficient data regarding the accommodative ocular system, its underlying mechanisms and the related problem of incomplete modeling, analysis of existing data provides a disjointed and incomplete understanding of ocular accommodation in humans and any implications resulting from age-related changes to ocular structures.

Various examples of prior art creating meshed finite element models include U.S. Patent Pub. No. 2007/0027667, U.S. Pat. Nos. 8,346,518, 7,798,641, and 7,096,166. U.S. Patent Publ. No. 2007/0027667 in particular serves as a general example how to specify "Computational Model of Human ocular accommodative biomechanics in young and old adults." These prior art applications generally do not perform simulations on an entire eye, particularly an entire human eye, and do not include simulations, analyzers, artificial intelligence and machine learning and other important concepts and aspects disclosed herein.

As such, systems, devices, and methods for a multi-component Finite Element Model (FEM) of an ocular accommodative mechanism that includes ocular structures including the ciliary muscle, lens, zonules, sclera, and choroid, in order to characterize the role of complex ciliary muscle action in producing ocular lens changes required for accommodative function between young and presbyopic adults are useful for simulation purposes. These simulations can then implement modeling techniques in order to gain a better understanding of how ciliary muscle function modification may lead to improved medical treatments, since most scientific research to date has been focused on the change in lens properties instead of muscle action.

Drug delivery to intraocular tissues is important in treating a variety of ocular diseases. As such, it would be useful to build models and simulations representative of drug delivery based on existing literature. Systemic administration of these agents is undesirable because it necessitates high plasma concentrations to achieve adequate intraocular dosing. Trans-corneal delivery by passive diffusion is difficult because the drug needs to have hydrophobic characteristics to pass through the corneal epithelium and endothelium and hydrophilic characteristics to pass through the corneal stroma. Furthermore, as soon as the agent enters the anterior chamber, it is carried out of the eye by the aqueous humor. Scleral delivery may be a more attractive route for drug administration, especially for drugs destined for the retina, since the tight epithelial barriers of the cornea are not present on the sclera. However, the scleral stroma is still a significant barrier, and a number of studies have examined the permeability of this tissue.

Scleral permeability to solute transport decreases with increasing solute molecular weight and increasing molecular radius, with the latter a better predictor of scleral permeability than the former. Additionally, the posterior sclera is more permeable to solute transport than the anterior sclera, further supporting the sclera as an ideal route for drug delivery to the retina.

The specific hydraulic conductivity of the sclera is $2 \times 10^{-14}$ cm$^2$, typical of dense connective tissues. With a typical pressure difference across the sclera of 15 mmHg; a scleral thickness, L, of 0.6 mm; and a filtering area, A, of 11.5 cm$^2$, so Darcy's law can be used to estimate a maximum flow rate (Q) across the sclera of 0.3 µl/min. The flow rate can be used to examine several issues related to fluid flow though the scleral stroma. The first question is the extent to which this flow impedes drug delivery across the sclera. The diffusional flux of a drug through a tissue can be estimated as $D_0(1-\text{phi})A(\text{Delta}*C)/L$, whereas the convective flux of a drug through that same tissue would be $QC(1-\text{phi}))$.

Here $D_0$ is the diffusion coefficient of the tracer in free solution (for albumin $6\times10^{-7}$ cm$^2$/sec); phi is the extent to which the tracer is retarded, relative to the fluid flow, from moving by the extracellular matrix (0 is unhindered, 1 completely hindered); and C is the concentration difference across the sclera, which we assume is the same as the concentration of drug at the surface of the sclera. Using these formulas, the ratio of diffusional transport to convective transport is computed to be approximately 20 for molecules the size of albumin. In other words, for these parameters, diffusional transport of a drug across the sclera is more than an order of magnitude higher than transport of the drug by convection. Thus, bulk flow across the sclera is estimated to have minimal impact on drug delivery through the sclera.

The value of Q can be used gain insight into the unconventional drainage pathway that normally carries a small fraction of the aqueous humor from the eye. Aqueous humor draining via this pathway passes through the ciliary muscle, into the suprachoroidal space, and then passes either through the sclera into the orbit or through the sclera to the vortex veins and choroidal circulation, where it is absorbed. Arguments have previously been provided for each of these pathways. The value of Q calculated above as 0.3 µl/min would appear to support the former pathway because this value is consistent with measured values of unconventional aqueous outflow rates. However, it is known that ciliary muscle contraction greatly affects the unconventional outflow, and that $PGF_{2\alpha}$ greatly increases unconventional outflow by decreasing the flow resistance of the interstitial spaces in the ciliary muscle. This is postulated to only be possible if the flow resistance of the ciliary muscle is of the same order of magnitude or even larger than that of the sclera; otherwise, changes in the muscle should make little difference. However, in that case the calculated flowrate of 0.3 µl/min must be an upper bound that does not consider the flow resistance of the ciliary muscle. A further argument against a trans-scleral flow is that unconventional outflow is not very pressure sensitive. Although this might be expected if the flow were primarily osmotically driven into the uveal vessels, this would not be the expected characteristic of a trans-scleral flow. Each of these considerations argue against trans-scleral flow, but are consistent with osmotic adsorption of the unconventional aqueous outflow by the choroidal circulation. As these questions still exist, accurate modeling and simulation would be beneficial.

It is therefore desirable to provide improved systems, devices and methods for performing simulations using a multi-component Finite Element Model (FEM) of an ocular accommodative mechanism that includes ocular structures including the ciliary muscle, lens, zonules, sclera, and choroid, in order to characterize the role of complex ciliary muscle action in producing ocular lens changes required for accommodative function between younger and older adults.

SUMMARY OF THE INVENTION

Disclosed are systems, devices and methods for a simulation execution using multi-component Finite Element Model (FEM) of ocular structures involved in optical biomechanics, including ocular accommodation. Developing and implementing a computational model can be critical to understanding how the complex movements and mechanics of the eye, for example ciliary muscle driving lens changes necessary for accommodation, and to understand how age-related changes lead to presbyopia and other medical conditions. For accommodation issues, most prior models focused solely on the actions of lens and zonules, simplifying ciliary movement to a single displacement. These models function by simulating the transition from the accommodated state where the lens is un-stretched but the muscle is contracted to the unaccommodated state where the muscle is at rest and the lens is stretched. As such, the disclosed developments of multi-component FEMs of the accommodative mechanism that include the ciliary muscle, lens, zonules, sclera, and choroid, to characterize the role of complex ciliary muscle action in producing the lens changes required for accommodative function.

Numerical simulation of the patient's eye can be created using 3D FEM meshing to accomplish methods such as adding a "pre-stretch" lens positioning in coding and manipulations of software, as executed by a computer processor. Similarly, methods of intricate meshing of zonular and other structures, methods of importing dynamic imaging into models for the purposes of modelling accommodation and accommodative movements including, but not limited to, simulation of central optical power and changes in the crystalline lens can be accomplished using computer based computations. Additionally, methods and software manipulation executed by a processor can be capable of performing numerical simulation of zonular apparatus movements, forces and impact on COP.

Systems, methods and devices disclosed herein can be used to perform other functions as well, such as those pertaining to simulations utilizing models of the back of the eye, including: lamina cribrosa, Ocular Nerve Head and others related to ocular structures and functions. For example, regarding the posterior globe: new insights and understanding of the lamina cribrosa are possible, as are insights into the complex structure of the peripapillary sclera, and attachments of the choroid using complex math for solving elastic and viscoelastic equations and simulations may provide additional benefits.

Virtual Eye Simulation Analyzers (VESAs) can include: 1) Virtual Eye 2-dimensional (2D) & 3-dimensional (3D) models; 2) an "ABACUS" Artificial Neural network including self-learning computer programs for categorizing all data inputs from Virtual Eye; 3) an "iRobot": able to take instructions from ABACUS; 4) Smart Applications (Apps) for remote robotic operating system, enabling remote laser surgery and Bluetooth operations; and 5) others.

Further, VESAs can be capable of evaluating, demonstrating, simulating, adjusting or modifying parameters, re-simulating, and solving for mechanisms of actions of various therapy manipulations, implantations, applications, forces, and features that are subjected or inputted as parts or all of a VESA model. The models can be dynamic and run in real-time, as well as retrospective. When combined with machine learning the models and intelligent programs are able to accurately and efficiently utilize data inputs to improve the accuracy of simulations run and solve for various solutions and outcomes of the therapy manipulations.

Mechanism of action for therapies and therapeutic or surgical outcomes include the ability of VESAs to make deterministic probabilities of how a particular therapy or surgery effects the whole eye system for physiological mechanisms of the eye, biomechanical mechanisms of the whole eye including but not limited to accommodative biomechanics, hydrodynamics functions of the eye, blood flow, neural feedback loops, mechanical properties, physical interactions, not accommodative functions and effects and others. Further, VESA is able to intelligently and accurately predict the optimal mechanism of action for particular individual surgeries, therapy manipulations, and others, as well as the most likely outcome of such therapies, surgeries, and other applications to individual structures and the whole eye.

"Virtual Eye" models for diagnostic image restoration during real-time, include intraoperative measurement of accommodation, manipulations of optics and others can include some or all of the following: 1) Image processing system of the whole eye integrating eye shape, corneal shape, optics, creation of treatment algorithms for present and future treatment; 2) Utilization of imaging such as OCT, UBM tomography, spectroscopy, video imaging and others to create reverse computer imaging in real-time from a human eye anatomy for the purpose of creating a 3D virtual computerized simulation; 3) Finite Element Model incorporated to mesh geometry, material property, biomechanics and applied physics input of a given eye.

Software systems of Virtual Eye can be: 1) Capable of Simulations of personalized age-related changes in (anatomy, biomechanics, material properties, geometry and others); 2) Capable of conducting an aging progression simulation from current day data to a particular age matrix in the future to predict maximum limitations of pattern and anatomical, material property and physics assumptions of graduated retreatments and prediction of how many will be needed a priori; 3) Registration of treatment patterns via smart memory for: a) Treatment enhancements, b) Retreatment and 3) added future treatments; and 4) others.

A simulator for simulating biomechanical models of the human ocular accommodation and whole eye function is proposed and employed in a finite element formulation for simulating the effects of surgical, therapeutic, and pharmacological manipulation on biomechanical properties of various ocular structures. Simulator systems of Virtual Eye can be used for applications including 1) performance of virtual clinical trials, 2) surgical education and training; 3) Virtual a-priori information on design of technologies, medical devices and treatment safety and efficacy; 4) real-time guidance or surgical guidance; 5) biomechanical predictions for future applications and surgeries; and 6) others.

In particular, the structural behavior of the whole eye, which is governed by the material properties, physics, biomechanics and behavior of the optics under various conditions and which is modeled as a 3D computer mathematical simulation can be used for predicting future ocular conditions. The proposed simulations using computational models and the effects of surgical procedures on them can be based on a number of important underlying simplified assumptions regarding the mechanical properties and structure of the ocular tissues at the ultrastructure level. The artificial intelligence software disclosed herein has capabilities allowing an interactive platform for diagnostic, surgical planning, intraoperative surgical adjustment, and virtual surgical simulation.

Thus, simulations using models of ocular structures, such as those used in ocular accommodation can be executed and repeated with different versions of an ocular mesh, along with various pluralities of external and internal manipulation of anatomical and geometrical or quasi-physical components.

BRIEF DESCRIPTION OF THE DRAWING(S)

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely. Illustrated in the accompanying drawing(s) is at least one of the best mode embodiments of the present invention.

FIGS. 1B-1C show an example embodiment of a cross-section of an eye diagram and illustrating changes in structural components of an eye for distance and near vision respectively.

FIG. 1D shows an example embodiment diagram of how an unaccommodated eye focuses an image through a lens.

FIG. 1E shows an example embodiment diagram of how an accommodated eye focuses an image through a lens.

FIG. 5A shows an example embodiment of a two-dimensional cross sectional diagram for a two-dimensional model design for an eye showing measurements of unaccommodated ocular structures.

FIG. 7G shows an example embodiment of a cross-sectional 3-dimensional model structure diagram showing various ocular structures of an eye.

FIG. 7H shows an example embodiment of a cross-sectional 3-dimensional model structure diagram showing a shaded ciliary muscle of an eye.

FIG. 7I shows an example embodiment of a cross-sectional 3-dimensional model structure diagram showing shaded zonules of an eye.

FIG. 7J shows an example embodiment of a cross-sectional 3-dimensional model structure diagram showing a sclera of an eye.

FIG. 7K shows an example embodiment of a cross-sectional 3-dimensional model structure diagram showing a shaded lens of an eye, including capsule, cortex, and nucleus.

FIG. 7L shows an example embodiment of a cross-sectional 3-dimensional model structure diagram showing a shaded choroid, vitreous membrane, and cornea.

FIG. 9A shows an example embodiment of a prior art diagram of ciliary fibers of an eye.

FIG. 9B shows an example embodiment of an accommodated eye diagram. As the schematic diagram of the eye is shown, major structures involved in accommodation include: a corneo-scleral shell, a crystalline lens, a ciliary body containing ciliary muscles, and the zonular fibers connecting the ciliary body to the crystalline lens.

FIG. 9C shows an example embodiment of a disaccomodated eye. Here, cornea is coupled with sclera.

FIG. 9D shows an example embodiment of a cross-sectional 3-dimensional model structure diagram showing an integrated composite ciliary fiber model of an eye including an exploded view with separate longitudinal layer model, radial layer model, and circular layer model.

FIG. 10A shows an example embodiment of a cross-sectional 3-dimensional model structure diagram of an eye with enlarged inset to show a meshing model.

FIG. 10B shows an example embodiment diagram of a meshing process.

FIG. 10C shows an example embodiment chart of material parameters of ocular structures.

FIG. 10D shows an example embodiment chart of various formulas governing transversely isotropic materials.

FIG. 10E shows an example embodiment chart of parameters for ciliary muscle and zonules.

FIG. 10F shows an example embodiment of a user interface screen for modifying various parameters during modeling.

FIG. 10G shows an example embodiment chart of strain energy density equations for ciliary muscle and zonules. These can be physically based strain invariants.

FIG. 10H shows an example embodiment chart of dilational strain equations.

FIG. 10I shows an example embodiment chart of along-fiber shear equations and diagram.

FIG. 10J shows an example embodiment chart of cross-fiber shear equations and diagrams.

FIG. 10L shows an example embodiment chart of along-fiber stretch equations and diagrams for zonules, including pretension versus time and stress versus fiber length.

FIG. 11B shows an example embodiment perspective view of a cross-sectional three-dimensional model structure diagram of an eye.

FIGS. 12A-12B show an example embodiment of a cross-sectional three-dimensional model structure diagram with upper and lower boundaries of an eye, respectively.

FIGS. 12C-12D shows an example embodiment of a cross-sectional three-dimensional quarter model structure diagram of an eye with radial symmetry and having a right and left boundary, respectively.

FIG. 14A shows an example embodiment of a simulation flowchart showing an initial model at rest undergoing zonule pre-tensioning to become an unaccommodated model and ciliary muscle contraction to become an accommodated model.

FIG. 14B shows an example embodiment of an unaccommodated eye diagram.

FIG. 14C shows an example embodiment of an accommodated eye diagram.

FIG. 14F shows an example embodiment diagram showing tension of zonules versus simulation time and ciliary muscle activation versus time.

FIG. 14G shows an example embodiment user interface diagram of an informational display during simulation screen.

FIG. 15A shows an example embodiment of a diagram including a cross-sectional diagram of an eye with expanded lens image, expanded ciliary muscle for confocal image, and expanded choroid image.

FIGS. 16A-16C are cross-sectional confocal images, respectively, showing ciliary fiber structures and fiber orientations.

FIG. 16D shows an example embodiment diagram of three parts of the ciliary muscle structure. The ciliary body contains the ciliary muscle.

FIGS. 16E-16F show example embodiment diagrams of a corneo-scleral shell with a ciliary body.

FIG. 16G shows an example embodiment diagram of changes in the eye between an unaccommodated eye in central section for distance vision and accommodated eye in right section for near vision.

FIGS. 16H-16I show example embodiments of a disaccomodated eye ciliary muscle diagram from a top view and accommodated eye ciliary muscle diagram from a top view, respectively.

FIGS. 16J-16K show example embodiments of a computer model of ciliary muscles of an eye from a top view and side cross-sectional view with inset respectively.

FIGS. 16L-16M show example embodiment diagrams of longitudinal fibers, radial fibers, and circular fibers, individually modeled and operable to be show simulations of their function during the accommodative process.

FIG. 16Q shows an example embodiment diagram of a simple spring model of ciliary muscle movement.

FIG. 16P shows an example embodiment of a disaccomodated and accommodated eye diagram.

FIG. 17E shows an example embodiment screenshot of a user interface model of ocular structures for use in simulation.

FIG. 17F shows an example embodiment image of ciliary muscle and lens movement during an accommodative process including diameter changes, as indicated by the arrows.

FIG. 17G shows an example embodiment diagram of ciliary muscle ring diameter versus accommodative amount.

FIG. 17H shows an example embodiment diagram of lens diameter versus accommodative amount.

FIG. 17L shows an example embodiment screenshot of a model of ocular structures for use in simulation.

FIG. 17M-17N show example embodiment images of lens thickness changes during an accommodative process, as indicated by the arrows.

FIG. 17O shows an example embodiment diagram of lens thickness changes versus accommodative amount.

FIGS. 17P-17Q show example embodiment screenshots of an accommodated eye and unaccommodated eye model of ocular structures for use in simulation, respectively.

FIGS. 17R-17S show example embodiment diagrams of changes to ciliary muscle and lens respectively, before, midway, and after an accommodative process.

FIG. 17T shows an example embodiment of a user interface diagram displaying measured results of positioning information during a simulation.

FIG. 19A shows an example embodiment of a 3-dimensional cross-sectional model structure diagram 1900 showing simulated accommodation of an eye through ciliary muscle contracting with varied muscle activation.

FIG. 19B shows an example embodiment of 3-dimensional cross-sectional model structure diagram showing simulated accommodation of an eye through longitudinal ciliary fiber contraction and its associated muscle fiber trajectories.

FIG. 19C shows an example embodiment of 3-dimensional cross-sectional model structure diagram showing simulated accommodation of an eye through ciliary contraction with varied muscle activation, particularly showing muscle fiber trajectories for radial fibers.

FIG. 19D shows an example embodiment of 3-dimensional cross-sectional model structure diagram showing simulated accommodation of an eye through ciliary contraction with varied muscle activation, particularly showing muscle fiber trajectories for circular fibers.

FIG. 20A shows an example embodiment of a chart showing accommodation of model results using a 3-dimensional cross-sectional model structure diagram showing as compared with a prior art model for anterior displacement of a lens in millimeters.

FIG. 20B shows an example embodiment of a chart showing accommodation of model results using a 3-dimensional cross-sectional model structure diagram showing as compared with a prior art model for apex thickness of ciliary muscle in millimeters.

FIG. 22A shows an example embodiment diagram of treatment regions from a particular three zone model protocol.

FIG. 22B shows an example embodiment diagram of treatment regions from a particular three zone model protocol.

FIG. 22C shows an example embodiment diagram of a simulated medical treatment of an eye.

FIG. 22D shows an example embodiment diagram of a simulated medical treatment of an eye, including treatment regions from a particular three zone model protocol.

FIG. 24A shows an example embodiment diagram of a simulated medical treatment of an eye, including treatment regions from a particular five zone model protocol.

FIG. 24B shows an example embodiment chart of macro results of therapy simulation methods.

FIG. 24C shows an example embodiment chart of apex thickness of the ciliary body for various zones simulated, along with a baseline, and results that affect scleral stiffness only.

FIG. 24D shows an example embodiment chart of length shortening of the ciliary body for various zones simulated, along with a baseline, and results that affect scleral stiffness only.

FIG. 24E shows an example embodiment chart of macro results of therapy simulation methods and results that affect scleral stiffness and attachment.

FIG. 24F shows an example embodiment chart of apex thickness of the ciliary body for various zones simulated, along with a baseline, and results that affect scleral stiffness and attachment.

FIG. 24G shows an example embodiment chart of length shortening of the ciliary body for various zones simulated, along with a baseline, and results that affect scleral stiffness and attachment.

FIG. 24H shows an example embodiment chart of effects of treatment density on ciliary deformation in accommodation that affect scleral stiffness only.

FIG. 24I shows an example embodiment chart of apex thickness of the ciliary body for various zones simulated versus volume faction percent removed.

FIG. 24J shows an example embodiment chart of length shortening of the ciliary body for various zones simulated versus volume faction percent removed.

FIG. 24K shows an example embodiment chart of effects of treatment density on ciliary deformation in accommodation that affect scleral stiffness and attachment.

FIG. 24L shows an example embodiment chart of apex thickness of the ciliary body for various zones simulated versus volume faction percent removed.

FIG. 24M shows an example embodiment chart of length shortening of the ciliary body for various zones simulated versus volume faction percent removed.

FIG. 31A shows an example embodiment diagram of an eye model with a plurality of implantable stents.

FIG. 31B shows an example embodiment diagram of effects of implantable stents on ocular structural movements during accommodation and other processes.

FIG. 31C shows an example embodiment diagram of a simulated eye and ocular stents.

FIG. 32A shows an example embodiment diagram of a MIGS device for treatment of ocular conditions, such as glaucoma.

FIG. 32B shows an example embodiment diagram of a MIGS device implanted in an eye for treatment.

FIG. 32C shows an example embodiment diagram of a MIGS device for implantation in an eye for treatment.

FIG. 32D shows an example embodiment diagram of a simulated eye and MIGS device for implantation simulation.

FIG. 34B shows an example embodiment diagram of applying accommodating eye drops to eye.

FIG. 34C shows an example embodiment diagram of effects of applying accommodating eye drops to eye.

DETAILED DESCRIPTION

Figure 1A:
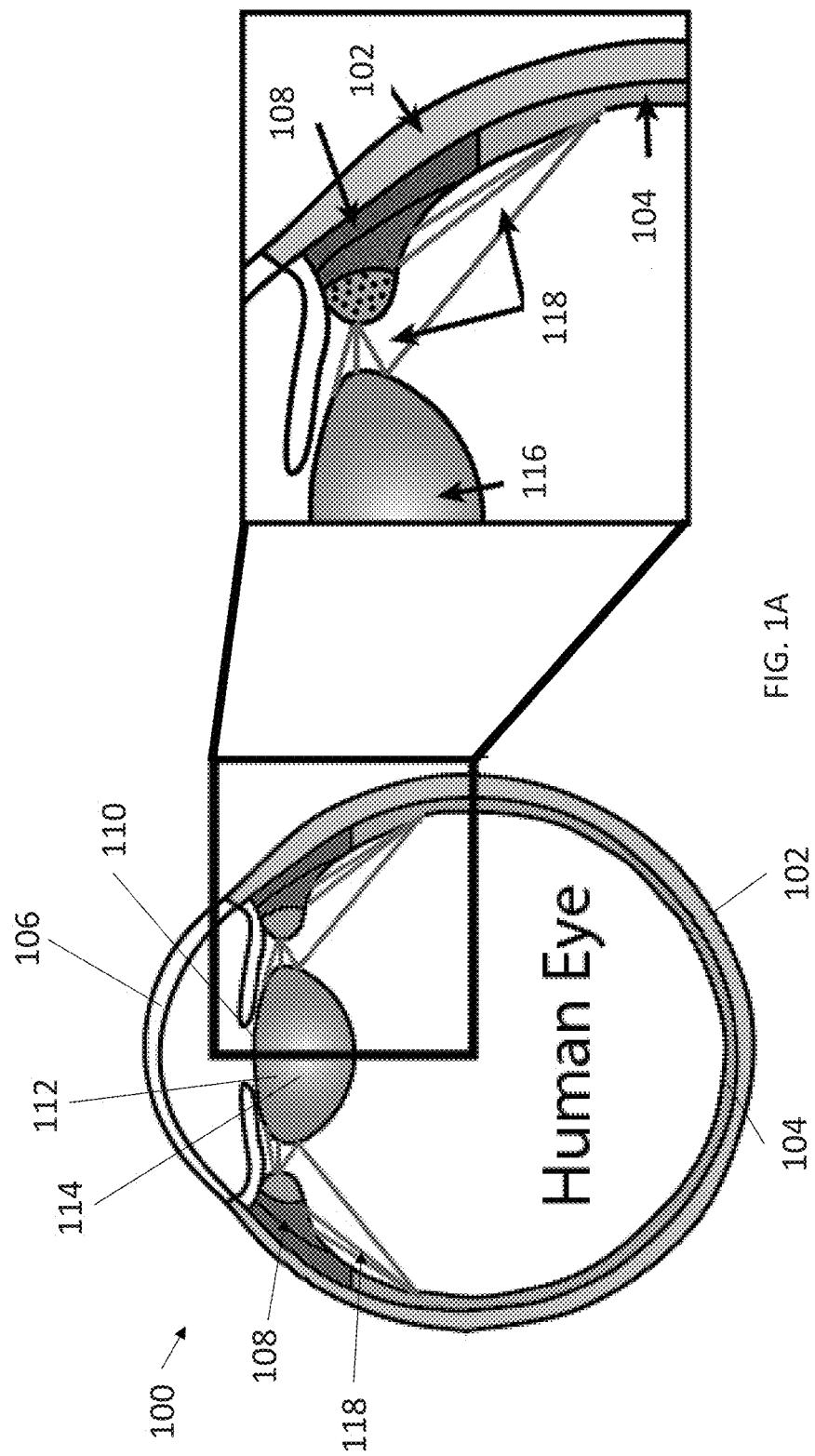
FIG. 1A shows an example embodiment of an anatomical diagram of an eye cross section with a reference key.

Before the present subject matter is described in detail, it is to be understood that this disclosure is not limited to the particular embodiments described, as such may vary. It should also be understood that the terminology used herein is for the purpose of describing particular embodiments only, and is not intended to be limiting, since the scope of the present disclosure will be limited only by the appended claims.

Accommodation of a human eye occurs through a change or deformation of the ocular lens when the eye transitions from distant focus to near focus. This lens change is caused by contraction of intraocular ciliary muscles (ciliary body), which relieves tension on the lens through suspensory zonule fibers and allows the thickness and surface curvature of the lens to increase. The ciliary muscle can have a ring-shaped and can be composed of three uniquely oriented ciliary fiber groups that contract toward the center and anterior of the eye. These three ciliary fiber groups are known as longitudinal, radial and circular. Deformation of the ciliary muscle due to the contraction of the different muscle fibers translates into or otherwise causes a change in tension to the surface of the ocular lens through zonule fibers, whose complex patterns of attachment to the lens and ciliary muscle dictate the resultant changes in the lens during accommodation. Ciliary muscle contraction also applies biomechanical strain at the connection locations between the ciliary muscle and the ocular sclera, known as the white outer coat of the eye. Additionally, biomechanical compression, strain or stress can be caused during accommodation can occur at connection locations between the ciliary muscle and the choroid, known as the inner connective tissue layer between the sclera and ocular retina. Ciliary muscle contraction can also cause biomechanical forces on the trabecular meshwork, lamina cribrosa, retina, optic nerve and virtually every structure in the eye.

Applying the techniques and models described with respect to the various embodiments herein, can lead to outputs and results that fall within known ranges of accommodation of a young adult human, as described in existing medical literature. This verifies the validity of the models with respect to the application of variables due to displacement and deformation of the ocular lens and ciliary muscle.

3D Mathematical Models can incorporate mathematics and non-linear Neohookean properties to recreate behavior of the structures of biomechanical, physiological, optical and clinical importance. Additionally, 3D FEM Models can incorporate data from imaging, literature and software relating to the human eye.

Developing a computational model can be critical to understanding how the complex movements of the ciliary muscle drive the lens changes necessary for accommodation, and to understand how age-related changes lead to presbyopia. Most prior models focused solely on the actions of lens and zonules, simplifying ciliary movement to a single displacement. In particular, these models function by simulating the transition from the accommodated state where the lens is un-stretched but the muscle is contracted to the unaccommodated state where the muscle is at rest and the lens is stretched. As such, the disclosed developments of multi-component FEMs of the accommodative mechanism that include the ciliary muscle, lens, zonules, sclera, and choroid, to characterize the role of complex ciliary muscle action in producing the lens changes required for accommodative function.

The principles and concepts disclosed herein can be used to create and facilitate visualization of accommodation structures. They can also be used to measure, evaluate and predict central optical power. Additionally, they can be used to simulate age specific whole or partial eye structures, functions, and biomechanics. Further, they can be used to independently simulate the ciliary muscle and its components, extra-lenticular, and lenticular movements, and functions on the lens. Also, individual simulations of anatomical structures and fibers can be performed that can reveal some biomechanical relationships that have otherwise been unknown or otherwise undefined and under-researched.

Numerical simulation of the patient's eye can be created using 3D FEM meshing to accomplish methods such as adding a "pre-stretch" lens positioning in coding and manipulations of software, as executed by a computer processor. Similarly, methods of intricate meshing of zonular and other structures, methods of importing dynamic imaging into models for the purposes of modelling accommodation and accommodative movements including, but not limited to, simulation of central optical power and changes in the crystalline lens can be accomplished using computer based computations. Additionally, methods and software manipulation executed by a processor can be capable of performing numerical simulation of zonular apparatus movements, forces and impact on Central Optical Power (COP).

Systems, methods and devices disclosed herein can be used to perform other functions as well, such as those pertaining to modelling other structures of the eye, such as the back of the eye, including: lamina cribrosa, Ocular Nerve Head and others, related to ocular structures and functions. For example, regarding the posterior globe: new insights and understanding of the lamina cribrosa are possible, as are insights into the complex structure of the peripapillary sclera, and attachments of the choroid using complex math for solving elastic and viscoelastic equations and simulations may provide additional benefits.

In particular, the structural behavior of the whole eye, which is governed by the material properties, physics, biomechanics and behavior of the optics under various conditions and can be modeled as a 3D computer mathematical simulation for later use in predicting future ocular conditions. The proposed simulations in creating computational models and the effects of surgical procedures implemented using them can be based on a number of important underlying simplified assumptions regarding the mechanical properties and structure of the ocular tissues at the ultra-structure level. As such, more accurate modeling is desirable for diagnostic, surgical planning, intraoperative surgical adjustment, and virtual surgical simulation.

Modeling of the eye can answer various questions about the eye. Some examples include: how does regional restoration of sclera stiffness improve ciliary deformation in accommodation? Do certain zones or combinations of zones have a greater effect? Does regional restoration of sclera attachment tightness (in addition to stiffness) augment improvements to ciliary deformation in accommodation? How do the treatment parameters relate to the change in scleral stiffness in the treated regions? How does regional restoration with different treatments (therefore different sclera stiffness's) improve ciliary deformation in accommodation?

Methods disclosed herein include: adding a "pre-stretch" lens positioning whether it be code, manipulations of software and the like; intricate meshing of zonular and other structures; importing dynamic imaging into the model for the purposes of modelling accommodation and accommodative movements including but not limited to simulation of central optical power changes in the crystalline lens; software manipulation capable of performing numerical simulation of zonular apparatus movements, forces and impact on COP; modelling the back of the eye: lamina cribrosa, Ocular Nerve Head, and others; posterior globe code for understanding lamina cribrosa; complex structuring of the peripapillary sclera, attachments of the choroid for example; complex math for solving elastic and viscoelastic equations and simulations; zonular reconstruction with relational lens effects by pretension modification of software code and mathematical assumptions along with simulations; simulations or presentations of imaging and math code to display functional relationships; and others.

Simulations performed using virtual models of ocular structures, such as those used in ocular accommodation processes, can be executed and repeated with different versions of an ocular mesh, along with various pluralities of external and internal manipulation of anatomical and geometrical or quasi-physical components. Additionally, other simulations using virtual models of ocular structures in different processes is also possible using the techniques described herein. These can include surgical or treatment related simulations and their effects, such as intraocular lens implantation, stent implantation, MIGS device implantation, drug delivery, and others.

Visualization of accommodation structures during and after simulations is included in addition to means for measuring, evaluating and predicting Central Optical Power (COP). These can be used to simulate and view age specific whole eye structures, optics, functions and biomechanics. Further, they can independently simulate properties of the ciliary muscle, extra-lenticular and lenticular movements of the ocular lens, and functions on the ocular lens. Individual simulations of anatomical structures and fibers can reveal biomechanical relationships which would otherwise be unknown and undefined. Numerical simulation of the patient's eye can be created using 3D FEM meshing to accomplish these operations.

To elaborate, representative 3D geometry of resting ocular structures can be computationally defined based on extensive review of literature measurements and medical images of the anatomy of young adult eyes and through modeling. Specialized methods implemented in software, such as AMPS software (AMPS Technologies, Pittsburgh, PA), can be used to perform geometric meshing, material property and boundary conditions definitions, and finite element analysis during the modeling stage. Ciliary muscle and zonules can be represented as a transverse isotropic material with orientations specified to represent complex fiber directions. Additionally, computational fluid dynamic simulations can be performed in order to produce fiber trajectories, which can then be mapped to the geometric model.

Initially, a lens modeling can include a lens in a relaxed configuration, before being stretched by pre-tensioning zonule fibers to an unaccommodated position and shape.

Figure 18B:
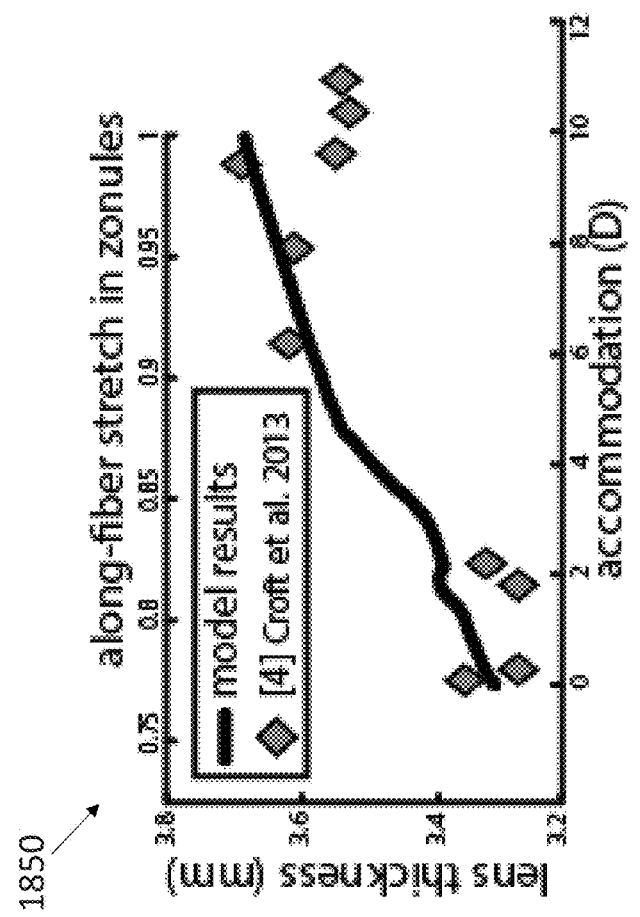
FIG. 18B shows an example embodiment of a chart showing accommodation of model results as a line using a 3-dimensional cross-sectional model, as compared with a prior art model that captured data points.
Figure 18A:
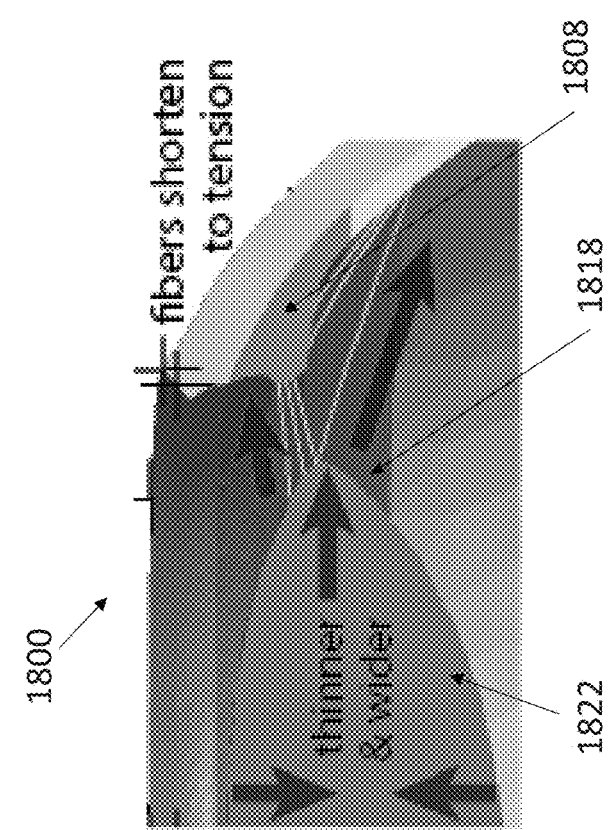
FIG. 18A shows an example embodiment of a 3-dimensional cross-sectional model structure diagram showing pre-tensioning of zonules and changes in the lens and ciliary body of an eye.

Unaccommodated lens position can be reached when zonules are shortened to between 75% and 80% of their starting length, and more particularly to about 77% of their starting length, as shown in FIG. 18A. Then accommodative motion can be simulated by performing active contraction of the various fibers of the ciliary muscle. In some embodiments this can be accomplished using previous models of skeletal muscle that are modified to represent dynamics particular or otherwise specific or unique to the ciliary muscle. Model results representing lens and ciliary anterior movement and deformed ocular lens thickness at a midline and apex can be validated or otherwise verified by comparing them to existing medical literature measurements for accommodation. In order to investigate contributions of the various different ciliary fiber groups to the overall action of the ciliary muscle, simulations can be performed for each fiber group by activating each in isolation while others remain passive or otherwise unchanged.

Various beneficial aspects of the embodiments described herein with respect to the various FIGs. are described with respect to simulations applying pre-tensioning zonules models and contracting ciliary muscle models.

With respect to the pre-tensioning zonules, modeling can include: 1) Creation of 3D material sheets oriented between measured zonular attachment points of insertion on the lens and origination on the ciliary/choroid; 2) specified fiber direction in the plane of the sheet (i.e. fibers directed from origin to insertion); and 3) Transversely isotropic constitutive material with tension development in the preferred direction. Further, with particular respect to 3), advantages have been achieved, including: a) Time-varying tension parameter input regulates the stress developed in the material; b) Time-varying tension input is tuned to produce required strain in the lens to match measurements of the unaccommodated configuration; c) Age variation in material properties and geometries to produce age-related impact; and d) others.

With respect to the contracting ciliary muscle models, modeling can include: 1) Modified constitutive model to represent smooth and skeletal aspects of ciliary mechanical response; 2) 3 sets of specified fiber directions to represent physiological orientation of muscle cells and lines of action of force production; and 3) Transversely isotropic constitutive material with active force development in the preferred direction. Further, with particular respect to 3), advantages have been achieved, including: a) Activation parameter input regulates the active stress developed in the material; b) Activation input is tuned to produce appropriate accommodative response to match literature measurements; c) Activation of individual muscle fiber groups can be varied in isolation to assess contributions to lens strain/stress; d) Activation of individual muscle fiber groups can be varied in isolation to assess contributions to ocular scleral strain/stress; e) Activation of individual muscle fiber groups can be varied in isolation to asses contributions to choroidal strain/stress; and f) others.

In various embodiments, simulation results can be governed by modification of tensioning and activation inputs to the zonule and ciliary materials, as opposed to performing an applied displacement to external node(s) of a mesh.

In various embodiments, three-dimensional circumferential and other force vectors can be simulated for various ocular structures, thus providing different effects and insights into ocular structures and their movement and relation to one another. Boundary conditions for ocular structures and material property values can be changed and their influence determined as well.

Thereafter, systems, methods and devices for providing a predictive outcome in the form of a 3D Computer Model with integrated Artificial Intelligence (AI) can be used to find predictive best instructions for a therapeutic ophthalmic correction, manipulation, or rehabilitation of a patient's vision defects, eye disease, or age-related dysfunction are disclosed. The predictive best instruction can be derived from physical structural inputs, neural network simulations, and prospective therapeutic-outcome-influencing. New information can be analyzed in conjunction with optimized, historical therapeutic-outcome information in order to provide various benefits. The concepts herein can be used to performs a multitude of simulations and has a knowledge based platform so that the system is able to improve its instruction response as the database is expanded.

The stored instructions contemplated can preferably be an optimized, custom, photoablative algorithm for driving a photoablative, photothermal laser. The instructions can be provided along with an AI processor via direct integration, stand-alone importation or remotely via a Bluetooth enabled application or connection. These instructions can be performed a priori or intraoperatively.

The stored instructions contemplated can preferably be an optimized custom ocular lens simulation algorithm used for simulating manipulation of an implantable intraocular lens in order to improve medical procedures and understanding.

The instructions can also be set up as a 'stand-alone' system for use as a Virtual Clinical trial system or Research and Development system, whereby the instructions can be provided with independent research design inputs and outputs to test various conditions and responses of the eye to surgical manipulations, implantation devices, or other therapeutic manipulations of the eye, in order to optimize design and outcome response.

Additionally, these instructions can also include one or more of: an algorithm for image processing interpretation, expansion of ophthalmic imaging data platforms and a companion diagnostic to an imaging device.

As described herein, methods for improving ophthalmic treatments, surgeries, or pharmacological interventions can include obtaining topological, topographical, structural, physiological, morphological, biomechanical, material property, and optical data for a human eye along with applied physics and analyzing through mathematical simulations using artificial intelligence networks.

Virtual clinical applications using simulation can include techniques executed via devices, systems and methods for automated design of an ophthalmic surgical procedure including physical measurements and applied physics of a patient's whole eye are obtained. Conventional techniques can be used to obtain these measurements. The information measured can be interpolated and extrapolated to fit nodes of a finite element model (FEM) of a human eye for analysis, which can then be analyzed to predict an initial state of stress of the eye and obtain pre-operative conditions of the cornea, lens and other structures. Incision data constituting an "initial" surgical plan can be incorporated into the finite element analysis model. A new analysis can then be performed to simulate resulting deformations, biomechanical effects, stresses, strains, curvatures of the eye as well as dynamic movements of the eye, more specifically the ciliary muscles, lens and accommodative structures. These can be compared to original values thereof and to a vision objective. If necessary, a surgical plan can be modified and resulting new ablation data can be entered into the FEM and the analysis is repeated. This procedure can be repeated as desired or necessary until the vision objectives are met.

Artificial Intelligence (AI) Software can use an artificial neural network to conduct machine learning, whereby the system can learn from the data, and therefore has a learning component based on the ongoing database expansion. It can be operative to improve reliability as the database is formulated and updated, heretofore unknown in the prior art of 3D predictive modeling systems, methods and devices.

Simulation can include Age Progression simulation of a patient's eye, having a predictive capacity to simulate ophthalmic surgical outcomes, determine rates of regression of treatments, as well as execute predictive algorithms for future surgical or therapeutic enhancement, heretofore unknown in the prior art of 3D predictive modeling systems, methods and devices.

Virtual Eye Simulation Analyzer can include integration of information related to all structures of an eye into a computer program for the purpose of simulating biomechanical and optical functioning of the eye, as well as age related simulations for clinical application purposes.

Virtual Eye Simulation Analyzer systems, devices and methods can include an output display that can be viewed by users as a standalone or integrated display system, along with other equipment.

Information used as inputs for the simulator can include imaging information for Biometry (UBM, OCT and others). Dynamic Imaging can be performed using UBM, OCT and others. Anatomy information can include geometry, histology, and others. Physiological function information can include dynamic accommodation, aqueous flow, intraocular pressures, pulsatile ocular blood flow, retinal performance or compromise and others. Material Properties of tissues of the eye, physics and biomechanical information related to relative biomechanics can also be used.

The simulator can incorporate mathematics and nonlinear Neohookean properties in order to recreate behavior of the structures of biomechanical, physiological, optical and others that may be valuable or otherwise of clinical importance. The simulator can use conventional methods to input data incorporated into a 3D FEM with a patient's unique data based on analysis of their own individual eye or eyes. Further, the simulator can use conventional methods to input data and create a numerical simulation of the patient's eye using a 3D FEM meshing—essentially creating a custom dynamic real-time "Virtual Eye," heretofore unknown in the prior art of 3D predictive modeling systems, methods and devices.

The AI is capable of learning via predictive simulation and can be operative to improve simulative predictions for surgical or therapeutic manipulations of the eye through artificial neural networks in an "ABACUS" program. ABACUS can also be capable of providing instructions directly to a communicatively coupled processor or processing system to create and apply algorithms, mathematical sequencing, formula generation, data profiling, surgical selection and others. It can also be capable of providing instructions directly to a workstation, an image processing system, a robotic controller or other device for implementation. Further, it can be capable of providing instructions indirectly through a Bluetooth or other remote connection to a robotic controller, an image system or other workstation.

The models herein can have various applications for clinical, research and surgical use, including: 1) use of prior evaluation and simulation of accommodation functions of the eye (examples including Presbyopia indication-IOL design and use, extra-lenticular therapeutics and their uses); 2) use of prior evaluation and simulation of aqueous flow of the eye, such as for glaucoma indications; 3) virtual simulations and real time simulations of efficacy of IOL's, therapeutic treatments and various biomechanical implications; 4) virtual simulations using the AI and CI to reproduce customized aging effects on an individual's biomechanical and physiological functions of their eye which have clinical importance; 5) Surgical Planning; 6) design model (such as FEM) importation and simulation, such as for IOL's and others; 7) Virtual clinical trials and analysis; 8) real-time intraoperative surgical analysis, planning and execution; 9) Performance of a crystalline lens of the eye as it relates to optical and biomechanical dysfunction, cataract formation and the like; and 10) others.

Additional components of simulators include: 1) Eye Scanning; 2) Optical inputs such as a) Cornea optics, Wavefronts, elastography, hysteresis, visual acuity topography, connective tissue macro and micro structure and b) lens optics such as Wavefront, visual acuity, topography, lens opacity, light scatter, Central optical power (COP) during accommodation and disaccommodation, elastography, viscoelastic properties and others; 3) Scleral biomechanics, viscoelastic, material properties, stress, strain mapping, connective tissue macro/micro structure; 4) Trabecular meshwork material, viscoelastic, connective tissue macro and micro structure; 5) Lamina cribrosa material properties, stress, strain viscoelastic, connective tissue macro and microstructure; 6) Physiological Inputs including a) Aqueous outflow and inflow, b) Intra Ocular Pressure (IOP), c) Ocular pulsatile blood flow, d) Retinal activity and others; 7) Surface Spectroscopy; 8) Collagen Fibril characterization of the cornea, sclera, lens, and others; and 9) others.

Benefits of simulators in an Accommodation embodiment include: 1) Measuring, analyzing and simulating Accommodation of an eye in real-time; 2) demonstrating accommodation biomechanics in real-time; 3) evaluating accommodation biomechanics; 4) Visualization of accommodation structures; 5) Measuring, evaluating and predicting Central Optical Power; 6) Simulating age progression of whole eye structures, functions and biomechanics; and 7) others.

Major structural component inputs can be based on the sclera, cornea, lens, trabecular meshwork, lamina cribrosa, retina and others. For the sclera, these can include: Scleral rigidity, viscoelasticity, Scleral thickness, Scleral depth, 3D surface topology, top surface spectral dimensions, 3D spectroscopy and others. For the cornea, these can include: Corneal Wavefront, viscoelasticity, Topography, Keratotomy, Corneal thickness, 3D topology, K readings, Corneal stiffness, 3D spectroscopy and others. For the lens these can include: Lenticular Wavefront, Central optical power, Accommodative amplitude, Light scattering, Opacity and others. For the trabecular meshwork, these can include: elasticity, outflow, inflow and others. For the lamina cribrosa this can include: porosity, mechanical dependence, perfusion, poroelasticity, cup floor depth, and others.

Some of the various major optical profiles, properties, information and visual acuity information outputs for a cornea can include: Total aberrations, Visual Strehl Ratio, Depth of focus, MRSE, Visual acuity, lens scatter and others. Some of the various major optical profiles, properties, information and visual acuity information outputs for a lens can include: Total aberrations, VSOF, Depth of focus and others.

FIG. 1A shows an example embodiment of an anatomical diagram 100 of an eye cross section with a reference key. As shown in the example embodiment, anatomical structures of the eye can include sclera 102; choroid 104; cornea 106; ciliary muscles 108 including circular, radial, and longitudinal fibers; lens 116, including lens capsule 110 and lens nucleus 114; lens cortex 112; and zonules 118 including three anterior, most anterior (MAZ), anterior vitreous, intermediate vitreous, and pars plana.

Accommodation is the process by which the eye changes optical power to focus on objects at various distances by deforming the lens. While age-related changes in the eye have been measured, it was only within the last few years that biomechanics of presbyopia have been brought into focus. Presbyopia causes a loss of accommodative function in the eye, making it harder to focus, especially on near objects or images.

FIGS. 1B-1C show an example embodiment of a cross-section of an eye diagram 120 and 130 illustrating changes in structural components of an eye for distance and near vision respectively. As shown in distance vision diagram 120, for distance vision the eye is relaxed and lens 122 has a lens thickness 124. Ciliary muscles 108 are generally relaxed, and zonules 118 are generally taut. However, as shown in near vision diagram 130, lens 122 changes to lens thickness 132 when the eye attempts to focus on something closer. Lens thickness 132 is greater than lens thickness 124 for a close-focused eye, caused by ciliary muscles 108 contracting and zonules 118 becoming more relaxed.

FIG. 1D shows an example embodiment diagram 140 of how an unaccommodated eye focuses an image through a lens.

FIG. 1E shows an example embodiment diagram of how an accommodated eye focuses an image through a lens.

Figure 1F:
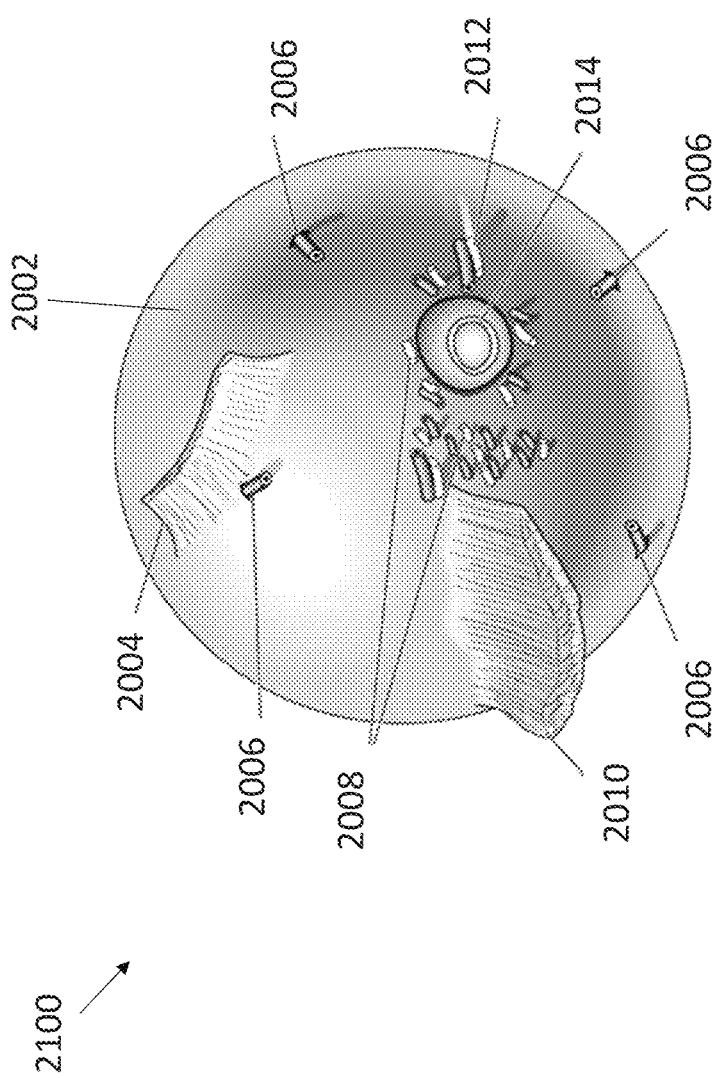
FIG. 1F shows an example embodiment of an ocular structure diagram showing ocular structures from a view of the back of a human eye.

FIG. 1F shows an example embodiment of an ocular structure diagram 2100 showing ocular structures from a view of the back of a human eye. As shown in the example embodiment, a posterior side of eye 2002 includes a superior oblique insertion 2004, vortex veins 2006, short posterior ciliary arteries and short ciliary nerves 2008, inferior oblique insertion 2010, long posterior ciliary artery and long ciliary nerve 2012, and optic nerve 2014.

Figure 1G:
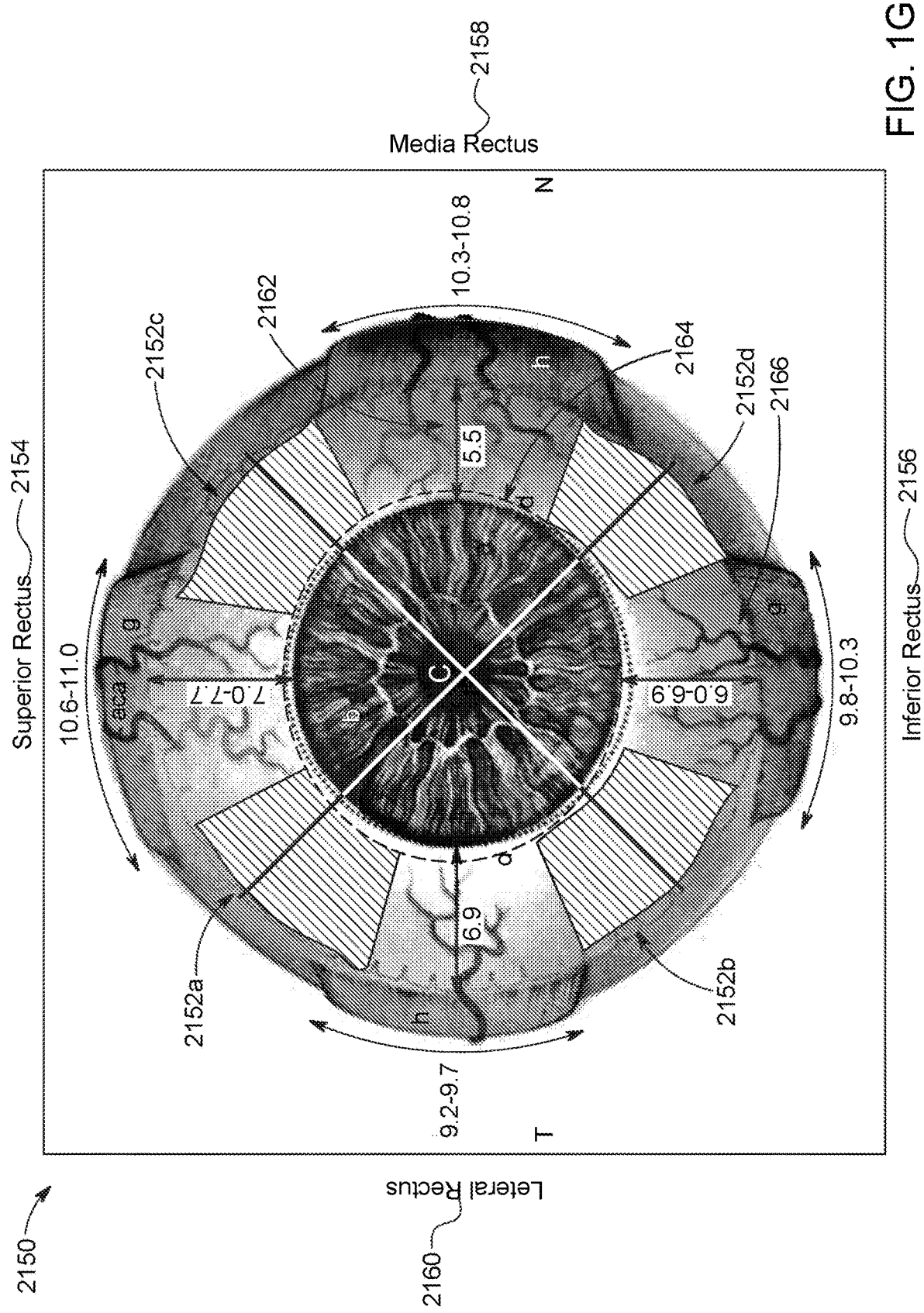
FIG. 1G shows an example embodiment of an ocular structure diagram showing ocular structures from a view of the front or anterior view of a human eye.

FIG. 1G shows an example embodiment of an ocular structure diagram 2150 showing ocular structures from a view of the front or anterior view of a human eye. As shown in the example embodiment, the approximate surface area of an entire ocular globe is about 75 mm. A meridional quadrant 2152a-2152d can be an average surface area of rectus muscles total, about 40.75 mm. As shown, shaded areas or meridional quadrants 2152a-2152d can be target zones for treatment of presbyopia and other conditions using medical techniques and procedures, such as ablation. Oblique quadrants 2152a-2152d can be an average surface area in a target area of about 75 mm-40.75 mm, which equals about 34 mm. As shown, quadrants 2152a-2152d can have different sizes temporal to nasally.

A superior rectus 2154 can be between 10.6 mm and 11 mm, or about 10.8 mm. An inferior rectus 2156 can be between 9.8 mm and 10.3 mm, or about 10.05. A medial rectus 2158 can be between 10.3 mm and 10.8 mm, or about 10.45 mm. A lateral rectus 2160 can be between 9.2 mm and 9.7 mm, or about 9.45 mm. An average combined cornea and limbus 2164 diameter 2162 can be about 12 mm. A distance from limbus 2164 in millimeters can have an approximate range of about 5.5 mm to about 7.7 mm, so for modeling and simulations, a distance of 6 mm can be used. Also shown are anterior ciliary arteries 2166.

Figure 2B:
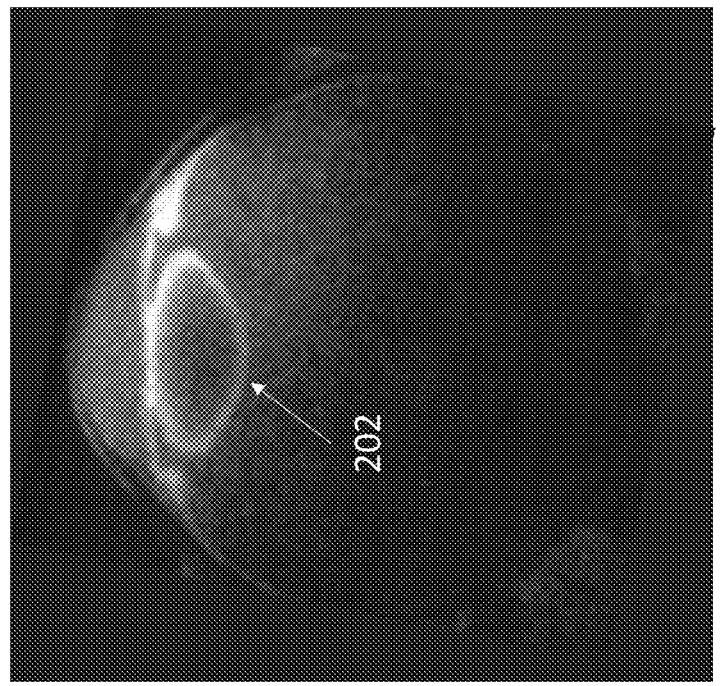
FIGS. 2A-2B shows an example embodiment of an unaccommodated eye cross sectional image and an accommodated eye cross sectional image, respectively.
Figure 2A:
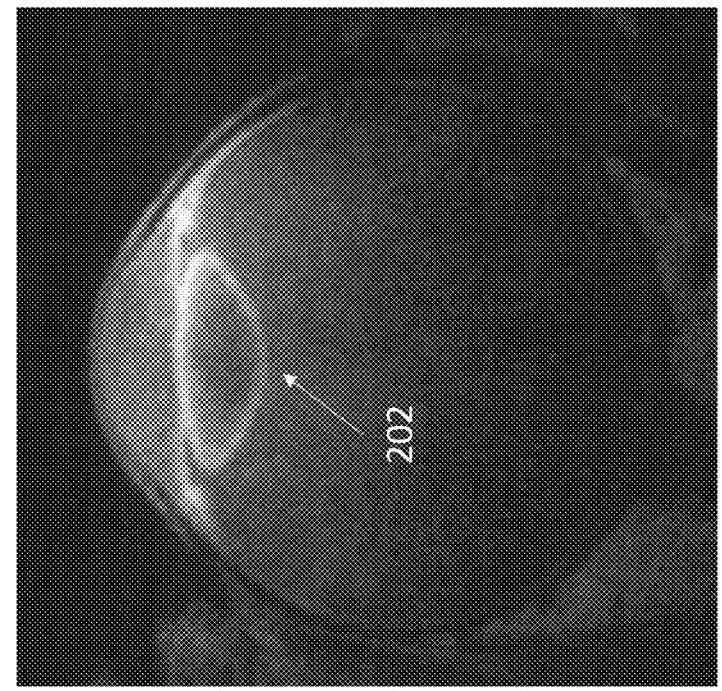

FIGS. 2A-2B shows an example embodiment of an unaccommodated eye cross sectional image 200 and an accommodated eye cross sectional image 210, respectively. As shown in the example embodiments, lens 202 changes from unaccommodated shape with a first thickness to an accommodated shape with a second thickness greater than the first thickness when changing from focusing on distant objects to near objects. The mechanisms underlying this principle are discussed with respect to FIGS. 1B-1C and elsewhere herein.

As discussed previously herein, it would be beneficial to develop improved modeling of ocular structures to better understand ocular mechanisms, including accommodation and dis-accommodation. One starting point is to use ocular imaging literature to understand ocular structures and their arrangement with one another.

Figure 3A:
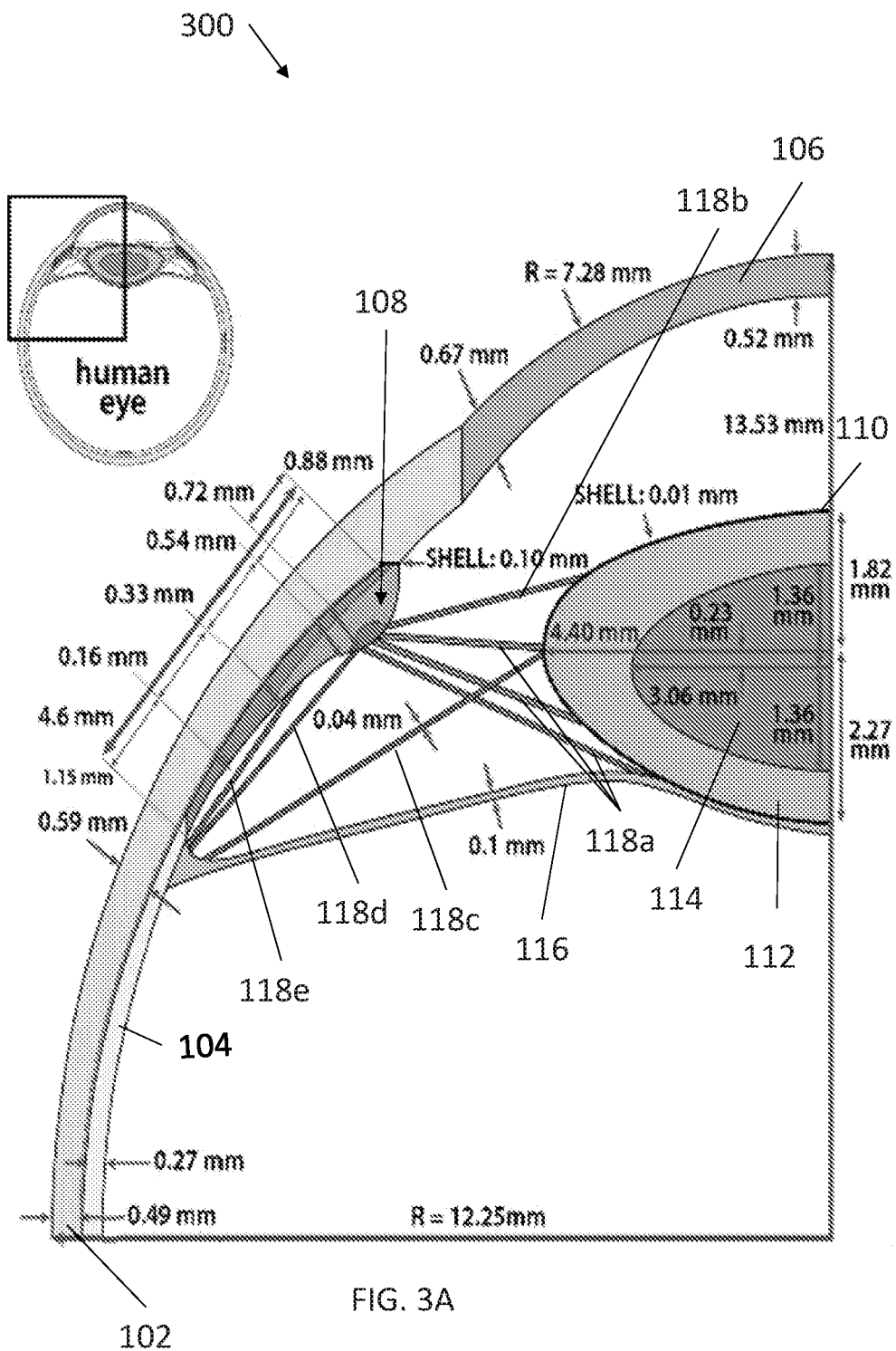
FIG. 3A shows an example embodiment of a cross sectional diagram of an eye based on model structures from existing imaging literature.

FIG. 3A shows an example embodiment of a cross sectional diagram 300 of an eye based on model structures from existing imaging literature. Like numbers have been included for sclera 102; choroid 104; cornea 106; ciliary muscles 108 including circular, radial, and longitudinal fibers; lens capsule 110; lens nucleus 114; lens cortex 112; and vitreous membrane 116, from FIG. 1A to maintain clarity. Zonules 118 of FIG. 1A are shown individually in FIG. 3A including three anterior zonules 118a, most anterior zonule (MAZ) 118b, anterior vitreous zonule 118c, intermediate vitreous zonule 118d, and pars plana zonule 118e.

Material properties can be defined by various equations and parameter values. Various factors affecting modelling include Neo-Hookean isotropic structures with material and stiffness references, how muscle structure and materials affect models, and how zonule models can be developed with an explanation of transverse isotropy with pre-tensioning.

As shown, various measurements can be implemented in modeling for an eye with a radius of 12.25 mm from a central optical axis to an exterior of sclera 102. Sclera 102 can range in thickness from 0.49 mm to 0.59 mm and choroid 104 can have a thickness of 0.27 mm. Cornea 106 can have a thickness ranging from 0.52 mm to 0.67 mm and a radius of 7.28 mm. A distance from lens capsule 110 to an outer edge of cornea 106 can be about 13.53 mm. Ciliary muscles 108 can have a length of 4.6 mm overall. Lens capsule 110 can be about 0.01 mm thick. Lens cortex 112 and lens nucleus 114 can have a combined radius of about 4.40 mm and a combined thickness of about 4.09 mm. Lens nucleus 114 can have a radius of about 3.06 mm and thickness of about 2.72 mm. Vitreous membrane 116 can be about 0.1 mm thick. Anterior vitreous zonule 118c can be about 0.4 mm thick.

Figure 3C:
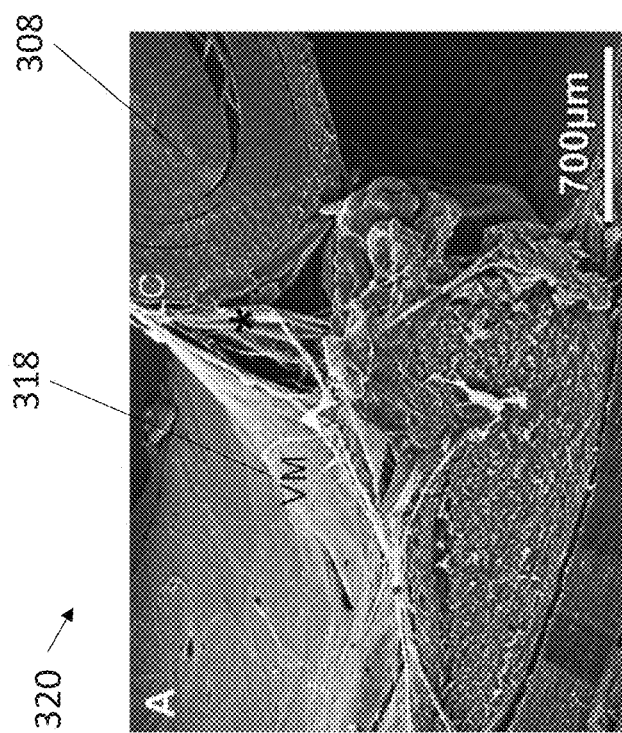
FIG. 3C shows an example embodiment of a Scanning Electron Microscopy image of Zonular fibers and relationship to the lens and the Vitreous membrane of an eye based on model structures from existing imaging literature.
Figure 3B:
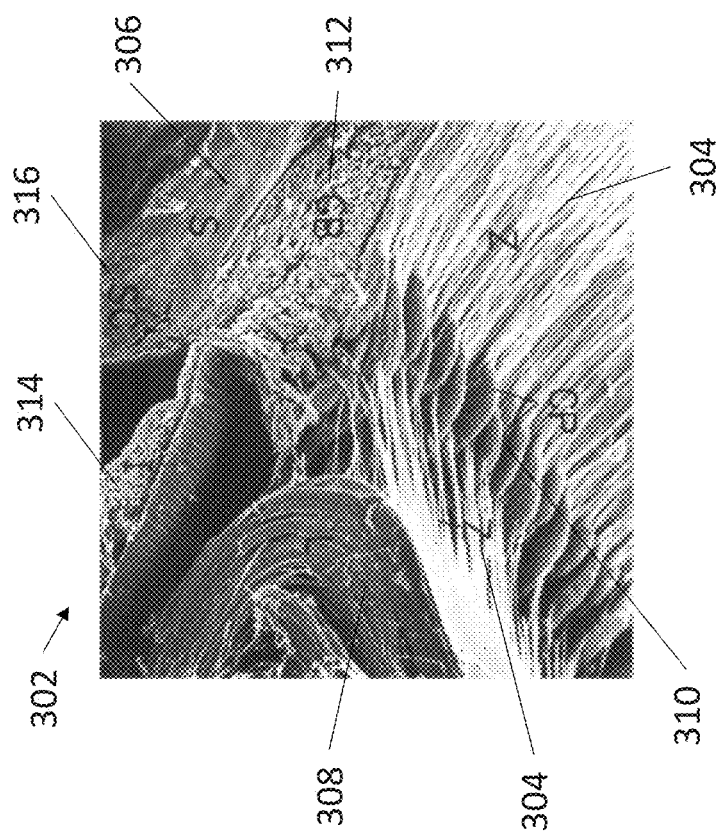
FIG. 3B shows an example embodiment of a Scanning Electron Microscopy image of Zonular fibers, and nodal attachments as well as pathway of the zonular proximal and distal insertion zones of an eye, based on model structures from existing imaging literature.

FIG. 3B shows an example embodiment of a Scanning Electron Microscopy image 302 of Zonular fibers 304, and nodal attachments as well as pathway of the zonular proximal and distal insertion zones of an eye, based on model structures from existing imaging literature. Also shown are sclera 306, lens 308, ciliary process 310, ciliary body 312, iris 314, and SC 316.

FIG. 3C shows an example embodiment of a Scanning Electron Microscopy image 320 of Zonular fibers 304 and relationship to the lens 308 and the Vitreous membrane 318 of an eye based on model structures from existing imaging literature.

Figure 3E:
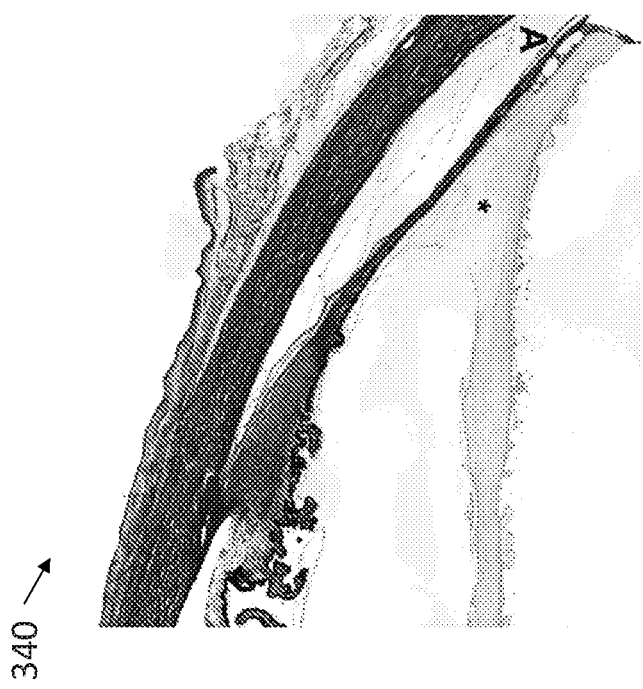
FIG. 3E shows an example embodiment image of a cross-section of the anterior segment of the eye showing the accommodation apparatus and related anatomy as well as the whole eye shell and cornea based on model structures from existing imaging literature.
Figure 3D:
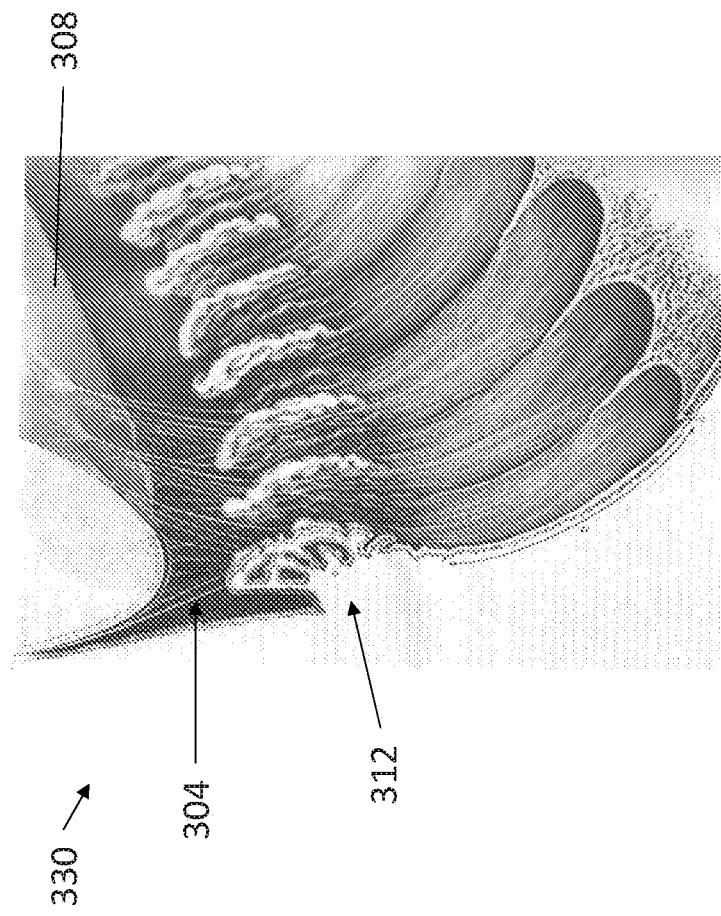
FIG. 3D shows an example embodiment diagram of a ciliary body. In general, ciliary body includes ciliary muscle.

FIG. 3D shows an example embodiment diagram 330 of a ciliary body 312. In general, ciliary body 312 includes ciliary muscle. Ciliary muscle includes circular fibers, radial fibers, and longitudinal fibers. Ciliary body 312 extends between the iris and the choroid. A cross section of ciliary body 312 has a generally triangular cross section. A base or anterior surface of this triangular cross section is continuous with an iris root. An apex of the triangular cross section is continuous with the choroid and directed posteriorly.

In general, ciliary body 312 includes an anterior surface or base and a posterior surface. The anterior surface is called the pars plicata and can contain about 60-70 different processes. In terms of its location and function within the eye, the anterior surface couples with or attaches lens zonules 304. The posterior surface of ciliary body 312 is called the pars plana. In terms of its location and function within the eye, the posterior surface lies against the sclera. . . . The posterior surface is known to be an important surgical landmark for many medical procedures.

FIG. 3E shows an example embodiment image 340 of a cross-section of the anterior segment of the eye showing the accommodation apparatus and related anatomy as well as the whole eye shell and cornea based on model structures from existing imaging literature.

Figure 3G:
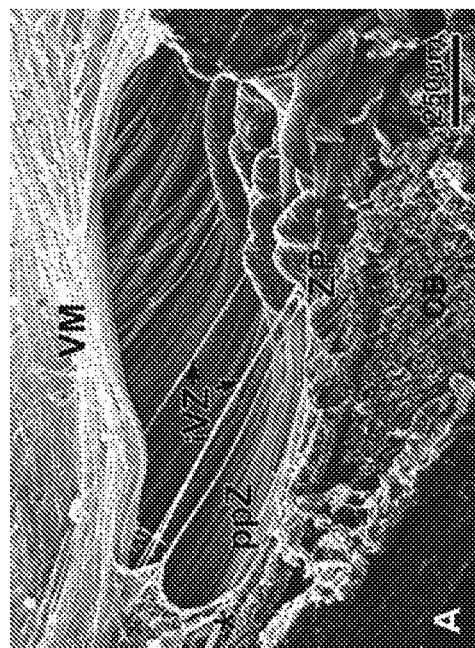
FIG. 3G shows an example embodiment of a Scanning Electron Microscopy image of the relationship between the vitreous membrane, the posterior vitreous zonule insertion and the other zonular structures of an eye based on model structures from existing imaging literature.
Figure 3F:
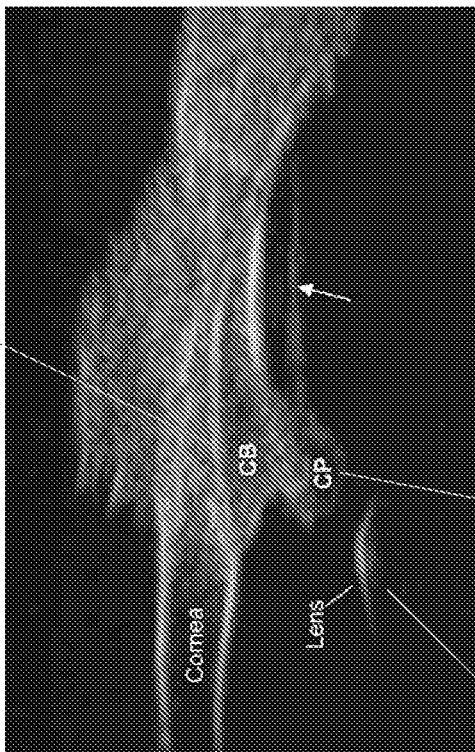
FIG. 3F shows an example embodiment of an ultrasound biometry image of a cross-section of the anterior segment showing the accommodation apparatus, specifically of the relationship of the ciliary process & ciliary body to the posterior vitreal zonule or pars plana, lens, and cornea of an eye, based on model structures from existing imaging literature.

FIG. 3F shows an example embodiment of an ultrasound biometry image 350 of a cross-section of the anterior segment showing the accommodation apparatus, specifically of the relationship of the ciliary process 310 & ciliary body 312 to the posterior vitreal zonule or pars plana, lens 308, and cornea of an eye, based on model structures from existing imaging literature.

FIG. 3G shows an example embodiment of a Scanning Electron Microscopy image 360 of the relationship between the vitreous membrane, the posterior vitreous zonule insertion and the other zonular structures of an eye based on model structures from existing imaging literature.

Figure 4A:
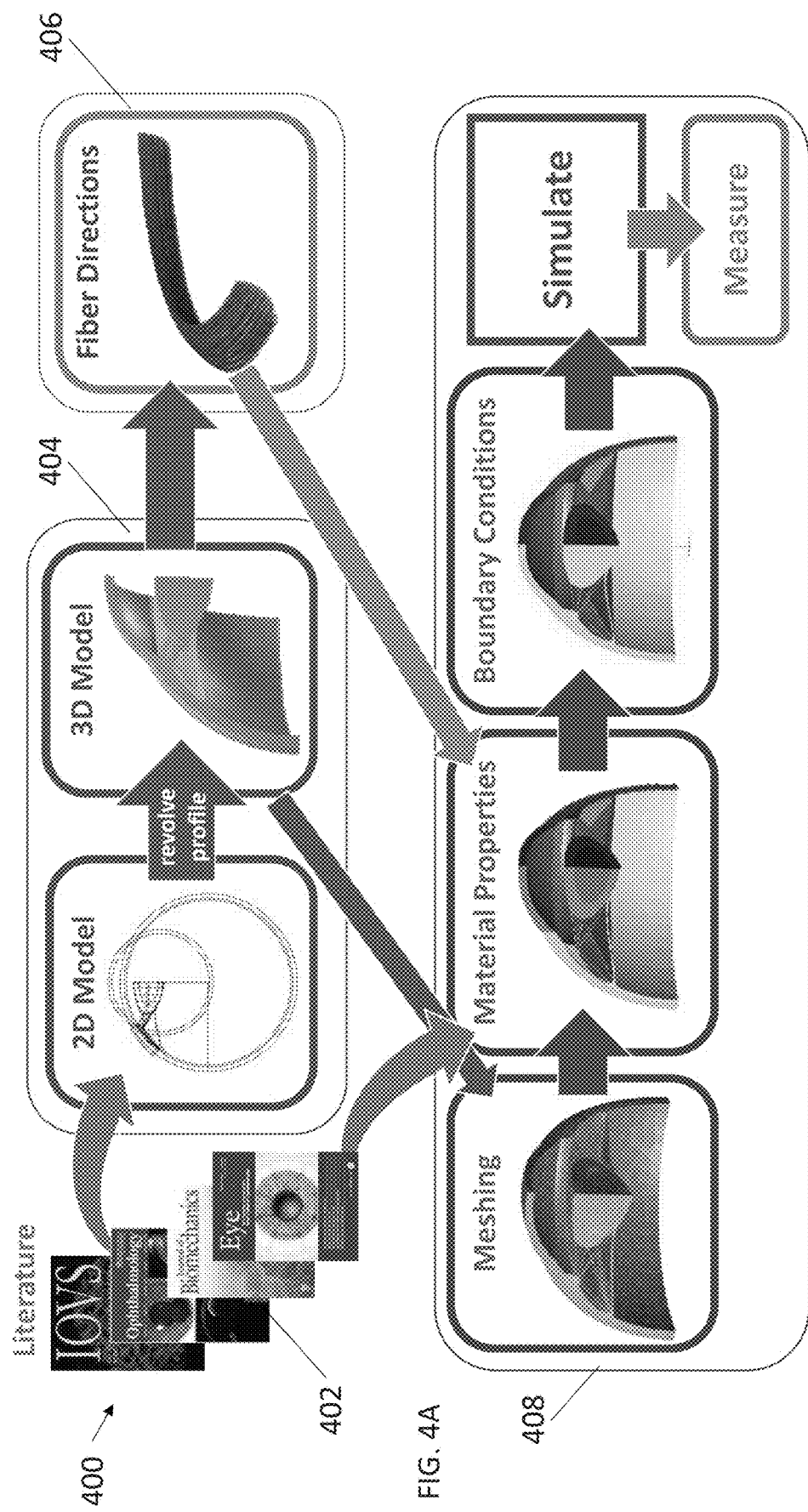
FIG. 4A shows an example embodiment flow diagram of a process of developing new ideas for improved treatments.

FIG. 4A shows an example embodiment flow diagram 400 of a process of developing new ideas for improved treatments. As shown in the example embodiment, prior research 402, in the form of papers, books, and others, along with mental modeling and known physical laws can be used to develop computational models using different computer programs for generating different models 404. This can also include the use of known physical laws. As shown, these can be two-dimensional models initial, which can then be used to create three-dimensional models. In some embodiments, revolving profiles can lead to improved three-dimensional models. Prior research 402 can also be used to generate structural models 406 of individual ocular structures in various computer programs. As discussed herein, this can include different fiber structural models for fibers of the ciliary body. These computational models 404 and 406 can then be put used in computer simulations 408 along with known physical laws to develop and reveal relationships between structures that may or may not be obvious. Steps such as meshing, inputting and manipulating material properties and boundary conditions can be performed before running the computational simulations and measuring various desired results. As such, simulations can be used to perform "what-if" scenarios in order to generate new ideas, which can be related to or reveal new insights about how to create or improve existing treatments.

To elaborate on the types of computer modeling that can be performed, computer aided design (CAD) programs can generate three-dimensional models of eyes. When inputting the model the computer needs various inputs, including what type of material it is. Examples include stiff, elastic, non-linear, and others. This may be required for each of the ocular structures. Neo-Hookean types of material models that describes the stress/strain relationships in materials. More simple versions of the model deal with non-linear tissues may also be important. Equations that import material properties for scleras, corneas, and lenses can be used for simulating those tissues' deformation when the ciliary muscle contracts.

These can be unaccommodated or accommodated inputs and allow for modeling to be constructed using measured values and medical images in the existing literature. In the example embodiment, CAD: 3D creation of the Model of unaccommodated 29-year-old eye geometry can be constructed based on literature values and medical images, for example by using Autodesk Inventor computer programs to create geometry and relationships. Once the 3D geometry model is developed, it can then be exported into AMPS which is the finite element analysis (FEA) solver. Other simulations can be used such as Autodesk Simulation CFD and Matlab.

FEA Solvers can be used for automated three-dimensional meshing of solid structures, enter material properties assigned to different components, define boundary conditions, and measure dynamics of accommodation through simulation.

Then there can be an automatic meshing in Amps that fragments complex geometry and is used to solve physics problems, discussed further with respect to FIG. 10. This is an example of simplification of smaller parts or finite element modeling ("FEM").

A FEM solver is where determination for physics of muscle contraction occurs and then all the corresponding reactions of the other anatomy of the accommodation complex can be determined and analyzed. After the mesh is created material properties can be assigned to each structure and each structure can therefore be understood as a set of elements. Scleral, lens, choroid, zonules, muscle material properties, and others can be unique to the anatomy. Then boundary conditions can be set and all structures can be fixed at an equator and at the limbus. There is no movement above or below those boundaries after being set. Corneal movement can be legitimately related to the lens. This can be used in a simplified model to understand the lens and the physics of the lens. Although the model may not be perfect, it can still be very useful in determining relationships. Once the mesh and boundary conditions are complete, dynamics simulations can be run.

Finite element analysis can include modeling details: meshing, boundary conditions, and solvers; performing multi-step simulations, such as pre-stretch and muscle contraction for accommodation; and description of measurements.

Another step can occur in which dynamics are determined in order to set up ciliary fiber directions. This is the first attempt to create a 3D modelling of not only the ciliary muscle fiber directions but of actual forces of action of ciliary muscles on the anatomical structures affecting accommodation.

Calibration and validation can also be important. Calibration can be performed using zonule tension modification that may match an average MRI measurement range and ciliary activation that may match an average OCT measurement range of actual subjects. Calibration results for individually tensioned zonules and "tuned" tension can be shown on a bar plot for lens Δradius and Δthickness. Additionally, results for individually activated muscle groups and "tuned" activation can be shown on a bar plot for Δlength and Δthickness Validation can include a comparison to imaging data of ciliary and lens deformation, which can be simultaneously checked against OCT and MRI averages. Validation results can be shown on a bar plot of Δapex thickness and Δlens thickness with bars for model and OCT experiments. Similarly, results can be shown on a bar plot of various deformations with bars for model and MRI experiments. These can include Δciliary apex thickness, Δlens thickness, Δspur to ora serrata distance, forward movement of vitreous zonule insertion zone, forward movement of lens equator, and centripetal lens equator movement.

As a result of validation, contributions of individual zonule sections on lens deformation role of initial lens tension in accommodation. For example, ciliary contraction with no pretension contribution of different muscle fiber groups to ciliary deformation in accommodation influence of ciliary's attachment to the sclera on its function can be examined, along with any differences between "tight" and "loose" attachments.

Figure 4B:
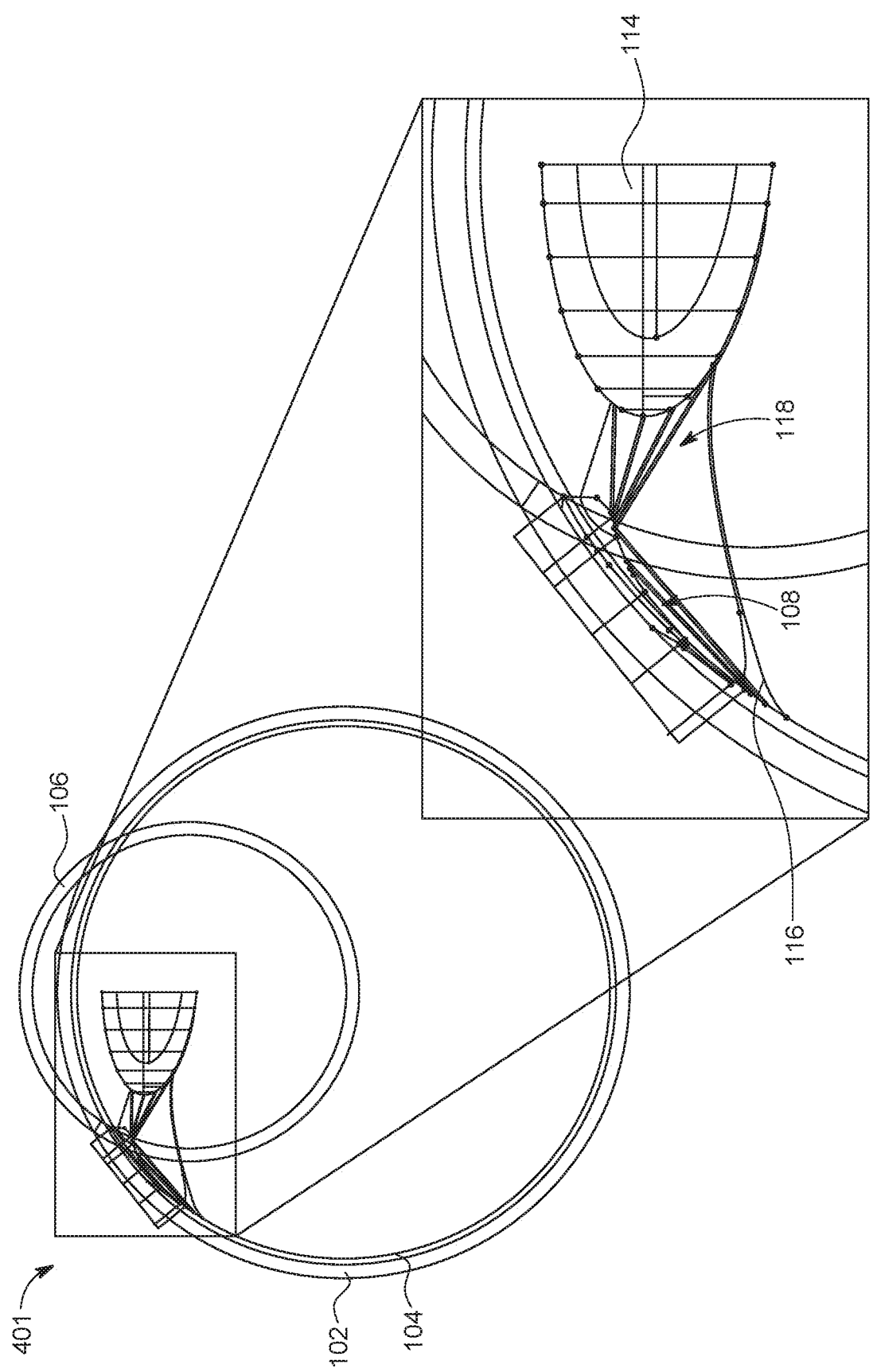
FIG. 4B shows an example embodiment of a cross sectional diagram for a two-dimensional model design for an eye with enlarged inset to show enhanced detail.

FIG. 4B shows an example embodiment 401 of a cross sectional diagram for a two-dimensional model design for an eye with enlarged inset to show enhanced detail. Like numbers have been included for sclera 102; choroid 104; cornea 106; ciliary muscles 108 including circular, radial, and longitudinal fibers; lens capsule 110; lens nucleus 114; vitreous membrane 116; and zonules 118 from FIG. 1A and FIG. 3A to maintain clarity.

As shown in the example embodiment, the eye and its various ocular structures can be effectively modeled using a computer modeling program. This can be accomplished by inputting various known structural measurements and structural measurement ranges of lengths, widths, diameters, thicknesses, and others to effectively create a general eye model that can be manipulated in simulations. Additionally, formulas can be developed and implemented based on known relationships between structural components to model different features and interactions. These can then be used to implement the simulations and to model interactions between the various structural components by changing or otherwise manipulating different variables in the formulas to find resulting effects.

Figure 4D:
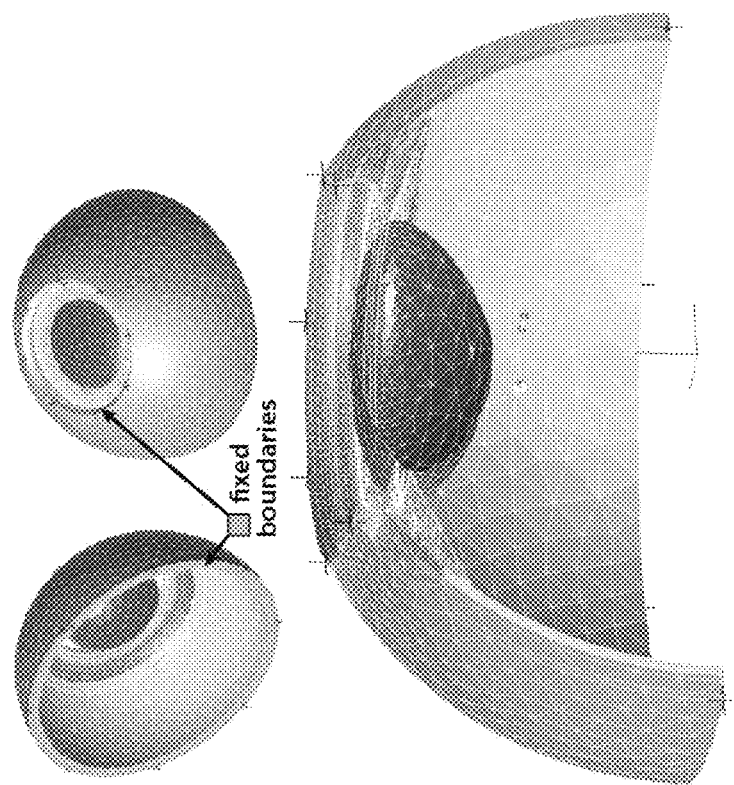
FIG. 4D shows an example embodiment diagram of a three-dimensional meshing model of an eye from a bottom perspective view, top perspective view, and side cross-sectional view.
Figure 4C:
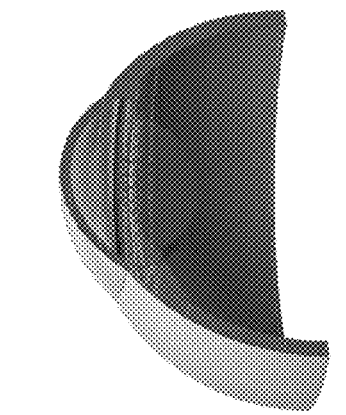
FIG. 4C shows an example embodiment diagram of a three-dimensional model of an eye from a perspective view, side view, and side cross-sectional view.

FIG. 4C shows an example embodiment diagram 403 of a three-dimensional model of an eye from a perspective view, side view, and side cross-sectional view.

FIG. 4D shows an example embodiment diagram 405 of a three-dimensional meshing model of an eye from a bottom perspective view, top perspective view, and side cross-sectional view. This will be discussed further with respect to FIG. 10.

FIG. 5A shows an example embodiment of a two-dimensional cross sectional diagram 500 for a two-dimensional model design for an eye showing measurements of unaccommodated ocular structures. Like numbers have been included for sclera 102; choroid 104; cornea 106; ciliary muscles 108 including circular, radial, and longitudinal fibers; lens capsule 110; lens nucleus 114; vitreous membrane 116; and zonules 118

Figure 5B:
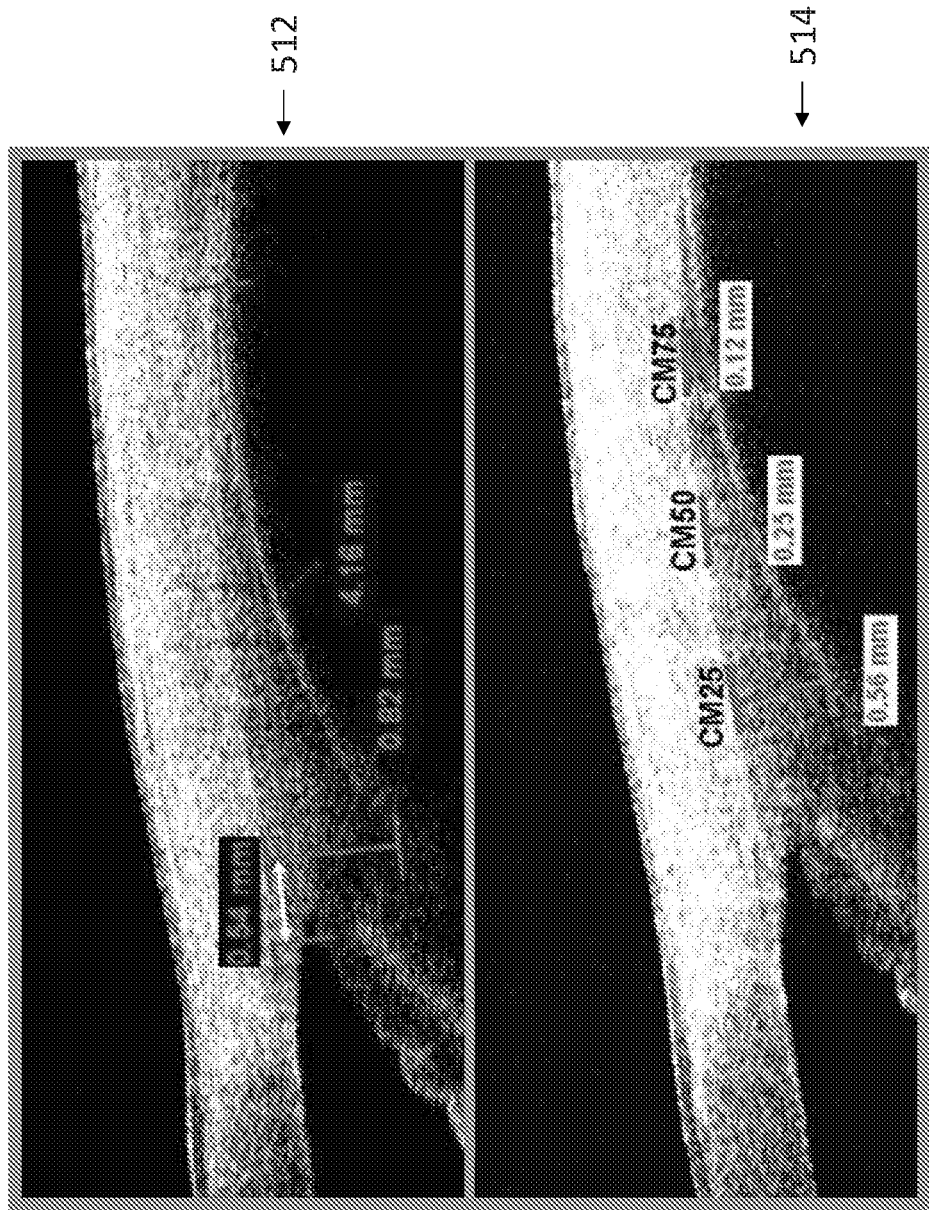
FIG. 5B shows an example embodiment of a prior art cross sectional image for a two-dimensional model design for an eye showing measurements of unaccommodated ocular structures.

FIG. 5B shows an example embodiment of a prior art cross sectional image 510 for a two-dimensional model design for an eye showing measurements of unaccommodated ocular structures. An upper section 512 and lower section 514 show different measurement values of the same unaccommodated eye. As shown in upper section 512, measurements of an unaccommodated eye's ocular structures have shown that a . . . has a length of 0.54 mm and a . . . of 0.82 mm while a . . . has a length of 4.16 mm. As shown in the lower section 514, a ciliary muscle measurement can show a thickness of 0.56 mm at a first point, a thickness of 0.25 mm at an intermediate point, and a thickness of 0.12 mm at a third point. All of these measurements can then be used as two dimensional measurements for a two-dimensional accommodation model. This can be used in developing effective formulas and implemented in simulations.

Figure 5C:
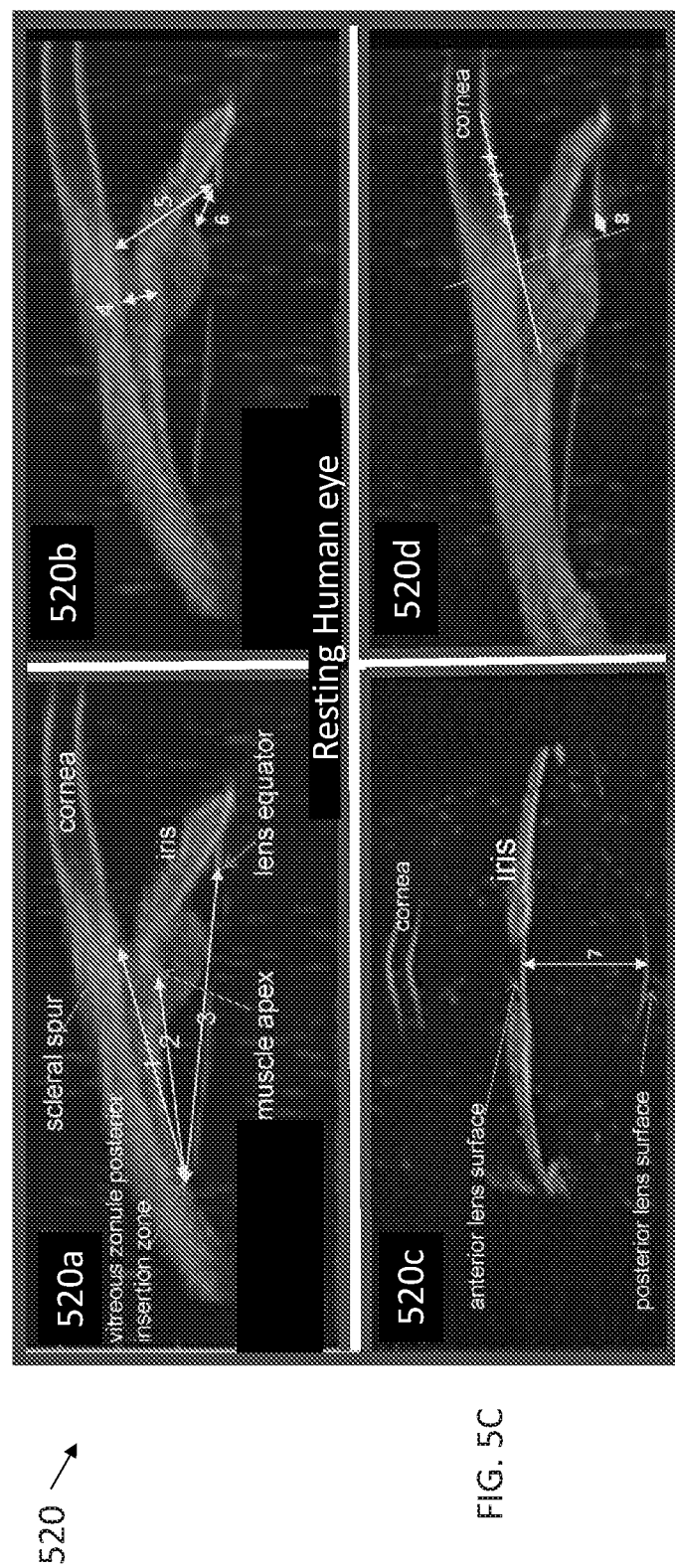
FIG. 5C shows an example embodiment diagram of prior art cross sectional images for a two-dimensional resting human eye showing measurements of unaccommodated ocular structures.

FIG. 5C shows an example embodiment diagram 520 of prior art cross sectional images 520a-520d for a two-dimensional resting human eye showing measurements of unaccommodated ocular structures. As shown in the example embodiment, measurements of various ocular structures can be conducted for the unaccommodated eye in order to develop an effective 2-dimensional model. Diagram 520a shows measurements from vitreous zonule posterior insertion zone to a scleral spur, muscle apex and lens equator.

Figure 6A:
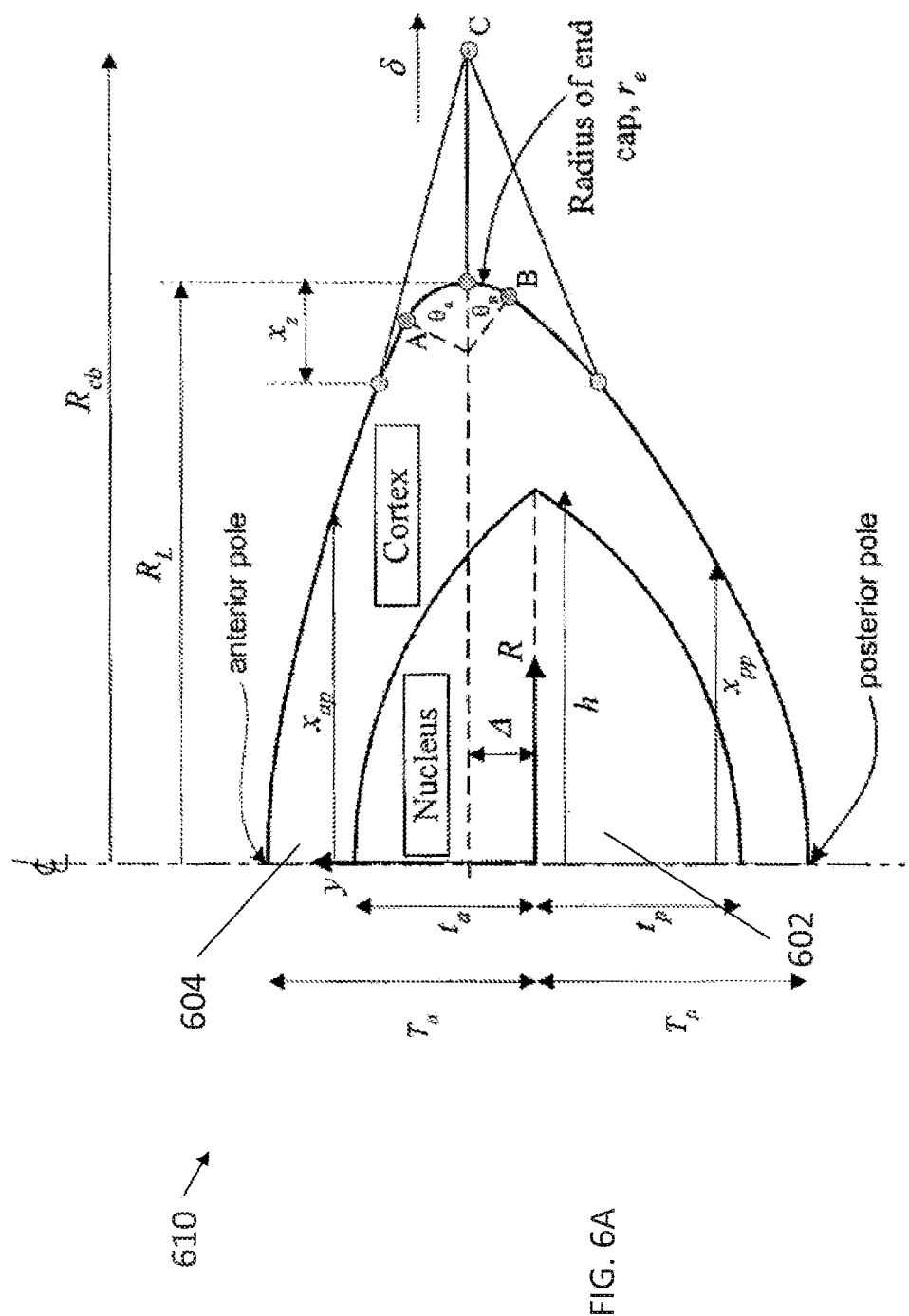
FIG. 6A shows an example embodiment of a cross sectional diagram for a two-dimensional model design for an eye showing variables of accommodated ocular structures.

FIG. 6A shows an example embodiment of a cross sectional diagram 610 for a two-dimensional model design for an eye showing variables of accommodated ocular structures. Here, the nucleus 602 and cortex 604 of the lens are modeled and are centered at the origin of the x-y plane. As shown in the example embodiment, various changes can be measured and modeled effectively in a two-dimensional x-y plane to account for all the changes that can occur during accommodation. These can include changes along the x-axis, including: $R_{cb}$, $R_L$, $R$, $x_{ap}$, $x_{ap}$, $x_z$, $h$, $x_{pp}$, and $\delta$. These can also include changes along the y-axis, including: $T_a$, $T_p$, $t_a$, $t_p$, and $\Delta$. Changes affecting an end cap, $r_e$ can be measured according to $\theta_a$ and $\theta_p$. These and other variables can be used to generate models of the lens and other ocular structures and their relationships.

Figure 6B:
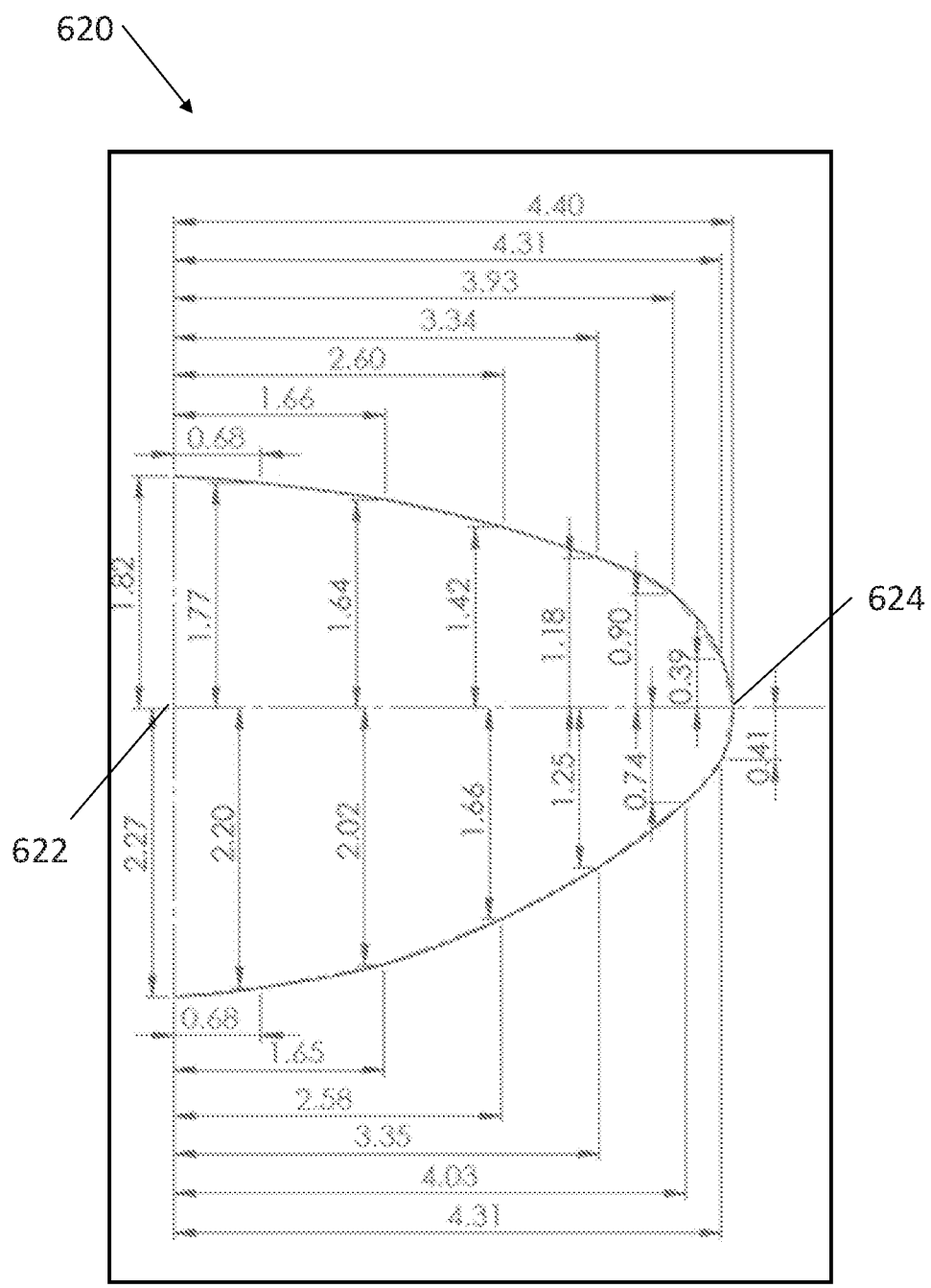
FIG. 6B shows an example embodiment of a cross sectional diagram for a two-dimensional model design for an eye showing dimensions of accommodated ocular structures.

FIG. 6B shows an example embodiment of a cross sectional diagram 620 for a two-dimensional model design for an eye showing dimensions of accommodated ocular structures. In the diagram, the outward facing surface of the lens is shown above the x-axis while the inward facing surface is below the x-axis. As shown in the example embodiment, standard measurements for x-axis distance and y-axis height of the lens centered at and moving away from the origin 622 toward the end cap 624 for the outward facing surface of the lens have been measured at (0, 1.82), (0.68, 1.77), (1.66, 1.64), (2.60, 1.42), (2.60, 1.18), (3.93, 0.90), (4.31, 0.39), and (4.40, 0). Similarly, standard measurements for x-axis distance and y-axis height of the lens centered at and moving away from the origin 622 toward the end cap 624 for the inward facing surface of the lens have been measured at (0, −2.27), (0.68, −2.20), (1.65, −2.02), (2.58, −1.66), (3.35, −1.25), (4.03, −0.74), and (4.40, 0).

Figure 7C:
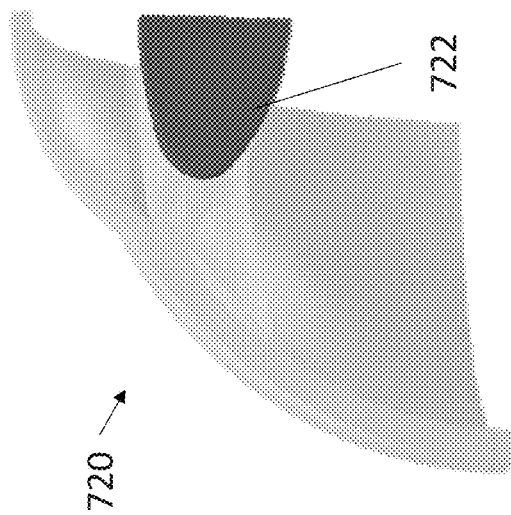
FIG. 7C shows an example embodiment of a cross-sectional 3-dimensional model structure diagram showing a shaded lens of an eye.
Figure 7B:
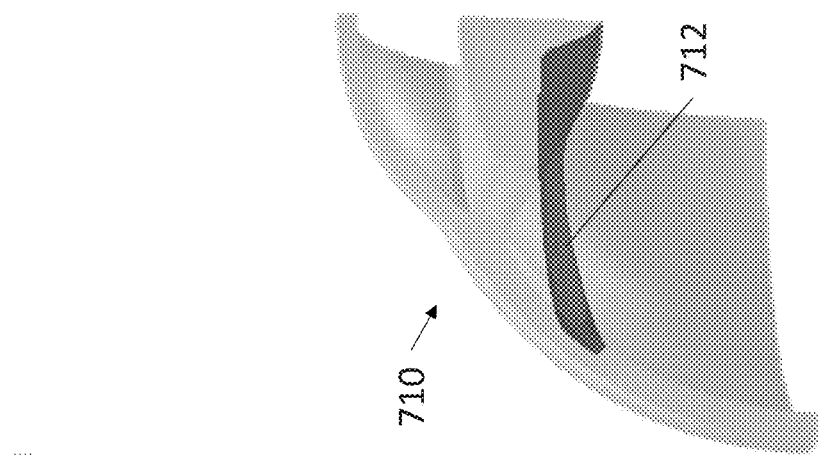
FIG. 7B shows an example embodiment of a cross-sectional 3-dimensional model structure diagram showing a shaded vitreous membrane of an eye.
Figure 7A:
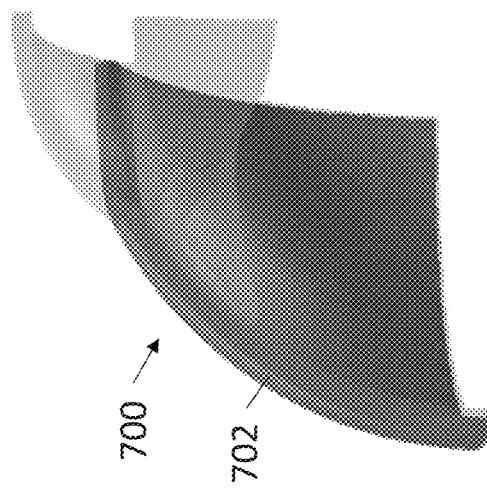
FIG. 7A shows an example embodiment of a cross-sectional 3-dimensional model structure diagram showing a shaded sclera of an eye.

FIG. 7A shows an example embodiment of a cross-sectional 3-dimensional model structure diagram 700 showing a shaded sclera 702 of an eye.

FIG. 7B shows an example embodiment of a cross-sectional 3-dimensional model structure diagram 710 showing a shaded vitreous membrane 712 of an eye.

FIG. 7C shows an example embodiment of a cross-sectional 3-dimensional model structure diagram 720 showing a shaded lens 722 of an eye.

Figure 7F:
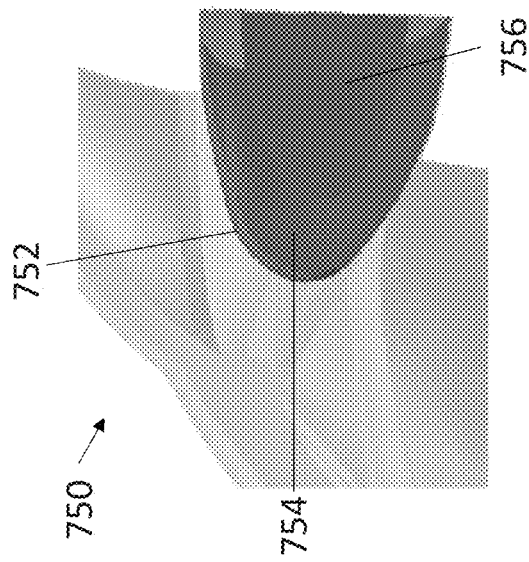
FIG. 7F shows an example embodiment of a cross-sectional 3-dimensional model structure diagram showing a capsule, cortex, and nucleus of an ocular lens.
Figure 7E:
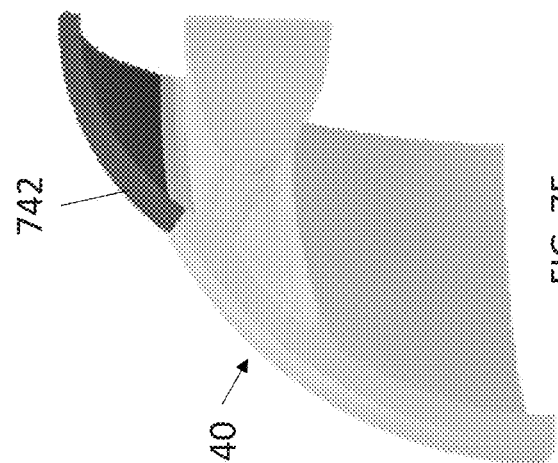
FIG. 7E shows an example embodiment of a cross-sectional 3-dimensional model structure diagram showing a cornea of an eye.
Figure 7D:
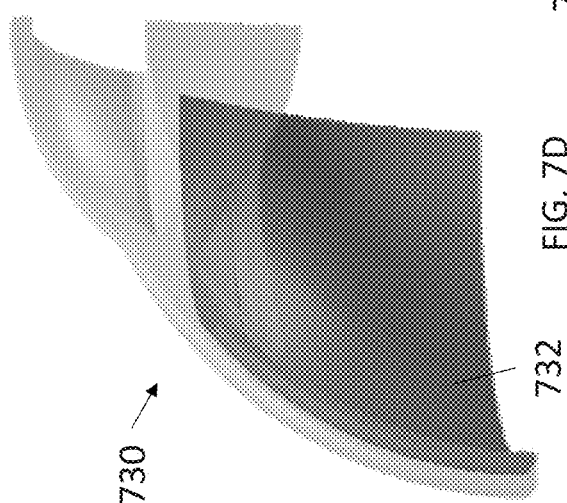
FIG. 7D shows an example embodiment of a cross-sectional 3-dimensional model structure diagram showing a choroid of an eye.

FIG. 7D shows an example embodiment of a cross-sectional 3-dimensional model structure diagram 730 showing a choroid 732 of an eye.

FIG. 7E shows an example embodiment of a cross-sectional 3-dimensional model structure diagram 740 showing a cornea 742 of an eye.

FIG. 7F shows an example embodiment of a cross-sectional 3-dimensional model structure diagram 750 showing a capsule 752, cortex 754, and nucleus 756 of an ocular lens.

FIG. 7G shows an example embodiment of a cross-sectional 3-dimensional model structure diagram 758 showing various ocular structures of an eye.

FIG. 7H shows an example embodiment of a cross-sectional 3-dimensional model structure diagram 760 showing a shaded ciliary muscle 762 of an eye.

FIG. 7I shows an example embodiment of a cross-sectional 3-dimensional model structure diagram 764 showing shaded zonules 766 of an eye.

FIG. 7J shows an example embodiment of a cross-sectional 3-dimensional model structure diagram 768 showing a sclera 770 of an eye. Also shown are subchoroid Lamellae 772 and scleral spur or shell 774.

FIG. 7K shows an example embodiment of a cross-sectional 3-dimensional model structure diagram 776 showing a shaded lens 778 of an eye, including capsule 780, cortex 782, and nucleus 784.

FIG. 7L shows an example embodiment of a cross-sectional 3-dimensional model structure diagram 786 showing a shaded choroid 788, vitreous membrane 790, and cornea 792.

It should be understood that various modeling programs can be used to develop ocular structural models. One example is Autodesk Inventor and another is Autodesk Simulation CFD, both by Autodesk, Inc.

Figure 8:
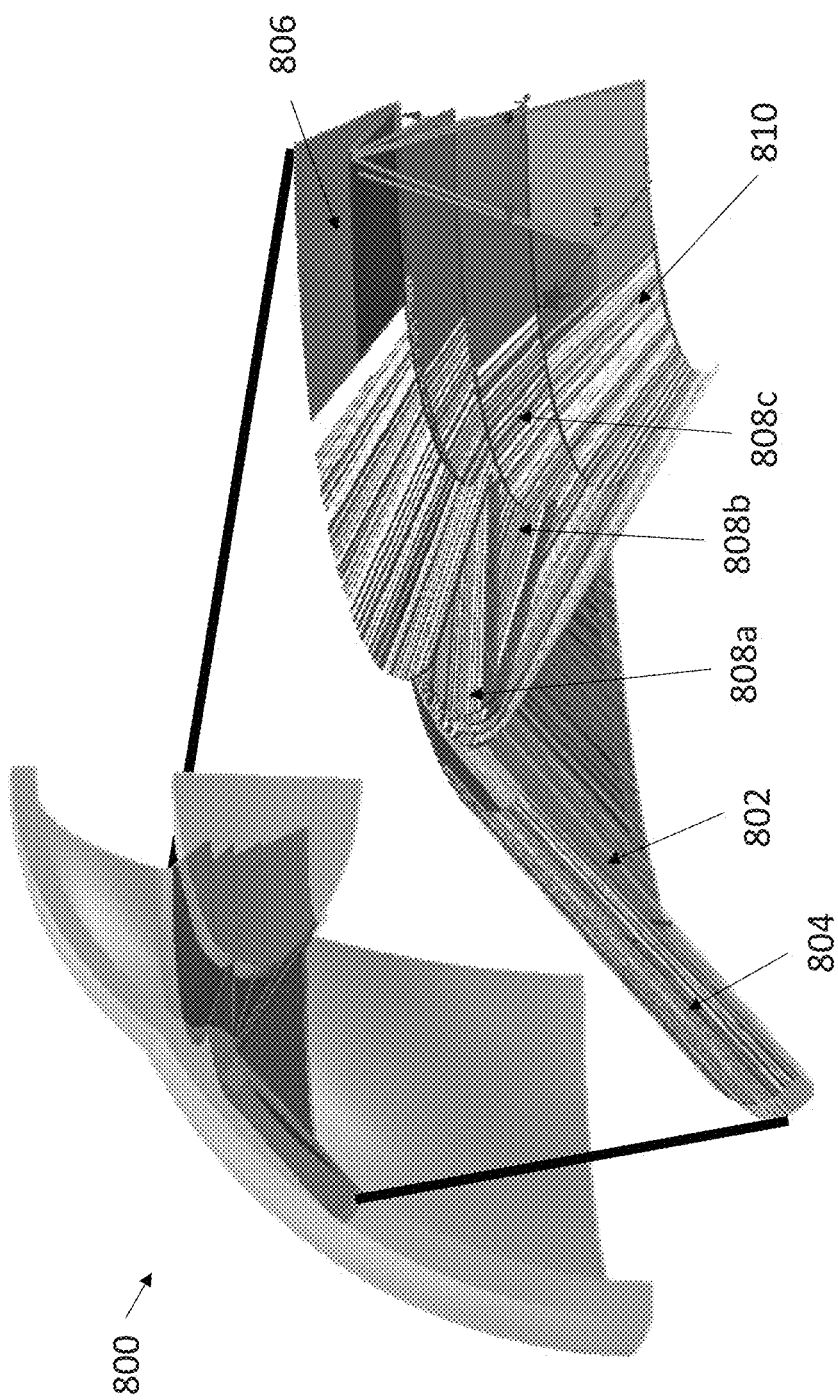
FIG. 8 shows an example embodiment of a cross-sectional 3-dimensional model structure diagram showing a zonules model of an eye with enlarged inset to show enhanced detail.

FIG. 8 shows an example embodiment of a cross-sectional 3-dimensional model structure diagram 800 showing a zonules model of an eye with enlarged inset to show enhanced detail. These are shown as various layers including intermediate vitreous zonule layer 802; pars plana zonule layer 804; most anterior zonule (MAZ) layer 806; three anterior zonule layers 808a, 808b, 808c; and anterior vitreous zonule layer 810. As shown, distances can be modeled from a central point in order to ensure modeling accuracy.

FIG. 9A shows an example embodiment of a prior art diagram 900 of ciliary fibers of an eye. The anatomical structure of ciliary muscles is known to include circular ciliary fibers 902, radial ciliary fibers 904, and longitudinal ciliary fibers 906. These are generally arranged with circular ciliary fibers 902 being the innermost ciliary fibers and arranged in circumferential fashion around a central location. Radial ciliary fibers 904 generally make up an intermediate layer. An outer layer of ciliary fibers are longitudinal ciliary fibers 906, which generally run outward in a radial fashion from a central location.

FIG. 9B shows an example embodiment of an accommodated eye diagram 1320. As the schematic diagram of the eye is shown, major structures involved in accommodation include: a corneo-scleral shell, a crystalline lens, a ciliary body containing ciliary muscles, and the zonular fibers connecting the ciliary body to the crystalline lens. For the accommodated eye a pars plicata portion of a ciliary body 1322 moves upward and inward while ciliary muscle 1324 contracts. Lens 1326 becomes steeper or thicker and leads to higher power for short distance vision. Zonules 1328 are relaxed and sclera 1330 is located exterior to ciliary muscle 1324.

FIG. 9C shows an example embodiment of a disaccommodated eye 1340. Here, cornea 1332 is coupled with sclera 1330. Zonules 1328 become taut and cause lens 1326 to become flatter or thinner, leading to lower power used for long distance vision. As is known in the art, other names for zonules 1328 include: suspensory ligaments, zonules of Zinn, zonular apparatus, and others. Zonular fibers can couple with lens 1326 are known as: anterior, central, and posterior. Ciliary muscle 1324 is contained within a ciliary body.

As shown in FIGS. 9B-9C, a schematic of the eye with the major structures involved in accommodation: the corneo-scleral shell, the crystalline lens, the ciliary body (containing the ciliary muscle), and the zonular fibers connecting the ciliary body to the crystalline lens. The relaxed, or disaccommodated eye is shown on the right. The ciliary muscle is relaxed and the zonules are pulled taut, flattening the lens for distance vision. The accommodated eye is shown on the left. Here, the ciliary muscle is contracted, relaxing the tension on the zonules and allowing the crystalline lens to take its more natural, curved shape for near vision.

FIG. 9D shows an example embodiment of a cross-sectional 3-dimensional model structure diagram 910 showing an integrated composite ciliary fiber model 912 of an eye including an exploded view with separate longitudinal layer model 914, radial layer model 916, and circular layer model 918.

FIG. 10A shows an example embodiment of a cross-sectional 3-dimensional model structure diagram 1000 of an eye with enlarged inset to show a meshing model 1010. Meshing is a technique that is known in modeling to be an effective way of representing three-dimensional structures with computer software. Meshing can include numerous cells 1012 of different sizes and shapes. As shown in the example embodiment, the cells in meshing model 1010 are triangular, although other regular and irregular polygonal shapes can be used. In general, smaller cells allow for closer approximation to any curves of the structure being modeled. As such, here highly rounded areas, such as the side of an ocular lens have smaller cells than comparatively larger round structures, such as a choroid wall. Meshing model 1010 in the example embodiment has been created using AMPS technologies software although many others are known.

FIG. 10B shows an example embodiment diagram 1020 of a meshing process. Here, meshing model geometry for finite element analysis can include using 260927 tetrahedral elements with 1787 triangular shell elements and 111970 nodes. As shown in the example embodiment, once the model has been created in step 1022, for example using Autodesk Inventor, the model can be converted to an intermediate stage 1024, for example in AMPSolid. Then the model can be converted to final meshed model 1026, for example in AMPView64.

FIG. 10C shows an example embodiment chart 1030 of material parameters of ocular structures. As shown in the example embodiment, isotropic Neo-Hookean materials properties of various ocular structures can be based on their elastic modulus E (MPa) and Poisson's ratio. These can be different for the cornea, sclera, scleral spur, subchoroid lamellae, choroid, vitreous membrane, lens cortex, lens nucleus, lens capsule, and other structures.

FIG. 10D shows an example embodiment chart 1032 of various formulas governing transversely isotropic materials.

FIG. 10E shows an example embodiment chart 1034 of parameters for ciliary muscle and zonules.

Various formulas and definitions used in modeling and simulation include: array size=side length of the square area of treatment (mm); treated surface area=surface area of sclera where treatment is applied (mm^2); treated surface area=array$^2$; thickness=thickness of sclera in the treated area (mm), assumed uniform; treated volume=volume of sclera where treatment is applied (mm^2); treated volume=treated surface area*thickness=array$^2$*thickness; density %=percent of treated surface area occupied by pores (%); spot size=surface area of one pore (mm^2); #pores=number of pores in the treated region;

$$\# \text{pores} = \frac{\text{density \%} * \text{treated surface area}}{\text{spot size} * 100} = \frac{\text{density \%} * \text{array}^2}{\text{spot size} * 100}$$

*round to nearest whole number; total pore surface area=total area within the treated surface area occupied by pores;

$$\text{total pore surface area} = \text{spot size} * \text{\#pores} \approx$$
$$\frac{\text{density \%} * \text{treated surface area}}{100} \approx \frac{\text{density \%} * \text{array}^2}{100};$$

depth=depth of one pore (mm); dependent on pulse per pore (ppp) parameter; depth %=percent of the thickness extended into by the pore depth (%);

$$\text{depth \%} = \frac{\text{depth}}{\text{thickness}} * 100;$$

total pore volume=total area within the treated surface area occupied by pores;

$$\text{total pore volume} =$$
$$\text{total pore surface area} * \text{depth} = \text{spot size} * \text{\# pores} * \text{depth} \approx$$
$$\frac{\text{density \%} * \text{treated surface area} * \text{depth}}{100} \approx \frac{\text{density \%} * \text{array}^2 * \text{depth}}{100};$$

volume fraction=percent of treated volume occupied by pores (%), i.e. percent of sclera volume removed by the laser; and $$\text{volume fraction} =$$
$$\frac{\text{total pore volume}}{\text{treated volume}} * 100 \approx \frac{\text{density \%} * \text{depth}}{\text{thickness}} = \frac{\text{density \%} * \text{depth \%}}{100}.$$

Array size, density %, spot size, depth, pulse per pore, and others can be parameters of a laser treatment. Thickness and others can be properties of the sclera. Inputs to calculate new stiffness can include volume fraction and others.

Further, calculating the new stiffness of a sclera in a treated region can be based on various factors including: volume fraction=percent of treated volume occupied by pores (%), i.e. percent of sclera volume removed by the laser;

$$\text{volume fraction} =$$
$$\frac{\text{total pore volume}}{\text{treated volume}} * 100 \approx \frac{\text{density \%} * \text{depth}}{\text{thickness}} = \frac{\text{density \%} * \text{depth \%}}{100};$$

stiffness=modulus of elasticity of sclera before treatment (MPa); treated stiffness=modulus of elasticity of sclera after treatment (MPa); estimated from microscale mixture model; and $$\text{treated stiffness} =$$
$$\left(1 - \frac{\text{volume fraction}}{100}\right) * \text{stiffness} \approx \left(1 - \frac{\text{density \%} * \text{depth}}{\text{thickness} * 100}\right) * \text{stiffness} =$$
$$\left(1 - \frac{\text{density \%} * \text{depth \%}}{10000}\right) * \text{stiffness}.$$

Input parameters to a finite element model of treated zones can be treated stiffness.

Information from FIGS. 10C-10E can be modified and measured in various embodiments to determine effects and changes. This can be done in AMPS software including AMPSView64 and others.

FIG. 10F shows an example embodiment of a user interface screen 1036 for modifying various parameters during modeling. Here, users can navigate using tabs 1038, enter information using fields 1040, select buttons 1042 that control different aspects of the model, select different drop down menus 1044, and execute computer controlled processes stored in memory by selecting buttons 1046.

FIG. 10G shows an example embodiment chart 1048 of strain energy density equations for ciliary muscle and zonules. These can be physically based strain invariants.

FIG. 10H shows an example embodiment chart 1050 of dilational strain equations.

FIG. 10I shows an example embodiment chart 1052 of along-fiber shear equations and diagram.

FIG. 10J shows an example embodiment chart 1054 of cross-fiber shear equations and diagrams.

Figure 10K:
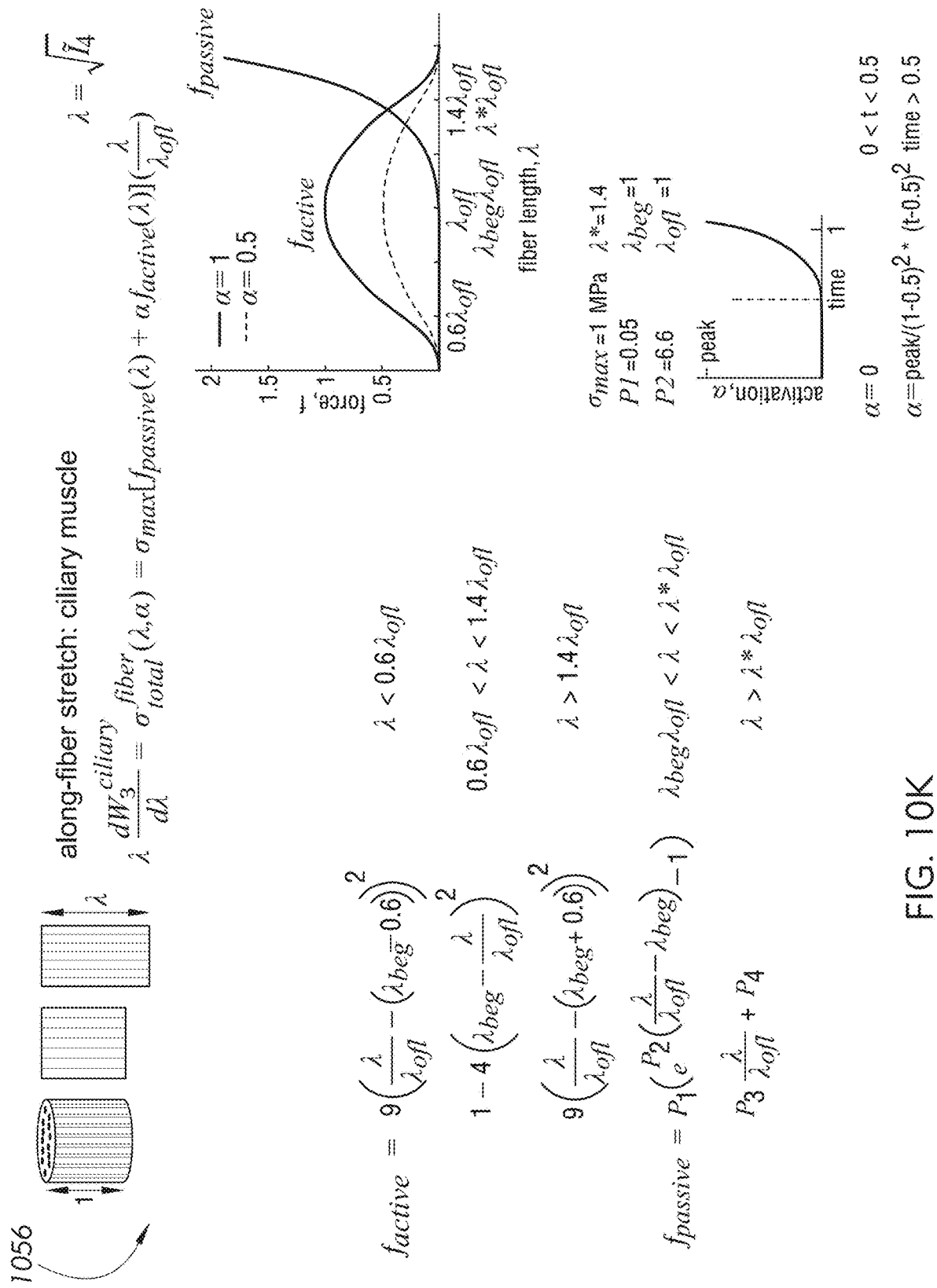
FIG. 10K shows an example embodiment chart of along-fiber stretch equations and diagrams for ciliary muscles, including activation versus time and force versus fiber length.

FIG. 10K shows an example embodiment chart 1056 of along-fiber stretch equations and diagrams for ciliary muscles, including activation versus time and force versus fiber length.

FIG. 10L shows an example embodiment chart 1058 of along-fiber stretch equations and diagrams for zonules, including pretension versus time and stress versus fiber length.

Figure 11A:
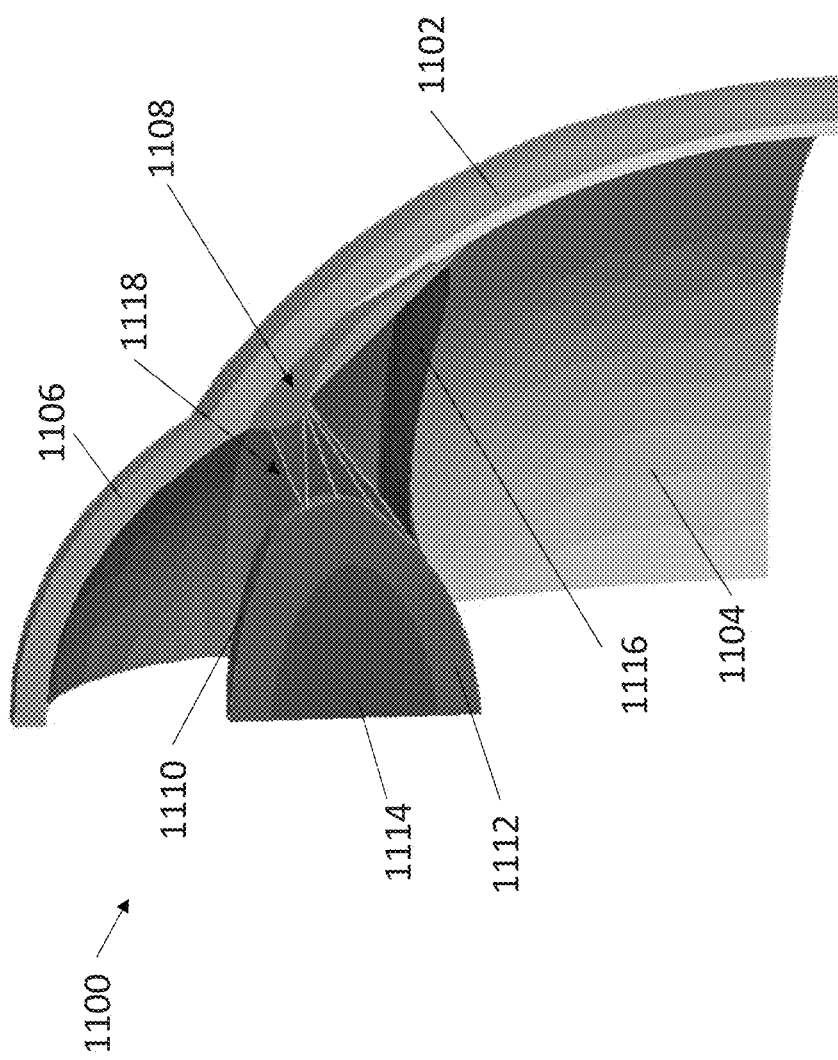
FIG. 11A shows an example embodiment perspective view of a cross-sectional three-dimensional model structure diagram of an eye.

FIG. 11A shows an example embodiment perspective view of a cross-sectional three-dimensional model structure diagram 1100 of an eye. When creating a three-dimensional model an initial step can be to define different structures. Here, ocular structures are being modeled. As such, each ocular structure is first defined as sclera 1102; choroid 1104; cornea 1106; ciliary muscles 1108; lens capsule 1110; lens cortex 1112; lens nucleus 1114; and vitreous membrane 1116, and zonules 1118.

FIG. 11B shows an example embodiment perspective view of a cross-sectional three-dimensional model structure diagram 1101 of an eye. Each ocular structure is first defined as sclera 1102; choroid 1104; cornea 1106; ciliary muscles 1108; lens capsule 1110; lens cortex 1112; lens nucleus 1114; and vitreous membrane 1116, and zonules 1118.

Figure 11C:
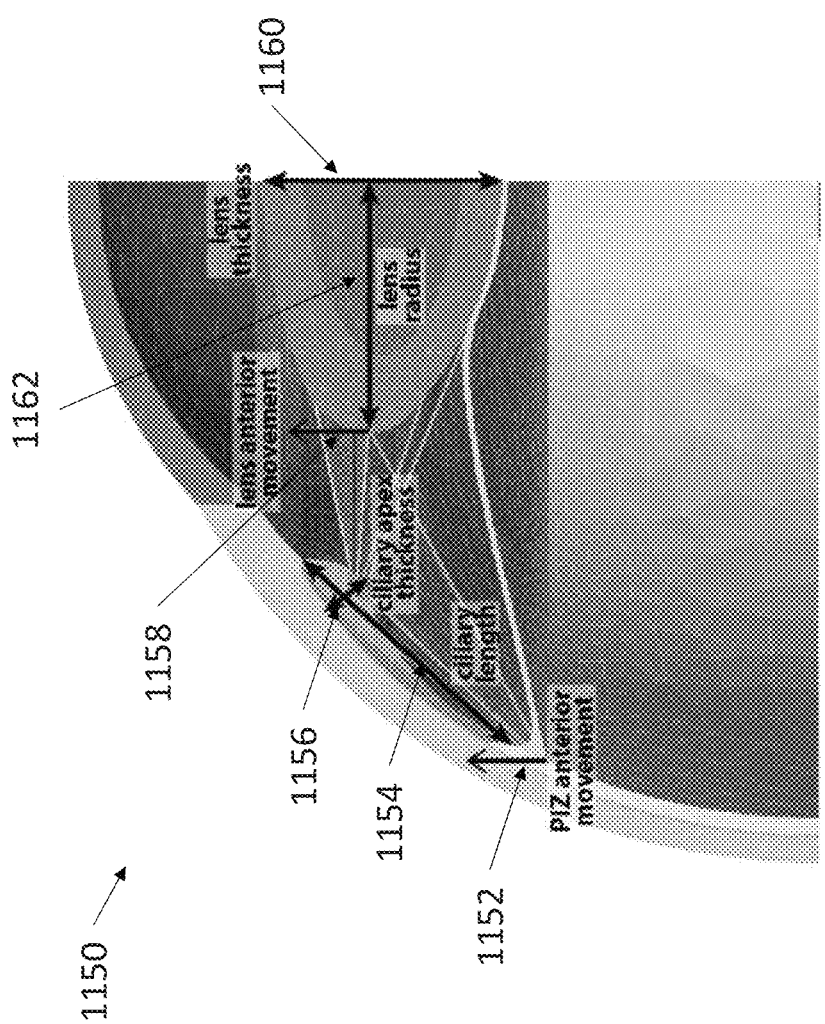
FIG. 11C shows an example embodiment side view of a cross-sectional three-dimensional model structure diagram of an eye.

FIG. 11C shows an example embodiment side view of a cross-sectional three-dimensional model structure diagram 1150 of an eye. Each ocular structure is first defined as sclera 1102; choroid 1104; cornea 1106; ciliary muscles 1108; lens capsule 1110; lens cortex 1112; lens nucleus 1114; and vitreous membrane 1116, and zonules 1118. Here, movement, dimensions and thicknesses are shown. Modelling, requires various dimensions, defining descriptions of included ocular structures in the form of geometry reference, and explaining required simplifications.

FIGS. 12A-12B show an example embodiment of a cross-sectional three-dimensional model structure diagram 1200, 1220 with upper and lower boundaries of an eye, respectively. After defining different structures in three-dimensional modeling, it can be important to define boundary positions. When modeling for changes in accommodation the entire ocular structure does not need to be modeled since portions of the back of the eye do not play a part in accommodative function. As such, areas near the lens are most important. Thus, defining boundary positions that are near the lens is useful in constraining any modeling and later simulations that may utilize the model.

As shown, the exterior structures are those which require boundary placement since they are the ones at the far extremes of the model. Here, the exterior structures that are constrained by selection of boundaries include sclera 1202 and choroid 1204. An upper boundary 1299 around a semi-circular area of sclera 1202 above the outward facing lens capsule 1210 is set to conserve modeling resources as shown in FIG. 12A. A rotation of the model in FIG. 12B shows a lower boundary 1201 affecting sclera 1202 and choroid 1204 in the rotated cutaway view. Boundary conditions can be fixed in the x, y, and z-directions in FIGS. 12A-12B.

FIGS. 12C-12D shows an example embodiment of a cross-sectional three-dimensional quarter model structure diagram 1240, 1260 of an eye with radial symmetry and having a right and left boundary, respectively. As shown in the models, no out of plane translation is allowed to occur due to left and right boundary setting. FIG. 12C shows how boundaries can be fixed in the x-direction, while FIG. 12D shows how boundaries can be fixed in the z-direction.

As shown, each of the modeled ocular structures requires boundary placement on the left and right here since each is being limited at the edge of the model. Here, the structures that are constrained by selection of boundaries include sclera 1202; choroid 1204; cornea 1206; ciliary muscles 1208; lens capsule 1210; lens cortex 1212; lens nucleus 1214; and vitreous membrane 1216, and zonules 1218. A right planar boundary 1225 along the desired plane is set to conserve modeling resources as shown in FIG. 12C. A left planar boundary 1275 along the desired plane is set to conserve modeling resources as shown in FIG. 12D. Global pressure on interior surfaces (2e−3 MPa) can be set at Intraocular pressure (IOP)—15 mmHg.

Figure 12E:
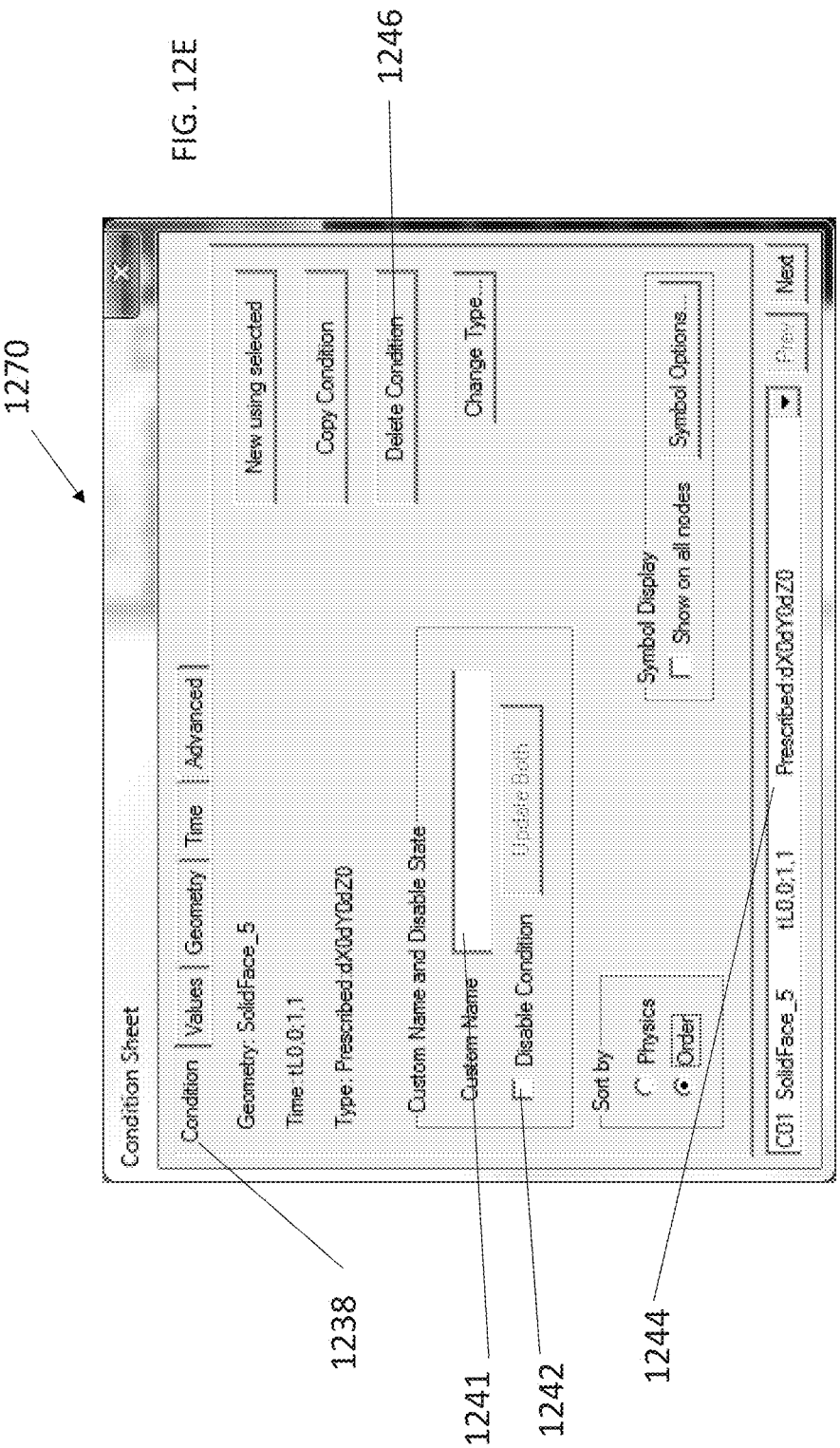
FIG. 12E shows an example embodiment of a user interface screen for modifying various parameters during modeling.

FIG. 12E shows an example embodiment of a user interface screen 1236 for modifying various parameters during modeling. Here, users can navigate using tabs 1238, enter information using fields 1241, select buttons 1242 that control different aspects of the model, select different drop down menus 1244, and execute computer controlled processes stored in memory by selecting buttons 1246.

Figure 13B:
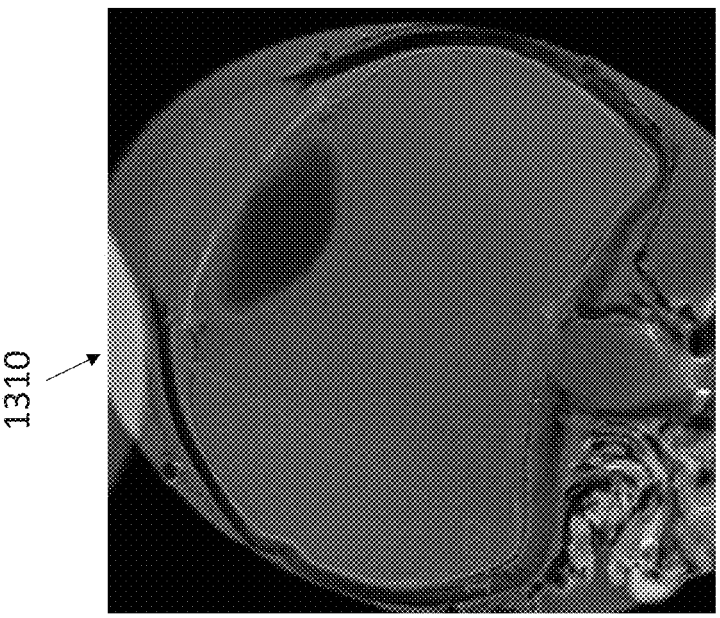
FIG. 13B shows an example embodiment of a close-up cross-sectional 7T MRI image of a small animal eye SE showing whole eye anatomy and the relationship of Sagittal macro and micro structures.
Figure 13A:
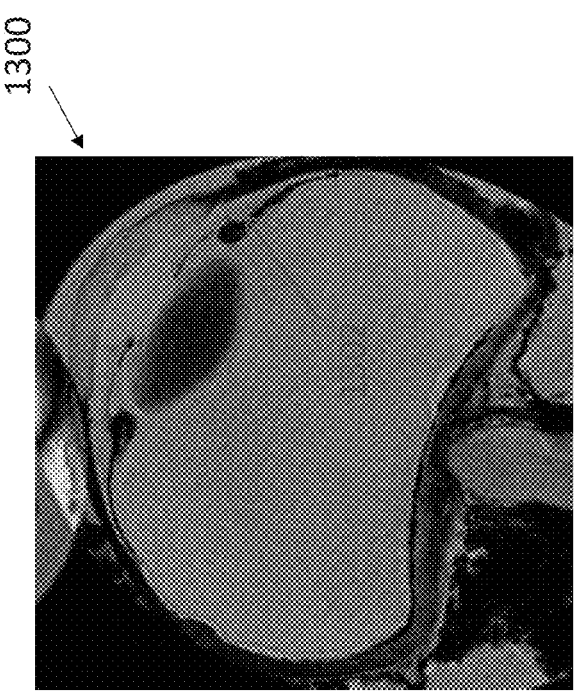
FIG. 13A shows an example embodiment of a cross-sectional 7T MRI image of a small animal eye showing anatomy and the relationship of Sagittal macro and micro structures.

FIG. 13A shows an example embodiment of a cross-sectional 7T MRI image 1300 of a small animal eye showing anatomy and the relationship of Sagittal macro and micro structures. Special attention here showing specifically the morphology of the ciliary muscles and body.

FIG. 13B shows an example embodiment of a close-up cross-sectional 7T MRI image 1410 of a small animal eye SE showing whole eye anatomy and the relationship of Sagittal macro and micro structures. Special attention here showing specifically the morphology of the ciliary muscles and body. This is a zoomed in version of FIG. 13A.

Figure 13C:
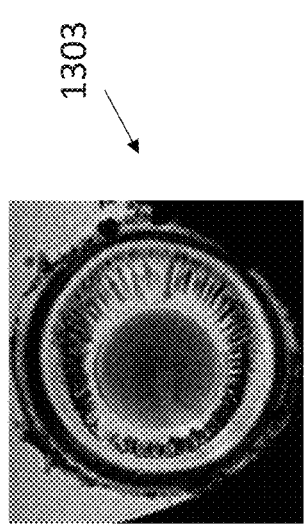
FIG. 13C shows an example embodiment of a cross-sectional 7T MRI image of a small animal eye GE showing a whole eye ciliary body.

FIG. 13C shows an example embodiment of a cross-sectional 7T MRI image 1320 of a small animal eye GE showing a whole eye ciliary body. FIGS. 13A-13C provide indications of ciliary muscles 1302.

FIG. 14A shows an example embodiment of a simulation flowchart 1400 showing an initial model at rest undergoing zonule pre-tensioning to become an unaccommodated model and ciliary muscle contraction to become an accommodated model. As shown in the example embodiment, a two-dimensional or three-dimensional initial model 1402 has been developed and implemented in a computer. Initial model 1402 represents the eye at rest. As a first simulation step, conditions that represent a zonule pre-tensioning can be applied in step 1404. This zonule pre-tensioning will lead to the simulation modeling an unaccommodated eye model 1406. As described herein, unaccommodated eye model 1406 represents the eye when viewing things at a distance. Unaccommodated eye model 1406 can then be subjected to conditions that represent a ciliary muscle contraction in a second simulation step 1408. This ciliary muscle contraction simulation step 1408 will then cause the simulation to present an accommodated eye model 1410.

FIG. 14B shows an example embodiment of an unaccommodated eye diagram 1401.

FIG. 14C shows an example embodiment of an accommodated eye diagram 1403. FIGS. 14B-14C are shown side by side so that differences in ocular structures and positions can be seen in order to highlight their distinctions. These distinctions are discussed elsewhere herein.

Figure 14D:
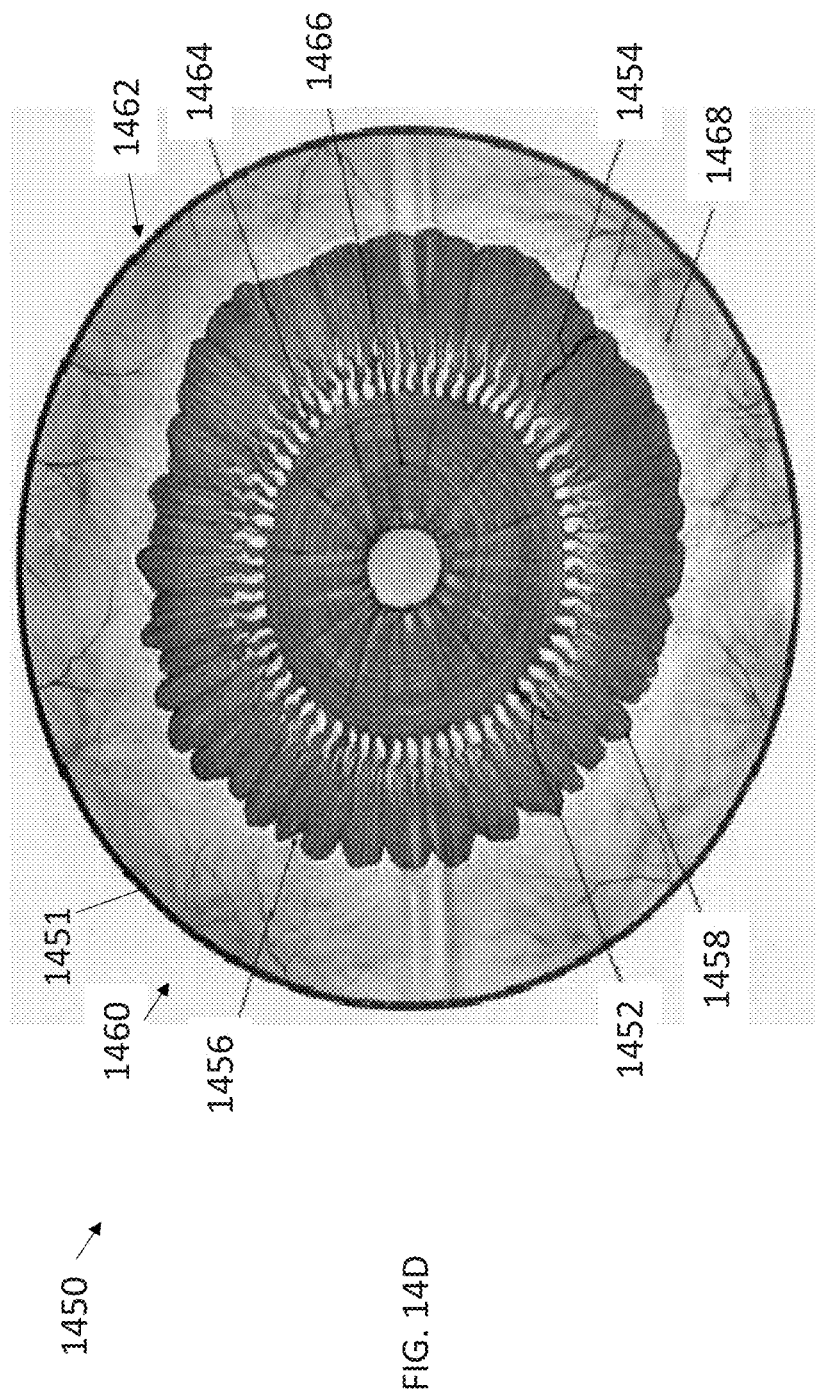
FIG. 14D shows example embodiment diagram calling out various components of the anatomy of an eye.

FIG. 14D shows example embodiment diagram 1450 calling out various components of the anatomy of an eye 1451. As shown in the example embodiment, the pars plicata 1452 and pars plana 1454 are important ocular structures. A nasal side 1460 of the ocular structures includes a proceso dentado 1456, pars plicata 1452, and ora serrata 1458. A temporal side 1462 includes a proceso ciliar 1464 and pars plana 1454. An iris 1466 is centrally located and retina is located exteriorly.

Figure 14E:
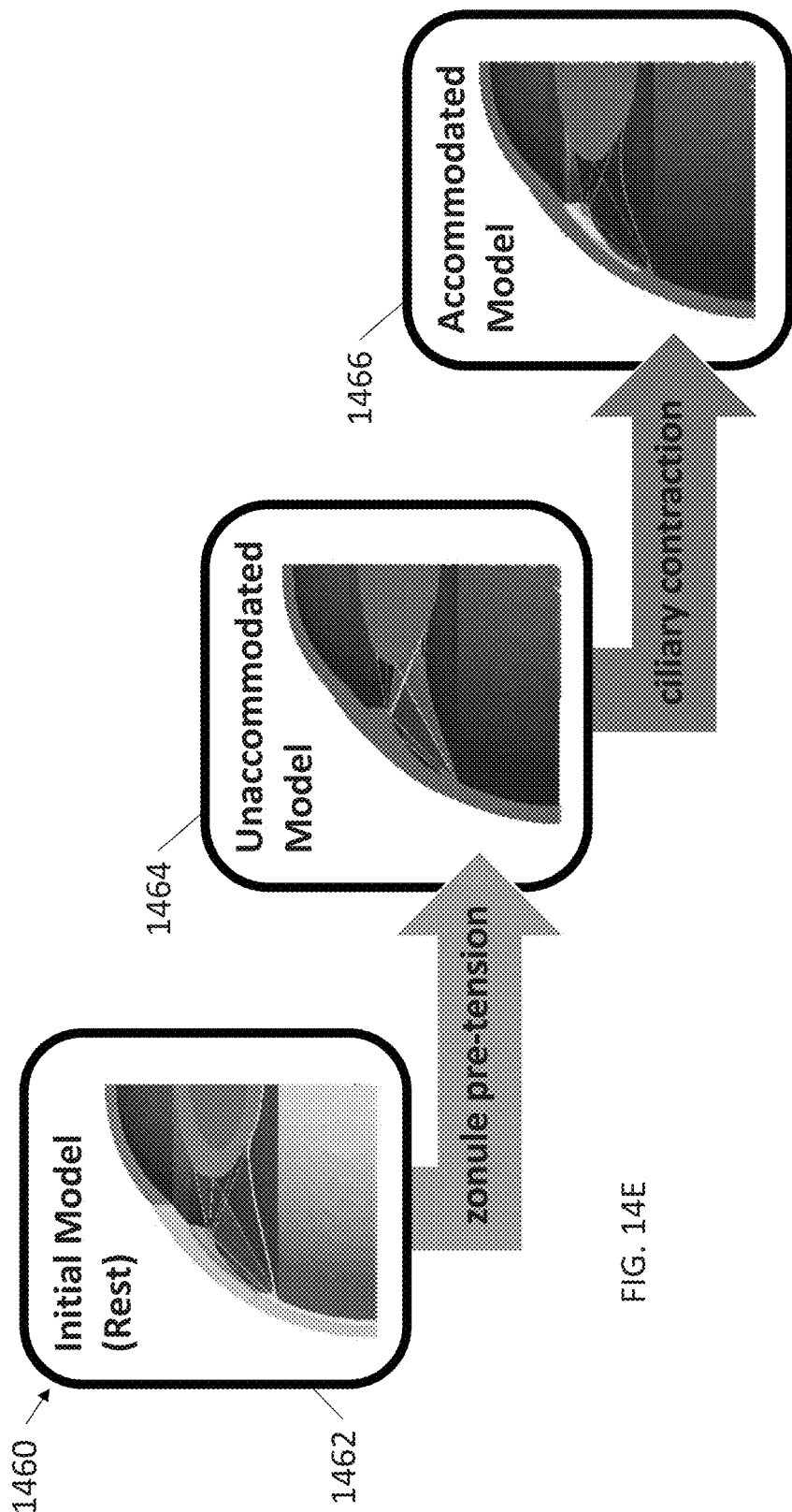
FIG. 14E shows an example embodiment diagram of an accommodation simulation process.

FIG. 14E shows an example embodiment diagram 1460 of an accommodation simulation process. As shown in the example embodiment, an initial model 1462 can be a resting model. After simulating zonule pre-tentioning, an unaccommodated model 1464 can be created. Next, ciliary contraction can be simulated and an accommodated model 1466 can be created. This can be performed using AMPSol64 or other programs executed by a computer.

FIG. 14F shows an example embodiment diagram 1470 showing tension of zonules versus simulation time and ciliary muscle activation versus time.

FIG. 14G shows an example embodiment user interface diagram 1472 of an informational display during simulation screen. As shown in the example embodiment, the process can be tracking by iteration and timing, and information such as status and others can be displayed for the user. Users can save, open, print, copy, cut, and stop simulations from running by selecting the appropriate buttons 1474.

FIG. 15A shows an example embodiment of a diagram 1500 including a cross-sectional diagram 1502 of an eye with expanded lens image 1504, expanded ciliary muscle for confocal image 1506, and expanded choroid image 1508 taken using a bright scope across plane A-A.

Figure 15B:
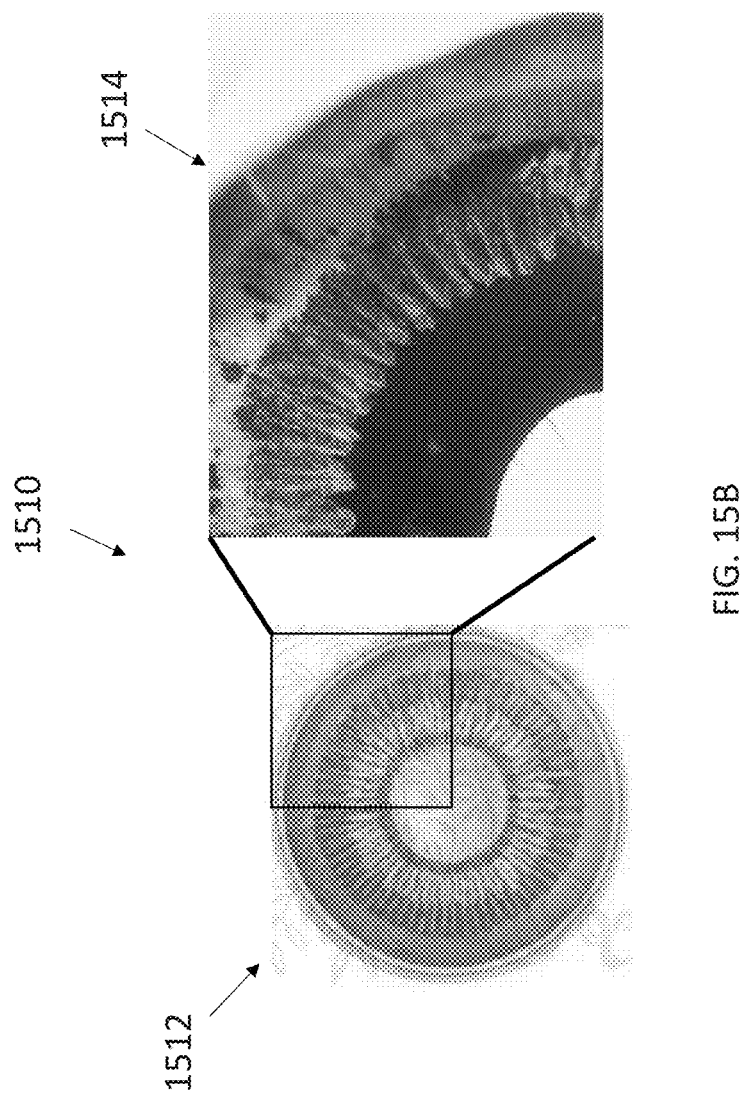
FIG. 15B shows an example embodiment diagram including a cross-sectional diagram of an eye including a ciliary muscle and processes image.

FIG. 15B shows an example embodiment diagram 1510 including a cross-sectional diagram of an eye 1512 including a ciliary muscle and processes image 1514 taken using a bright scope.

FIGS. 16A-16C are cross-sectional confocal images 1600, 1602, 1604 respectively, showing ciliary fiber structures and fiber orientations. This data can be taken from cadaver eyes to determine fiber directions during movements. Here, eye imaging includes: Confocal Imaging of the 3 different fiber directions of the radial, longitudinal and circular muscles of the ciliary muscle or ciliary body. Each FIG. 16B is a zoomed version of FIG. 16A, and FIG. 16C is a further zoomed image that shows an example embodiment of an image of fiber orientation and branching.

FIG. 16D shows an example embodiment diagram 1610 of three parts of the ciliary muscle structure. The ciliary body 1612 contains the ciliary muscle. There are three types of muscle fibers: circular 1614, radial or oblique 1616, and longitudinal or meridonal 1618. Longitudinal muscle 1618 is also known as Bruke's muscle. The radial 1616 and longitudinal 1618 muscle fibers terminate in the scleral spur 1620. The longitudinal muscle fibers 1618 terminate in "epichoroidal stars" 1622 for attachment to the choroid layer at the ora serrata.

FIGS. 16E-16F show example embodiment diagrams 1630, 1650 of a corneo-scleral shell with a ciliary body. As shown in the example embodiment, sclera 1624 can be exterior to a choroid layer 1626. A transition from the choroid layer 1626 to the ciliary body 1612 is shown at the ora serrata 1628. Also shown is the cornea 1632.

FIG. 16G shows an example embodiment diagram 1660 of changes in the eye between an unaccommodated eye in central section 1662 for distance vision and accommodated eye in right section 1664 for near vision. As shown in the example embodiment, lens 1666 becomes thicker and more curved in accommodated vision and zonule fibers 1668 are under more tension.

FIGS. 16H-16I show example embodiments of a disaccomodated eye ciliary muscle diagram 1670 from a top view and accommodated eye ciliary muscle diagram 1672 from a top view, respectively. Muscle force during accommodation in shown by the arrows in FIG. 16I FIGS. 16J-16K show example embodiments of a computer model of ciliary muscles of an eye from a top view 1674 and side cross-sectional view 1676 with inset respectively. As shown in the example embodiment, circular fibers 1614, radial fibers 1616, and longitudinal fibers 1618 can each be individually modeled.

FIGS. 16L-16M show example embodiment diagrams of longitudinal fibers 1678, radial fibers 1680, and circular fibers 1682, individually modeled and operable to be show simulations of their function during the accommodative process.

Figure 16N:
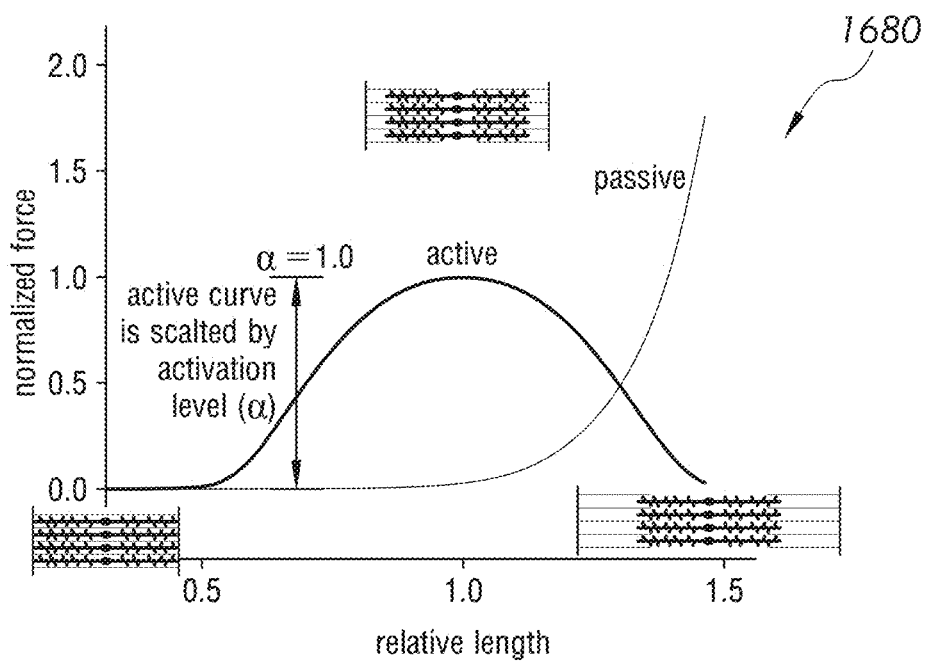
FIG. 16N shows an example embodiment diagram of normalized force versus relative length of ciliary muscle.

FIG. 16N shows an example embodiment diagram 1680 of normalized force versus relative length of ciliary muscle. This indicates that it is transversely isotropic, incompressible material with active contraction and three sets of fiber directions. Here, contraction is the force produced along muscle fibers. This indicates that ciliary muscle is best matched as "smooth striated" muscle.

Here, arrows indicate the contraction and movement of the ciliary body 1612. When the ciliary muscle 1612 contracts, the longitudinal fibers stretch choroid 1626 and pull ora serrata 1628 upwards toward cornea 1632. The end of the ciliary body 1612 close to the scleral spur 1620 is called the pars plicata. As the ciliary muscle 1612 contracts, the pars plicata moves inward and upward. This relaxes the tension on zonules attached to the crystalline lens, allowing the lens to take a steeper shape for near vision. As such, contraction of ciliary body 1612 stretches choroid 1626 and causes inward and upward movement of the pars plicata, relaxing zonules. Additionally, circular fibers 1614 have an increase in the cross-sectional size of their bundle.

The contraction of muscle is governed by protein interactions in the sub-units, called sarcomeres. When this contraction occurs, force is produced in the muscle in the direction of its fibers. The force produced is a function of the sarcomere length, where more force is produced at midlength and much less is produced at the extremes of long and short. To model the forces in the ciliary muscle, assumptions about lengths during contraction are made based on previous research. Which direction the fibers are contracting to estimate the directions of the forces that the muscle produces are also important.

The longitudinal fibers run from the scleral spur to the ora serrata. The circular fibers run circumferentially around the lens. Between these are the intermediate fibers which transition between the two previous groups. Our model will include two muscle sections with longitudinal and circular fiber directions and a joined boundary between them. When the muscle fibers of the ciliary contract during accommodation, forces will be produced toward the center and front of the eye.

Muscle fiber arrangement and the directions of individual forces produced during accommodation can be used to specifically see their structure and function for each of the different fiber directions. To do this in the model fiber directions for the model must first be incorporated because the muscle forces flow through the fibers. Fiber direction determination is necessary in order to know the exact forces when simulated. A last step in setting up a model to accommodate through simulation. Thus, at this point all the things required for model creation are complete and ready for simulation, including: geometry, material properties, physics, fiber direction, and others.

Validation of the model can be performed by comparing measurements of known eye accommodation movements. In general, the lens may be simplified and move in a general way or be more specific. As such, adding a preload to the lens can assure that when the eye is unaccommodated the lens is stretched. Deformation in accommodation can also balance out the ratio of lens A/P movement and lens centripetal movement. Further refinement of lens movement with preloading can be performed and quantification and correlation of central optical power with lens movement as well. Once the accommodated-unaccommodated model is completed elastic forces and storage of energy potential can be measured and analyzed. This can allow for quantifying the potential energy stored in the choroid during stretching movements and also the longitudinal forces upon disaccommodation of the eye.

Validation of the modeling can occur by comparing results from the model with experimental data by different people and organization. This can allow for greater understanding of how the model operates and known ocular changes. Changes in both shape and position of ciliary muscles and the lens can be measured and compared with any measurements from imaging studies.

Comparison of model results may indicate that additional data needs to be collected since measured data is highly variable. Resolution and accuracy of the images themselves can be a cause of this variability. Thus, the question of "Is the model working as expected" can be answered yes, since it shows a similar trend even there is variability in the actual measured data.

Changes in ciliary ring lens equator diameters can also occur due to accommodation. Previously, measurements of the diameter of both the ciliary muscles and the lens have been performed on unaccommodated and accommodated eyes. This data is shown by two lines. In the figure. Unaccommodated points on the left figure and accommodated points are shown on the right figure. These were measured over a range. Previously, it was reported that there was no real correlation between ciliary ring diameter and optical power. Validation of the model using trends has been shown to match this data.

Changes in lens forward A/P displacement with accommodation has been shown to match the model as well, as shown in the figure. Further, changes in lens thickness with accommodation can be validated. Here, even though the model is right at the median or average of the data, not much thickening of the lens is shown. Thus, it appears too flat. However, this can be explained by the forces of the pre-stressing.

Refining the model can be performed by: modifying lens movement by adding the pre-stress, performing ciliary muscle fiber studies using 3D imaging (such as by imaging cadaver eyes). And by adding the Limbal ring. Further, model parameters can be varied to investigate measured physiologic changes associated with presbyopia. Additionally, utility of the model can be demonstrated by examining the effect of surgical corrections to presbyopia. Since the model demonstrates accommodation of a young healthy eye, varying the model can demonstrate accommodation in presbyopic eyes.

Figure 16O:
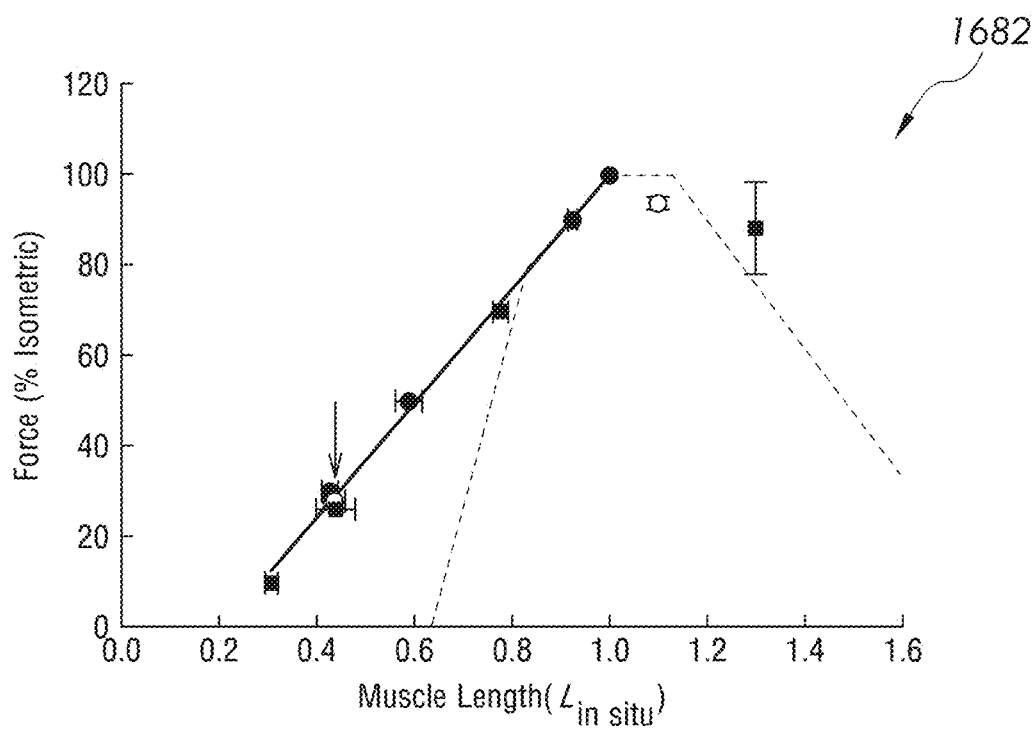
FIG. 16O shows an example embodiment chart of force versus muscle length.

FIG. 16O shows an example embodiment chart 1682 of force versus muscle length, indicating that the top of the pyramidal shape could be the "sweet spot."

FIG. 16P shows an example embodiment of a disaccomodated eye diagram 1684 and accommodated eye diagram 1686. Here, a scleral spur 1688 is shown at the top of the figure. When accommodation occurs, meridional muscle 1690 contracts, ora serrata 1692 is pulled up and retina/choroid 1694 stretches with respect to sclera 1696 due to a weak shearing.

FIG. 16Q shows an example embodiment diagram 1698 of a simple spring model of ciliary muscle movement. Here, average radial choroid modulus can be about $8 \times 10^5$ N m$^{-2}$ (0.8 MPa), while average radial sclera modulus can be about $2 \times 10^6$ N m$^{-2}$ (2.0 MPa).

Figure 17A:
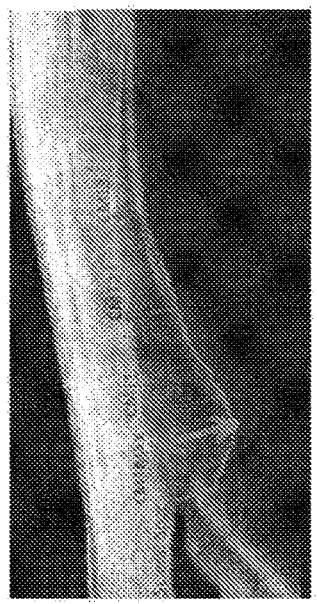
FIG. 17A shows an example embodiment screenshot of a model of ocular structures for use in simulation.

FIG. 17A shows an example embodiment screenshot 1700 of a model of ocular structures for use in simulation. As shown, ciliary muscle 1702 movement can be simulated by inputting initial conditions and running simulations, such as during an accommodative process, along with other ocular structural movement. Thickness changes are shown by the arrows.

Figure 17B:
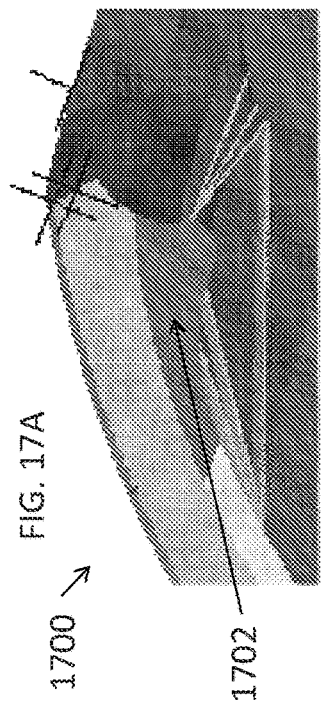
FIG. 17B shows an example embodiment image of individual ciliary fiber movement during an accommodative process including thickness changes, as indicated by the arrows.

FIG. 17B shows an example embodiment image 1708 of individual ciliary fiber movement during an accommodative process including thickness changes, as indicated by the arrows.

Figure 17D:
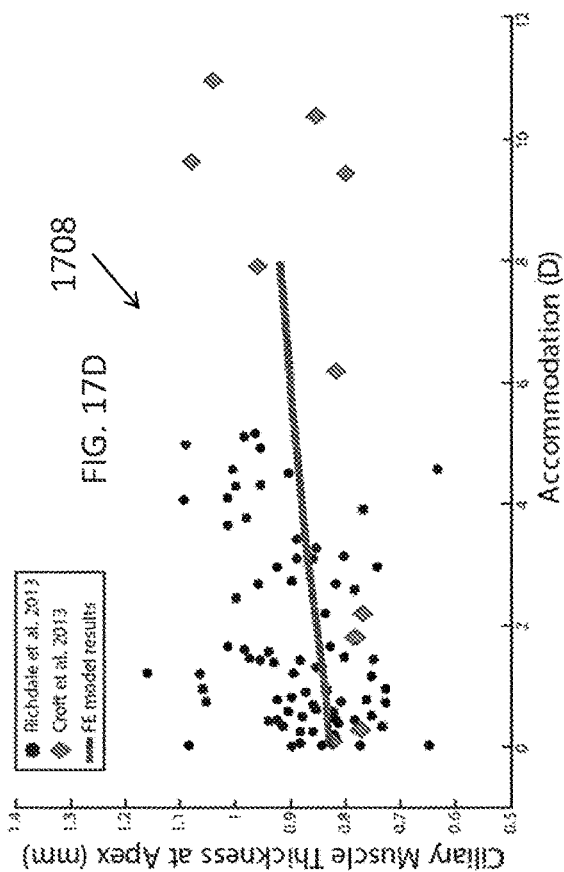
FIG. 17D shows an example embodiment diagram of ciliary muscle thickness at ciliary muscle apex versus accommodative amount.
Figure 17C:
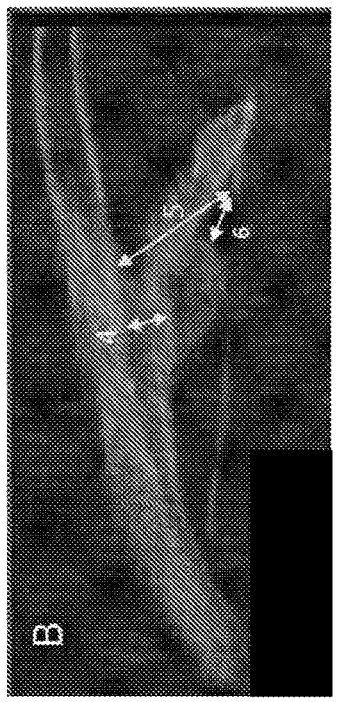
FIG. 17C shows an example embodiment image indicating overall ciliary muscle movement during an accommodative process including changes in thickness, as indicated by the arrows.

FIG. 17C shows an example embodiment image 1706 indicating overall ciliary muscle movement during an accommodative process including changes in thickness, as indicated by the arrows.

FIG. 17D shows an example embodiment diagram 1708 of ciliary muscle thickness at ciliary muscle apex versus accommodative amount. As shown in the example embodiment, a simulation was run using finite element modeling, as shown by the line. Various individual data points from clinical studies performed previously are also mapped, indicating that the model and simulator effectively shows the thickness changes measured.

FIG. 17E shows an example embodiment screenshot 1710 of a model of ocular structures for use in simulation. As shown in the example embodiment, diameters of ciliary body 1702 and lens 1712 can be measured and simulated according to the model.

FIG. 17F shows an example embodiment image 1714 of ciliary muscle and lens movement during an accommodative process including diameter changes, as indicated by the arrows.

FIG. 17G shows an example embodiment diagram 1716 of ciliary muscle ring diameter versus accommodative amount. As shown in the example embodiment, a simulation was run using finite element modeling, as shown by the line. Various individual data points from clinical studies performed previously are also mapped, indicating that the model and simulator effectively shows the diameter changes measured.

FIG. 17H shows an example embodiment diagram 1718 of lens diameter versus accommodative amount. As shown in the example embodiment, a simulation was run using finite element modeling, as shown by the line. Various individual data points from clinical studies performed previously are also mapped, indicating that the model and simulator effectively shows the lens diameter changes measured.

Figure 17J:
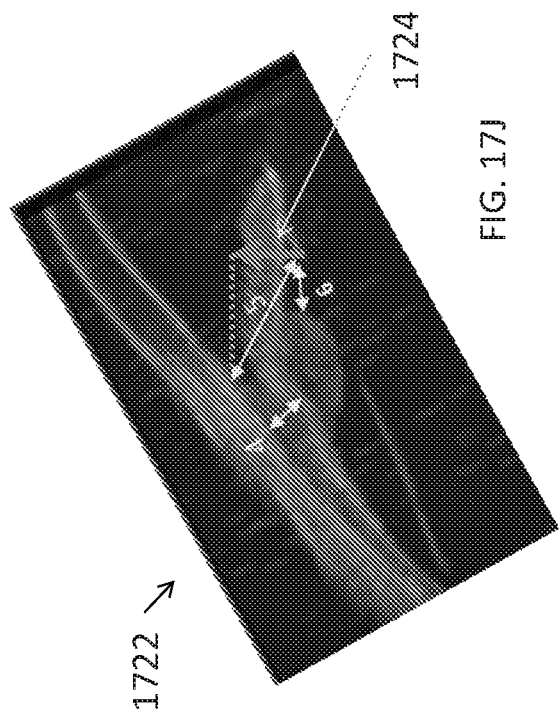
FIG. 17J shows an example embodiment image of forward displacement of lens during an accommodative process, as indicated by arrow.
Figure 17K:
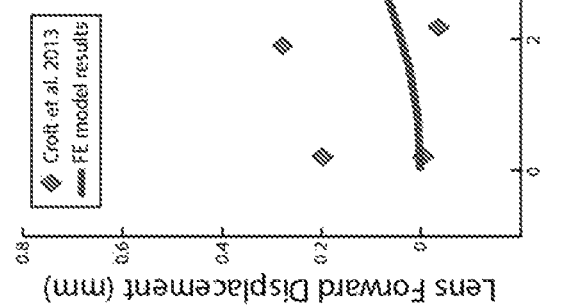
FIG. 17K shows an example embodiment diagram of forward displacement of the lens versus accommodative amount.
Figure 17I:
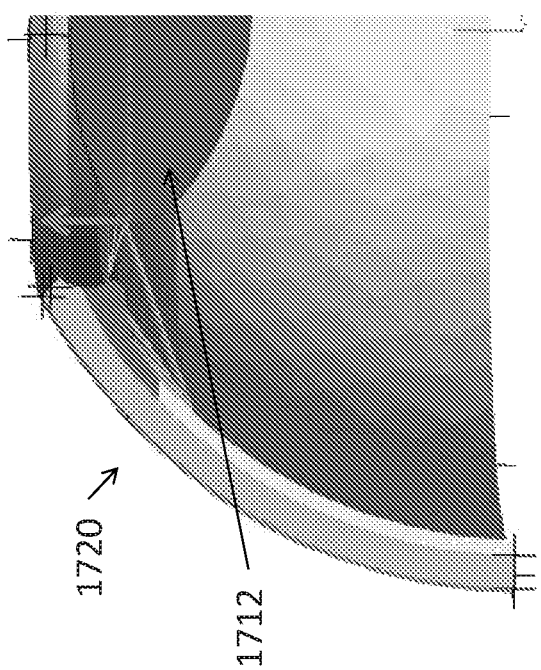
FIG. 17I shows an example embodiment screenshot of a model of ocular structures for use in simulation.

FIG. 17I shows an example embodiment screenshot 1720 of a model of ocular structures for use in simulation. As shown in the example embodiment, forward displacement of lens 1712 can be measured and simulated according to the model.

FIG. 17J shows an example embodiment image 1722 of forward displacement of lens during an accommodative process, as indicated by arrow 1724. Other arrows show changes in other ocular structures.

FIG. 17H shows an example embodiment diagram 1726 of forward displacement of the lens versus accommodative amount. As shown in the example embodiment, a simulation was run using finite element modeling, as shown by the line. Various individual data points from clinical studies performed previously are also mapped, indicating that the model and simulator effectively shows the forward displacement of the lens during accommodation.

FIG. 17L shows an example embodiment screenshot 1728 of a model of ocular structures for use in simulation. As shown in the example embodiment, changes in thickness of lens 1712 can be measured and simulated according to the model.

FIG. 17M-17N show example embodiment images 1730, 1732 of lens thickness changes during an accommodative process, as indicated by the arrows.

FIG. 17O shows an example embodiment diagram 1734 of lens thickness changes versus accommodative amount. As shown in the example embodiment, a simulation was run using finite element modeling, as shown by the line. Various individual data points from clinical studies performed previously are also mapped, indicating that the model and simulator effectively shows lens thickness changes during accommodation.

FIGS. 17P-17Q show example embodiment screenshots of an accommodated eye 1736 and unaccommodated eye 1738 model of ocular structures for use in simulation, respectively. As shown in the example embodiment, changes in ciliary muscle 1702 and lens 1712 can be measured and simulated according to the model. Here, lens 1712 can gain thickness and ciliary muscle 1702 can change position during accommodation.

FIGS. 17R-17S show example embodiment diagrams 1740, 1744 of changes to ciliary muscle 1742 and lens 1744 respectively, before, midway, and after an accommodative process. The solid lines indicate an unaccommodated shape, the medium dashed lines indicate midway accommodated, and the dark dashed lines indicate full accommodative shape.

FIG. 17T shows an example embodiment of a user interface diagram 1748 displaying measured results of positioning information during a simulation. As shown in the example embodiment, users can select particular features to follow or select positions of particular features during a simulation. Coordinates and distances between points or changes in position can be entered and displayed in various embodiments.

FIG. 18A shows an example embodiment of a 3-dimensional cross-sectional model structure diagram 1800 showing pre-tensioning of zonules 1818 and changes in the lens 1822 and ciliary body 1808 of an eye. As shown in the example embodiment, during modeling zonules 1818 can be pre-tensioned to change lens 1818 from normal or otherwise unaltered anatomic measurements of a resting shape to those of an unaccommodated shape. As such, lens 1822 becomes thinner and wider as a result of zonules 1818 pulling outward and downward into the eye, while fibers of ciliary body 1808 shorten to tension. Pre-tensioning of zonules 1822 prior to muscle contraction may be applied in order for a model to produce appropriate lens 1818 deformation. After applying the simulation to the model, results of displacement and deformation of lens 1822 and ciliary muscle 1808 can fall within the range of known values for accommodation of a young adult human eye, as described in existing medical literature and shown in FIG. 18B.

FIG. 18B shows an example embodiment of a chart 1850 showing accommodation of model results as a line using a 3-dimensional cross-sectional model, as compared with a prior art model that captured data points. Chart 1850 shows distance along fiber stretch in zonules versus lens thickness in millimeters. As shown, accuracy of three-dimensional modeling can be proven to be comparable an effective modeling technique compared with known data that exists in current medical literature. As described herein, systems, methods and devices including the pretensioning of ocular zonules conducts an instruction to modeling that elicits novel exploitation of biomechanical relationships and functions of the extra-lenticular structures of the eye as it relates to the mechanisms of accommodation and COP.

FIG. 19A shows an example embodiment of a 3-dimensional cross-sectional model structure diagram 1900 showing simulated accommodation of an eye through ciliary muscle 1908 contracting with varied muscle activation. As shown in the example embodiment, anterior and central contraction of ciliary muscles 1908 can be used to simulate accommodation of the eye. As such, this contraction causes lens 1922 to become thicker and more curved, as well as to shift in an anterior direction. However, it is known that ciliary muscles include sets of fibers, such as longitudinal fibers, radial fibers, and circular fibers. These fibers are known to function differently and produce different results, such that the contraction of specific fiber groups within ciliary muscle 1908 can contribute disproportionately to different aspects of lens 1918 shape-change during accommodation. FIGS. 19B-19D model each of these fiber groups independently.

FIG. 19B shows an example embodiment of 3-dimensional cross-sectional model structure diagram 1930 showing simulated accommodation of an eye through longitudinal ciliary fiber contraction and its associated muscle fiber trajectories. Further description of longitudinal ciliary fibers is shown and given with respect to FIGS. 9A-9B. As shown in the example embodiment, longitudinal fibers 1908a may be generally located on an exterior of ciliary muscle 1908. Thus, when longitudinal fibers 1908a are activated, the outer portions of ciliary muscle 1908 move. This is a movement with a shallow slope, compared to other fibers, as shown in muscle trajectory depiction 1962.

FIG. 19C shows an example embodiment of 3-dimensional cross-sectional model structure diagram showing simulated accommodation of an eye through ciliary contraction with varied muscle activation, particularly showing muscle fiber trajectories for radial fibers. Further description of radial ciliary fibers is shown and given with respect to FIGS. 9A-9D. As shown in the example embodiment, radial fibers 1908b may be generally located in a central or internal portion of ciliary muscle 1908. Thus, when radial fibers 1908b are activated, central or internal portions of ciliary muscle 1908 move. This is a movement with a steeper slope, compared to other fibers, as shown in muscle trajectory depiction 1964.

FIG. 19D shows an example embodiment of 3-dimensional cross-sectional model structure diagram showing simulated accommodation of an eye through ciliary contraction with varied muscle activation, particularly showing muscle fiber trajectories for circular fibers. Further description of circular ciliary fibers is shown and given with respect to FIGS. 9A-9D. As shown in the example embodiment, circular fibers 1908c may be generally located on an interior of ciliary muscle 1908. Thus, when circular fibers 1908c are activated, the inner portions of ciliary muscle 1908 move. This is a small movement, compared to other fibers, as shown in muscle trajectory depiction 1966.

For example, contraction of radial ciliary fibers 1908b can significantly contribute to anterior displacement of the lens, as shown in FIG. 19C. Contraction of circular ciliary fibers 1908c can contribute most significantly to thickening of the ciliary muscle at or near the apex, as shown in FIG. 19D, which can result in lens thickening and increased lens curvature.

FIG. 20A shows an example embodiment of a chart 2000 showing accommodation of model results using a 3-dimensional cross-sectional model structure diagram showing as compared with a prior art model for anterior displacement of a lens in millimeters. As shown in the example embodiment, the prior measurements were unable to determine which fibers were moving, and where. However, the three-dimensional simulation was able to monitor function of all fibers active, represented by line 2008; longitudinal fibers, represented by line 2008a, radial fibers, represented by line 2008b; and circular fibers, represented by 2008c. This is a vast improvement over the prior art.

FIG. 20B shows an example embodiment of a chart 2050 showing accommodation of model results using a 3-dimensional cross-sectional model structure diagram showing as compared with a prior art model for apex thickness of ciliary muscle in millimeters. As shown in the example embodiment, the prior measurements were unable to determine which fibers were moving, and where. However, the three-dimensional simulation was able to monitor function of all fibers active, represented by line 2058; longitudinal fibers, represented by line 2058a, radial fibers, represented by line 2058b; and circular fibers, represented by 2058c. This is a vast improvement over the prior art.

Figure 21:
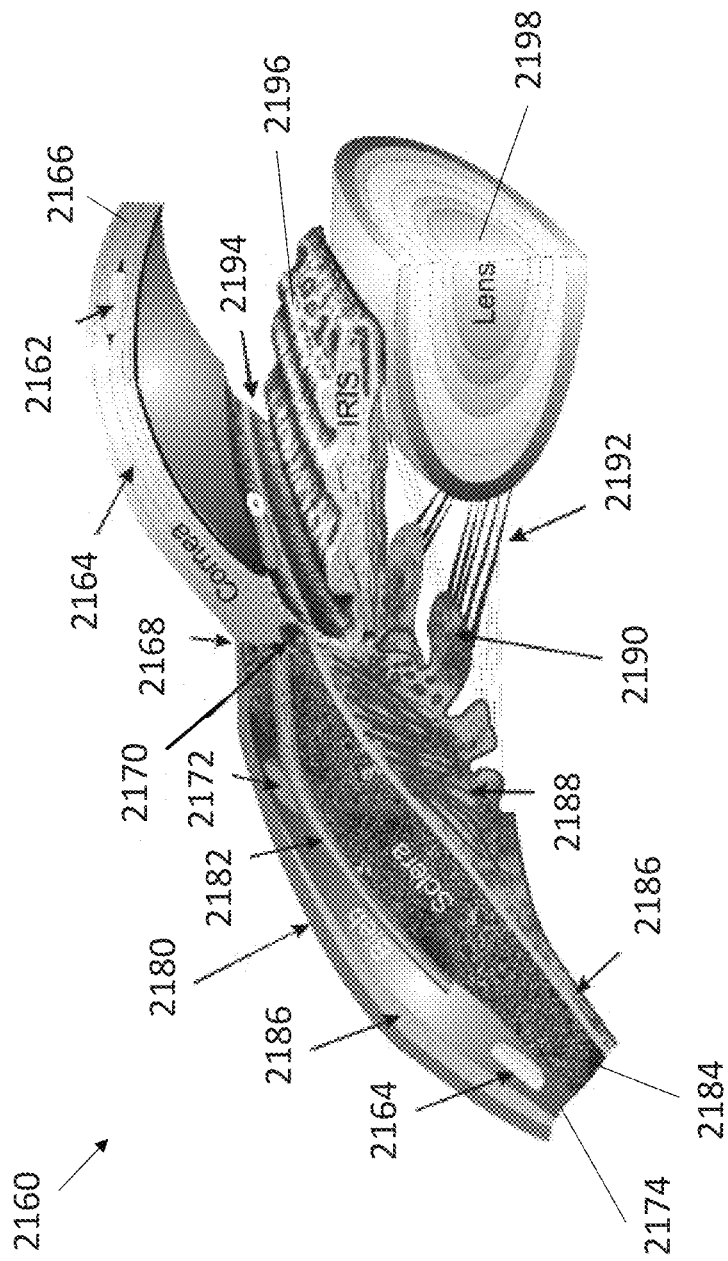
FIG. 21 shows an example embodiment of a cross-sectional ocular structure diagram 2160 showing ocular structures of a human eye.

FIG. 21 shows an example embodiment of a cross-sectional ocular structure diagram 2160 showing ocular structures of a human eye. As shown in the example embodiment, an intra stromal disk implant 2162 can be placed within layers of a corneal stroma 2164 of cornea 2166. Cornea 2166 is coupled with limbus 2168 and canal of Schlemm 2170 is located posteriorly in cornea 2166. Fin 2172 is located anteriorly in bleb 2174 and sub-tenon SIBS disk implants 2176 can be placed posteriorly. Tenons 2178 can be located exterior to bleb 2174 and covered by conjunctiva 2180. MIDI Tube 2182 can be located between bleb 2174 and sclera 2184, which is located exterior to retina 2186. Ciliary muscles 2188 are coupled with ciliary body 2190, which are in turn coupled with ligaments of zonules 2192. Trabecular network 2194 is coupled with iris 2196, in turn covering a portion of lens 2198.

FIG. 22A shows an example embodiment diagram 2200 of treatment regions from a particular three zone model protocol. As shown, an inner zone1 2202, middle zone2 2204 and outer zone3 2206 can be circumferentially located about a central axis.

FIG. 22B shows an example embodiment diagram 2210 of treatment regions from a particular three zone model protocol. As shown, an inner zone1 2202 is shown individually in the upper left quadrant, middle zone2 2204 is shown in the upper right quadrant, outer zone3 is shown in the lower right quadrant, and composite of all three zones 2208 is shown in the lower left quadrant.

FIG. 22C shows an example embodiment diagram 2212 of a simulated medical treatment of an eye. As shown in the example embodiment, treatment to achieve a desired effect can be simulated using an eye model 2216. Here, a laser 2214 is generating a beam of energy for application at location 2220 on a sclera 2218 of eye model 2216. This simulation can be used to determine potential effects of treatment on an eye, for instance to help treat accommodative problems due to aging.

FIG. 22D shows an example embodiment diagram 2230 of a simulated medical treatment of an eye, including treatment regions from a particular three zone model protocol. As shown, an inner zone1 2202, middle zone2 2204 and outer zone3 2206 can be circumferentially located about a central axis at the right of the figure. These zones are shown as sections of sclera 2218.

Figure 22E:
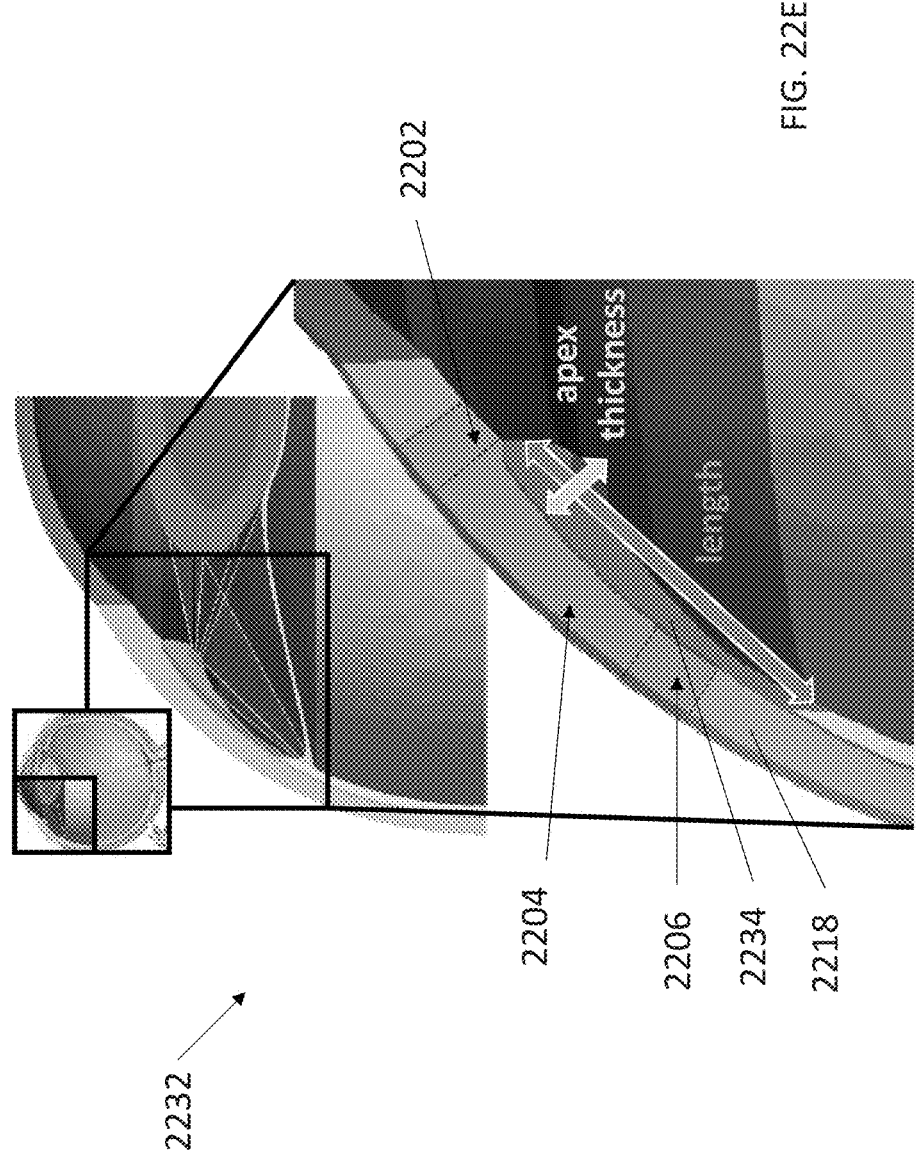
FIG. 22E shows an example embodiment diagram of a simulated medical treatment of an eye, including treatment regions from a particular three zone model protocol.

FIG. 22E shows an example embodiment diagram 2232 of a simulated medical treatment of an eye, including treatment regions from a particular three zone model protocol. As shown, an inner zone1 2202, middle zone2 2204 and outer zone3 2206 can be circumferentially located about a central axis at the right of the figure. These zones are shown as sections of sclera 2218. Here, treatment of sclera 2218 can affect the movement of ciliary body by applying a laser to it. This beam may remove parts, portions, or sections of tissue, thus changing the biomechanical properties of the underlying ciliary muscle 2234. This can affect the length and apex thickness of the ciliary muscle during an accommodative process.

Figures 22F, 22G, 22H:
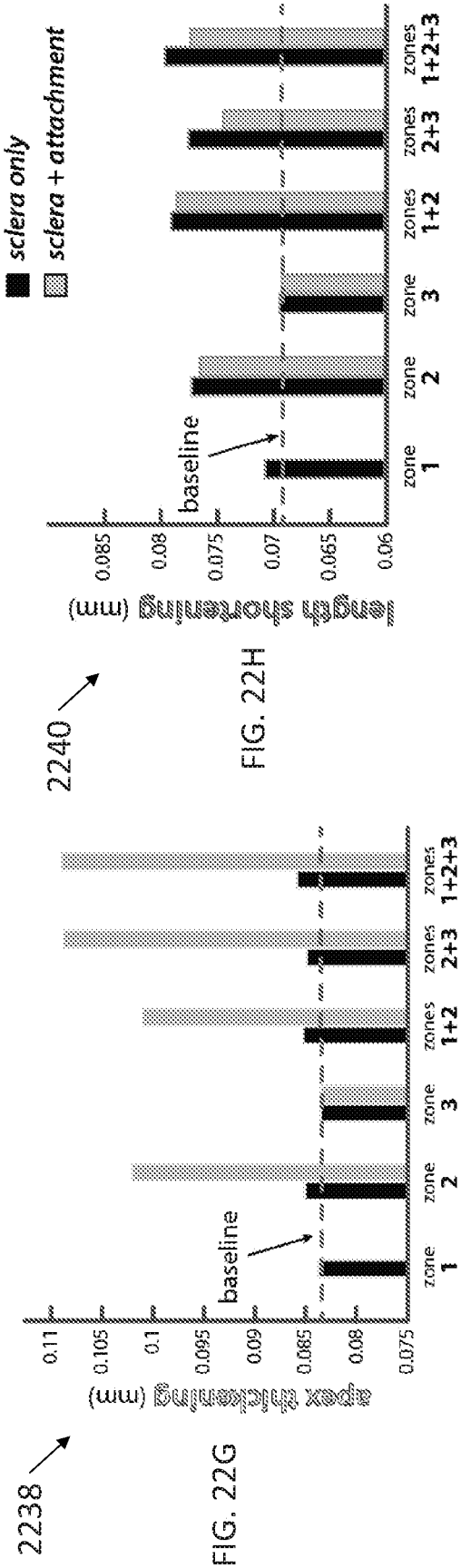
FIG. 22F shows an example embodiment chart of macro results of therapy simulation methods.
FIG. 22G shows an example embodiment chart of apex thickness of the ciliary body for various zones simulated, along with a baseline.
FIG. 22H shows an example embodiment chart of length shortening of the ciliary body for various zones simulated, along with a baseline.

FIG. 22F shows an example embodiment chart 2236 of macro results of therapy simulation methods. As shown in the example embodiment, a baseline simulation can include a first accommodation model with an "old" sclera. An initial presumption is that age-related changes that contribute to presbyopia cause various effects. For example, the eye lens may become more stiff, the ciliary body may be impeded by stiffening of its posterior attachments, the ciliary muscle may lose contractility, and the lens itself may grow, which can lead to reduced tension in the zonules when at rest. Therefore, when creating a simulation, previous computational models can be applied to assess the individual effects of various structures on accommodative function. These changes can be applied in isolation using these new simulations by applying individual changes to various factors. These can include: lens stiffness, sclera stiffness, the sclera attachment to the ciliary muscles and choroid, which can also be coupled with stiffness changes, zonular tension changes, ciliary muscle contraction, and others. In various embodiments, it is beneficial to run simulations with changes from the eye of a thirty-year-old individual to that of a seventy-year-old individual. These simulations can be used to determine which structural changes cause the greatest effects and can highlight the most likely mechanisms of presbyopia. As such, ideal candidates for actual treatments can be identified based on the influence of different changes by simulated age.

Here, a stiff sclera can be set with a modulus of elasticity (E)=2.85 MPa, equivalent to that of an individual of about 50 years old. A tight attachment between the sclera and the ciliary body and choroid can occur and all other parameters can be changed. These include ciliary activation, stiffness of other components, and others as appropriate.

Next, treatment simulations can include use of the baseline model with regionally "restored" sclera stiffness and attachment tightness. This can simulate treated combinations of changes to different zones, both with and without changing attachment by modifying parameters. These changes can be performed in zones: 1, 2, 3, 1+2, 2+3, 1+2+3, and others. As such, a restored sclera can have a modulus of elasticity (E)=1.61 MPa, equivalent to an individual of about 30 years old. These values can simulate a loose attachment between sclera and the ciliary body and choroid. An effect of regional treatment on ciliary deformation in accommodation can be seen in FIGS. 22G-22H, including apex thickening and length shortening, both in millimeters, as shown.

FIG. 22G shows an example embodiment chart 2238 of apex thickness of the ciliary body for various zones simulated, along with a baseline. Here, better results are shown by higher locations on the chart.

FIG. 22H shows an example embodiment chart 2240 of length shortening of the ciliary body for various zones simulated, along with a baseline. Here, better results are shown by higher locations on the chart.

Figures 22I, 22J:
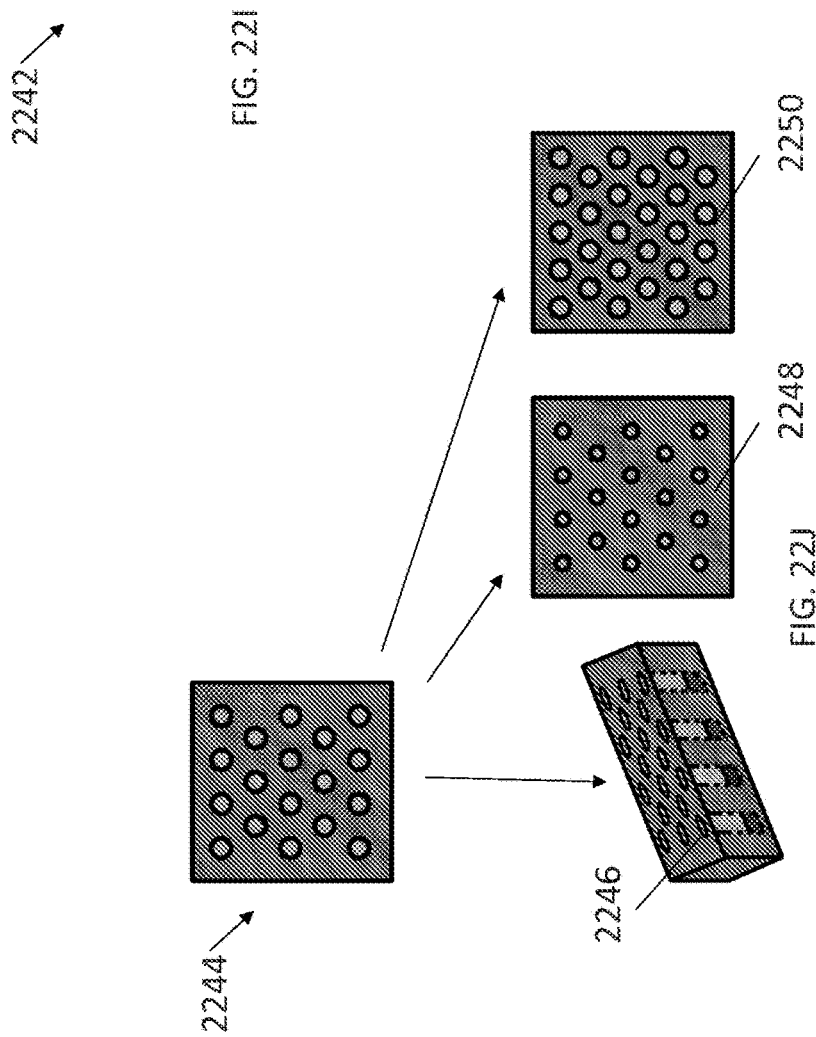
FIG. 22I shows an example embodiment chart of micro results for therapy simulation methods.
FIG. 22J shows an example embodiment diagram of different characteristics of pore density that can be changed. First is depth, pore width, and quantity.

FIG. 22I shows an example embodiment chart 2242 of micro results for therapy simulation methods. Here, pores are made in tissue that can affect biomechanics in the tissue and surrounding or coupled tissues. As shown in the example embodiment, a restored sclera stiffness can be dependent on the treatment, based on the density of pores. Pore density can be a factor of the percent volume of material removed, and can be varied by changing parameters of these pore ablation holes. Parameters can include depth, diameter, quantity, and others as appropriate. Therefore, the resultant stiffness is estimated as a microscale mixture of holes and is assumed to be parallel or evenly spaced and sized with volume equals treatment density or percent of the total. The remaining volume is "old" sclera (E=2.85 MPa). In some embodiments, it has been shown in simulation that remove of about 43.5% of volume operates to change sclera stiffness from older, about 50 years old, to younger, about 30 years old.

FIG. 22J shows an example embodiment diagram 2244 of different characteristics of pore density that can be changed. First is depth 2246, pore width 2248, and quantity 2250.

As a result of these simulations, various questions can be answered by using the model, as follows: First, how does regional restoration of sclera stiffness improve ciliary deformation in accommodation and do certain zones or combinations of zones have a greater effect? Here, treating all 3 zones resulted in the most improved deformation at the ciliary's length and apex; individually treating zone 2 had the greatest effect, while treating zone 3 had the least.

Second, does regional restoration of sclera attachment tightness, in addition to stiffness, augment improvements to ciliary deformation in accommodation? Here, treatment in zones 2 and 3 had a much greater affect in improving ciliary deformation at the apex, corresponding with increasing lens thickness, if the attachment of the sclera to the ciliary/choroid was assumed to return too loose instead of tight.

Third, how do the treatment parameters relate to the change in scleral stiffness in the treated regions? Here, sclera stiffness decreases linearly with increasing treatment density, by the amount of volume removed, that can be determined by the hole diameter and depth as well as the total number of holes. Thus 43% of the volume needs to be removed achieve the same stiffness as the sclera in the accommodating model of an individual about 30 years old.

Fourth, how does regional restoration with different treatments, including different sclera stiffness's, improve ciliary deformation in accommodation? Here, treatments with increasing density improve ciliary deformation at the apex and length. However, changing the stiffness has a limited affect without also changing the attachment tightness.

Additional questions that may be answered with further experimentation include: does sclera's attachment to ciliary become tighter with age, do procedures alter the tightness of this attachment in addition to changing regional sclera stiffness, and others.

Figure 23:
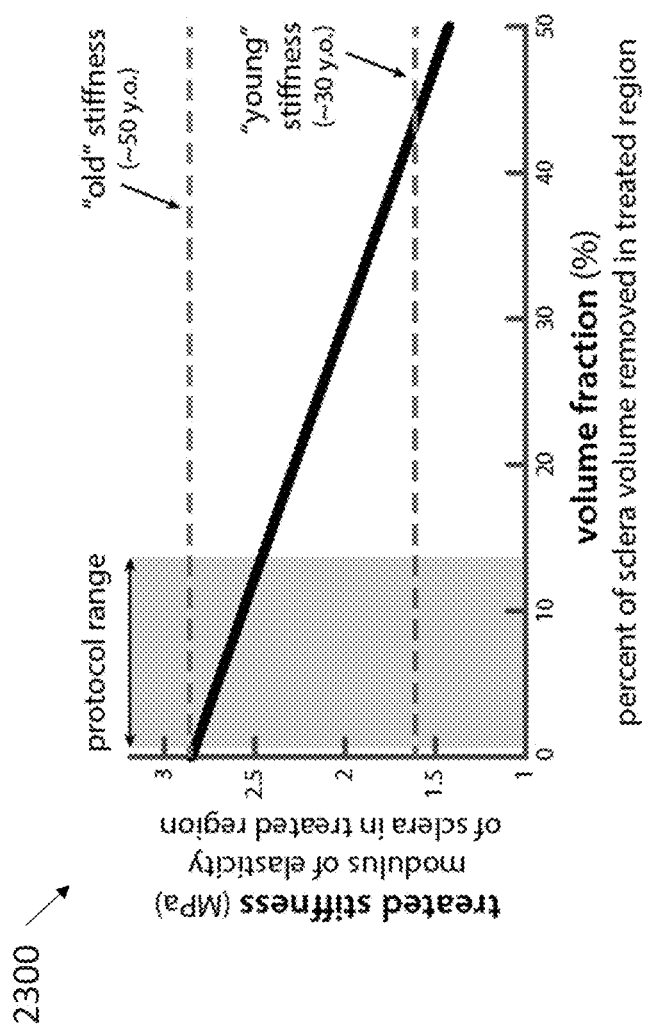
FIG. 23 shows an example embodiment diagram of treated stiffness including modulus of elasticity of sclera in a treated region versus volume fraction or percent of sclera volume removed in the treated region for the simulation.

FIG. 23 shows an example embodiment diagram 2300 of treated stiffness including modulus of elasticity of sclera in a treated region versus volume fraction or percent of sclera volume removed in the treated region for the simulation.

FIG. 24A shows an example embodiment diagram 2251 of a simulated medical treatment of an eye, including treatment regions from a particular five zone model protocol. As shown, an inner zone0 2252, second inner zone1 2202, zone2 2204 and outer zone3 2206, and additional outer zone 2256 can be circumferentially located about a central axis at the right of the figure. These zones are shown as sections of sclera 2218. Here, treatment of sclera 2218 can affect the movement of ciliary body by applying a laser to it. This beam may remove parts, portions, or sections of tissue, thus changing the biomechanical properties of the underlying ciliary muscle 2234. This can affect the length and apex thickness of the ciliary muscle during an accommodative process.

FIG. 24B shows an example embodiment chart 2260 of macro results of therapy simulation methods. In the example embodiment, baseline simulation: original model of healthy accommodation with "old" sclera with a stiff sclera: modulus of elasticity (E)=2.85 MPa, equivalent to about a 50-year old's eye. This can have a tight attachment between the sclera and the ciliary/choroid. All other parameters changed, including ciliary activation, stiffness of other components, and others. Treatment simulations include a baseline model with regionally "treated" sclera stiffness and attachment tightness. These can include treated combinations of zones (with & without changing attachments individually for zones: 0, 1, 2, 3, 4; combined: 1+2+3, 1+2+3+4, 0+1+2+3+4. The treated sclera can have a modulus of elasticity (E)=1.61 MPa, equivalent to that of about a 30 years' old's eye. This eye has a loose attachment between the sclera and the ciliary/choroid and values in an original accommodation model.

FIG. 24C shows an example embodiment chart 2262 of apex thickness of the ciliary body for various zones simulated, along with a baseline, and results that affect scleral stiffness only. Here, better results are shown by higher locations on the chart.

FIG. 24D shows an example embodiment chart 2264 of length shortening of the ciliary body for various zones simulated, along with a baseline, and results that affect scleral stiffness only. Here, better results are shown by higher locations on the chart.

FIG. 24E shows an example embodiment chart 2266 of macro results of therapy simulation methods and results that affect scleral stiffness and attachment.

FIG. 24F shows an example embodiment chart 2268 of apex thickness of the ciliary body for various zones simulated, along with a baseline, and results that affect scleral stiffness and attachment. Here, better results are shown by higher locations on the chart.

FIG. 24G shows an example embodiment chart 2270 of length shortening of the ciliary body for various zones simulated, along with a baseline, and results that affect scleral stiffness and attachment. Here, better results are shown by higher locations on the chart.

FIG. 24H shows an example embodiment chart 2400 of effects of treatment density on ciliary deformation in accommodation that affect scleral stiffness only. Here, sclera in all zones changed to stiffness corresponding with volume fraction of treatment for tight attachment. Treatment stiffness= (1−(volume fraction)/100)×baseline stiffness.

FIG. 24I shows an example embodiment chart 2402 of apex thickness of the ciliary body for various zones simulated versus volume faction percent removed. A protocol range is shown as well as decreased scleral thickness and "young" stiffness.

FIG. 24J shows an example embodiment chart 2404 of length shortening of the ciliary body for various zones simulated versus volume faction percent removed. A protocol range is shown as well as decreased scleral thickness and "young" stiffness.

FIG. 24K shows an example embodiment chart 2406 of effects of treatment density on ciliary deformation in accommodation that affect scleral stiffness and attachment. Here, sclera in all zones changed to stiffness corresponding with volume fraction of treatment for tight attachment.

FIG. 24L shows an example embodiment chart 2408 of apex thickness of the ciliary body for various zones simulated versus volume faction percent removed. A protocol range is shown as well as decreased scleral thickness and "young" stiffness and healthy apex thickening line reference. These results are shown for, tight attachments, loose attachments and changing attachments.

FIG. 24M shows an example embodiment chart 2410 of length shortening of the ciliary body for various zones simulated versus volume faction percent removed. A protocol range is shown as well as decreased scleral thickness and "young" stiffness and healthy length shortening line reference. These results are shown for, tight attachments, loose attachments and changing attachments.

Here, the "treated" sclera stiffness is dependent on volume fraction percent sclera volume removed by treatment. The resultant stiffness estimated as microscale mixture of holes that are assumed to be parallel evenly spaced, sized within a volume that equals the volume fraction or is a percentage of total sclera volume. As such, any remaining volume is "old" sclera (E=2.85 MPa). It was found that there is a need to remove about 43.5% of volume to change sclera stiffness from old a fifty-year old simulated eye to receive the benefits of having a younger thirty-year-old eye. Protocols or combinations of density percentage and depth allow for a maximum volume fraction of 13.7 percent, equivalent to a new stiffness of 2.46 MPa. It should be understood that different numbers of zones and pores can be used in different treatment methods.

FIGS. 24A-24M are able to prove various answers to important questions, as follows. First, how does regional restoration of sclera stiffness improve ciliary deformation in accommodation and do certain zones or combinations of zones have a greater effect? Here, treating all 5 zones resulted in the most improved deformation at the ciliary's length and apex, but not much more than just treating zones 1+2+3. Individually treating zone 1 had the greatest effect on apex thickening and zone 2 had the greatest on length shortening, while treating zone 3 had the least for both.

Next, does regional restoration of sclera attachment tightness and stiffness augment improvements to ciliary deformation in accommodation? Here, individually treating zones 1 & 2 had a much greater affect in improving ciliary deformation at the apex (corresponding with increasing lens thickness) if the attachment of the sclera to the ciliary/choroid was assumed to return too loose instead of tight. Simultaneously treating zones 1-4 (+/−zone 0) had a very large effect on deformation of both ciliary length and apex.

Further, how do the treatment parameters relate to the change in scleral stiffness in the treated regions? Here, scleral stiffness decreases linearly with increasing volume fraction of the amount of volume removed that can be determined by the pore density percentage as a function of the spot size and number of pores, and depth. This resulted in 43% of the volume needs to be removed achieve the same stiffness as the sclera in the accommodating model of about a 30-year-old eye.

Additionally, how does regional restoration with different treatments (therefore different sclera stiffness's) improve ciliary deformation in accommodation? Here, treatments with increasing density improved ciliary deformation at the apex and length. However, changing the stiffness has a limited affect without also changing the attachment tightness. As such, treatments can be designed using these results.

Figure 25A:
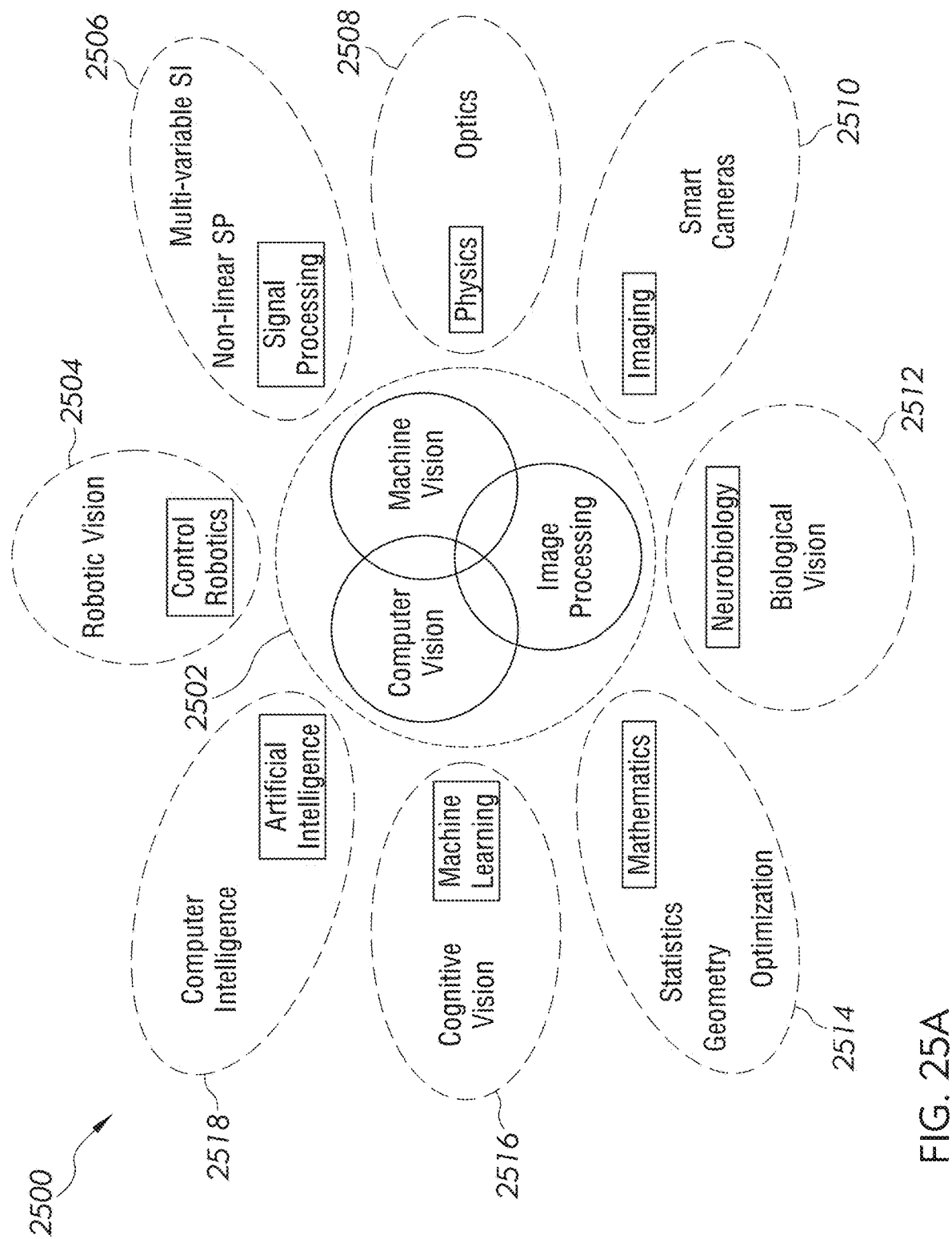
FIG. 25A shows an example embodiment of a conceptual diagram for an artificial neural network for ocular structures of an entire human eye via virtual analysis and particularly for spherically human ocular accommodation procedures.

FIG. 25A shows an example embodiment of a conceptual diagram 2500 for an artificial neural network for ocular structures of an entire human eye via virtual analysis and particularly for spherically human ocular accommodation procedures. As shown in the example embodiment, an overall concept of virtual eye simulation and analysis systems and methods can be modeled as central Venn diagram, including computer vision, machine vision, image processing, and others. These can each be broken down into subsets of one or more of control robotics 2504, signal processing 2506, physics implementation and analysis 2508, imaging 2510, neurobiology 2512, mathematics 2514, machine learning 2516, artificial intelligence 2518, and others. These can further be broken down into robotic vision, multi-variable SI, non-linear SP, optics, smart cameras, biological vision, statistics, geometry and optimization, cognitive vision, computer intelligence, and others.

Algorithms and other software used to implement the systems and methods disclosed herein are generally stored in non-transitory computer readable memory and generally contain instructions that, when executed by one or more processors or processing systems coupled therewith, perform steps to carry out the subject matter described herein. Implementation of the imaging, machine-learning, prediction, automated correcting and other subject matter described previously can be used with current and future developed medical systems and devices to perform medical procedures that provide benefits that are, to date, unknown in the art.

In some instances, the previously described systems, methods and devices are performed prior to or contemporaneous with various medical procedures. Example embodiments of medical systems, methods and devices benefitting from implementation of the prior described subject matter will now be described with respect to various figures. In some embodiments, the prior described subject matter can be implemented in some of the systems, devices and methods described below. In some embodiments they may be implemented in their own systems, methods and devices, along with any required components to accomplish their respective goals, as would be understood by those in the art. It should be understood that medical procedures benefitting from the previously described material are not limited to implementation using the material described hereafter, but other previous, currently performed and future developed procedures can benefit as well.

Figure 25B:
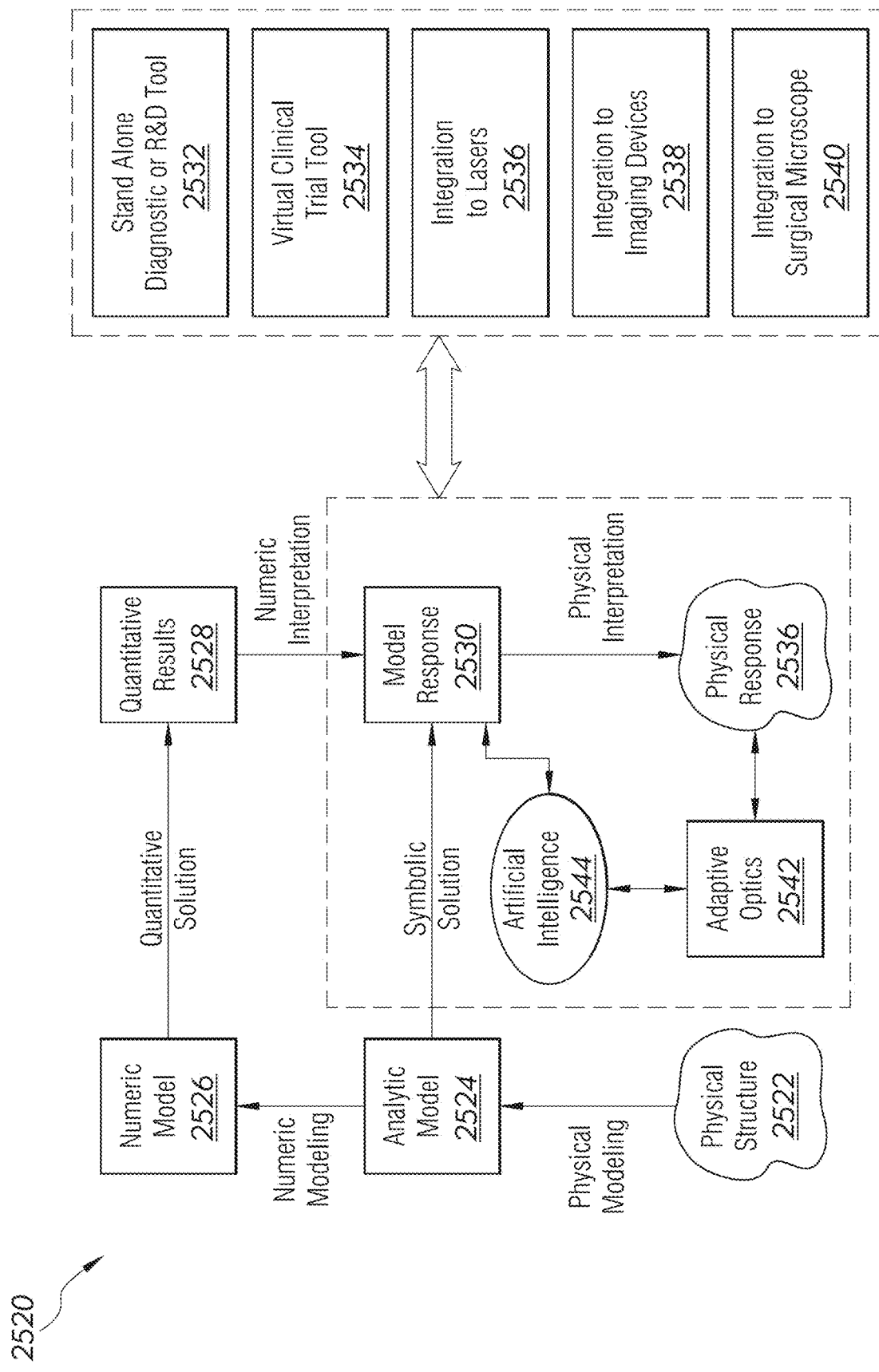
FIG. 25B shows an example embodiment diagram of Artificial Intelligence, Simulations and Field Applications of a simulation structure.

FIG. 25B shows an example embodiment diagram 2520 of Artificial Intelligence, Simulations and Field Applications of a simulation structure. In the example embodiment, physical structure information 2522 can be used for physical modeling input to an analytic model 2524. This can output numeric modeling to a numeric model 2526 and symbolic solutions to a model response 2530. Numeric model 2526 output can be quantitative solutions for a quantitative results analysis 2528. This can output numeric interpretations to model response 2530 which can output a physical interpretation of a physical response 2536. Thus, adaptive optics 2542 can be used in combination with AI module 2544. These can be used to control or affect a standalone diagnostic or R&D tool 2532; virtual clinical trial tool 2534; integration with lasers 2536; imaging devices 2538; surgical microscopes 2540; and others. These can also be implemented provide feedback to model response 2530, and affect adaptive optics 2542, AI 2544 and physical response 2536.

Figure 25C:
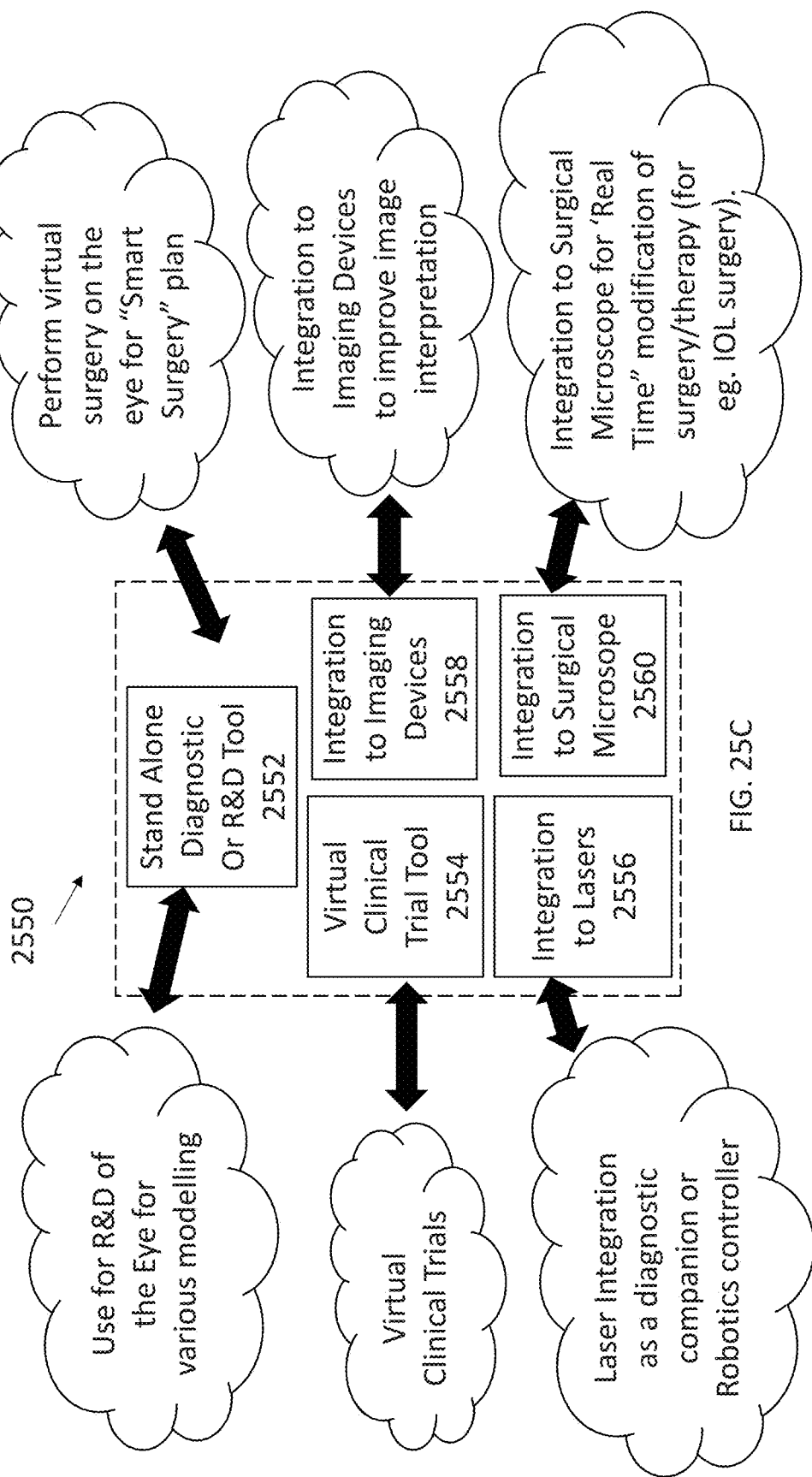
FIG. 25C shows an example embodiment diagram of preferred applications of Artificial Intelligence, Simulations and Field Applications.

FIG. 25C shows an example embodiment diagram 2550 of preferred applications of Artificial Intelligence, Simulations and Field Applications. One or more preferred applications can include: 1) use for standalone research and development tools of ocular structures for various modeling implementations 2552; 2) use in virtual clinical trials via one or more virtual clinical trial tools 2554; 3) integration with lasers 2556 for use as or with a diagnostic companion or robotics controller 2556; 4) use during for or with virtual surgery performance on the an eye model to help develop a "Smart Surgery" plan; 5) integration with imaging devices 2558 to improve image interpretations; 6) integration with surgical microscopes 2560 for "real time" modifications of surgery or therapeutic procedures, such as intraocular lens (IOL) implantation surgery or other scleral surgeries; and 7) others. As discussed herein, these applications can include manipulation and changes to material properties, as they relate to the aging process, dysfunction relative to average ocular abilities, and others.

Functions of simulations can include: 1) simulations of ideal biomechanics for optimizing total visual function and best central optical power for accommodation; 2) simulations of ideal biomechanics for optimizing total visual function and best optical power of the cornea 3) simulations for optimizing ideal scleral biomechanics to maximize ciliary muscle function; 4) simulation optimization for scleral material properties and lens properties which maximize ciliary function; 5) simulations with variable tuning of ciliary muscle fibers, including circular, radial, and longitudinal fibers, in proportionate amounts to optimize lens deformation during accommodation and discommendation; 6) stress, strain, and other mapping of forces on ocular structures; 7) simulations of ideal biomechanics for optimizing decreased outflow of aqueous from the trabecular meshwork; 8) simulations of ideal biomechanics for optimizing retinal decompression of lamina cribrosa and parapapillary sclera; 9) simulations for optimizing scleral rejuvenation; 10) simulations for optimizing surgical outcomes of intra ocular lens surgery; 11) simulations for optimizing surgical or therapeutic outcomes for corneal surgery; 12) age progression simulations to evaluate long term effects of aging on eye function; 13) age progression simulations to evaluate long term stability and outcomes of various surgical procedures of the eye; 14) simulations for analyzing testing of applications, therapies, surgical manipulation, implantation devices and pharmacological treatments of the eye via virtual clinical trials; 15) simulations for demonstrating ideal ocular drug delivery and penetration locations and pathway; and 16) others.

Figure 25D:
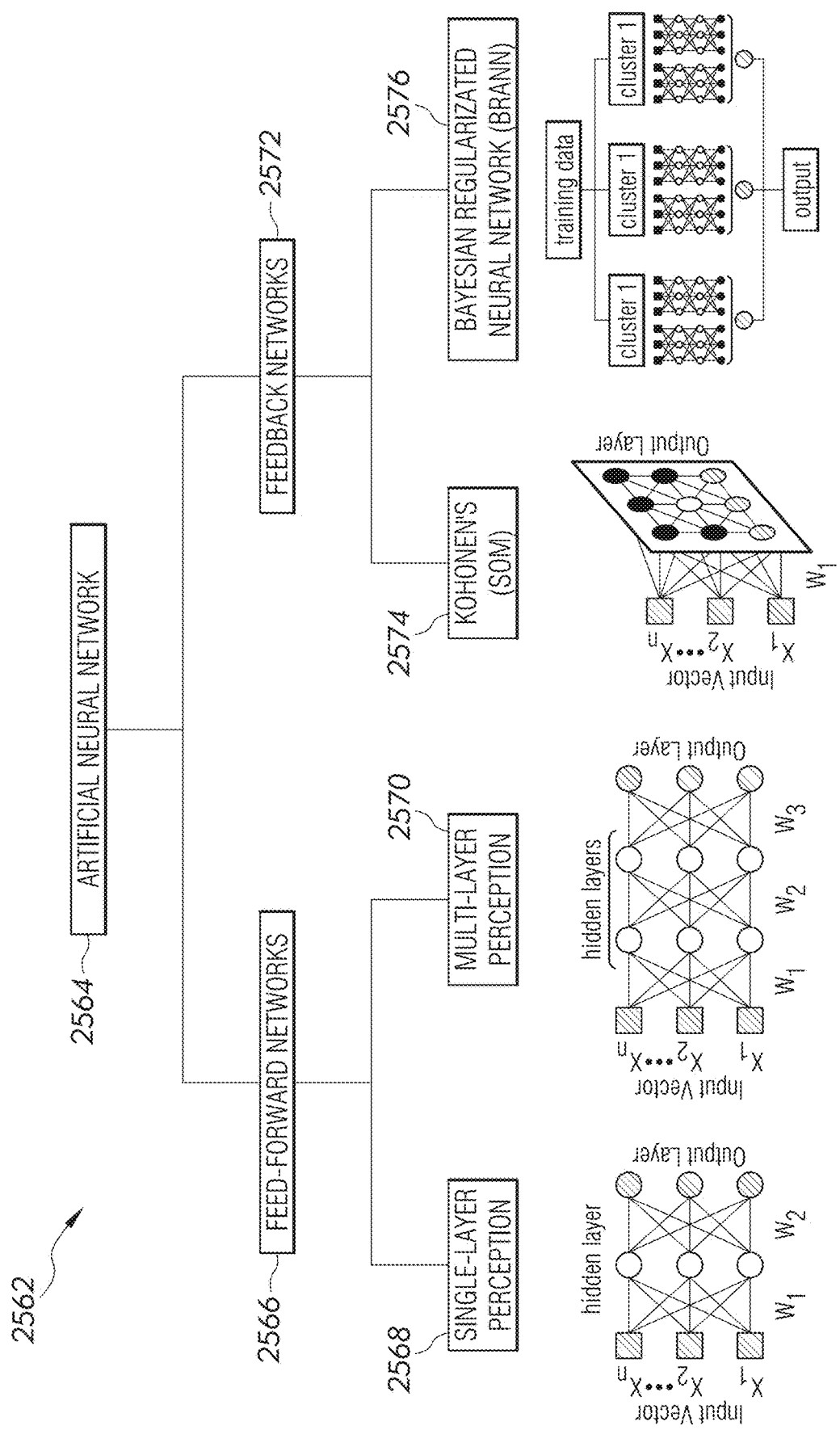
FIG. 25D shows an example embodiment of a prior art artificial neural network model diagram.

FIG. 25D shows an example embodiment of a prior art artificial neural network model diagram 2562. As shown in the example embodiment, an artificial neural network 2564 can be a one or more of a feed-forward network 2566, feedback network 2572, or combinations thereof. Feed-forward networks can be one or more of single layer perceptron networks 2568, multi-layer perceptron networks 2570, or combinations thereof. Feedback networks 2572 can be one or more of Kohonen's (SOM) networks 2574, Bayesian Regualrizated neural networks 2576, (BRANN), or combinations thereof.

Figure 25E:
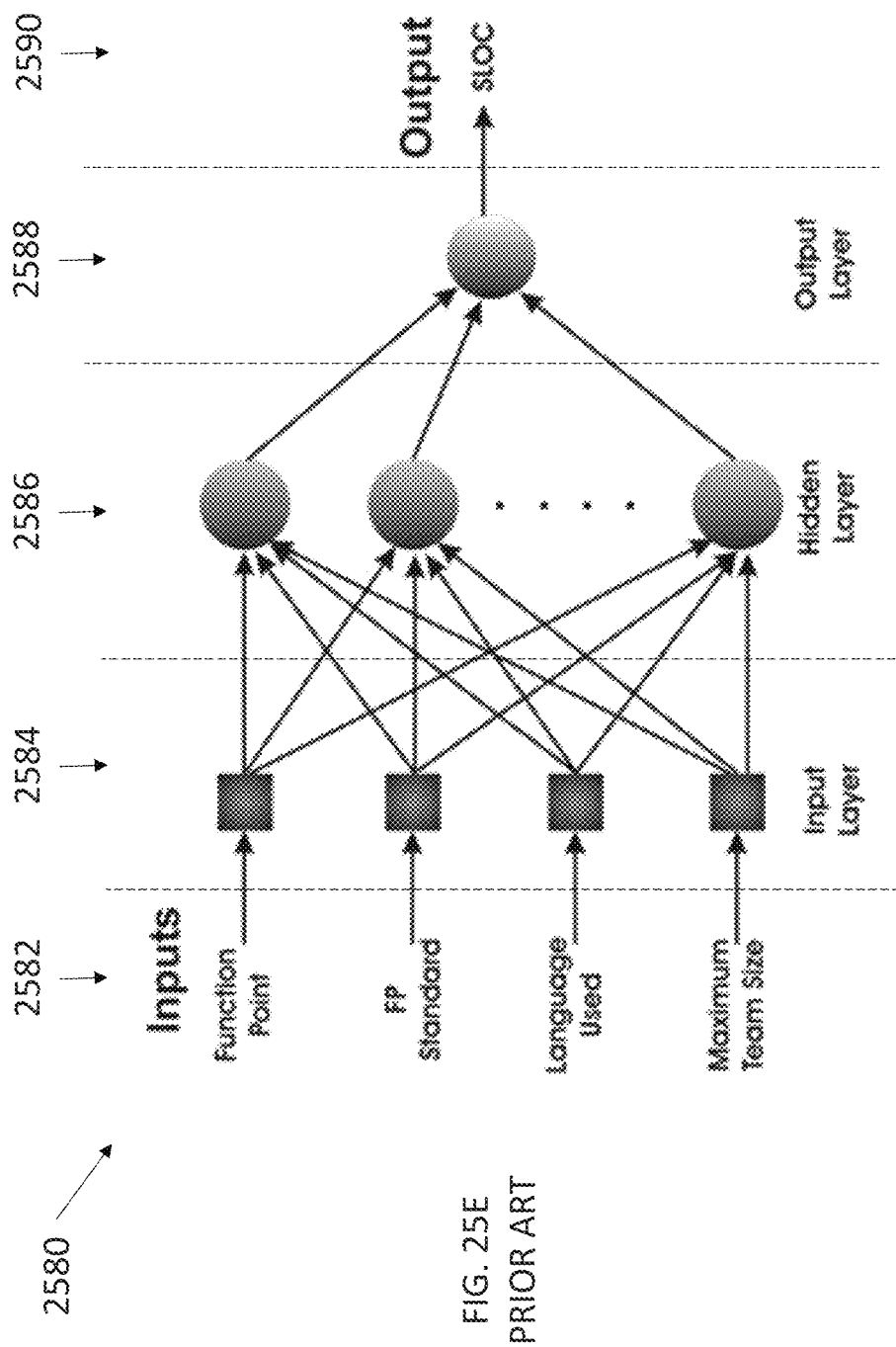
FIG. 25E shows an example embodiment of a prior art artificial neural network diagram including complex relationship inputs and outputs for shape accommodation biophysics.

FIG. 25E shows an example embodiment of a prior art artificial neural network diagram 2580 including complex relationship inputs and outputs for shape accommodation biophysics. As shown in the example embodiment, various inputs 2582 can include function points, function point standards, languages used, maximum team sizes, and others. These can be transmitted or entered in an input layer 2584 for initial processing before being sent to a hidden layer for further processing, depending on what structures and functions they affect. Once processed, they can be sent to an output layer 2588 and transmitted, applied, or displayed as outputs, for example as an SLOC.

Figure 26A:
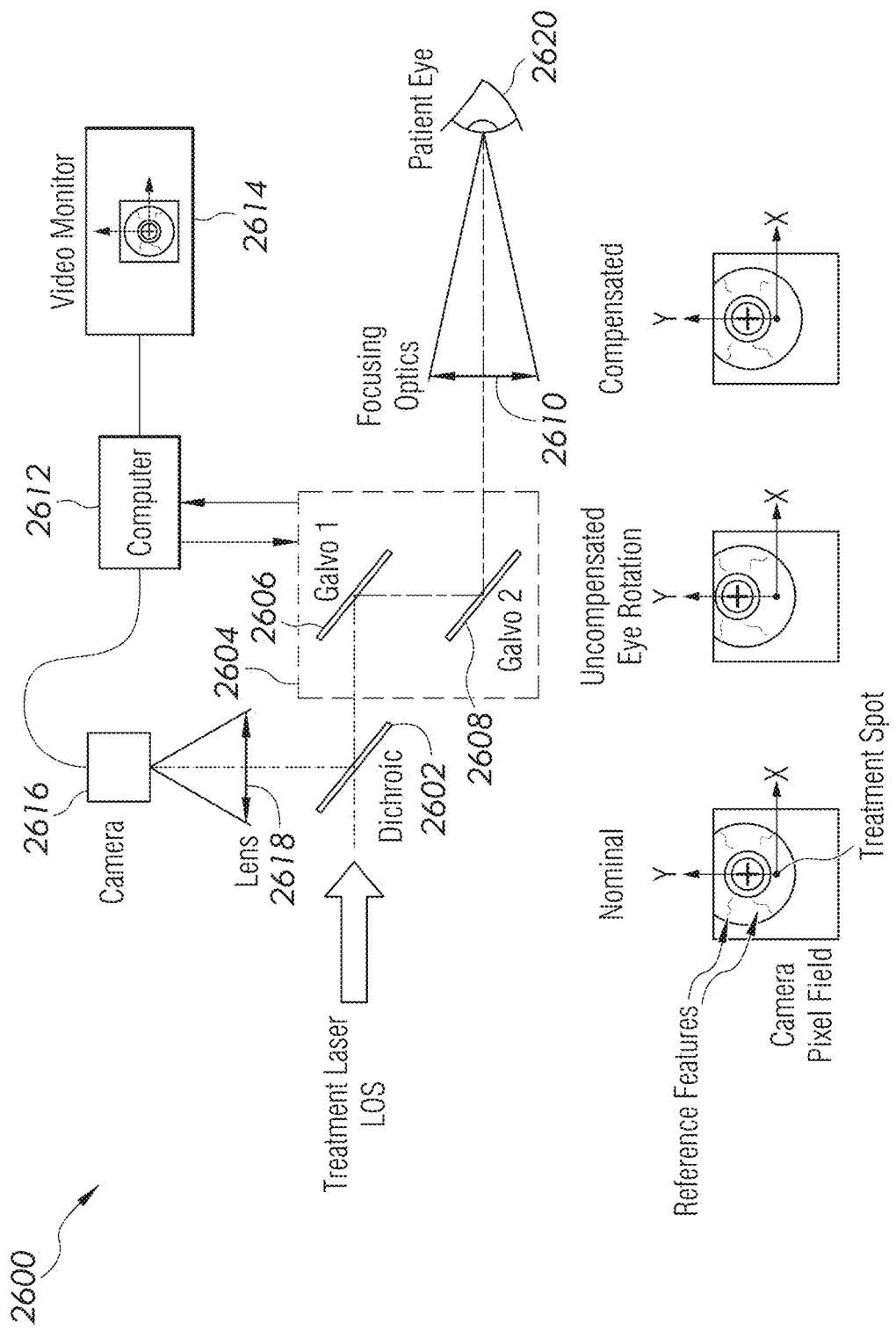
FIG. 26A illustrates a laser treatment system according to an embodiment of the present invention.

FIG. 26A illustrates a laser treatment system according to an embodiment of the present invention. Turning to FIG. 26A, a laser treatment system 2600 according to an embodiment of the present invention is shown. In this embodiment, a treatment laser beam travels to dichroic 2602. At dichroic 2602 the laser beam travels to Galvo Setup 2604 which consists of Galvo1 2606 and Galvo2 2608. The beam then passes from Galvo Setup 2604 to focusing optics 2610 and ultimately to patient eye 2620.

Also provided for in this embodiment is a control and monitoring system which broadly consists of a computer 2612, video monitor 2614, and camera 2616. Camera 2616 provides monitoring of the laser beam at dichroic 2602 via lens 2618. Camera 2616 transmits its feed to computer 2612. Computer 2612 is also operable monitor and control Galvo Setup 2604. Computer 2612 is also coupled to video monitor 2614 to provide a user or operator a live feed from camera 2616.

In some embodiments of the invention a dual axis closed loop galvanometer optics assembly is used.

Since multiple lasers systems may be used for treatment in some embodiments, additional laser systems will now be described.

The laser system may include a cage mount galvanometer containing a servo controller, intelligent sensor, feedback system and mount assembly with an optical camera. Some embodiments may include use of a cage mount galvanometer optics assembly. Some embodiments may include ultra-high resolution nano-positioners to achieve sub-nanometer resolution.

To expand, FIG. 26A shows more detail of a CCD (or CMOS) camera-based eye tracker subsystem. Dichroic 2602 beamsplitter is used to pick off visible light, while allowing the IR treatment beam to transmit. The beamsplitter 2602 is located in front of the steering elements, shown here as galvo mirrors 2604. Lens 2618 images the tissue plane (eye) onto the camera. Features in the image field (e.g. blood vessels, edge of the iris, etc.) are identified by image processing and their coordinates in the camera pixel field computed. If the eye moves within the pixel field frame-to-frame, the change in position of the reference features can be computed. An error function is computed from the change in reference feature position and commands issued to the galvo mirrors 2604 to minimize the error function. In this configuration, the optical line of sight is always centered on the treatment spot, which is at a fixed coordinate in the camera pixel field. The apparent motion from repositioning the galvos 2604 will be to move the eye image relative to the fixed treatment spot.

Figure 26B:
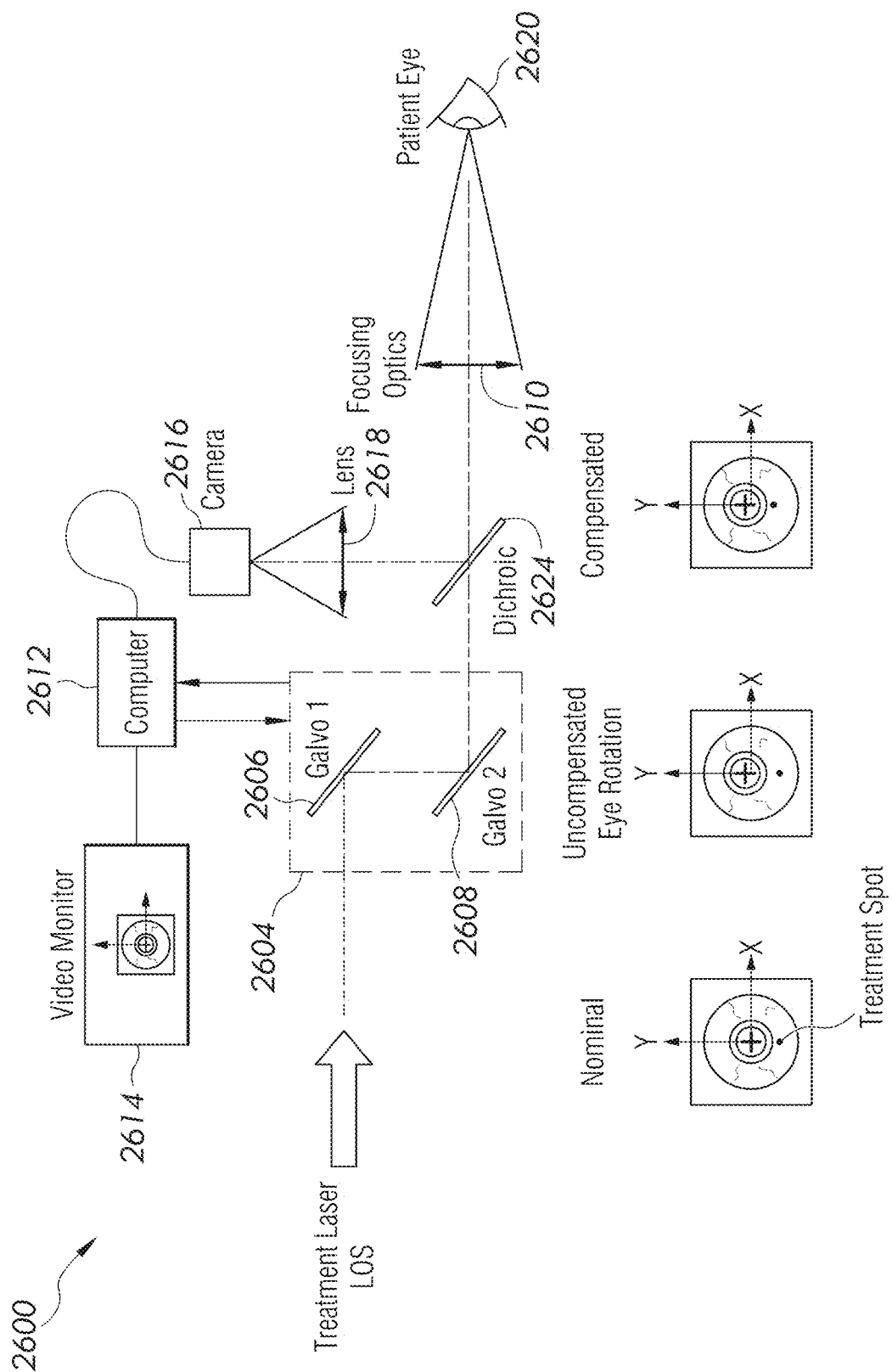
FIG. 26B illustrates a laser treatment system according to an embodiment of the present invention.

FIG. 26B illustrates a laser treatment system according to an embodiment of the present invention. Turning to FIG. 26B, another embodiment of a laser treatment system 2622 according to an embodiment of the present invention is shown. FIG. 26B is similar to FIG. 26A, except that the eye tracking subsystem is located after galvo mirrors 2604.

In this embodiment, a treatment laser beam travels to Galvo Setup 2604 which consists of Galvo1 2606 and Galvo2 2608. The beam then passes from Galvo Setup 2604 to dichroic 2624. At dichroic 2624 the laser beam travels to focusing optics 2610 and ultimately to patient eye 2620.

Also provided for in this embodiment is a control and monitoring system which broadly consists of a computer 2612, video monitor 2614, and camera 2612. Camera 308 provides monitoring of the laser beam at dichroic 2624 via lens 2618. Camera 2612 transmits its feed to computer 2612. Computer 2612 is also operable monitor and control Galvo Setup 2604. Computer 2612 is also coupled to video monitor 2614 to provide a user or operator a live feed from camera 308.

Here, the eye image is shown centered in the pixel field. When eye motion is detected within the pixel field, the galvos 2604 are repositioned to move the treatment spot to a new position within the pixel field corresponding to the movement of the eye, and to a desired fixed position relative to the eye reference features.

With reference to the aforementioned biofeedback loop, eye tracking includes in some embodiments includes use of light source producing an infrared illumination beam projected onto an artificial reference affixed to an eye. The infrared illumination beam is projected near the visual axis of the eye and has a spot size on the eye greater than the reference and covering an area when the reference moves with the eye.

In some embodiments the reference has a retro-reflective surface that produces backward scattering orders of magnitude stronger than backward scattering from the eye would. An optical collector may be configured and positioned a distance from the eye to collect this backward scattered infrared light in order to form a bright image spot of the reference at a selected image location.

The bright image spot appears over a dark background with a single element positioning detector positioned at the selected image location to receive the bright image spot and configured to measure a two-dimensional position of the bright image spot of the reference on the positioning detector. An electric circuit may be coupled to the positioning detector to produce positioning signals indicative of a position of the reference according to a centroid of the bright image spot based on the measured two-dimensional position of the bright image spot on the positioning detector.

Figure 26C:
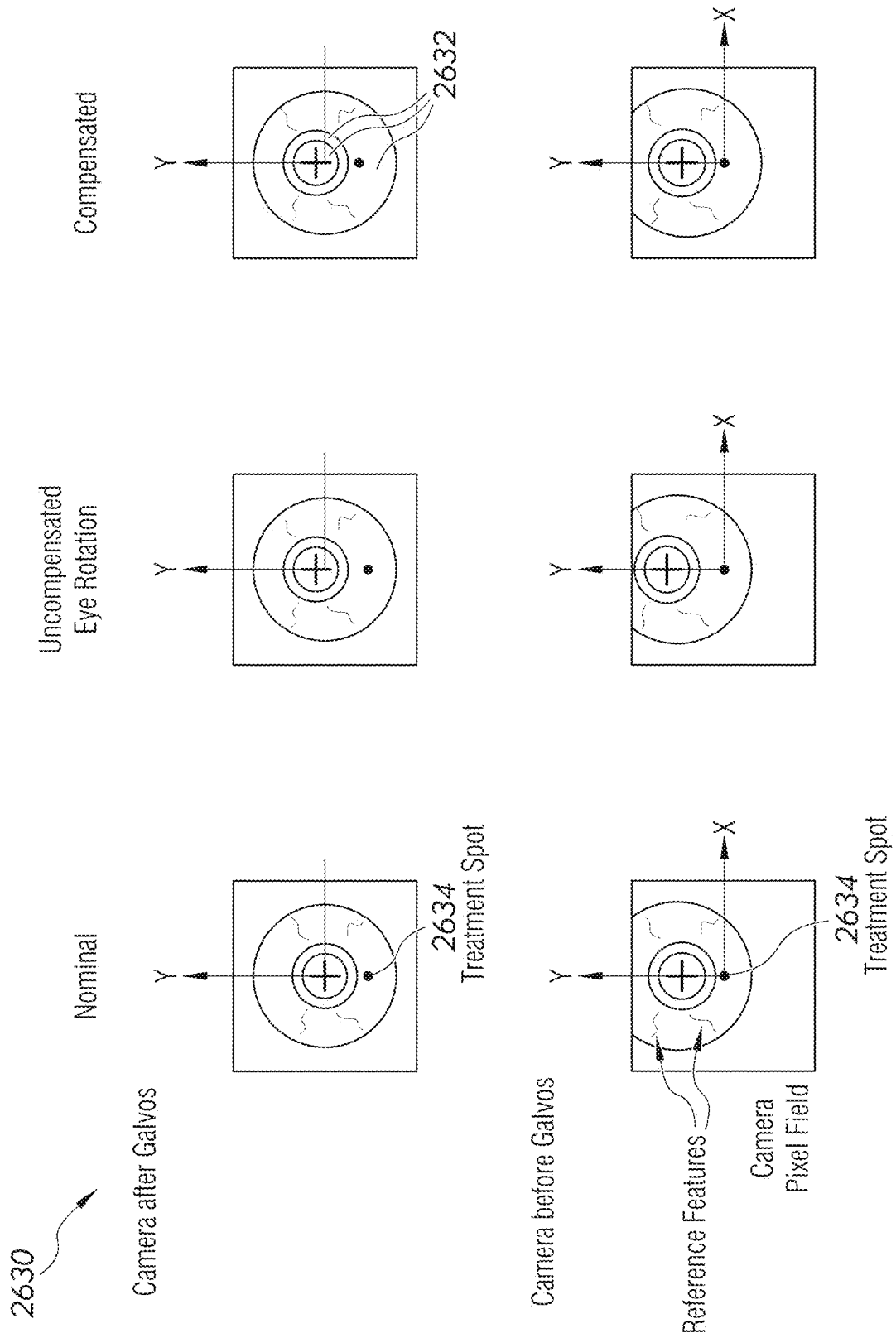
FIG. 26C illustrates a camera correction system according to an embodiment of the present invention.

FIG. 26C illustrates a camera correction system with images diagram 2630 according to an embodiment of the present invention. In the example embodiment, the top row illustrates the camera focus location after galvos have been used and the bottom row illustrates the camera focus location before galvos. Various landmarks 2632 may be seen in the example embodiments including capillaries, iris, pupil, etc. Treatment spot 2634 may also be seen in each embodiment.

As is shown in the example embodiment the top row of focus before the galvos each show the pupil of as the center pixel of each image. Compensation after galvos in the bottom row allows the treatment spot 2634 to remain the focus of the camera's attention in each image and thereby allow the system to remain in position for the associated procedure.

Figure 26D:
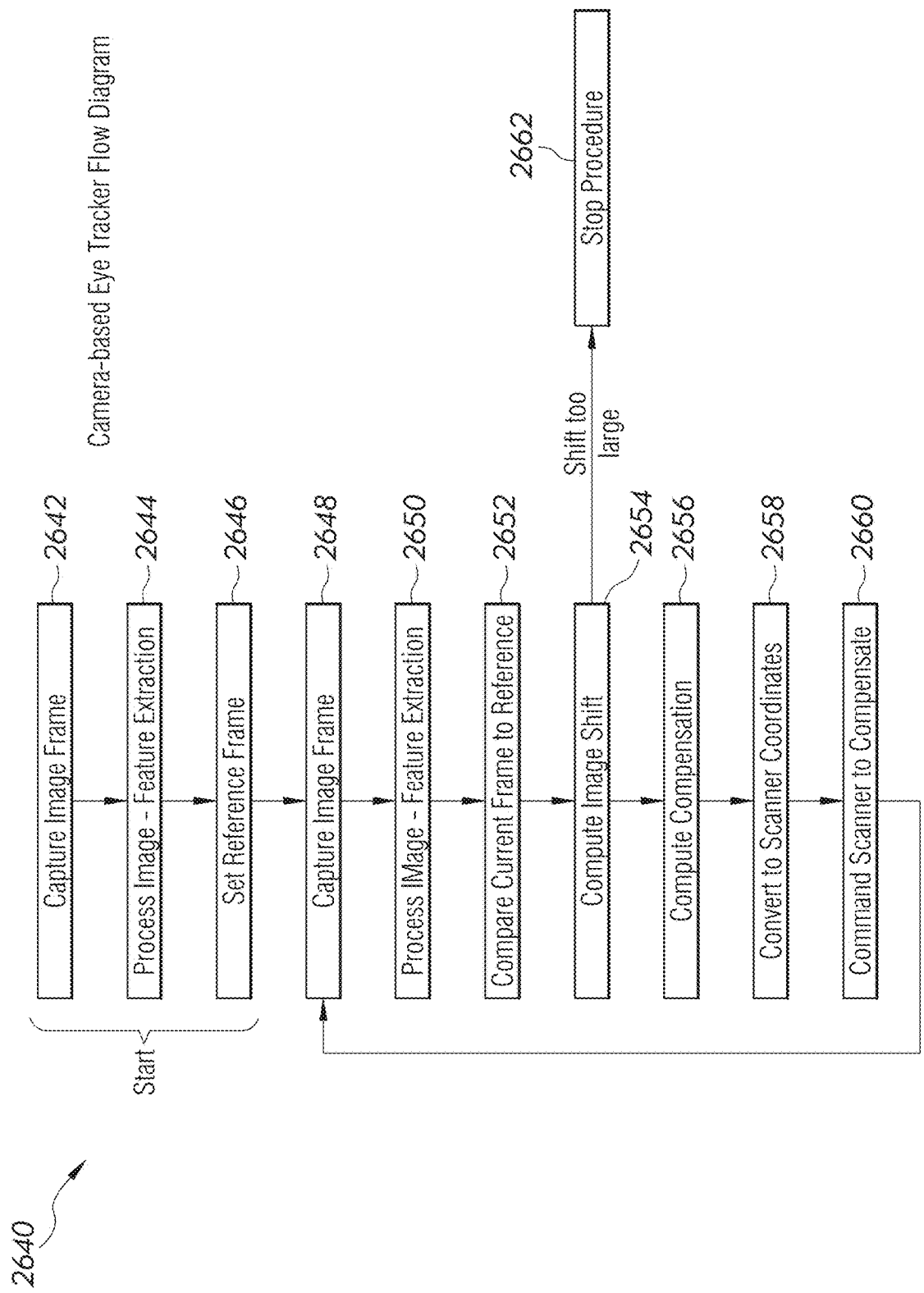
FIG. 26D illustrates a flow diagram of a camera-based eye tracker process according to an embodiment of the present invention.

FIG. 26D illustrates a flow diagram of a camera-based eye tracker process 2640 according to an embodiment of the present invention. Turning to FIG. 26D, a camera-based eye tracker flow diagram 2640 is depicted showing a process according to an embodiment of the present invention.

Broadly put, the diagram represents the use of a CCD or CMOS camera to capture an image of eye. Image data is transmitted to a computer, where key features are segmented/extracted (e.g. blood vessels, iris features, edge of pupil). The image is stored as a reference frame. Subsequent images are then compared to reference frame. A shift is computed after comparing reference features in pixel coordinates. Conversion of pixel coordinates to scanning system coordinates then occurs before commanding the scanning system to deviate treatment beam line of site to restore relationship relative to reference features. If the shift is too large or out of range of scanning system, halt procedure and take steps to reacquire the target image field.

As a more detailed explanation referencing each step, an initialization or starting sequence according to some embodiments requires capture image frame in step 2642 before processing the captured image frame in order to extract features in step 2644. This captured frame with extracted features is then used to set a reference frame in step 2646.

After a reference frame is set, step 2648 consists of capturing an additional image frame, called a current frame. This image or current frame is processed in step 26500 in order to extract features. Step 2652 consists of comparing the current frame to the reference frame which was set in step 2656. An image shift is computed between the current frame and the reference frame in order to determine the difference between the frames. A comparison to a pre-set threshold allows the system to determine if the image shift exceeds the pre-set threshold and stops the procedure at this point by going to step 2662.

If an image shift does not exceed the pre-set threshold and therefore is not too large, the system computes a compensation level in step 2656 in order to compensate for the change or shift between the current frame and the reference frame. This compensation level is computed into physical coordinates used by a scanner in step 2658. The scanner is then commanded to compensate using the coordinates in step 2660. After this compensation step 2648 occurs and another current image frame is captured and the cycle continues.

Figure 27A:
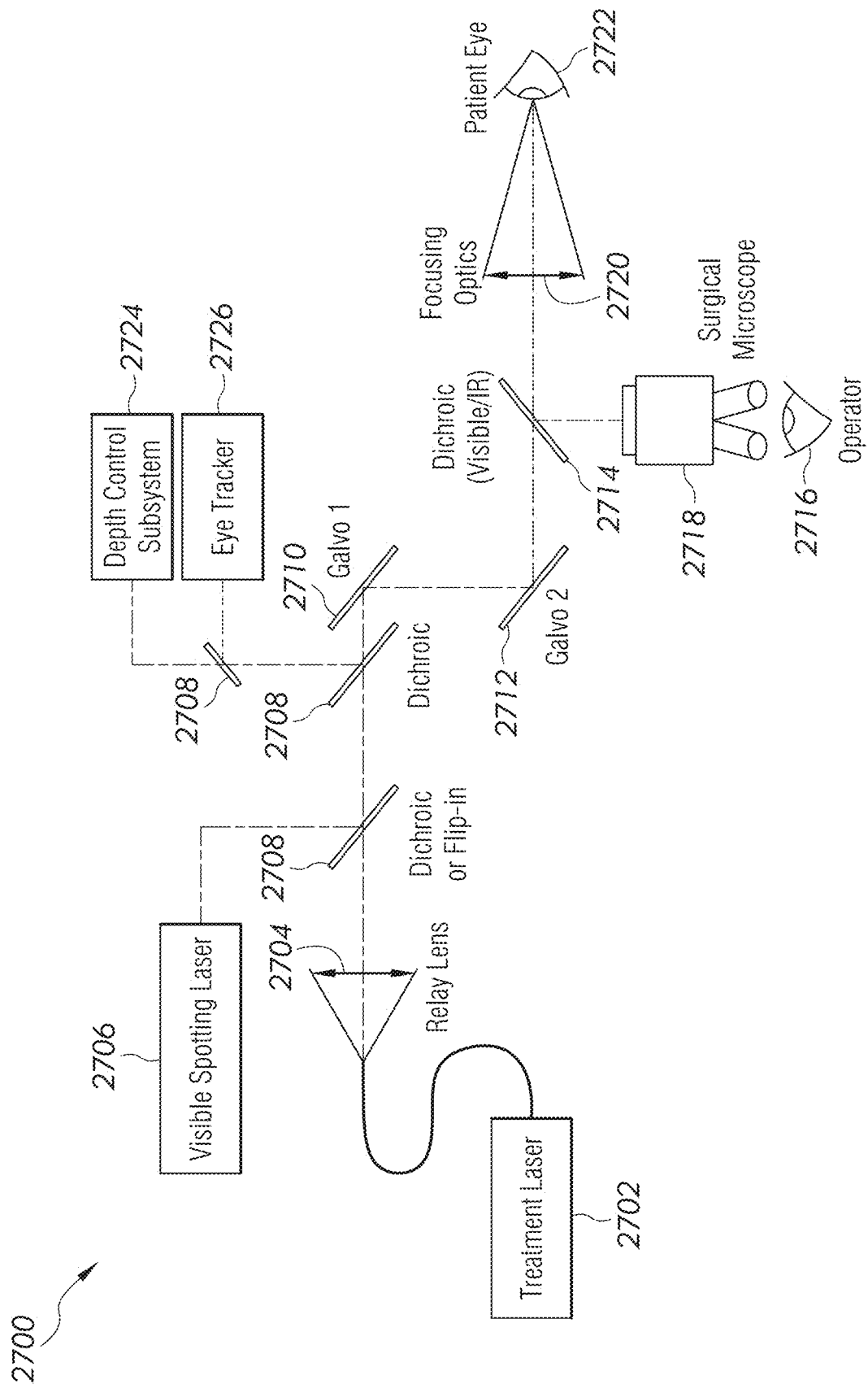
FIG. 27A illustrates a laser treatment system according to an embodiment of the present invention.

FIG. 27A illustrates a laser treatment system diagram 2700 according to an embodiment of the present invention. In the example embodiment, laser treatment system 2700 consists of a treatment laser 2702 emitting a laser beam which travels through relay lens 2704 to dichroic or flip-in 2708. Visible spotting laser 2706 emits a laser beam which also travels to dichroic or flip-in 2708. In some embodiments, the beams from treatment laser 2702 and visible spotting laser 2706 may meet simultaneously at first dichroic or flip-in 2708. In other embodiments, the beams may reach first dichroic or flip-in 2708 at staggered times.

The beam or beams leave first dichroic or flip-in 2708 and travels to a second dichroic 2708. The beam or beams leave second dichroic 2708 and travel to Galvo1 2710. Galvo1 2710 may consist of a mirror which rotates through a galvanometer set-up in order to move a laser beam. The beam or beams leave Galvo1 2710 and travel to Galvo2 2712 which may be a similar setup to Galvo1 2710. The beam or beams leave Galvo2 2712 and travel to dichroic (visible/IR) 2714. Operator 2716 may monitor the beam or beams at dichroic (visible/IR) 2714 by using a surgical microscope 2718. The beam or beams travel from dichroic (visible/IR) 2714 through focusing optics 2720 to patient eye 2722.

In FIG. 27A, additional monitoring elements are provided for use by operator 2716 to aid in medical procedures. Depth control subsystem 2724 assists in controlling the depth of ablation procedures in accordance with the present invention and receives input from second dichroic 2708.

Similarly, eye tracker 2726 assists in tracking landmarks on patient eye 2722 during medical procedures in accordance with the present invention and also receives input from second dichroic 2708. Another dichroic 2708 is shown in the example embodiment splitting the beam with outputs to eye tracker 2726 and depth control subsystem 2724.

Figure 27B:
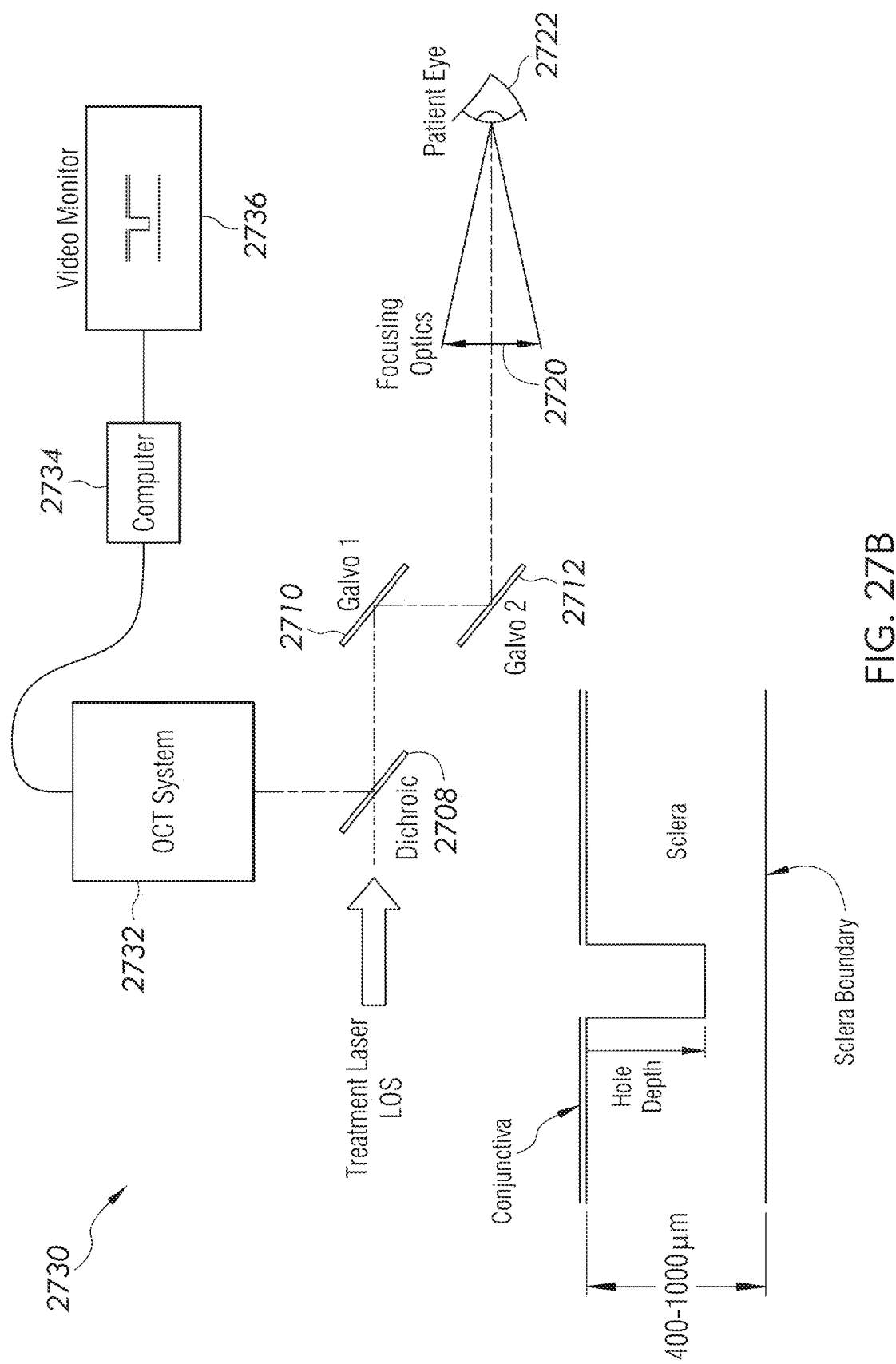
FIG. 27B illustrates a laser treatment system including ablation pore depth according to an embodiment of the present invention.

FIG. 27B illustrates a laser treatment system diagram 2730 including ablation pore depth according to an embodiment of the present invention. FIG. 27B generally shows a treatment laser beam traveling to dichroic 2708 before travelling to Galvo1 2710, then to Galvo2 2712, through focusing optics 2720, and to patient eye 2722.

An OCT system 2732 is an Optical Coherence Tomography system used to obtain subsurface images of the eye. As such, when coupled to computer 2734 which is coupled to video monitor 2736, OCT system 2732 provides a user or operator the ability to see subsurface images of the tissue ablation.

In at least some embodiments OCT provides a real-time, intraoperative view of depth levels in the tissue. OCT may provide for image segmentation in order to identify sclera interior boundary to help better control depth.

OCT system 2732 uses an OCT measurement beam, injected into the treatment beam line of sight via a dichroic beam splitter 208, located before the scanning system. In this way, the OCT system 2732 line of sight is always centered on the pore being ablated. The OCT system 2732 is connected to a computer 2734 for processing the images and for control of the laser. In various embodiments, OCT system 2732 can be on axis, off axis, or combinations thereof.

In some embodiments of the invention an anatomy avoidance subsystem is provided to identify critical biological obstacles or locations during procedures (e.g. blood vessels and others). As such, subsurface visualization may be provided to identify obstacles such as blood vessels intraoperatively.

Also shown in FIG. 27B is a simple diagram of an ablation pore in the sclera showing an example of the depth of an ablation in relation to the inner boundary of the sclera.

Figure 27C:
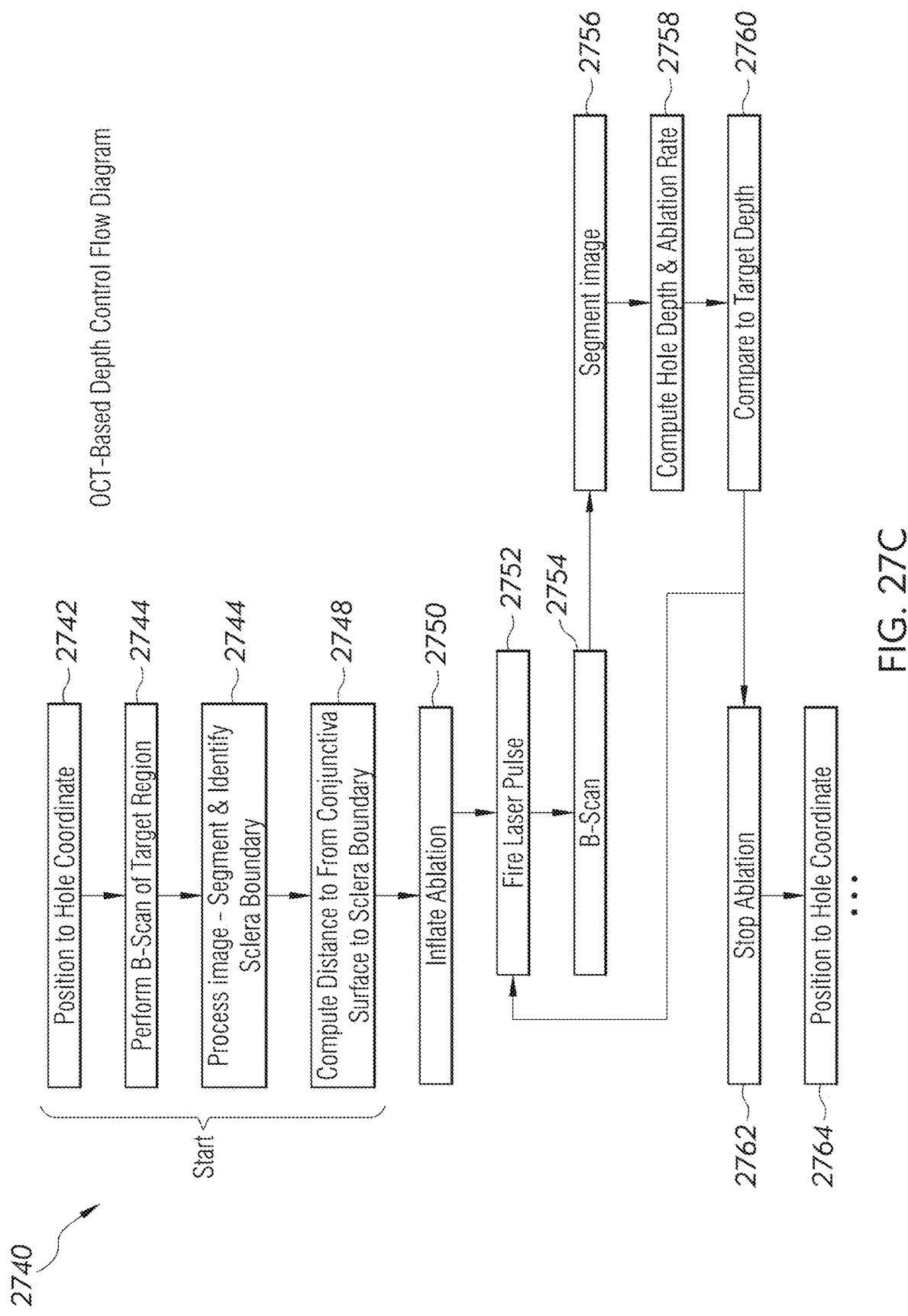
FIG. 27C illustrates a flow diagram of OCT-based depth control according to an embodiment of the present invention.

FIG. 27C illustrates a flow diagram 2740 of OCT-based depth control according to an embodiment of the present invention. In general, The OCT system executes a repetitive B-scan, synchronized with the laser. In some embodiments, OCT system can be a swept source OCT. The B-scan shows the top surface of the conjunctiva and/or sclera, the boundaries of the pore being ablated, and the bottom interface between the sclera and the choroid or ciliary body. Automatic image segmentation algorithms are employed to identify the top and bottom surfaces of the sclera (typically 400-1000 microns thick) and the boundaries of the ablated pore. The distance from the top surface of the sclera to the bottom surface of the pore is automatically computed and compared to the local thickness of the sclera. In some embodiments this occurs in real time. When the pore depth reaches a predefined number or fraction of sclera thickness, ablation is halted and the scanning system indexed to the next target ablation location. In some embodiments images may be segmented to identify interior sclera boundaries.

With reference to the steps in the figure, in the example embodiment a starting or initialization set of steps occurs first. This starting set of steps begins with positioning to a pore coordinate in step 2742. AB-scan of the target region occurs in step 2744. This scan creates an image which is processed in step 2746 in order to segment and identify the sclera boundary. A distance is then computed in step 2748 between the conjunctive surface and the sclera boundary.

After completion of this starting set of steps ablation is initiated in step 2750. A laser beam pulse is fired in step 2752 followed by a B-scan in step 2754. This B-scan creates an image that is then segmented in step 2756 and pore depth and ablation rate are computed from the image in step 2758. This pore depth and ablation rate are compared to the target depth in step 2760. If the target depth has not been reached, then the process loops back to step 2752 and repeats. Upon reaching a target depth step 2760 stops the ablation process in step 2762 and the starting process begins again at step 2742 with positioning to a next pore coordinates.

Figure 28:
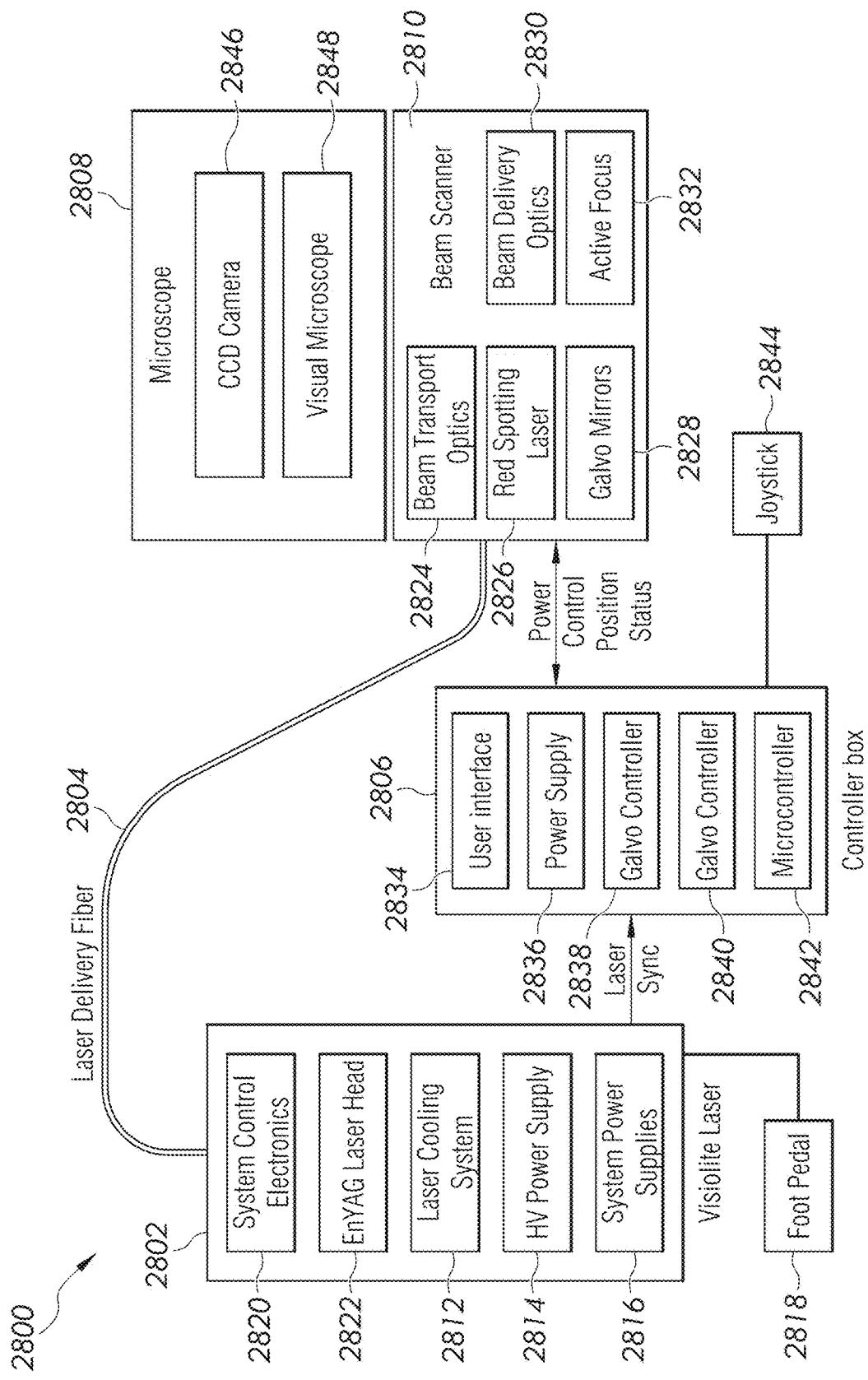
FIG. 28 illustrates a laser treatment system component map showing relation of related subsystems according to an embodiment of the present invention.

FIG. 28 illustrates a laser treatment system component diagram 2800 showing relation of related subsystems according to an embodiment of the present invention. In general laser treatment system component map 2800 shows a laser 2802, a laser delivery fiber 2804, laser control system 2806, monitoring system 2808, and beam control system 2810.

Laser 2802 is generally made up of several subsystems. In the example embodiment, these subsystems include system control electronics 2820, Er:YAG laser head 2822, laser cooling system 2812, HV power supply 2814, and system power supplies 2816. Foot pedal 2818 provides some control for the system user. Laser 2802 transmits a laser beam via laser delivery fiber 2804 to beam control system 2810.

Beam control system 2810 is generally made up of beam transport optics 2824, red spotting laser 2826, galvo mirrors 2828, beam delivery optics 2830, and active focus 2832.

Laser control system 2806 maintains a link to laser 2802 via a laser sync and to beam control system 2810 via power control position status. Laser control system 2806 is generally made up of a user interface 2834, power supply 2836, galvo controller 2838, galvo controller 2840, and microcontroller 2842. Laser control system 2806 is also manipulable via joystick 2844.

Monitoring system 2808 is generally made up of CCD camera 2846 and visual microscope 2848.

In some embodiments, a fiber laser is used which is composed of an undoped cladding and a doped core of higher refraction. The laser beam travels through the fiber guided within the fiber core and experiences a high amplification due to the length of interaction. Fiber lasers are considered advantageous to other laser systems because, among other qualities, they have simple thermal management properties, high beam quality, high electrical efficiency, high optical efficiency, high peak energy, in addition to being low cost, requiring low maintenance, having superior reliability, a lack of mirror or beam path alignment, and they are lightweight and generally compact.

In some embodiments of the invention spot arrays may be used in order to ablate multiple pores at once. These spot arrays may, in some cases, be created using microlenses and also be affected by the properties of the laser. A larger wavelength may lead to a smaller number of spots with increased spot diameter.

Figure 29:
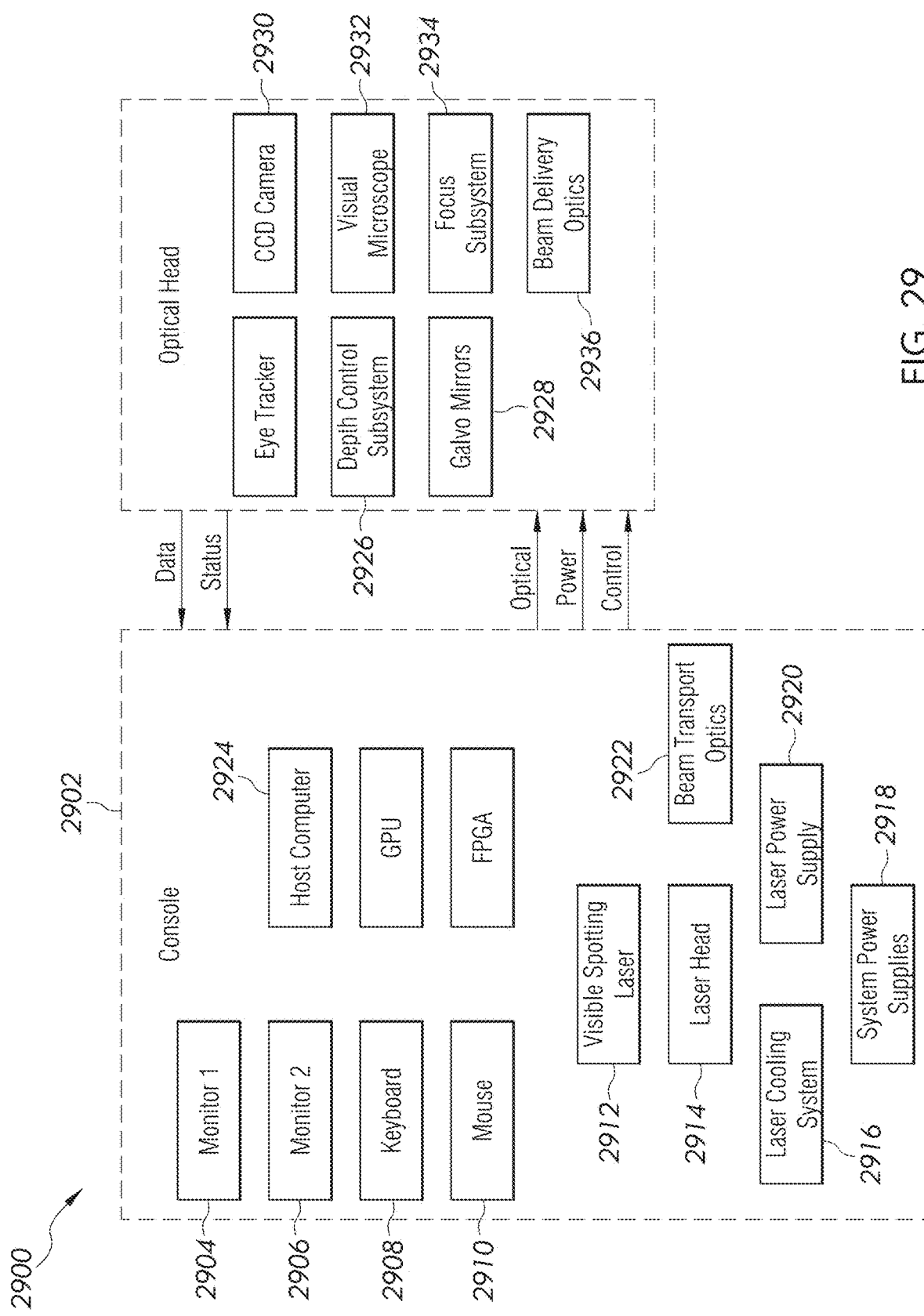
FIG. 29 illustrates a laser treatment system according to an embodiment of the present invention.

Turning to FIG. 29, a laser treatment system 2900 is shown according to an embodiment of the present invention. Laser treatment system 2900 is generally made up of control system 2902, optics and beam controls.

Control system 2902 includes monitor1 2904 and monitor2 2906 as well as keyboard 2908 and mouse 2910 to provide a user the ability to interact and control with a host computer 2924 running computer programs. In many embodiments the computer programs running on host computer 2924 include control programs for controlling visible spotting laser 2912, laser head 2914, laser cooling system 2916, system power supplies 2918, laser power supply 2920, and beam transport optics 2922.

Also provided for in this embodiment are depth control subsystem 2926, galvo mirrors 2928, CCD Camera 2930, visual microscope 2932, focus subsystem 2934, and beam delivery optics 2936.

Preoperative measurement of ocular properties and customization of treatment to an individual patient's needs is beneficial in many embodiments. Preoperative measurement of ocular properties may include measuring intraocular pressure (IOP), scleral thickness, scleral stress/strain, anterior vasculature, accommodative response, refractive error, and accommodation including depth of focus, extended range of focus, Visual Strehl Optical Function, accommodative amplitude and multiple optical components of the eye. Measurement of scleral thickness may include use of optical coherence tomography (OCT). Measurement of scleral stress/strain may include using Brillouin scattering, OCT elastography, photo-acoustics with light plus ultrasound, and others. Measurement of anterior vasculature may include using OCT or Doppler OCT. Measurement of refractive error may include using the products such as the iTrace trademarked product from Tracey Technologies Corp.

Intraoperative biofeedback loops may be important during the procedure in order to keep the physician informed on the progress of the procedure. Such feedback loops may include use of topographical measurements and monitoring "keep away" zones such as anterior ciliary arteries.

Biofeedback loops may include a closed-loop sensor to correct for nonlinearity in the piezo scanning mechanism. The sensor in some embodiments may offer real-time position feedback in a few milliseconds and utilizing capacitive sensors for real-time position feedback.

Sensor/feedback apparatus may also perform biological or chemical "smart sensing" to allow ablation of target tissue and protect or avoid surrounding tissue. Other embodiments can include smart sensing of nanoparticles, robotic smart sensing, combinations of sensing types, and others. In some instances, this smart sensing may be accomplished by using a biochip incorporation in a mask which is activated by light irradiation and senses location, depth, size, shape, or other parameters of an ablation profile. Galvo-optic assemblies are also contemplated in some embodiments and may be used to gage numerous parameters of laser steering and special function.

Figure 30B:
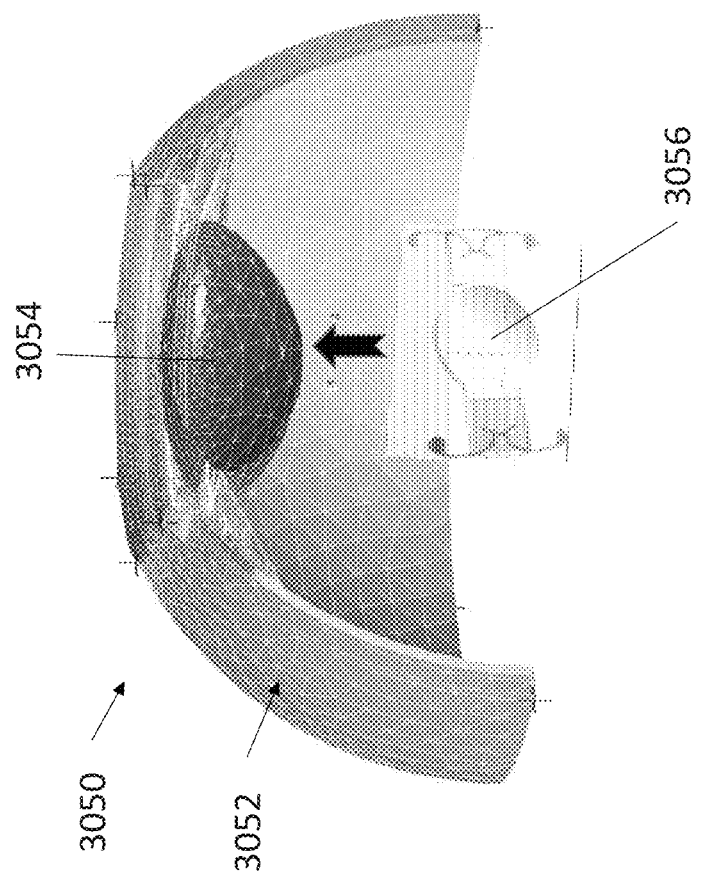
FIG. 30B shows an example embodiment diagram 3050 of a simulated eye 3052 and implantable IOL.
Figure 30A:
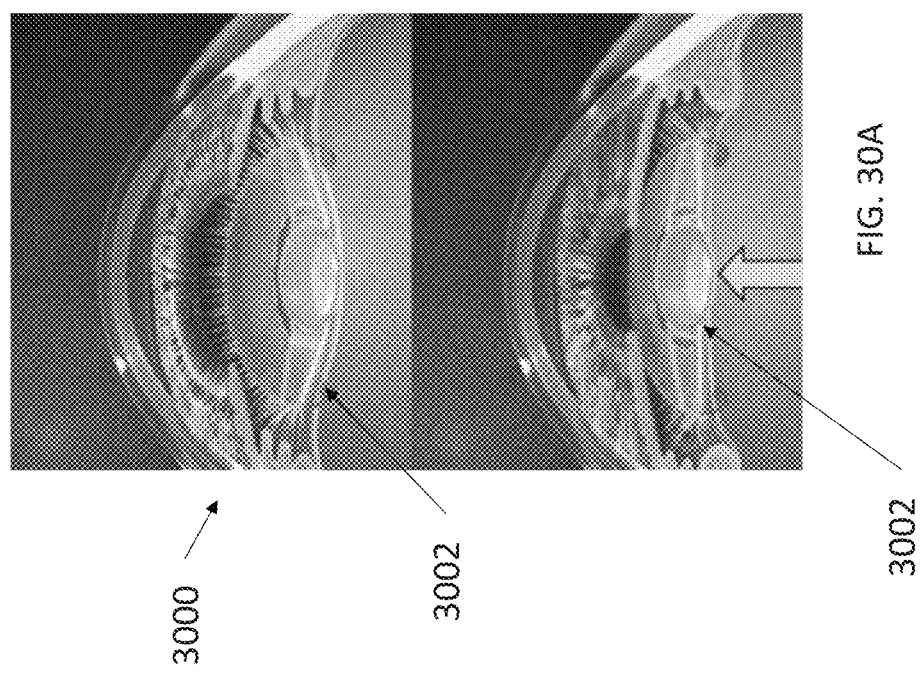
FIG. 30A shows an example embodiment cross-sectional diagram of effects of an accommodating intraocular lens (IOL) on an eye, including location placement.

FIG. 30A shows an example embodiment cross-sectional diagram 3000 of effects of an accommodating intraocular lens (IOL) on an eye, including location placement. As shown in the example embodiment, an intraocular lens 3002 can cause changes in accommodation functionality when implanted, by making the eye act in a healthier manner between an unaccommodated state in the upper portion of FIG. 30A and an accommodated state in the lower portion of the figure. In various embodiments, IOL's can be monofocal, multifocal, or other types, and may or may not be exclusively for accommodative purposes. Here, mechanisms of action are shown as well as optical outcomes of the IOL devices. Other implications, features, and effects of the devices can be visualized, analyzed, and assessed via one or more simulations after modeling.

FIG. 30B shows an example embodiment diagram 3050 of a simulated eye 3052 and implantable IOL 3056. As shown in the example embodiment, effects of IOL 3056 can be modeled according to physical and material principles, as discussed elsewhere herein, and then simulations can be run in order to determine the effects on muscles and ocular structures, such as lens 3054.

FIG. 31A shows an example embodiment diagram 3100 of an eye model 3102 with a plurality of implantable stents 3156. Here, stent 3156 can be used in minimally invasive glaucoma surgery, or for other types of procedures.

FIG. 31B shows an example embodiment diagram 3120 of effects of implantable stents 3156 on ocular structural movements during accommodation and other processes. Here, simulation can include analysis of hydrodynamics of aqueous flow upon implementation of the MIGS device with and without accommodation function in various embodiments. Other physiological impacts of the treatment device can also be visualized, simulated, and analyzed.

FIG. 31C shows an example embodiment diagram 3150 of a simulated eye 3152 and ocular stents 3156. As shown in the example embodiment, effects of ocular stents 3156 can be modeled according to physical and material principles, as discussed elsewhere herein, and then simulations can be run in order to determine the effects on muscles and ocular structures, such as lens 3154.

FIG. 32A shows an example embodiment diagram 3200 of a MIGS device 3202 for treatment of ocular conditions, such as glaucoma. As shown in the example embodiment, MIGS device 3202 can include a hollow cylindrical snorkel 3204, having a lumen 3206 therein. Lumen 3206 can turn at a right angle down a body 3208, which can have one or more exterior retention arches 3210. Body 3208 can have an interior rail 3212 extending along its length, about 1 mm. Body 3208 can end at a self-trephining tip 3214.

FIG. 32B shows an example embodiment diagram 3220 of a MIGS device 3202 implanted in an eye 3222 for treatment. As shown in the example embodiment, body 3208 of MIGS device 3202 can extend in a canal 3226, while lumen 3206 of cylindrical snorkel 3204 allows for fluid to travel through it to relieve ocular pressure.

FIG. 32C shows an example embodiment diagram 3230 of a MIGS device 3202 for implantation in an eye 3252 for treatment. As shown in the example embodiment, trabecular meshwork 3254 can be an implantation site.

FIG. 32D shows an example embodiment diagram 3240 of a simulated eye 3252 and MIGS device 3202 for implantation simulation. As shown in the example embodiment, effects of implantation of MIGS device 3202 can be modeled according to physical and material principles, as discussed elsewhere herein, and then simulations can be run in order to determine the effects on muscles and ocular structures, such as intraocular pressure at or near a trabecular framework site 3254. Aqueous biomechanics and aqueous flow can also be simulated and analyzed.

Figure 33:
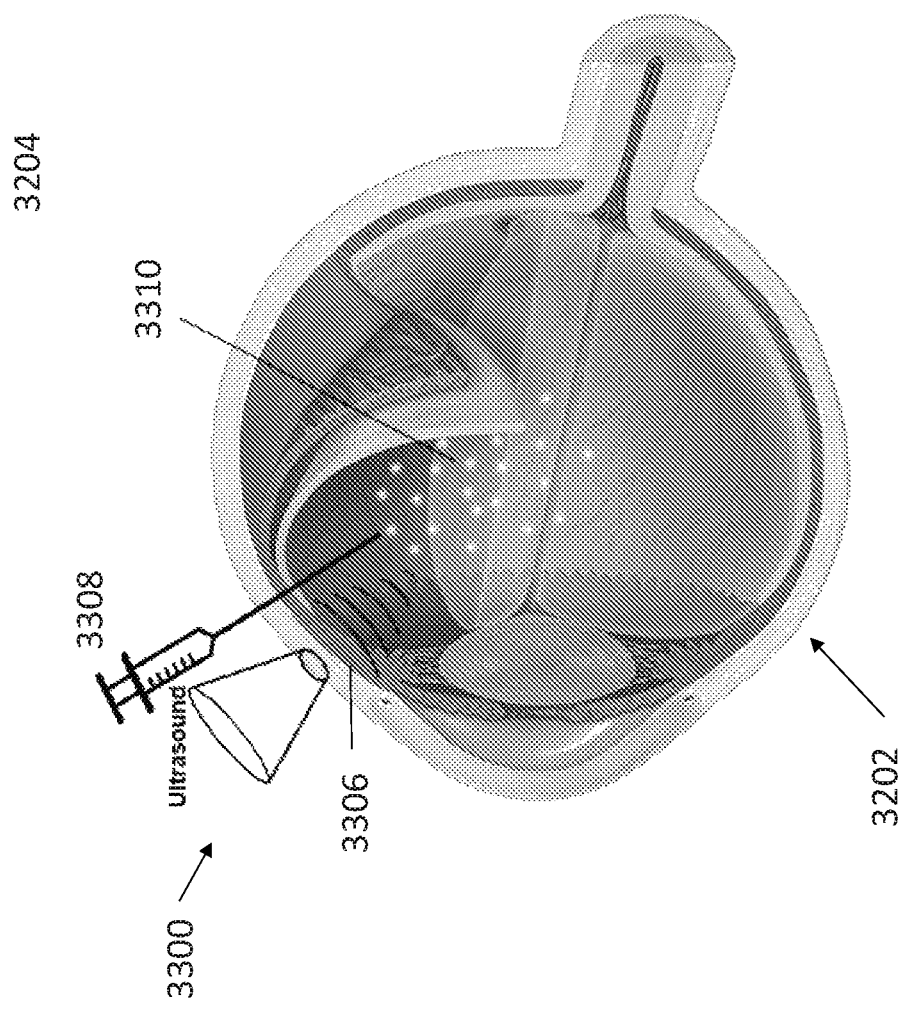
FIG. 33 shows an example embodiment diagram of ocular drug delivery to an eye.

FIG. 33 shows an example embodiment diagram 3300 of ocular drug delivery to an eye 3202. As shown in the example embodiment, a treatment site 3306 of eye 3202 can be selected intravitreal injection 3208 or other delivery of particles 3210 to the eye. In some embodiments, these can be drug-carrying, drug-coated, or drug loaded nano-particles. This can be monitored, for example by ultrasound or other processes.

Figure 34A:
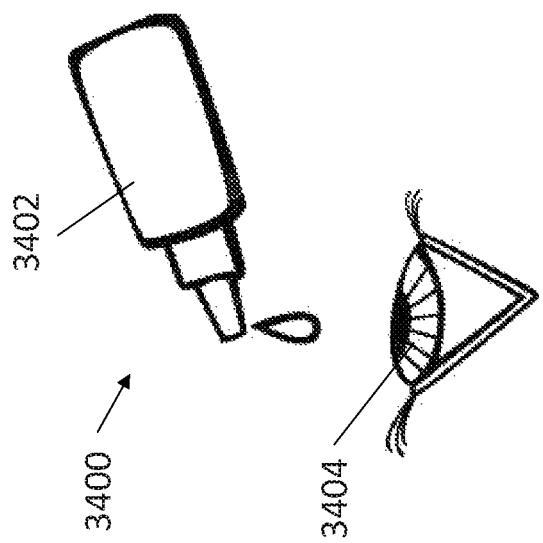
FIG. 34A shows an example embodiment diagram of applying accommodating eye drops to eye.

FIG. 34A shows an example embodiment diagram 3400 of applying accommodating eye drops 3402 to eye 3404.

FIG. 34B shows an example embodiment diagram 3410 of applying accommodating eye drops 3402 to eye 3404. As shown in the example embodiment, these can be injected in some embodiments, and can also move through channels 3406 of eye 3402.

FIG. 34C shows an example embodiment diagram 3400 of effects of applying accommodating eye drops to eye 3404. As shown in the example embodiment, drops can cause moderate accommodation effects and a strong pinhole effect on the pupil, iris, and lens. These effects can also be modeled and simulated, as described by the processes, systems, and methods herein. In some embodiments, other eye drops which soften the lens, lens capsule, or other structures can also be simulated by changing material properties of the lens material in the model or simulation. Such eye drops include and are not limited to EVO 06 sterile lens drop which break bonds in the lens and restore lens flexibility. This can be simulated, analyzed, and otherwise manipulated to see the accommodation and physiological impact and effect on the eye.

Figure 35A:
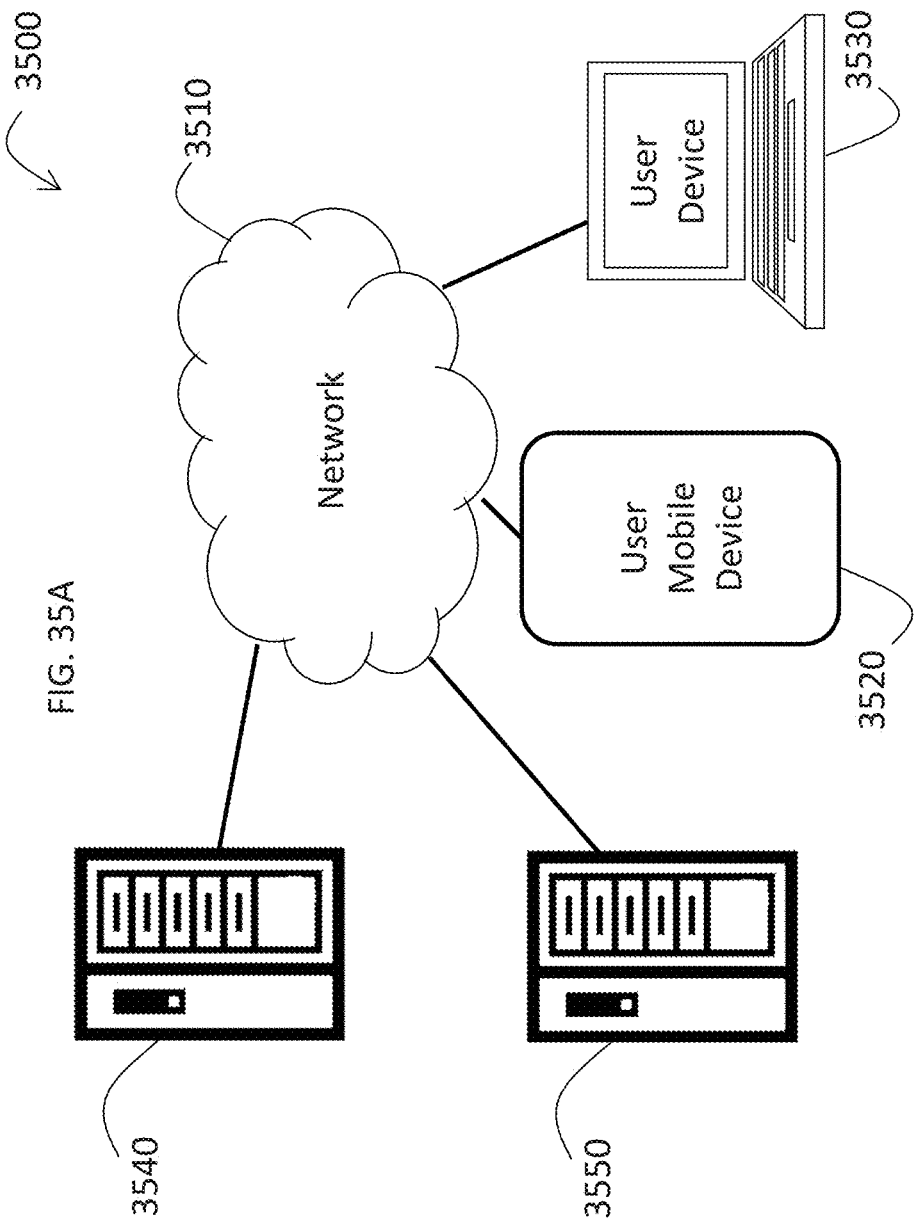
FIG. 35A is an example embodiment of a basic network setup diagram.

FIG. 35A is an example embodiment of a basic network setup diagram 3500. As shown in the example embodiment, network setup diagram 3500 of can include multiple servers 3540, 3550 which can include applications distributed on one or more physical servers, each having one or more processors, memory banks, operating systems, input/output interfaces, power supplies, network interfaces, and other components and modules implemented in hardware, software or combinations thereof as are known in the art. These servers can be communicatively coupled with a wired, wireless, or combination network 3510 such as a public network (e.g. the Internet, cellular-based wireless network, cloud-based network, or other public network), a private network or combinations thereof as are understood in the art. Servers 3540, 3550 can be operable to interface with websites, webpages, web applications, social media platforms, advertising platforms, and others. As shown, a plurality of end user devices 3520, 3530 can also be coupled to the network and can include, for example: user mobile devices such as smart phones, tablets, phablets, handheld video game consoles, media players, laptops; wearable devices such as smartwatches, smart bracelets, smart glasses or others; and other user devices such as desktop devices, fixed location computing devices, video game consoles or other devices with computing capability and network interfaces and operable to communicatively couple with network 3510.

Figure 35B:
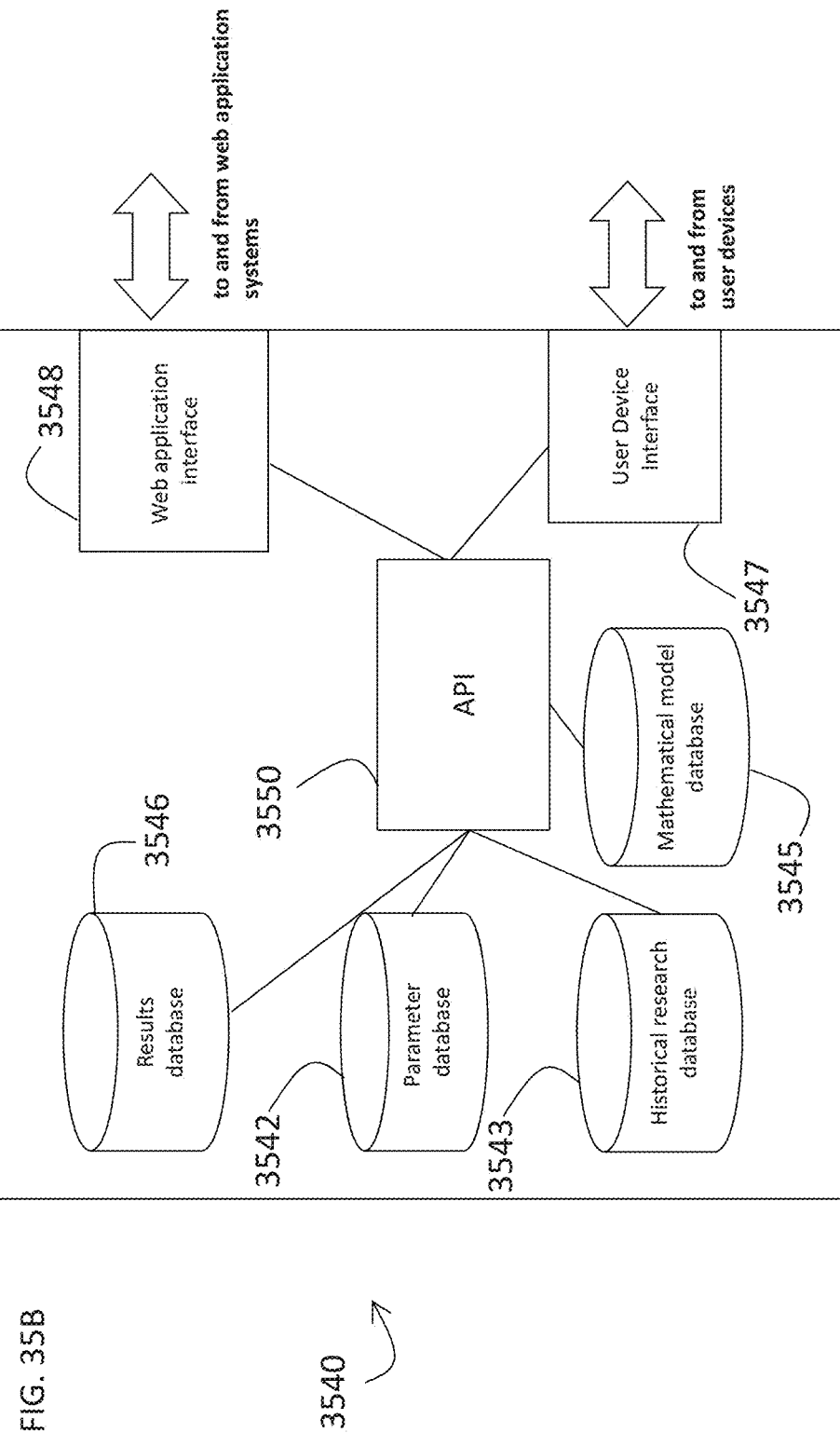
FIG. 35B is an example embodiment of a network connected server system diagram.

FIG. 35B is an example embodiment of a network connected modeling and simulation system diagram 3540. As shown in the example embodiment, a modeling and simulation server system can include at least one user device interface 3547 implemented with technology known in the art for facilitating communication between system user devices and the server and communicatively coupled with a server-based application program interface (API) 3550. API 3550 of the server system can also be communicatively coupled to at least one tracking and routing engine 3548 for communication with web applications, websites, webpages, websites, social media platforms, and others. As such, it can access information via a network when needed. API 3550 can also be communicatively coupled with a parameter database 3542, a historical research informational database 3543, a mathematical model database 3545, and results database 3546 combinations thereof or other databases and other interfaces. API 3550 can instruct databases 3542, 3543, 3545, 3546 to store (and retrieve from the databases) information such as variables, models, best practices, results, or others as appropriate. Databases 3542, 3543, 3545, 3546 can be implemented with technology known in the art, such as relational databases, object oriented databases, combinations thereof or others. Databases 3542, 3543, 3545, 3546 can be a distributed database and individual modules or types of data in the database can be separated virtually or physically in various embodiments.

Figure 35C:
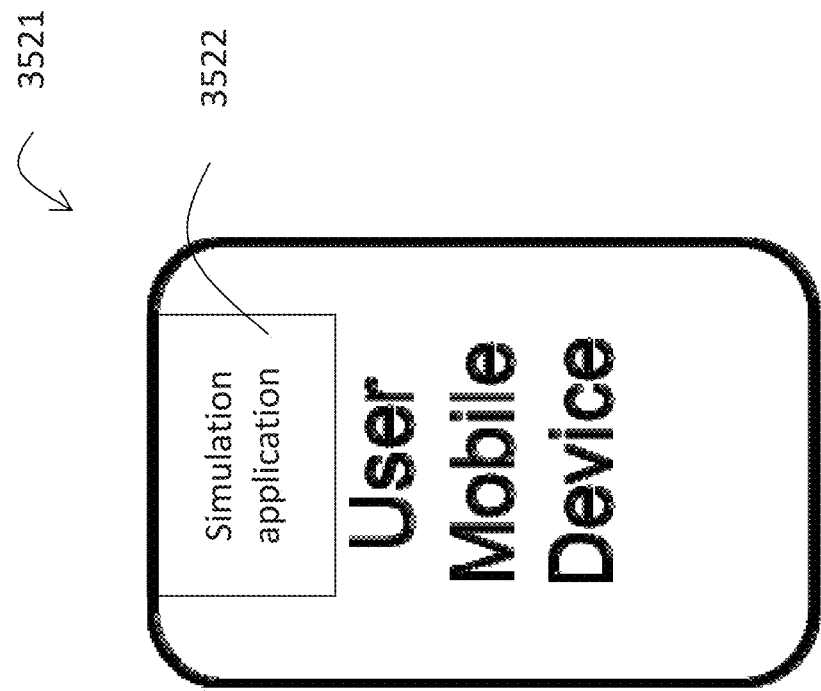
FIG. 35C is an example embodiment of a user mobile device diagram.

FIG. 35C is an example embodiment of a user mobile device diagram 3521. As shown in the example embodiment, a user mobile device 3521, can includes a network connected simulation application 3522 that is installed in, pushed to, or downloaded to the user mobile device or its internet browser application. In many embodiments user devices are touch screen devices such as smart phones, phablets or tablets which have at least one processor, network interface, camera, power source, memory, speaker, microphone, input/output interfaces, operating systems and other typical components and functionality. It should be understood that user mobile device 3521 can be replaced with equivalent functionality by user devices such as desktop or laptop computers in various embodiments.

In some embodiments, simulation application 3522 may not be installed on user device 3521. Instead, it may be replaced by one or more of a system administrator application, an advertiser application, an affiliate application, a consumer application, or others. In some embodiments, a dedicated application for any of these may not be installed on user device 3521. Instead, users may access a portal via a web browser installed on device 3521, which may be dedicated or hybrids of various portals or websites.

Although FIGS. 35A-35C are directed to a network based system, it should be understood that simulations and modeling systems and processes and data storage in non-transitory memory as disclosed herein can be performed on non-network connected devices as well or implemented on a single device. Further, in some embodiments, they are distributed in different fashions than those shown.

As used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

In many instances, entities are described herein as being coupled to other entities. It should be understood that the terms "coupled" and "connected" (or any of their forms) are used interchangeably herein and, in both cases, are generic to the direct coupling of two entities (without any non-negligible (e.g., parasitic) intervening entities) and the indirect coupling of two entities (with one or more non-negligible intervening entities). Where entities are shown as being directly coupled together, or described as coupled together without description of any intervening entity, it should be understood that those entities can be indirectly coupled together as well unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A computer-implemented virtual eye analyzing and simulation method for treatment of accommodation of an eye of a patient using neural networks, the method comprising:

measuring elasticity of sclera and potential energy stored in a choroid during transition from unaccommodated state to accommodated state of the eye of the patient;

simulating the elasticity of sclera and potential energy stored in the choroid during transition from unaccommodated state to accommodated state based on a first Finite Element Model (FEM) of one or more structures of an accommodative mechanism of the eye of the patient, wherein the one or more structures is associated with at least one of a ciliary muscle, lens, zonules, sclera, lamina cribrosa, retina, and choroid, wherein the ciliary muscle represents the eye at rest, a second FEM of one or more structures of the accommodative mechanism of the eye of the patient, wherein the one or more structures is associated with at least one of the ciliary muscle, lens, zonules, sclera, lamina cribrosa, retina, and choroid, wherein the ciliary muscle represents the eye at unaccommodated state, and wherein the ciliary muscle undergoing zonule pre-tensioning and a third FEM of one or more structures of the accommodative mechanism of the eye of the patient, wherein the one or more structures is associated with at least one of the ciliary muscle, lens, zonules, sclera, lamina cribrosa, retina, and choroid, wherein the ciliary muscle represents the eye at accommodated state; and analyzing the measured and the simulated elasticity of sclera and potential energy stored in the choroid during transition from unaccommodated state to accommodated state in real-time using neural networks.

2. The computer-implemented virtual eye analyzing and simulation method of claim 1, wherein all steps are performed in real-time at a plurality of time points.

3. The computer-implemented virtual eye analyzing and simulation method of claim 2, wherein the plurality of time points includes intraoperative time and preoperative time.

4. The computer-implemented virtual eye analyzing and simulation method of claim 1 further comprising simulating ocular nerve head, lamina cribrosa, and central optical power changes in a crystalline lens.

5. The computer-implemented virtual eye analyzing and simulation method of claim 1 further comprising validating each of the first, second and third model by comparing results from each of the first, second and third model with experimental data by different patients.

6. The computer-implemented virtual eye analyzing and simulation method of claim 1 further comprising validating each of the first, second and third model by comparing results from each of the first, second and third model with experimental data by different organizations.

7. The computer-implemented virtual eye analyzing and simulation method of claim 1, wherein determining and simulating each of the first, second and third model comprises simulating direction of force of the ciliary muscle.

8. The computer-implemented virtual eye analyzing and simulation method of claim 7, wherein the direction of force comprises a force of a longitudinal fiber of the ciliary muscle.

9. The computer-implemented virtual eye analyzing and simulation method of claim 7, wherein the direction of force comprises a force of a circular fiber of the ciliary muscle.

10. The computer-implemented virtual eye analyzing and simulation method of claim 7, wherein the direction of force comprises a force of a radial fiber of the ciliary muscle.

11. The computer-implemented virtual eye analyzing and simulation method of claim 1, wherein the third model comprises circular, radial, and longitudinal ciliary muscle fibers contracting independently of one another or in a plurality of contractile forces.

12. The computer-implemented virtual eye analyzing and simulation method of claim 1 further comprising refining each of the first, second and third model, wherein the refining includes modifying lens movement by adding prestress, ciliary muscle fibers using 3D imaging.

13. The computer-implemented virtual eye analyzing and simulation method of claim 1 further comprising refining each of the first, second and third model output for standalone or integrated enhanced display.

14. A virtual eye analyzing and simulation system for treatment of accommodation of an eye of a patient using neural networks, the system comprises one or more processors for performing:
measuring modulus of elasticity of sclera and potential energy stored in a choroid during transition from unaccommodated state to accommodated state of the eye of the patient;
simulating the elasticity of sclera and potential energy stored in the choroid during transition from unaccommodated state to accommodated state based on a first Finite Element Model (FEM) of one or more structures of an accommodative mechanism of the eye of the patient, wherein the one or more structures are associated with at least one of a ciliary muscle, lens, zonules, sclera, lamina cribrosa, retina, and choroid, wherein the ciliary muscle represents the eye at rest, a second FEM of one or more structures of the accommodative mechanism of the eye of the patient, wherein the one or more structures are associated with at least one of the ciliary muscle, lens, zonules, sclera, lamina cribrosa, retina, and choroid, wherein the ciliary muscle represents the eye at unaccommodated state, and wherein the ciliary muscle undergoing zonule pre-tensioning and a third FEM of one or more structures of the accommodative mechanism of the eye of the patient, wherein the one or more structures are associated with at least one of the ciliary muscle, lens, zonules, sclera, lamina cribrosa, retina, and choroid, wherein the ciliary muscle represents the eye at accommodated state; and
analyzing the measured and the simulated elasticity of sclera and potential energy stored in the choroid during transition from unaccommodated state to accommodated state in real-time using neural networks.

15. The system of claim 14 further comprising simulating, in real time biomechanical interactions and changes in preoperative time and in real-time at intraoperative time, ocular nerve head, lamina cribrosa, and central optical power changes in a crystalline lens.

16. The system of claim 14 further comprising validating, in real time at preoperative time and in real-time at intraoperative time, each of the first, second and third model by comparing results from each of the first, second and third model with experimental data by different patients.

17. The system of claim 14, wherein the third model comprises the ciliary muscle contracting.

18. The system of claim 14, wherein determining and simulating each of the first, second and third model comprises simulating direction of force of the ciliary muscle.

19. The system of claim 18 wherein the direction of force comprises a force of a longitudinal fiber of the ciliary muscle.

20. The system of claim 18, wherein the direction of force comprises a force of a circular fiber of the ciliary muscle.

* * * * *